(12) United States Patent
Cianchetta et al.

(10) Patent No.: US 9,365,545 B2
(45) Date of Patent: Jun. 14, 2016

(54) THERAPEUTIC COMPOUNDS AND COMPOSITIONS

(71) Applicant: AGIOS PHARMACEUTICALS, INC, Cambridge, MA (US)

(72) Inventors: Giovanni Cianchetta, Waltham, MA (US); Janeta Popovici-Muller, Windham, NH (US); Robert Zahler, Pennington, NJ (US); Sheldon Cao, Fuyang (CN); Xiaolei Wang, Shanghai (CN); Zhixiong Ye, Beijing (CN)

(73) Assignee: AGIOS PHARMACEUTICALS, INC, Cambridge, MA (US)

(*) Notice: Subject to any disclaimer, the term of this patent is extended or adjusted under 35 U.S.C. 154(b) by 0 days.

(21) Appl. No.: 14/814,862

(22) Filed: Jul. 31, 2015

(65) Prior Publication Data

US 2015/0336931 A1 Nov. 26, 2015

Related U.S. Application Data

(63) Continuation of application No. 14/210,583, filed on Mar. 14, 2014, now Pat. No. 9,108,921.

(51) Int. Cl.

| | |
|---|---|
| *C07D 401/12* | (2006.01) |
| *C07D 417/12* | (2006.01) |
| *C07D 211/52* | (2006.01) |
| *C07D 401/14* | (2006.01) |
| *C07D 413/12* | (2006.01) |
| *C07D 211/48* | (2006.01) |
| *C07D 405/12* | (2006.01) |
| *C07D 417/14* | (2006.01) |

(52) U.S. Cl.
CPC ............ *C07D 401/12* (2013.01); *C07D 211/48* (2013.01); *C07D 211/52* (2013.01); *C07D 401/14* (2013.01); *C07D 405/12* (2013.01); *C07D 413/12* (2013.01); *C07D 417/12* (2013.01); *C07D 417/14* (2013.01)

(58) Field of Classification Search
USPC ............ 514/314, 321; 546/172, 198; 544/353
See application file for complete search history.

(56) References Cited

U.S. PATENT DOCUMENTS

| | | | |
|---|---|---|---|
| 3,046,122 A | 7/1962 | Siis et al. | |
| 3,097,210 A | 7/1963 | Bicking | |
| 4,474,599 A | 10/1984 | Rogers et al. | |
| 4,775,762 A | 10/1988 | Knox et al. | |
| 4,849,424 A | 7/1989 | Ikeda et al. | |
| 4,881,965 A | 11/1989 | Yamamoto et al. | |
| 4,889,553 A | 12/1989 | Rowson et al. | |
| 4,959,094 A | 9/1990 | Wegner et al. | |
| 5,122,530 A | 6/1992 | Tomioka et al. | |
| 5,180,732 A | 1/1993 | Tomioka et al. | |
| 5,220,028 A | 6/1993 | Iwasawa et al. | |
| 5,252,590 A | 10/1993 | Tomioka et al. | |
| 6,150,356 A | 11/2000 | Lloyd et al. | |
| 6,172,005 B1 | 1/2001 | Selby | |
| 6,492,368 B1 | 12/2002 | Dorsch et al. | |
| 6,511,977 B1 | 1/2003 | Lloyd et al. | |
| 6,818,631 B1 | 11/2004 | Nakagawa et al. | |
| 7,288,554 B2 | 10/2007 | Finkelstein et al. | |
| 7,524,848 B2 | 4/2009 | Powers et al. | |
| 7,863,444 B2 | 1/2011 | Calderwood et al. | |
| 8,642,660 B2 | 2/2014 | Goldfarb | |
| 8,742,119 B2 | 6/2014 | Salituro et al. | |
| 9,108,921 B2 * | 8/2015 | Cianchetta ........... C07D 211/52 |
| 2003/0187001 A1 | 10/2003 | Calderwood et al. | |
| 2004/0198979 A1 | 10/2004 | Dhanak et al. | |
| 2007/0282101 A1 | 12/2007 | Ericsson et al. | |
| 2008/0004269 A1 | 1/2008 | Xu et al. | |
| 2008/0051414 A1 | 2/2008 | Hurley et al. | |
| 2008/0214495 A1 | 9/2008 | Alstermark et al. | |
| 2009/0054453 A1 | 2/2009 | Alcaraz et al. | |
| 2009/0163545 A1 | 6/2009 | Goldfarb | |
| 2009/0247499 A1 | 10/2009 | Fletcher et al. | |
| 2010/0105657 A1 | 4/2010 | Nordvall et al. | |
| 2011/0224252 A1 | 9/2011 | Dumeunier et al. | |

FOREIGN PATENT DOCUMENTS

| | | |
|---|---|---|
| CA | 2235621 A1 | 5/1997 |
| CN | 102112131 A | 6/2011 |

(Continued)

OTHER PUBLICATIONS

Adveenko, et al., "Thiocyanation of N-arylsulfonyl-, N-aroyl-, and N-[(N-arylsulfonyl)benzimidoyl]-1,4-benzoquinone imines" Russian Journal of Organic Chemistry, vol. 45, No. 3 (2009), 408-416.

Baxter I et al: "Preparation and some reactions of 6-arylsulphonimidobenzoxazol-2(3H)-one" Journal of the Chemical Society, Section C: Organic Chemistry, Chemical Society. Letchworth, GB LNKD-DOI:10.1039/J39700000850, Jan. 1, 1970, pp. 850-853.

Beutler et al. "Elevated Pyruvate Kinase Activity in Patients with Hemolytic Anemia Due to Red Cell Pyruvate Kinase 'Deficiency'" The American Journal of Medicine (1987) vol. 83, pp. 899-904.

(Continued)

*Primary Examiner* — Charanjit Aulakh
(74) *Attorney, Agent, or Firm* — Lando & Anastasi, LLP

(57) ABSTRACT

Compounds of general formula I:

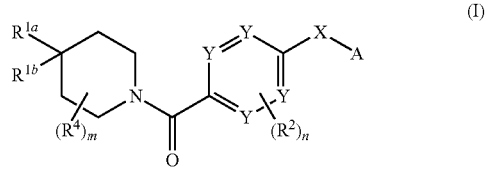

and compositions comprising compounds of general formula I that modulate pyruvate kinase are described herein. Also described herein are methods of using the compounds that modulate pyruvate kinase in the treatment of diseases.

31 Claims, No Drawings

(56) References Cited

FOREIGN PATENT DOCUMENTS

| | | |
|---|---|---|
| CN | 102805860 A | 12/2012 |
| DE | 3813886 A1 | 11/1989 |
| EP | 0246749 A2 | 11/1987 |
| EP | 0628551 A1 | 12/1994 |
| IT | 1176770 B | 8/1987 |
| JP | S61129129 A | 6/1986 |
| JP | 06-025177 | 2/1994 |
| JP | 2002-193710 A | 7/2002 |
| JP | 2007/238458 A | 9/2007 |
| WO | 8501289 A1 | 3/1985 |
| WO | 9211761 A1 | 7/1992 |
| WO | 97/28141 A1 | 8/1997 |
| WO | 9916751 A1 | 4/1999 |
| WO | 9948490 A1 | 9/1999 |
| WO | 0017202 A1 | 3/2000 |
| WO | 01/07440 A1 | 2/2001 |
| WO | 0117956 A1 | 3/2001 |
| WO | 03022277 A1 | 3/2003 |
| WO | 03037252 A2 | 5/2003 |
| WO | 03/062235 A1 | 7/2003 |
| WO | 03/076422 A1 | 9/2003 |
| WO | 03093297 A2 | 11/2003 |
| WO | 2004/004730 A2 | 1/2004 |
| WO | 2004014851 A2 | 2/2004 |
| WO | 2004/037251 A1 | 5/2004 |
| WO | 2004110418 A2 | 12/2004 |
| WO | 2006033628 A1 | 3/2006 |
| WO | 2006043950 A1 | 4/2006 |
| WO | 2006052190 A1 | 5/2006 |
| WO | 2006117762 A2 | 11/2006 |
| WO | 2007016354 A1 | 2/2007 |
| WO | 2007019346 A1 | 2/2007 |
| WO | 2008/019139 A2 | 2/2008 |
| WO | 2008024284 A2 | 2/2008 |
| WO | 2008/026658 A1 | 3/2008 |
| WO | 2008047198 A1 | 4/2008 |
| WO | 2008/050168 A1 | 5/2008 |
| WO | 2009012430 A1 | 1/2009 |
| WO | 2009/053102 A1 | 4/2009 |
| WO | 2009086303 A2 | 7/2009 |
| WO | 2010023445 A1 | 3/2010 |
| WO | 2010/042867 A2 | 4/2010 |
| WO | 2010124082 A1 | 10/2010 |
| WO | 2010/129596 A1 | 11/2010 |
| WO | 2010130638 A1 | 11/2010 |
| WO | 2011002817 A1 | 1/2011 |
| WO | 2011094708 A2 | 8/2011 |
| WO | 2011109441 A1 | 9/2011 |
| WO | 2011137089 A1 | 11/2011 |
| WO | 2012052102 A1 | 4/2012 |
| WO | 2012069503 A1 | 5/2012 |
| WO | 2012083246 A1 | 6/2012 |

OTHER PUBLICATIONS

Boxer et al. "Identification of activators for the M2 isoform of human pyruvate kinase Version 3" Probe Reports from the NIH Molecular Libraries Program [Internet] (2009) pp. 1-25.
Boxer, et al. "Evaluation of Substituted N,N'-Diarylsulfonamides as Activators of the Tumor Cell Specific M2 Isoform of Pyruvate Kinase" Journal of Medicinal Chemistry (2010) vol. 53, pp. 1048-1055.
Cecil Textbook of Medicine, edited by Bennet, J.C., and Plum F., 20th edition, vol. 1, 1004-1010, 1996.
Cohen et al., "The development and therapeutic potential of protein kinase inhibitors", Current Opinion in Chemical Biology, 3, 459-465, 1999.
Conti et al. "Su alcuni analoghi assigenati della benzo-tiazine 2-3-diidro-3-cheto-benzo-1-4-ossazine 6-sostitute" Bollettino Scientifico Della Facolta Di Chimica Industriale Di Bologna (1957) vol. XV, No. 2, pp. 33-36.
Crawford et al., Caplus an 2010:1218943.
Database Chemcats, Chemical Abstracts Service, Columbus, OH, US "Bionet Screening Compounds" Key Organics Ltd., Camelford, Cornwall (2001).
Dermer et al., "Another Anniversary for the War on Cancer", Bio/Technology, 1994, 12:320.
Dombrauckas, et al., Structural Basis for Tumor Pyruvate Kinasa M2 Allosteric Regulation and Catalysis, Biochemistry, vol. 44, p. 9717-9429 (2005).
European Search report for EP Application No. 10 794 667.5 dated Oct. 9, 2013.
European Search Report for European Application No. 11811257.2 dated Apr. 23, 2014.
Fabbro et al. "Protein kinases as targets for anticancer agents: from inhibitors to useful drugs." Pharmacology & Therapeutics 93, 79-98, 2002.
Freshney et al., Culture of Animal Cells, A Manual of Basic Technique, Alan R. Liss, Inc., 1983, New York, p. 4.
Golub et al., "Molecular Classification of Cancer: Class Discovery and Class Prediction by Gene Expression Monitoring", Science, 286, 531-537, 1999.
Hitosugi, et al., "Tyrosine Phosphorylation Inhibits PKM2 to Promote the Warburg Effect and Tumor Growth" Sci. Signal., Nov. 17, 2009, vol. 2, Issue 97, p. ra73.
International Search Report & Written Opinion for PCT/US10/030139 dated Dec. 10, 2010.
International Search Report & Written Opinion for PCT/US10/40485 dated Aug. 11, 2010.
International Search Report and Written Opinion for International Application No. PCT/CN2013/072688 dated Dec. 12, 2013.
International Search Report and Written Opinion for International Application No. PCT/CN2014/000260 dated Jun. 5, 2014.
International Search Report and Written Opinion for International Application No. PCT/US2012/036390 dated Sep. 21, 2012.
International Search Report and Written Opinion for International Application No. PCT/US2012/036406 dated Jul. 6, 2012.
International Search Report and Written Opinion for International Application No. PCT/US2012/036411 dated Oct. 9, 2012.
International Search Report and Written Opinion for International Application No. PCT/US2012/036412 dated Jul. 6, 2012.
International Search Report and Written Opinion for International Application No. PCT/US2012/036413 dated Jul. 6, 2012.
International Search Report and Written Opinion for International Application No. PCT/US2013/069193 dated Feb. 26, 2014.
International Search Report dated May 3, 2012 for related application PCT/US2011/066595.
International Search Report for PCT/US2010/033610 dated Jul. 22, 2010.
Jiang et al. "Evaluation of thieno[3,2-b]pyrrole[3,2-d]pyridazinones as activators of the tumor cell specific M2 isoform of pyruvate kinase" Bioorganic & Medicinal Chemistry Letters (2010) vol. 20, pp. 3387-3393.
Komoriya et al. "Design, synthesis, and biological activity of non-basic compounds as factor Xa inhibitors: SAR study of S1 and aryl binding sites" Bioorganic & Medicinal Chemistry 13 (2005) 3927-3954.
Korsakov et al. "Synthesis and Properties of Sulfonamide Derivatives of 3,5-Dimethylisoxazole" Khim. Tekhnol (2005) vol. 21, pp. 114-117. Abstract Only.
Mass, R. D., "The HER receptor family: a rich target for therapeutic development", Int. J. Radiation Oncology Bio. Phys. vol. 58(3): 932-940, 2004.
Pan et al. "Research Status of Pyruvate Deficiency" Chinese Journal of Hematology (1999) vol. 20, No. 4, pp. 223.
Patel et al. "Synthesis of some new idolinone derivatives containing piperazine moiety" Bulgarian Chemical Communications, 2003 Bol 35 No. 4 pp. 242-244.
Petz et al. "Increased IgG Molecules Bound to the Surface of Red Blood Cells of Patients With Sickle Cell Anemia" Blood (1984) vol. 64, No. 1, pp. 301-304.
Proisy et al. "Rapid Synthesis of 3-Aminoisoquinoline-5-sulfonamides Using the Buchwald-Hartwig Reaction" Synthesis 2009, No. 4, pp. 0561-0566.

(56) References Cited

OTHER PUBLICATIONS

Steiner et al. "Synthesis and Antihypertensive Activity of New 6-Heteroaryl-3-hydrazinopyridazine Derivatives" Journal of Medicinal Chemistry (1981) vol. 24, No. 1, pp. 59-63.
Supplemental EP Search Report & Written Opinion for EP 10 79 4667 dated Jan. 15, 2013.
Supplemental EP Search Report for European Application No. 10714131.9 dated Oct. 17, 2014.
Tawaka, et al., Caplus an 1998:794998.
VanElemen et al, Caplus am 2003:737742.
Walsh et al. "2-oxo-N-aryl-1,2,3,4-tetrahydroquinoline-6-sulfonamides as activators of the tumor cell specific M2 isoform of pyruvate kinase" Bioorg Med Chem Lett. Nov. 1, 2011; 21(21): 6322-6327.
Wong et al. "PKM2, a Central Point of Regulation in Cancer Metabolism" International Journal of Cell Biology (2013) vol. 2013, pp. 1-11.

* cited by examiner

THERAPEUTIC COMPOUNDS AND COMPOSITIONS

CLAIM OF PRIORITY

This application is a continuation of U.S. Ser. No. 14/210,583, filed Mar. 14, 2014, which claims priority from International Patent Application Number PCT/CN2013/072688, filed Mar. 15, 2013, the contents of each of which is incorporated herein by reference in its entirety.

BACKGROUND OF INVENTION

Pyruvate kinase deficiency (PKD) is one of the most common enzyme defects in erythrocytes in human due to autosomal recessive mutations of the PKLR gene (Zanella, A., et al., *Br J Haematol* 2005, 130 (1), 11-25). It is also the most frequent enzyme mutation in the central glycolytic pathway and only second to glucose-6 phosphate dehydrogenase (G6PD) deficiency (Kedar, P., et al., *Clin Genet* 2009, 75 (2), 157-62) of the hexose monophosphate shunt.

Human erythrocytes are unique in that they anucleate when mature Immature erythocytes have nuclei but during early erythropoiesis prior to becoming circulating reticulocytes they extrude nuclei as well as other organelles such as mitochondria, endoplasmic reticulum, and golgi aparatus, in order to make room for oxygen-carrying hemoglobin. As a result of lacking mitochondria, mature red blood cells do not utilize any of the oxygen they transport to economically synthesize adenosine triphosphate (ATP) as other normal differentiated cells do. Instead, red blood cells depend entirely on anaerobic glycolysis to cycle nicotinamide adenine dinucleotide ($NAD^+$) and to make ATP, an essential energy source largely used to drive ATPase-dependent $K^+/Na^+$ and $Ca^{2+}$ pumps, in order to maintain cell membrane integrity and pliability as they navigate through blood vessels. In PKD disorder, two major distinctive metabolic abnormalities are ATP depletion and concomitant increase of 2,3-diphosphoglycerate consistent with accumulation of upper glycolytic intermediates. Moreover, one of the consequences of decreased ATP and pyruvate level is lowered lactate level leading to inability to regenerate NAD through lactate dehydrogenase for further use in glycolysis. The lack of ATP disturbs the cation gradient across the red cell membrane, causing the loss of potassium and water, which causes cell dehydration, contraction, and crenation, and leads to premature destruction and diminished lifetime of the red blood cells (RBCs). Such defective RBCs are destroyed in the spleen, and excessive hemolysis rate in the spleen leads to the manifestation of hemolytic anemia. The exact mechanism by which PKD sequesters newly matured RBCs in the spleen to effectively shorten overall half-lives of circulating RBCs is not yet clear, but recent studies suggest that metabolic dysregulation affects not only cell survival but also the maturation process resulting in ineffective erythropoiesis (Aizawa, S. et al., *Exp Hematol* 2005, 33 (11), 1292-8).

Pyruvate kinase catalyzes the transfer of a phosphoryl group from phosphoenolpyruvate (PEP) to ADP, yielding one molecule of pyruvate and one molecule of ATP. The enzyme has an absolute requirement for $Mg^{2+}$ and $K^+$ cations to drive catalysis. PK functions as the last critical step in glycolysis because it is an essentially irreversible reaction under physiological conditions. In addition to its role of synthesizing one of the two ATP molecules from the metabolism of glucose to pyruvate, pyruvate kinase is also an important cellular metabolism regulator. It controls the carbon flux in lower-glycolysis to provide key metabolite intermediates to feed biosynthetic processes, such as pentose-phosphate pathway among others, in maintaining healthy cellular metabolism. Because of these critical functions, pyruvate kinase is tightly controlled at both gene expression and enzymatic allostere levels. In mammals, fully activated pyruvate kinase exists as a tetrameric enzyme. Four different isozymes (M1, M2, L and R) are expressed from two separate genes. Erythrocyte-specific isozyme PKR is expressed from the PKLR gene ("L gene") located on chromosome 1q21. This same gene also encodes the PKL isozyme, which is predominately expressed in the liver. PKLR consists of 12 exons with exon 1 is erythroid-specific whereas exon 2 is liver-specific. The two other mammalian isozymes PKM1 and PKM2 are produced from the PKM gene ("M gene") by alternative splicing events controlled by hnRNP proteins. The PKM2 isozyme is expressed in fetal tissues and in adult proliferating cells such as cancer cells. Both PKR and PKM2 are in fact expressed in proerythroblasts. However, upon erythroid differentiation and maturation, PKM2 gradually is decreased in expression and progressively replaced by PKR in mature erythrocytes.

Clinically, hereditary PKR deficiency disorder manifests as non-spherocytic hemolytic anemia. The clinical severity of this disorder range from no observable symptoms in fully-compensated hemolysis to potentially fatal severe anemia requiring chronic transfusions and/or splenectomy at early development or during physiological stress or serious infections. Most affected individuals who are asymptomatic, paradoxically due to enhanced oxygen-transfer capacity, do not require any treatment. However, for some of the most severe cases, while extremely rare population-wise with estimated prevalence of 51 per million (Beutler, E. *Blood* 2000, 95 (11), 3585-8), there is no disease-modifying treatment available for these patients other than palliative care (Tavazzi, D. et al., *Pediatr Ann* 2008, 37 (5), 303-10). These hereditary non-spherocytic haemolytic anemia (HNSHA) patients present a clear unmet medical need.

Heterogenous genetic mutations in PKR lead to dysregulation of its catalytic activity. Since the initial cloning of PKR and report of a single point mutation $Thr^{384}$>Met associated with a HNSHA patient (Kanno, H. et al., *Proc Natl Acad Sci USA* 1991, 88 (18), 8218-21), there are now nearly 200 different reported mutations associated with this disease reported worldwide (Zanella, A. et al., *Br J Haematol* 2005, 130 (1), 11-25; Kedar, P., et al., *Clin Genet* 2009, 75 (2), 157-62; Fermo, E. et al., *Br J Haematol* 2005, 129 (6), 839-46; Pissard, S. et al., *Br J Haematol* 2006, 133 (6), 683-9). Although these mutations represent wide range genetic lesions that include deletional and transcriptional or translational abnormalities, by far the most common type is missense mutation in the coding region that one way or another affects conserved residues within domains that are structurally important for optimal catalytic function of PKR. The pattern of mutation prevalence seems to be unevenly distributed toward specific ethnic backgrounds. For instance, the most frequent codon substitutions reported for North American and European patients appear to be $Arg^{486}$>Trp and $Arg^{510}$>Gln, while mutations $Arg^{479}$>His, $Arg^{490}$>Trp and $Asp^{331}$>Gly were more frequently found in Asian patients (Kedar, P., et al., *Clin Genet* 2009, 75 (2), 157-62).

Cancer cells rely primarily on glycolysis to generate cellular energy and biochemical intermediates for biosynthesis of lipids and nucleotides, while the majority of "normal" cells in adult tissues utilize aerobic respiration. This fundamental difference in cellular metabolism between cancer cells and normal cells, termed the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

All tumor cells exclusively express the embryonic M2 isoform of pyruvate kinase, suggesting PKM2 as a potential target for cancer therapy. PKM2 is also expressed in adipose tissue and activated T-cells. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation will lead to the loss of allosteric control of PKM2 needed for shunting biochemical intermediates from glycolysis into biosynthesis of nucleotides and lipids. Thus, the activation of PKM2 can inhibit the growth and proliferation of cancer cells, activated immune cells, and fat cells. Activation of PKM2 may therefore be effective in the treatment of cancer, obesity, diabetes, autoimmune conditions, and proliferation-dependent diseases, e.g., benign prostatic hyperplasia (BPH).

SUMMARY OF INVENTION

Described herein are compounds that activate pyruvate kinase and pharmaceutically acceptable salts, solvates, and hydrates thereof, for example, compounds that activate PKR and/or PKM2.

Also provided are pharmaceutical compositions comprising a compound provided herewith and the use of such compositions in methods of treating diseases and conditions that are related to pyruvate kinase function, e.g., PKR function, and/or PKM2 function (including, e.g., cancer, diabetes, obesity, autoimmune disorders, and benign prostatic hyperplasia (BPH)).

In one embodiment, provided herein is a compound of Formula (I):

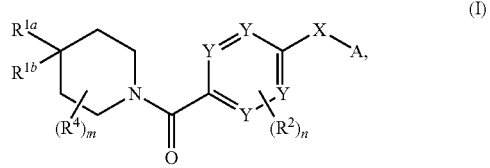

or a pharmaceutically acceptable salt thereof, wherein:

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —NH—S(O)$_2$—CH$_2$—, —CH$_2$—S(O)—NH— or —CH$_2$—S(O)$_2$—NH—;

Y is C(H) or N; provided that no more than two Y groups are N;

$R^{1a}$ is hydroxyl, —CH$_2$OH, —CHO, —CO$_2$H or —CO$_2$—C$_{1-6}$ alkyl;

$R^{1b}$ is C$_{1-8}$ alkyl optionally substituted with one to four R$^5$ groups; C$_{1-8}$ alkenyl optionally substituted with one to four R$^5$ groups; cycloalkyl; heterocycle; aryl; heteroaryl; cycloalkylalkyl; cycloalkylalkenyl; heterocyclylalkyl; heterocyclylalkenyl; aralkyl; aralkenyl; heteroaralkyl; heteroaralkenyl; or —OH, with the proviso that when $R^{1a}$ is OH, $R^{1b}$ is not OH; wherein each cycloalkyl, heterocycle, aryl, heteroaryl, cycloalkylalkyl, cycloalkylalkenyl, heterocyclylalkyl, heterocyclylalkenyl, aralkyl, aralkenyl, heteroaralkyl, or heteroaralkenyl is optionally substituted;

each R$^2$ is independently selected from halo, alkyl, CN, OH, and alkoxy, wherein said alkyl or alkoxy is optionally substituted with one to four R$^5$ groups; or two adjacent R$^2$ groups are taken together with the ring atoms they are attached to form a 5- or 6-membered carbocyclic, aryl, heterocyclic or heteroaryl ring;

each R$^4$ is independently selected from halo, alkyl, alkoxy, haloalkyl, haloalkoxy and hydroxyl;

each R$^5$ is independently selected from halo, OH, C$_{1-6}$ alkoxy, CN, NH$_2$, —SO$_2$—C$_{1-6}$ alkyl, —NH(C$_{1-6}$ alkyl), and —N(C$_{1-6}$ alkyl)$_2$;

n is 0, 1, 2 or 3; and m is 0, 1 or 2; provided that a compound of Formula (I) is not the following:

(1) 4-[[4-hydroxy-4-(4-methylphenyl)-1-piperidinyl]carbonyl]-N-2-thiazolyl-benzenesulfonamide;
(2) 4-[[4-(4-chlorophenyl)-4-hydroxy-1-piperidinyl]carbonyl]-N-2-thiazolyl-benzenesulfonamide;
(3) 4-[[4-(3-fluorophenyl)-4-hydroxy-1-piperidinyl]carbonyl]-N-2-thiazolyl-benzenesulfonamide;
(4) 4-[[4-(2-fluoro-5-methylphenyl)-4-hydroxy-1-piperidinyl]carbonyl]-N-2-thiazolyl-benzenesulfonamide;
(5) 4-phenyl-1-[4-[(phenylamino)sulfonyl]benzoyl]-4-piperidinecarboxylic acid methyl ester;
(6) 1-[4-[[(2-methylphenyl)amino]sulfonyl]benzoyl]-4-phenyl-4-piperidinecarboxylic acid methyl ester;
(7) 1-[4-[methyl[(4-methylphenyl)sulfonyl]amino]benzoyl]-4-phenyl-4-piperidinecarboxylic acid;
(8) 1-[4-[(methylphenylamino)sulfonyl]benzoyl]-4-phenyl-4-piperidinecarboxylic acid;
(9) 1-[4-[(cyclopropylamino)sulfonyl]benzoyl]-4-phenyl-4-piperidinecarboxylic acid; or
(10) 4-phenyl-1-[4-[[(2-thienylmethyl)amino]sulfonyl]benzoyl]-4-piperidinecarboxylic acid methyl ester.

In another embodiment, provided is a method for treating or preventing (e.g., treating) a disease, condition or disorder as described herein comprising administering a compound provided herein, a pharmaceutically acceptable salt, solvate or hydrate thereof, or pharmaceutical composition thereof.

In another embodiment, provided is a method for increasing lifetime of the red blood cells (RBCs) in need thereof comprising contacting blood with an effective amount of (1) a compound disclosed herein or a pharmaceutically acceptable salt, solvate or hydrate thereof; (2) a composition comprising a compound disclosed herein or a salt, solvate or hydrate thereof and a carrier; or (3) a pharmaceutical composition comprising a compound disclosed herein or a pharmaceutically acceptable salt, solvate or hydrate thereof, and a pharmaceutically acceptable carrier.

In another embodiment, provided is a method for regulating 2,3-diphosphoglycerate levels in blood in need thereof comprising contacting blood with an effective amount of (1) a compound disclosed herein or a pharmaceutically acceptable salt, solvate or hydrate thereof; (2) a composition comprising a compound disclosed herein or a salt, solvate or hydrate thereof and a carrier; or (3) a pharmaceutical composition comprising a compound disclosed herein or a pharmaceutically acceptable salt, solvate or hydrate thereof, and a pharmaceutically acceptable carrier.

In another embodiment, provided is a method for treating hereditary non-spherocytic haemolytic anemia comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating sickle cell anemia comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

Compounds and compositions described herein are activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Examples 2-5. Compounds described herein are also activators of wild type PKR.

In an embodiment, to increase the lifetime of the red blood cells, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibrium to the R, or oxygenated state, thus producing a therapeutic inhibition of the intracellular polymerization that underlies sickling by increasing oxygen affinity due to the 2,3-DPG depletion, thereby stabilizing the more soluble oxyhemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes).

In another embodiment, provided is a method of increasing the level of PKM2 activity and/or glycolysis in a patient in need thereof. The method comprises the step of administering an effective amount of a compound described herein to the patient in need thereof, thereby increasing the level of PKM2 activity and/or glycolysis in the patient. In some embodiments, a compound or a composition described herein is used to maintain PKM2 in its active conformation or activate pyruvate kinase activity in proliferating cells as a means to divert glucose metabolites into catabolic rather than anabolic processes in the patient.

In another embodiment, provided is a method of inhibiting cell proliferation in a patient in need thereof. The method comprises the step of administering an effective amount of a compound described herein to the patient in need thereof, thereby inhibiting cell proliferation in the patient. In one aspect this method can inhibit growth of a transformed cell, more specifically a cancer cell. In another aspect the method generally inhibits growth of a PKM2-dependent cell that undergoes aerobic glycolysis.

In another embodiment, provided is a method of treating a patient suffering from or susceptible to a disease or disorder associated with reduced PKM2 activity or reduced glycolysis in a patient in need thereof. The method comprises the step of administering an effective amount of a compound described herein to the patient in need thereof, thereby treating, preventing or ameliorating the disease or disorder in the patient. In certain embodiment the compound described herein is provided in a pharmaceutical composition. In certain embodiments, the method includes the step of identifying or selecting a patient who would benefit from activation of PKM2 prior to treatment. Identifying or selecting such a patient can be on the basis of the level of PKM2 activity in a cell of the patient. In one aspect, the selected patient is suffering from or susceptible to unwanted cell growth or proliferation, e.g., cancer, obesity, diabetes, atherosclerosis, restenosis, and autoimmune diseases. In another aspect, the selected patient is suffering from a cancer associated with PKM2 function.

In another embodiment, the compound described herein is administered at a dosage and frequency sufficient to increase lactate production or oxidative phosphorylation.

DETAILED DESCRIPTION

The details of construction and the arrangement of components set forth in the following description or illustrated in the drawings are not meant to be limiting. Embodiments can be practiced or carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term "halo" or "halogen" refers to any radical of fluorine, chlorine, bromine or iodine.

The term "alkyl" refers to a monovalent hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. In certain aspects, the term "alkyl" refers to a monovalent hydrocarbon chain that may be a straight chain or branched chain, containing 1 to 6 carbon atoms. In other aspects, the term "alkyl" refers to a monovalent hydrocarbon chain that may be a straight chain or branched chain, containing 1 to 4 carbon atoms.

The term "haloalkyl" refers to an alkyl in which one or more hydrogen atoms are replaced by halo, and includes alkyl moieties in which all hydrogens have been replaced by halo (e.g., perfluoroalkyl). The term "haloalkoxy" refers to an alkoxy in which one or more hydrogen atoms are replaced by halo.

The term "alkenyl" refers to a monovalent straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent. In certain aspects, the term "alkenyl" refers to a monovalent straight or branched hydrocarbon chain containing 2-6 carbon atoms and having one or more double bonds. In other aspects, the term "alkenyl" refers to a monovalent straight or branched hydrocarbon chain containing 2-4 carbon atoms and having one or more double bonds.

The term "alkoxy" refers to an —O-alkyl radical.

The term "aryl" refers to a monocyclic, bicyclic, or tricyclic aromatic hydrocarbon ring system. Examples of aryl moieties include, but are not limited to, phenyl, naphthyl, and anthracenyl.

The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" or "carbocyclyl" refers to saturated or unsaturated cyclic, bicyclic, tricyclic, or polycyclic non-aromatic hydrocarbon groups having 3 to 12 carbons. Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms selected independently from N, O, or S if monocyclic, bicyclic, or tricyclic, respectively).

The term "heterocyclyl" refers to a saturated or unsaturated, 3-10 membered non-aromatic monocyclic, 8-12 membered non-aromatic bicyclic, or 11-14 membered non-aromatic tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl.

Bicyclic and tricyclic ring systems containing one or more heteroatoms and both aromatic and non-aromatic rings are considered to be heterocyclyl groups according to the present definition. Such bicyclic or tricyclic ring systems are considered to be an aryl or a heteroaryl fused to a carbocyclyl or heterocyclyl, where the ring bound to the rest of the molecule is required to be aromatic.

The terms "heteroarylalkyl" and "heteroaralkyl", as used herein, refers to an alkyl group substituted with a heteroaryl group.

The term "heterocyclylalkyl", as used herein, refers to an alkyl group substituted with a heterocyclyl group.

All ring systems (i.e, aryl, heteroaryl, carbocyclyl, cycloalkyl, heterocyclyl, etc.) or ring system portions of groups (e.g., the aryl portion of an aralkyl group) are optionally substituted at one or more substitutable carbon atoms with substituents independently selected from: halo, —C≡N, $C_1$-$C_4$ alkyl, =O, $C_{3-7}$ cycloalkyl, $C_{1-6}$ alkyl, —OH, —O—($C_{1-6}$ alkyl), —SO$_2$—($C_{1-6}$ alkyl), —($C_{1-4}$ alkyl)-N(R$^\circ$)(R$^\circ$), —N(R$^\circ$)(R$^\circ$), —O—($C_{1-4}$ alkyl)-N(R$^\circ$)(R$^\circ$), —C(O)—N(R$^\circ$)(R$^\circ$), —($C_{1-4}$ alkyl)-C(O)—N(R$^\circ$)R$^\circ$), —O-(heteroaryl), —O-(heterocycle), —O-phenyl, -heteroaryl, -heterocycle, and -phenyl, wherein:

each R$^\circ$ is independently selected from hydrogen, and —$C_{1-4}$ alkyl; or two R$^\circ$s are taken together with the nitrogen atom to which they are bound to form a 4- to 8-membered saturated heterocycle optionally comprising one additional heteroatom selected from N, S, S(=O), S(=O)$_2$, and O, any alkyl substituent is optionally further substituted with one or more of —OH, —O—($C_{1-4}$ alkyl), halo, —$NH_2$, —NH($C_{1-4}$ alkyl), or —N($C_{1-4}$ alkyl)$_2$; and any carbon atom on a phenyl, cycloalkyl, heteroaryl or heterocycle substituent is optionally further substituted with one or more of —($C_1$-$C_4$ alkyl), —($C_{1-4}$ fluoroalkyl), —OH, —O—($C_{1-4}$ alkyl), —O—($C_{1-4}$ fluoroalkyl), halo, —$NH_2$, —NH($C_{1-4}$ alkyl), or —N($C_{1-4}$ alkyl)$_2$.

All heterocyclyl ring systems (and any heterocyclyl substituents on any ring system) are optionally substituted on one or more any substitutable nitrogen atom with —$C_{1-4}$ alkyl, or fluoro-substituted $C_{1-4}$ alkyl.

The term "substituted" refers to the replacement of a hydrogen atom by another group.

The term "oxo" refers to an oxygen atom, which forms a carbonyl when attached to carbon, an N-oxide when attached to nitrogen, and a sulfoxide or sulfone when attached to sulfur.

The term "selective" in association with a PKM2 activator is meant at least 2-fold, 3-fold, 4-fold, 5-fold, 6-fold, or 10-fold greater activation of PKM2 than PKM1.

The term "activator" of pyruvate kinase R as used herein means an agent that (measurably) increases the activity of wild type pyruvate kinase R (wtPKR) or causes wild type pyruvate kinase R (wt PKR) activity to increase to a level that is greater than wt PKR's basal levels of activity or an agent that (measurably) increases the activity of a mutant pyruvate kinase R (mPKR) or causes mutant pyruvate kinase R (mPKR) activity to increase to a level that is greater than that mutant PKR's basal levels of activity, for examples, to a level that is 20%, 40%, 50%, 60%, 70%, 80%, 90% or 100% of the activity of wild type PKR.

The term "activator" of pyruvate kinase M2 as used herein means an agent that (measurably) increases the activity of PKM2 or causes PKM2 activity to increase to a level that is greater than PKM2's basal levels of activity. For example, the activator may mimic the effect caused by a natural ligand (e.g., FBP). The activator effect caused by a compound provided herein may be to the same, or to a greater, or to a lesser extent than the activating effect caused by a natural ligand, but the same type of effect is caused. A compound provided herein can be evaluated to determine if it is an activator by measuring either directly or indirectly the activity of the pyruvate kinase when subjected to said compound. The activity of PKM2 can be measured, for example, by monitoring the concentration of a substrate such as ATP or NADH.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

Compounds

Provided herein is a compound of Formula (I) or a pharmaceutically acceptable salt, solvate or hydrate thereof as described above in the Summary of the Invention, e.g, useful for activating wild type PKR and/or various mutant PKRs such as those mutants described herein, and/or useful for selectively activating PKM2.

In one embodiment, provided herein is a compound of Formula (I):

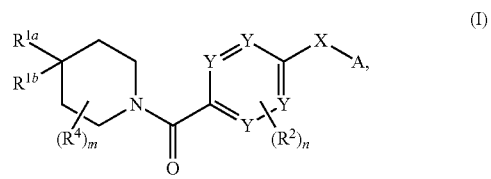

or a pharmaceutically acceptable salt thereof, wherein:

A is aryl or heteroaryl, wherein the aryl or heteroaryl is optionally substituted, and the aryl or heteroaryl is optionally fused to an optionally substituted carbocyclyl or an optionally substituted heterocyclyl;

X is selected from —NH—S(O)$_2$—, —NH—S(O)$_2$—$CH_2$—, —$CH_2$—S(O)—NH— or —$CH_2$—S(O)$_2$—NH—;

Y is C(H) or N; provided that no more than two Y groups are N;

$R^{1a}$ is hydroxyl, —$CH_2OH$, —CHO, —$CO_2H$ or —$CO_2$—$C_{1-6}$ alkyl;

$R^{1b}$ is $C_{1-8}$ alkyl optionally substituted with one to four $R^5$ groups; $C_{1-8}$ alkenyl optionally substituted with one to four $R^5$ groups; cycloalkyl; heterocycle; aryl; heteroaryl; cycloalkylalkyl; cycloalkylalkenyl; heterocyclylalkyl; heterocyclylalkenyl; aralkyl; aralkenyl; heteroaralkyl; heteroaralkenyl; or —OH, with the proviso that when $R^{1a}$ is OH, $R^{1b}$ is not OH; wherein each cycloalkyl, heterocycle, aryl, heteroaryl, cycloalkylalkyl, cycloalkylalkenyl, heterocyclylalkyl, heterocyclylalkenyl, aralkyl, aralkenyl, heteroaralkyl, or heteroaralkenyl is optionally substituted;

each $R^2$ is independently selected from halo, alkyl, CN, OH, and alkoxy, wherein said alkyl or alkoxy is optionally substituted with one to four $R^5$ groups; or two adjacent $R^2$ groups are taken together with the ring atoms they are attached to form a 5- or 6-membered carbocyclic, aryl, heterocyclic or heteroaryl ring;

each $R^4$ is independently selected from halo, alkyl, alkoxy, haloalkyl, haloalkoxy and hydroxyl;

each $R^5$ is independently selected from halo, OH, $C_{1-6}$ alkoxy, CN, $NH_2$, —$SO_2$—$C_{1-6}$ alkyl, —NH($C_{1-6}$ alkyl), and —N($C_{1-6}$ alkyl)$_2$;

n is 0, 1, 2 or 3; and m is 0, 1 or 2; provided that a compound of Formula (I) is not the following:

(1) 4-[[4-hydroxy-4-(4-methylphenyl)-1-piperidinyl]carbonyl]-N-2-thiazolyl-benzenesulfonamide;

(2) 4-[[4-(4-chlorophenyl)-4-hydroxy-1-piperidinyl]carbonyl]-N-2-thiazolyl-benzenesulfonamide;

(3) 4-[[4-(3-fluorophenyl)-4-hydroxy-1-piperidinyl]carbonyl]-N-2-thiazolyl-benzenesulfonamide;

(4) 4-[[4-(2-fluoro-5-methylphenyl)-4-hydroxy-1-piperidinyl]carbonyl]-N-2-thiazolyl-benzenesulfonamide;

(5) 4-phenyl-1-[4-[(phenylamino)sulfonyl]benzoyl]-4-piperidinecarboxylic acid methyl ester;

(6) 1-[4-[[(2-methylphenyl)amino]sulfonyl]benzoyl]-4-phenyl-4-piperidinecarboxylic acid methyl ester;

(7) 1-[4-[methyl[(4-methylphenyl)sulfonyl]amino]benzoyl]-4-phenyl-4-piperidinecarboxylic acid;

(8) 1-[4-[(methylphenylamino)sulfonyl]benzoyl]-4-phenyl-4-piperidinecarboxylic acid;

(9) 1-[4-[(cyclopropylamino)sulfonyl]benzoyl]-4-phenyl-4-piperidinecarboxylic acid; or

(10) 4-phenyl-1-[4-[[(2-thienylmethyl)amino]sulfonyl]benzoyl]-4-piperidinecarboxylic acid methyl ester.

In one embodiment, provided is a compound of formula (I), wherein m is 1. In some aspects of these embodiments, $R^4$ is hydroxyl.

In one embodiment, provided is a compound of formula (I), wherein m is 0 (i.e., there are no $R^4$ substituents on the piperidinyl ring) and $R^{1a}$ is hydroxyl, the compound having formula (Ia):

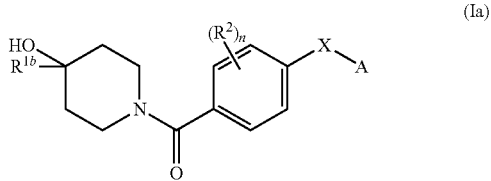

(wherein each Y is CH), or a pharmaceutically acceptable salt thereof, wherein A, X, $R^{1b}$, $R^2$ and n are as described for formula (I).

In certain aspects of formula (I) or (Ia), n is 0. In certain aspects of formula (I) or (Ia), n is 1. In a more specific aspect, $R^2$ is $C_{1-6}$ alkyl (e.g., methyl). In another more specific aspect, $R^2$ is $C_{1-6}$ alkoxy (e.g., methoxy). In another more specific aspect, $R^2$ is halo (e.g., fluoro or chloro). In another more specific aspect, $R^2$ is $C_4$ haloalkoxy (e.g., trifluoromethoxy or difluoromethoxy). In another more specific aspect, $R^2$ is cyano.

In certain aspects of formula (I) or (Ia), n is 2. In a more specific aspect, two $R^2$ moieties, taken together with the atoms to which they are attached, form an optionally substituted cyclyl (e.g., unsubstituted phenyl, unsubstituted isothiazolyl). In another more specific aspect, each $R^2$ moiety is halo (e.g., fluoro).

In certain aspects of formula (I) or (Ia), A is an optionally substituted monocyclic aryl. In a more specific aspect, A is an optionally substituted phenyl (e.g., 2,3-dichlorophenyl, 2-chlorophenyl, 3-chlorophenyl, 4-chlorophenyl, 3-cyanophenyl, 4-cyanophenyl, 2-trifluoromethylphenyl, 3-trifluoromethylphenyl, 4-trifluoromethyphenyl, 3-trifluoromethoxyphenyl, 4-trifluoromethoxyphenyl, 2,3-diamino-4-fluorophenyl). In certain aspects of formula (I) or (Ia), A is an optionally substituted bicyclic aryl. In a more specific aspect, A is an optionally substituted naphthyl (e.g., unsubstituted naphthyl).

In certain aspects of formula (I) or (Ia), A is an optionally substituted monocyclic heteroaryl. In a more specific aspect, A is an optionally substituted pyridyl (e.g., an optionally substituted 3-pyridyl or optionally substituted 2-pyridyl). In an even more specific aspect, A is unsubstituted 3-pyridyl. In an even more specific aspect, A is unsubstituted 2-pyridyl.

In certain aspects of formula (I) or (Ia), A is an optionally substituted bicyclic heteroaryl. In a more specific aspect, A is an optionally substituted quinolin-8-yl (e.g., unsubstituted quinolin-8-yl). In another more specific aspect, A is substituted quinolin-8-yl (e.g., 2-fluoroquinolin-8-yl, 3-fluoroquinolin-8-yl, 5-fluoroquinolin-8-yl or 6-fluoroquinolin-8-yl). In another more specific aspect, A is an optionally substituted quinolin-3-yl (e.g., unsubstituted quinolin-3-yl). In another more specific aspect, A is an optionally substituted quinolin-5-yl (e.g., unsubstituted quinolin-5-yl or 2-fluoroquinolin-5-yl). In another more specific aspect, A is an optionally substituted isoquinolin-5-yl (e.g., unsubstituted isoquinolin-5-yl). In another more specific aspect, A is an optionally substituted quinolin-5-yl (e.g., unsubstituted quinolin-5-yl). In another more specific aspect, A is substituted quinolin-5-yl (e.g., 2-fluoroquinolin-5-yl). In another more specific aspect, A is an optionally substituted benzo[1,2,5]oxadiazole (e.g., unsubstituted benzo[1,2,5]oxadiazole). In another more specific aspect, A is an optionally substituted quinoxalin-5-yl (e.g., unsubstituted quinoxalin-5-yl or 8-hydroxyquinoxalin-5-yl). In another more specific aspect, A is substituted quinoxalin-5-yl (e.g., 8-fluoroquinoxalin-5-yl or 8-hydroxyquinoxalin-5-yl). In another more specific aspect, A is an optionally substituted chromanyl (e.g., chroman-8-yl). In another more specific aspect, A is an optionally substituted 2,3-dihydrobenzo[b][1,4]dioxinyl (e.g., unsubstituted 2,3-dihydrobenzo[b][1,4]dioxin-5-yl). In another more specific aspect, A is an optionally substituted benzo[d]thiazol-4-yl (e.g., unsubstituted benzo[d]thiazol-4-yl, 6-fluorobenzo[d]thiazol-4-yl, 7-fluorobenzo[d]thiazol-4-yl, 2-methylbenzo[d]thiazol-4-yl or 2-amino-6-fluorobenzo[d]thiazol-4-yl). In another more specific aspect, A is an optionally substituted benzofuranyl (e.g., benzofuran-7-yl). In another more specific aspect, A is an optionally substituted benzo[1,2,5]thiadiazol-5-yl (e.g., unsubstituted benzo[1,2,5]thiadiazol-5-yl). In another more specific aspect, A is an optionally substituted benzo[1,2,5]thiadiazol-4-yl (e.g., unsubstituted benzo[1,2,5]thiadiazol-4-yl). In another more specific aspect, A is an optionally substituted benzo[c]thiazolyl (e.g., unsubstituted benzo[c]thiazol-4-yl). In another more specific aspect, A is an optionally substituted 1,2,3,4-tetrahydroquinolin-8-yl (e.g., unsubstituted 1,2,3,4-tetrahydroquinolin-8-yl). In another more specific aspect, A is an optionally substituted 1H-indol-2(7aH)-on-5-yl (e.g., 1-methyl-1H-indol-2(7aH)-on-5-yl). In another more specific aspect, A is an optionally substituted thieno[3,2-b]pyridin-3-yl (e.g., unsubstituted thieno[3,2-b]pyridin-3-yl). In another more specific aspect, A is an optionally substituted benzo[1,3]dioxol-5-yl (e.g., unsubstituted benzo[1,3]dioxol-5-yl or 2,2-difluorobenzo[1,3]dioxol-5-yl). In another more specific aspect, A is an optionally substituted benzo[d]thiazol-7-yl (e.g., unsubstituted benzo[d]thiazol-7-yl or 6-methylbenzo[d]thiazol-7-yl or 6-fluorobenzo[d]thiazol-7-yl). In another more specific aspect, A is an optionally substituted cinnolin-8-yl (e.g., unsubstituted cinnolin-8-yl). In another more specific aspect, A is an optionally substituted imidazo[1,2-a]pyridine-8-yl (e.g., unsubstituted imidazo[1,2-a]pyridine-8-yl). In another more specific aspect, A is an optionally substituted thiazolo[5,4-b]pyridin-7-yl (e.g., unsubstituted thiazolo[5,4-b]pyridine-7-yl). In another more specific aspect, A is an optionally substituted 1H-pyrrolo[3,2-b]pyridin-3-yl (e.g., unsubstituted 1H-pyrrolo[3,2-b]pyridin-3-yl). In another more specific aspect, A is an optionally substituted 1H-pyrrolo[2,3-b]pyridin-1-yl (e.g., unsubstituted 1H-pyrrolo[2,3-b]pyridin-1-yl). In another more specific aspect, A is an optionally substituted benzo[d]oxazol-2(3H)-on-6-yl (e.g., 3-methylbenzo[d]oxazol-2(3H)-on-6-yl). In another more specific aspect, A is an optionally substituted benzo[c]isothiazol-7-yl (e.g., unsubstituted benzo[c]isothiazol-7-yl).

In certain aspects of formula (I) or (Ia), A is:

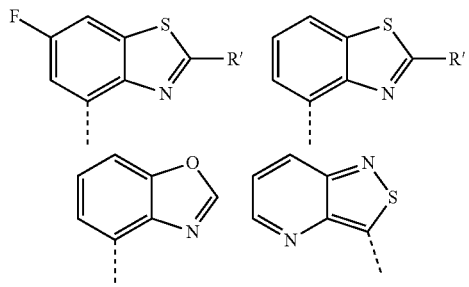

13

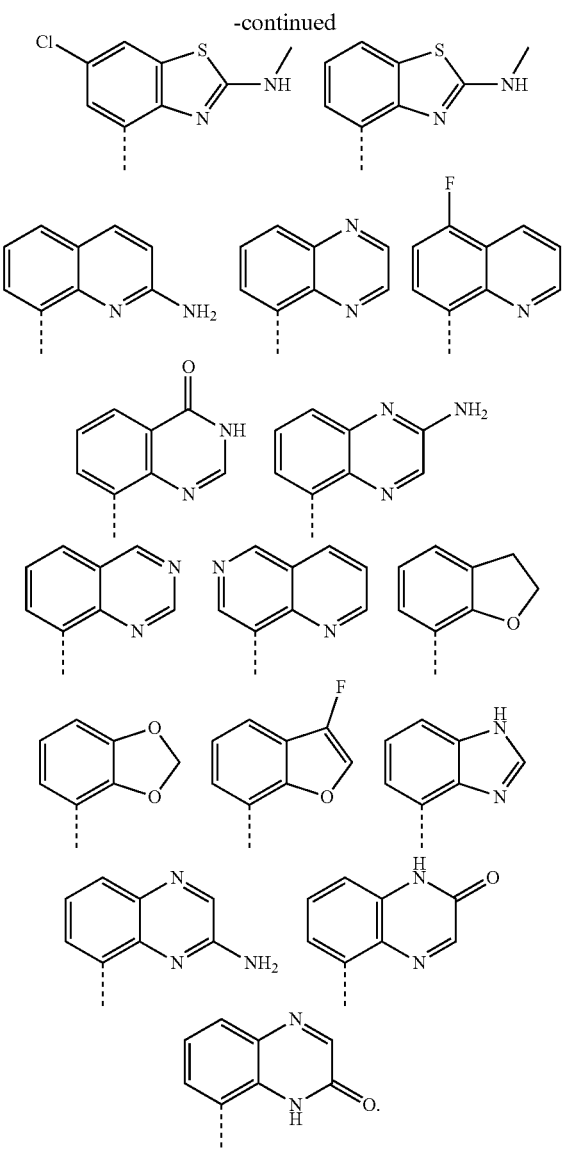

R' = H, NH₂

In certain aspects of formula (I) or (Ia), X is —NH—S(O)₂—, —NH—S(O)₂—CH₂—, or —CH₂—S(O)₂—NH—. In certain aspects of formula (I) or (Ia), X is —NH—S(O)₂—. In an even more specific aspect of formula (I), A is an optionally substituted quinolin-8-yl and X is —NH—S(O)₂— and the compound has the structure set forth in formula (II) or a pharmaceutically acceptable salt thereof:

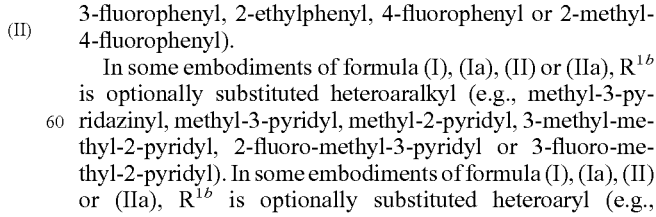

(II)

wherein $R^{1b}$, $R^2$, $R^4$, m and n are as defined for Formula (I).

14

In an even more specific aspect of formula (Ia), A is an optionally substituted quinolin-8-yl and X is —NH—S(O)₂— and the compound has the structure set forth in formula (IIa) or a pharmaceutically acceptable salt thereof:

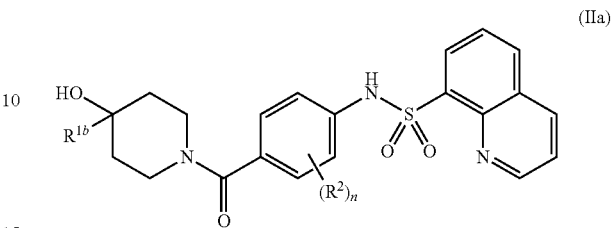

(IIa)

wherein $R^{1b}$, $R^2$, and n are as defined for Formula (Ia).

In certain embodiments of formula (I) or (Ia), A is an optionally substituted monocyclic aryl (e.g., optionally substituted phenyl). In some embodiments, A is 4-chlorophenyl. In some embodiments, A is 3-cyanophenyl. In some embodiments, A is 2-chlorophenyl. In some embodiments, A is 4-cyanophenyl. In some embodiments, A is 2-trifluoromethylphenyl. In some embodiments, A is 4-trifluoromethylphenyl. In some embodiments, A is 3-trifluoromethylphenyl. In some embodiments, A is 3-chlorophenyl. In some embodiments, A is 4-trifluoromethoxyphenyl. In some embodiments, A is 2,3-dichlorophenyl. In some embodiments, A is 2,4-difluorophenyl. In some embodiments, A is 3-trifluoromethoxyphenyl.

In certain embodiments of formula (I) or (Ia), A is phenyl substituted with two substituents on adjacent carbons which form an optionally substituted heterocyclyl or carbocyclyl ring (e.g., resulting in A comprising a bicycle).

In some embodiments of formula (I), $R^{1a}$ is hydroxyl. In some embodiments of formula (I), $R^{1a}$ is —C(O)H. In some embodiments of formula (I), $R^{1a}$ is —CH₂OH. In some embodiments of formula (I), $R^{1a}$ is —CO₂—$C_{1-6}$ alkyl (e.g., —CO₂Et). In some embodiments of formula (I), $R^{1a}$ is —CO₂H.

In some embodiments of formula (I), (Ia), (II) or (IIa), $R^{1b}$ is optionally substituted aralkyl (e.g., benzyl, 2,3-difluorobenzyl, 2-fluorobenzyl, 3-fluorobenzyl, 2-methylbenzyl, 3-methylbenzyl, 2-trifluoromethylbenzyl, 3-trifluoromethylbenzyl, 2-methoxybenzyl, 3-methoxybenzyl).

In some embodiments of formula (I), (Ia), (II) or (IIa), $R^{1b}$ is optionally substituted aryl (e.g., unsubstituted phenyl, 2-(2-chlorophenyl)phenyl, 4-cyanophenyl, 3-cyanophenyl, 2-cyanophenyl, 2-hydroxyphenyl, 2-(methylsulfonyl)phenyl, 3-(methylsulfonyl)phenyl, 2-chloro-4-methylphenyl, 2-chloro-4-fluorophenyl, 2-chloro-3-fluorophenyl, 2-chloro-5-fluorophenyl, 2,3-difluorophenyl, 2,6-difluorophenyl, 2-methylphenyl, 2-fluorophenyl, 2-methoxyphenyl, 2-trifluoromethylphenyl, 2-difluorophenyl, 3-methoxyphenyl, 3-trifluoromethoxyphenyl, 3-trifluoromethylphenyl, 2-trifluoromethoxyphenyl, 3-chlorophenyl, 2-chlorophenyl, 3-fluorophenyl, 2-ethylphenyl, 4-fluorophenyl or 2-methyl-4-fluorophenyl).

In some embodiments of formula (I), (Ia), (II) or (IIa), $R^{1b}$ is optionally substituted heteroaralkyl (e.g., methyl-3-pyridazinyl, methyl-3-pyridyl, methyl-2-pyridyl, 3-methyl-methyl-2-pyridyl, 2-fluoro-methyl-3-pyridyl or 3-fluoro-methyl-2-pyridyl). In some embodiments of formula (I), (Ia), (II) or (IIa), $R^{1b}$ is optionally substituted heteroaryl (e.g., 3-fluoro-2-pyridyl, 3-methyl-2-pyridyl, 3-fluoro-4-pyridyl, 4-pyridyl, 4-isothiazolyl, 3-methyl-4-fluoro-2-pyridyl, 2-chloro-4-pyridyl, 4-fluoro-2-methyl-3-pyridyl, 4-fluoro-3-bromo-2-pyridyl, 2-methoxy-3-pyridyl, 6-methoxy-2-pyridyl, 6-fluoro-2-pyridyl, 6-methyl-2-pyridyl, 2-methyl-3-pyridyl, 6-chloro-2-pyridyl, 3-trifluoromethyl-2-pyridyl, 6-trifluoromethyl-2-pyridyl, 2-fluoro-3-pyridyl, 2-trifluoromethyl-3-pyridyl or 6-difluoromethyl-2-pyridyl).

In some embodiments of formula (I), (Ia), (II) or (IIa), $R^{1b}$ is optionally substituted $C_{1-8}$ alkyl (e.g., methyl, ethyl, n-propyl, isopropyl, t-butyl, isobutyl, n-butyl, t-pentyl, 2-hydroxyethyl, 1-hydroxyethyl, 3-hydroxypropyl, 2-hydroxy-2-methylpropyl, 3-hydroxy-3-methylbutyl, 3,3,3-trifluoropropyl, 2-methoxyethyl, 3,3-difluoropropyl, ethoxymethyl, N,N-dimethylmethyl, pyrrollomethyl or 2-hydroxypropyl). In some embodiments of formula (I), (Ia), (II) or (IIa), $R^{1b}$ is optionally substituted cycloalkyl (e.g., cyclopropyl). In some embodiments of formula (I), (Ia), (II) or (IIa), $R^{1b}$ is optionally substituted cycloalkylalkyl (e.g., cyclopropylmethyl, 1-methyl-cyclopropylmethyl, cyclobutylmethyl, 2,2-difluorocyclopropylmethyl). In some embodiments of formula (I), (Ia), (II) or (IIa), $R^{1b}$ is optionally substituted $C_{2-8}$ alkenyl (e.g., 2-methyl-2-propenyl or 3,3-difluoro-2-propenyl).

In some embodiments of formula (I), (Ia), (II) or (IIa), $R^{1b}$ is —NH—$R^5$. In some further aspects of these embodiments, $R^5$ is optionally substituted aryl (e.g., 2-methoxyphenyl). In some further aspects of these embodiments, $R^5$ is optionally substituted aralkyl (e.g., unsubstituted benzyl).

In some embodiments of formula (I), (Ia), (II) or (IIa), $R^{1b}$ is —NH—C(O)—$R^5$. In some further aspects of these embodiments, $R^5$ is optionally substituted heteroaryl (e.g., unsubstituted 2-pyridyl).

In some embodiments of formula (I), (Ia), (II) or (IIa), $R^{1b}$ is:

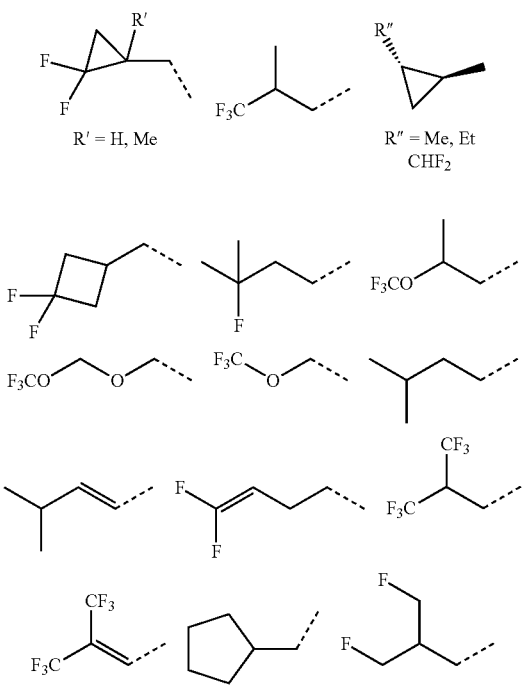

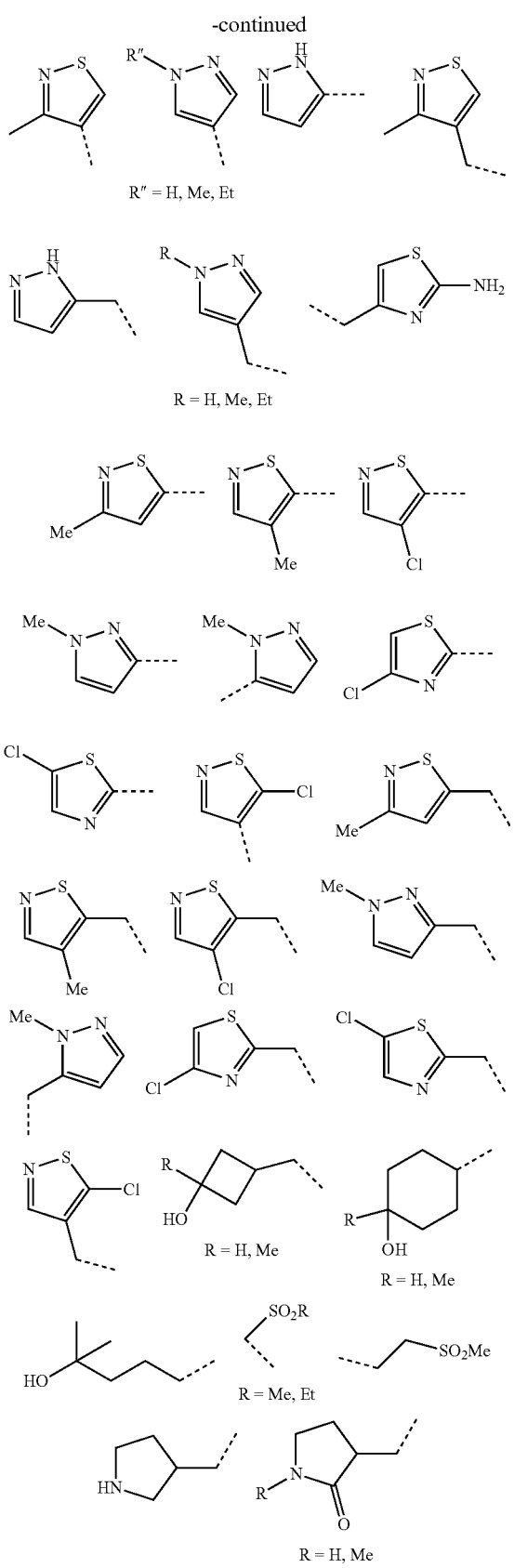

In yet another embodiment, the compound is selected from any one of the compounds set forth in Table 1, below:

TABLE 1

Exemplary Compounds of Formula I:

| Compound # | Structure |
|---|---|
| 100 | 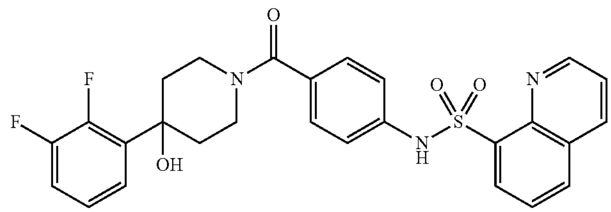 [SMILES: O=C(c1ccc(NS(=O)(=O)c2cccc3cccnc23)cc1)N1CCC(O)(c2cccc(F)c2F)CC1] |
| 101 | 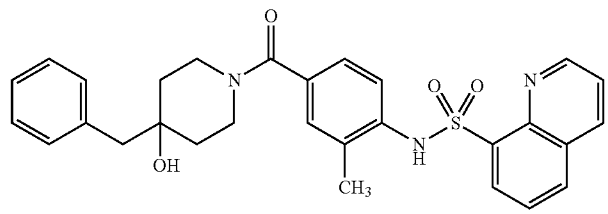 [SMILES: Cc1cc(C(=O)N2CCC(O)(Cc3ccccc3)CC2)ccc1NS(=O)(=O)c1cccc2cccnc12] |
| 102 | 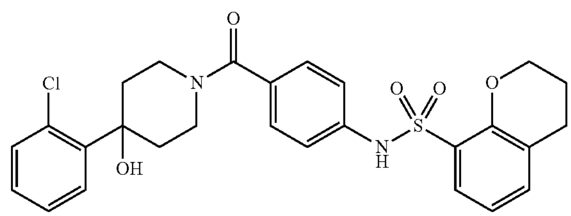 [SMILES: O=C(c1ccc(NS(=O)(=O)c2cccc3c2OCCC3)cc1)N1CCC(O)(c2ccccc2Cl)CC1] |
| 103 | 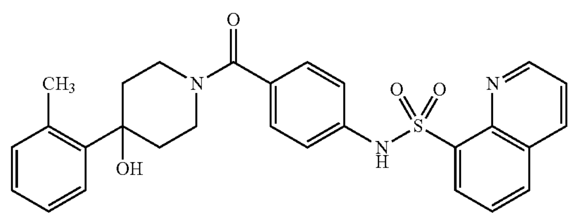 |
| 104 | 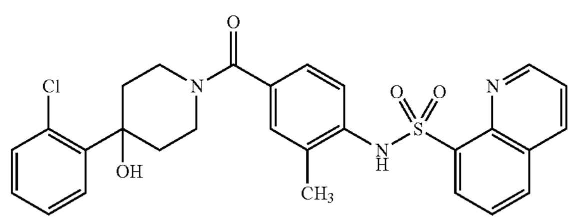 |
| 105 | 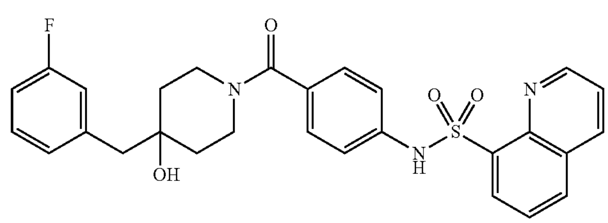 [SMILES: O=C(c1ccc(NS(=O)(=O)c2cccc3cccnc23)cc1)N1CCC(O)(Cc2cccc(F)c2)CC1] |
| 106 | 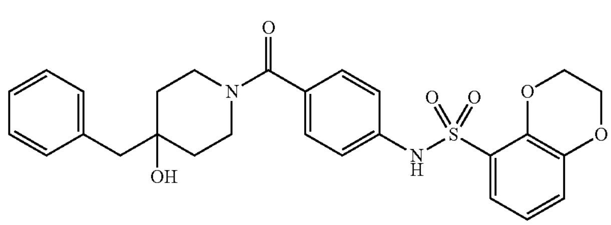 [SMILES: O=C(c1ccc(NS(=O)(=O)c2cccc3c2OCCO3)cc1)N1CCC(O)(Cc2ccccc2)CC1] |

TABLE 1-continued
Exemplary Compounds of Formula I:
| Compound # | Structure |
|---|---|
| 108 | 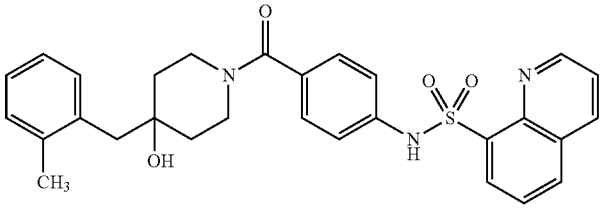 [SMILES: Cc1ccccc1CC1(O)CCN(C(=O)c2ccc(NS(=O)(=O)c3cccc4cccnc34)cc2)CC1] |
| 109 | 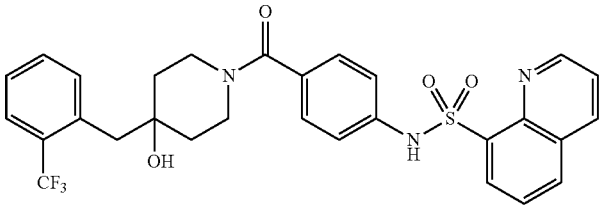 [SMILES: O=C(c1ccc(NS(=O)(=O)c2cccc3cccnc23)cc1)N1CCC(O)(Cc2ccccc2C(F)(F)F)CC1] |
| 110 | 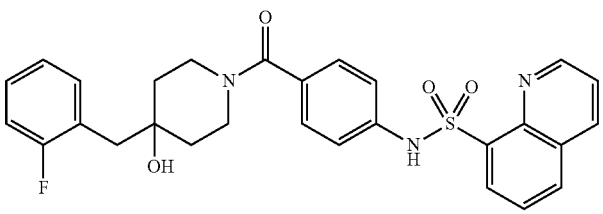 [SMILES: O=C(c1ccc(NS(=O)(=O)c2cccc3cccnc23)cc1)N1CCC(O)(Cc2ccccc2F)CC1] |
| 111 | 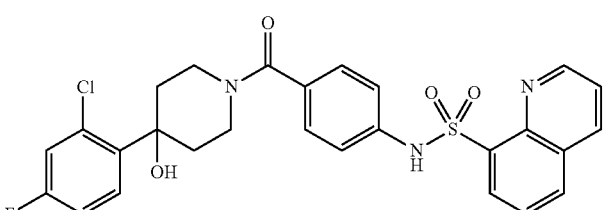 |
| 112 | 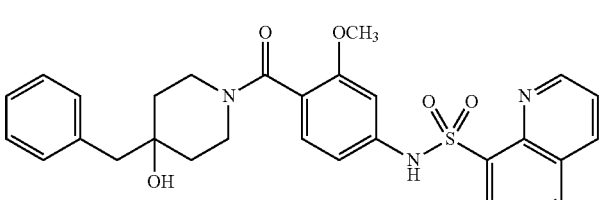 |
| 113 | 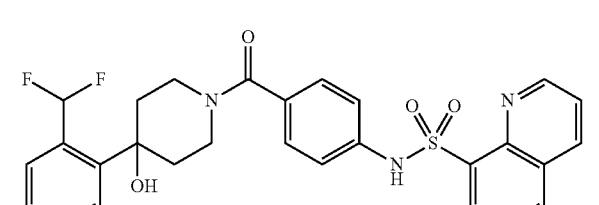 |
| 114 | 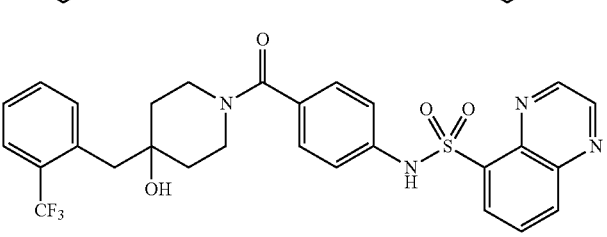 |

TABLE 1-continued

Exemplary Compounds of Formula I:

| Compound # | Structure |
|---|---|
| 115 | 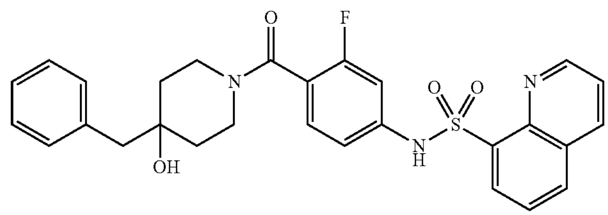 [SMILES: O=C(c1ccc(NS(=O)(=O)c2cccc3cccnc23)cc1F)N1CCC(O)(Cc2ccccc2)CC1] |
| 116 | 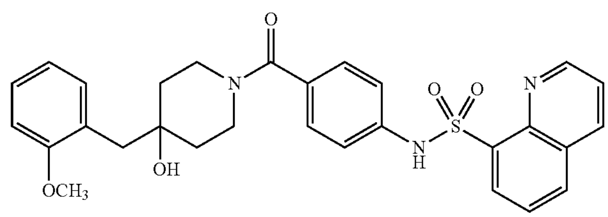 [SMILES: COc1ccccc1CC1(O)CCN(C(=O)c2ccc(NS(=O)(=O)c3cccc4cccnc34)cc2)CC1] |
| 117 | 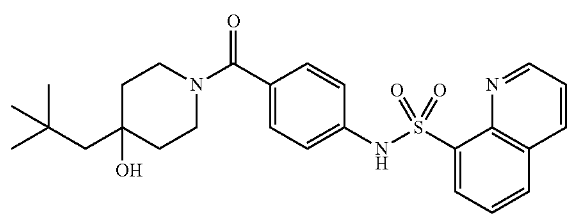 [SMILES: CC(C)(C)CC1(O)CCN(C(=O)c2ccc(NS(=O)(=O)c3cccc4cccnc34)cc2)CC1] |
| 118 | 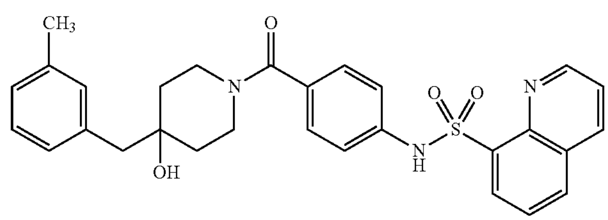 [SMILES: Cc1cccc(CC2(O)CCN(C(=O)c3ccc(NS(=O)(=O)c4cccc5cccnc45)cc3)CC2)c1] |
| 119 | 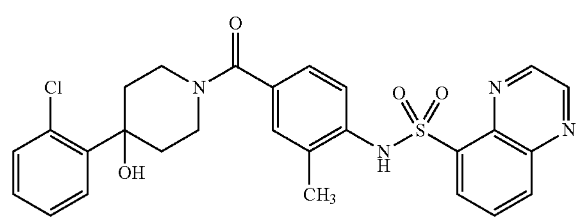 [SMILES: Cc1cc(C(=O)N2CCC(O)(c3ccccc3Cl)CC2)ccc1NS(=O)(=O)c1cccc2nccnc12] |
| 120 | 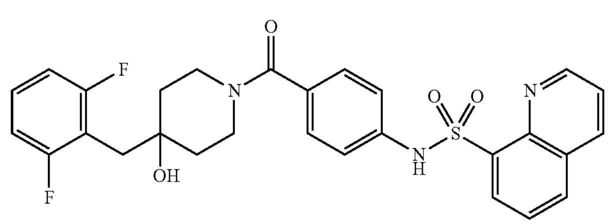 [SMILES: O=C(c1ccc(NS(=O)(=O)c2cccc3cccnc23)cc1)N1CCC(O)(Cc2c(F)cccc2F)CC1] |
| 121 | 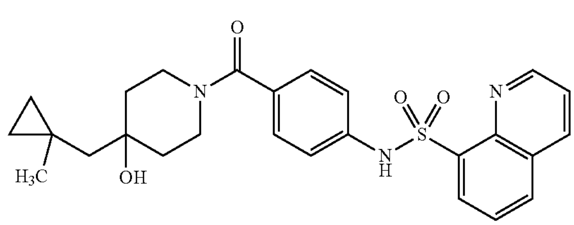 [SMILES: CC1(CC2(O)CCN(C(=O)c3ccc(NS(=O)(=O)c4cccc5cccnc45)cc3)CC2)CC1] |

TABLE 1-continued

Exemplary Compounds of Formula I:

| Compound # | Structure |
|---|---|
| 122 | 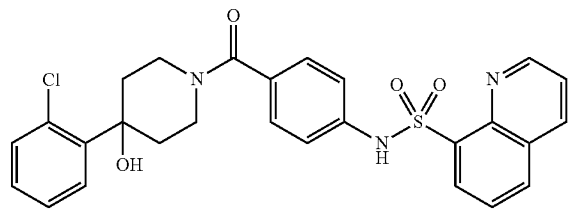 [SMILES: O=C(c1ccc(NS(=O)(=O)c2cccc3cccnc23)cc1)N1CCC(O)(c2ccccc2Cl)CC1] |
| 123 | 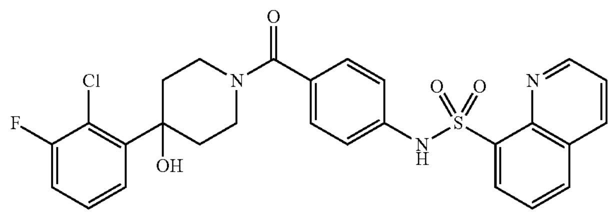 [SMILES: O=C(c1ccc(NS(=O)(=O)c2cccc3cccnc23)cc1)N1CCC(O)(c2cccc(F)c2Cl)CC1] |
| 124 | 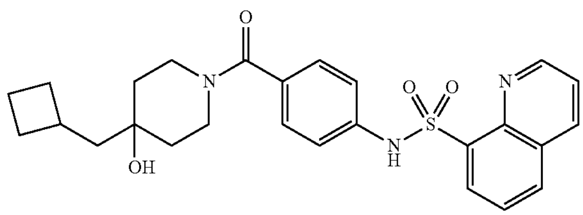 [SMILES: O=C(c1ccc(NS(=O)(=O)c2cccc3cccnc23)cc1)N1CCC(O)(CC2CCC2)CC1] |
| 125 | 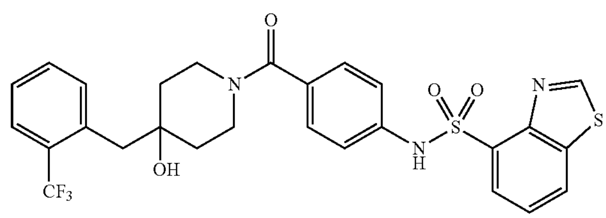 [SMILES: O=C(c1ccc(NS(=O)(=O)c2cccc3scnc23)cc1)N1CCC(O)(Cc2ccccc2C(F)(F)F)CC1] |
| 126 | 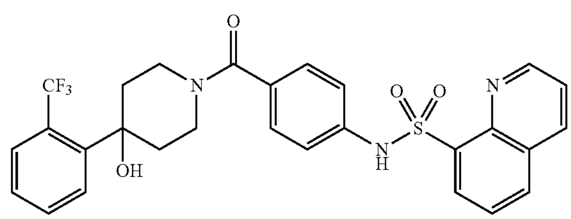 [SMILES: O=C(c1ccc(NS(=O)(=O)c2cccc3cccnc23)cc1)N1CCC(O)(c2ccccc2C(F)(F)F)CC1] |
| 127 | 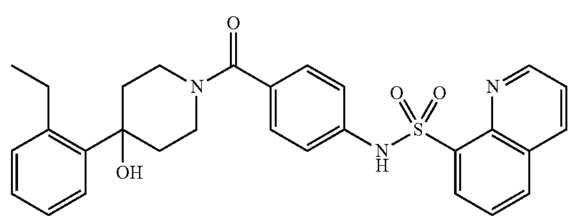 [SMILES: CCc1ccccc1C1(O)CCN(C(=O)c2ccc(NS(=O)(=O)c3cccc4cccnc34)cc2)CC1] |
| 128 | 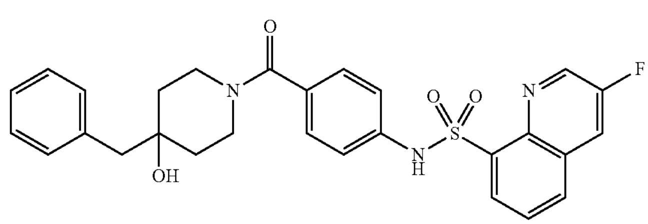 [SMILES: O=C(c1ccc(NS(=O)(=O)c2cccc3cc(F)cnc23)cc1)N1CCC(O)(Cc2ccccc2)CC1] |

TABLE 1-continued

Exemplary Compounds of Formula I:

| Compound # | Structure |
|---|---|
| 129 | (4-(6-fluoro-2-methylpyridin-3-yl)-4-hydroxypiperidin-1-yl)(4-(quinoline-8-sulfonamido)phenyl)methanone |
| 130 | (4-hydroxy-4-neopentylpiperidin-1-yl)(4-(quinoxaline-5-sulfonamido)phenyl)methanone |
| 131 | (4-benzyl-4-hydroxypiperidin-1-yl)(4-(quinoline-8-sulfonamido)phenyl)methanone |
| 132 | (4-((1-methylcyclopropyl)methyl)-4-hydroxypiperidin-1-yl)(4-(benzo[d]thiazole-7-sulfonamido)phenyl)methanone |
| 133 | (4-(6-bromo-5-fluoropyridin-2-yl)-4-hydroxypiperidin-1-yl)(4-(quinoline-8-sulfonamido)phenyl)methanone |
| 134 | (4-hydroxy-4-neopentylpiperidin-1-yl)(4-(benzo[d]thiazole-7-sulfonamido)phenyl)methanone |

TABLE 1-continued

Exemplary Compounds of Formula I:

| Compound # | Structure |
|---|---|
| 135 | 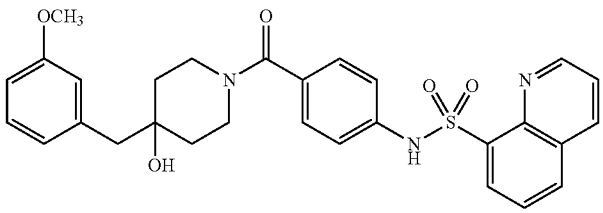 [SMILES: COc1cccc(CC2(O)CCN(C(=O)c3ccc(NS(=O)(=O)c4cccc5cccnc45)cc3)CC2)c1] |
| 136 | 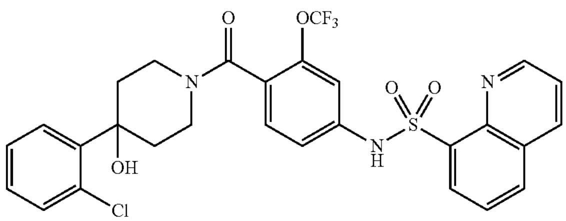 [SMILES: O=C(c1ccc(NS(=O)(=O)c2cccc3cccnc23)cc1OC(F)(F)F)N1CCC(O)(c2ccccc2Cl)CC1] |
| 137 | 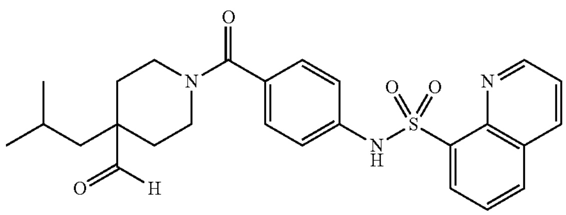 [SMILES: CC(C)CC1(C=O)CCN(C(=O)c2ccc(NS(=O)(=O)c3cccc4cccnc34)cc2)CC1] |
| 138 | 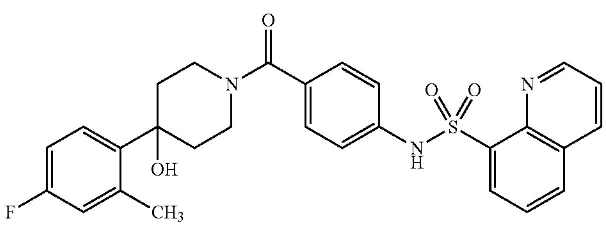 |
| 140 | 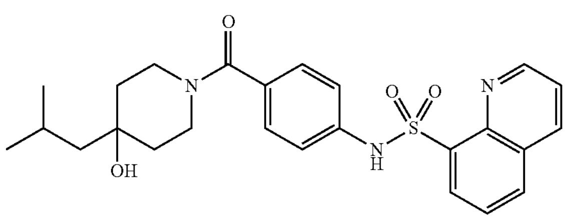 [SMILES: CC(C)CC1(O)CCN(C(=O)c2ccc(NS(=O)(=O)c3cccc4cccnc34)cc2)CC1] |
| 141 | 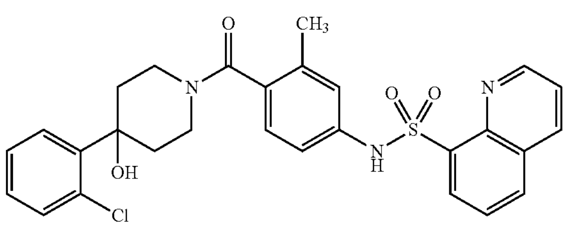 [SMILES: Cc1cc(NS(=O)(=O)c2cccc3cccnc23)ccc1C(=O)N1CCC(O)(c2ccccc2Cl)CC1] |
| 142 | 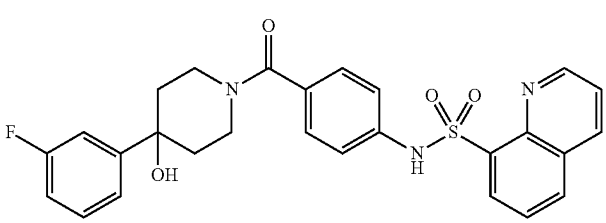 [SMILES: O=C(c1ccc(NS(=O)(=O)c2cccc3cccnc23)cc1)N1CCC(O)(c2cccc(F)c2)CC1] |

TABLE 1-continued
Exemplary Compounds of Formula I:
| Compound # | Structure |
|---|---|
| 143 | 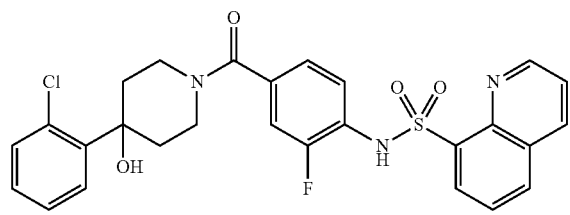 [SMILES: O=C(c1ccc(NS(=O)(=O)c2cccc3cccnc23)c(F)c1)N1CCC(O)(c2ccccc2Cl)CC1] |
| 144 | 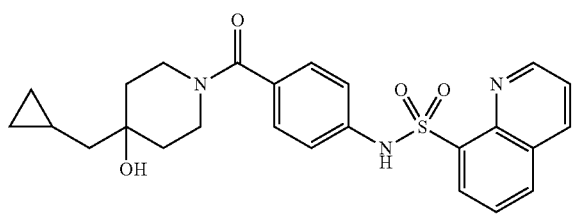 [SMILES: O=C(c1ccc(NS(=O)(=O)c2cccc3cccnc23)cc1)N1CCC(O)(CC2CC2)CC1] |
| 145 | 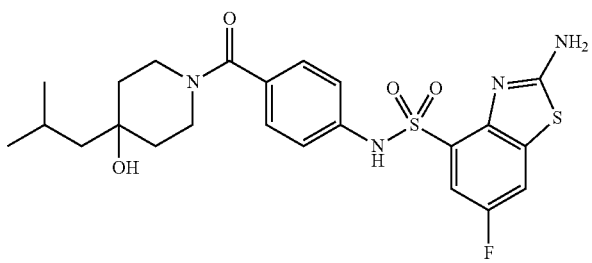 [SMILES: CC(C)CC1(O)CCN(C(=O)c2ccc(NS(=O)(=O)c3cc(F)cc4sc(N)nc34)cc2)CC1] |
| 146 | 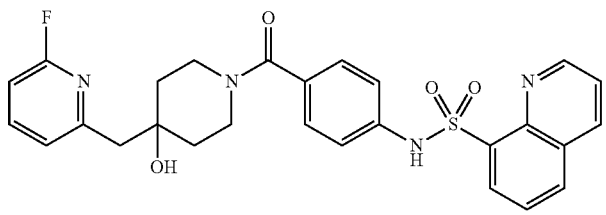 [SMILES: O=C(c1ccc(NS(=O)(=O)c2cccc3cccnc23)cc1)N1CCC(O)(Cc2cccc(F)n2)CC1] |
| 147 | 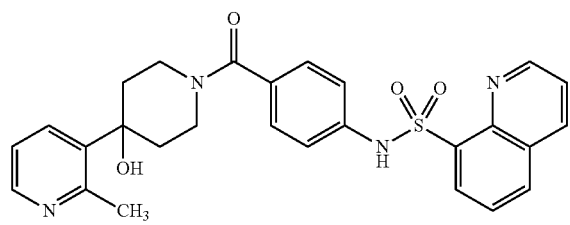 [SMILES: Cc1ncccc1C1(O)CCN(C(=O)c2ccc(NS(=O)(=O)c3cccc4cccnc34)cc2)CC1] |
| 148 | 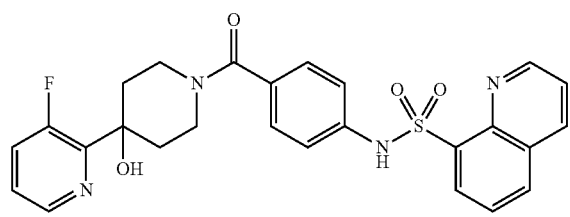 [SMILES: O=C(c1ccc(NS(=O)(=O)c2cccc3cccnc23)cc1)N1CCC(O)(c2ncccc2F)CC1] |

TABLE 1-continued
Exemplary Compounds of Formula I:
| Compound # | Structure |
| --- | --- |
| 149 | 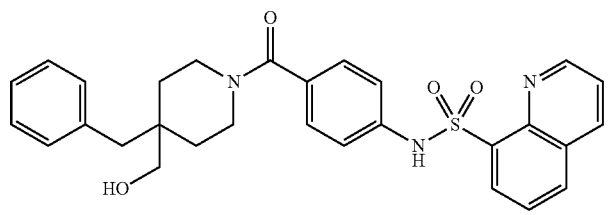 [SMILES: O=C(c1ccc(NS(=O)(=O)c2cccc3cccnc23)cc1)N1CCC(CO)(Cc2ccccc2)CC1] |
| 150 | 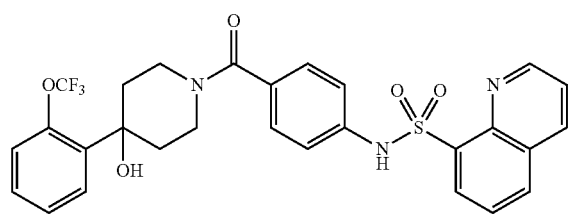 [SMILES: O=C(c1ccc(NS(=O)(=O)c2cccc3cccnc23)cc1)N1CCC(O)(c2ccccc2OC(F)(F)F)CC1] |
| 151 | 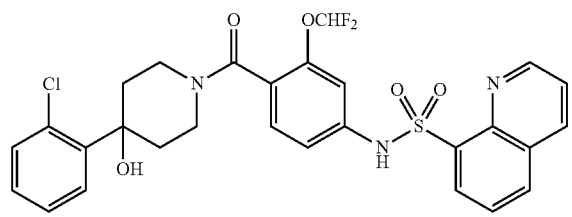 |
| 152 | 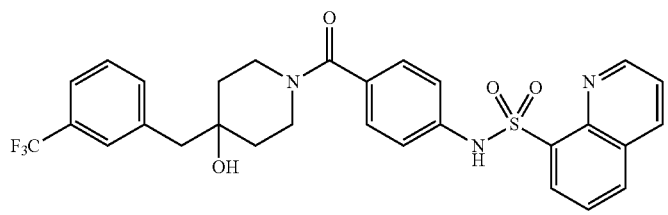 [SMILES: O=C(c1ccc(NS(=O)(=O)c2cccc3cccnc23)cc1)N1CCC(O)(Cc2cccc(C(F)(F)F)c2)CC1] |
| 153 | 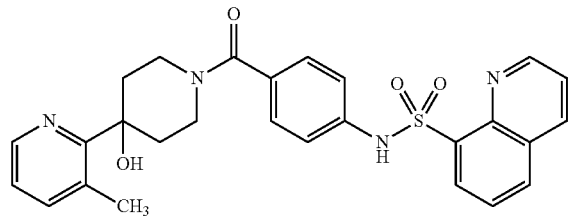 [SMILES: Cc1cccnc1C1(O)CCN(C(=O)c2ccc(NS(=O)(=O)c3cccc4cccnc34)cc2)CC1] |
| 154 | 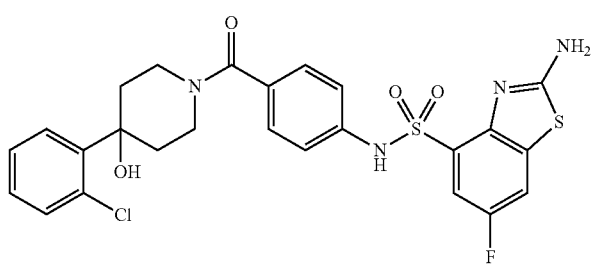 [SMILES: Nc1nc2c(S(=O)(=O)Nc3ccc(C(=O)N4CCC(O)(c5ccccc5Cl)CC4)cc3)cc(F)cc2s1] |

TABLE 1-continued

Exemplary Compounds of Formula I:

| Compound # | Structure |
|---|---|
| 155 | 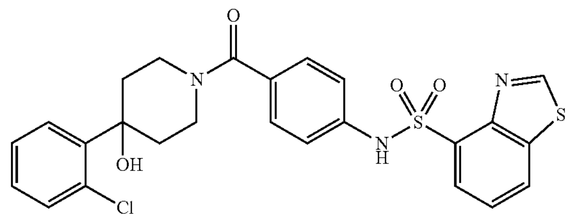 [SMILES: O=C(c1ccc(NS(=O)(=O)c2cccc3scnc23)cc1)N1CCC(O)(c2ccccc2Cl)CC1] |
| 156 | 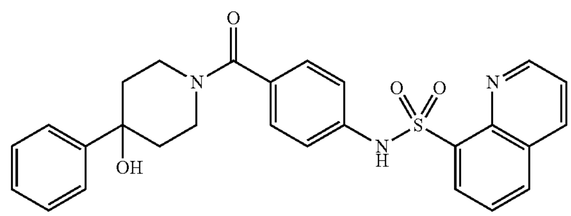 |
| 157 | 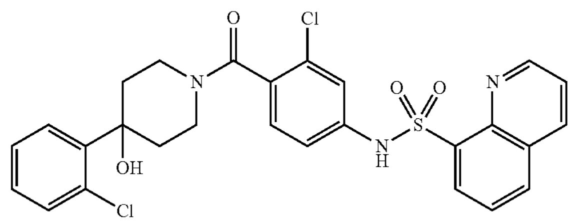 |
| 158 | 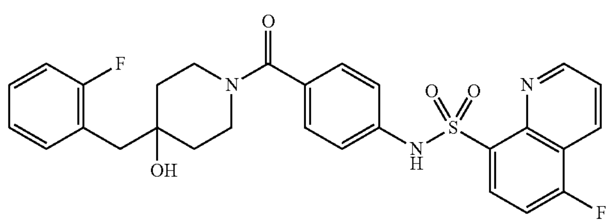 [SMILES: O=C(c1ccc(NS(=O)(=O)c2ccc(F)c3cccnc23)cc1)N1CCC(O)(Cc2ccccc2F)CC1] |
| 159 | 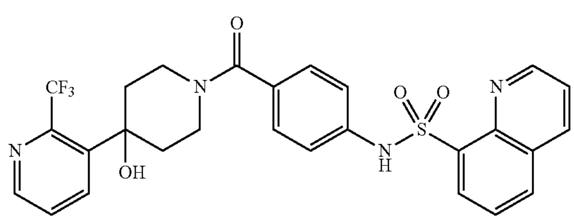 [SMILES: O=C(c1ccc(NS(=O)(=O)c2cccc3cccnc23)cc1)N1CCC(O)(c2cccnc2C(F)(F)F)CC1] |
| 160 | 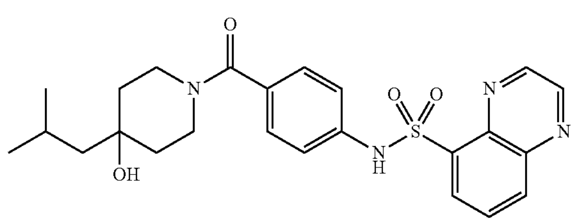 [SMILES: CC(C)CC1(O)CCN(C(=O)c2ccc(NS(=O)(=O)c3cccc4nccnc34)cc2)CC1] |
| 161 | 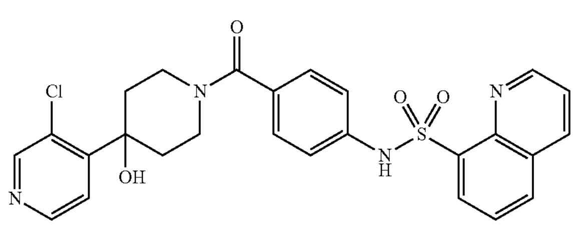 [SMILES: O=C(c1ccc(NS(=O)(=O)c2cccc3cccnc23)cc1)N1CCC(O)(c2ccncc2Cl)CC1] |

TABLE 1-continued

Exemplary Compounds of Formula I:

| Compound # | Structure |
| --- | --- |
| 162 | 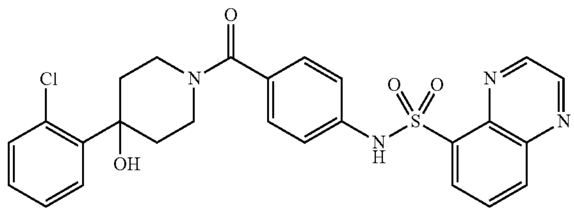 [SMILES: O=C(c1ccc(NS(=O)(=O)c2cccc3nccnc23)cc1)N1CCC(O)(c2ccccc2Cl)CC1] |
| 163 | 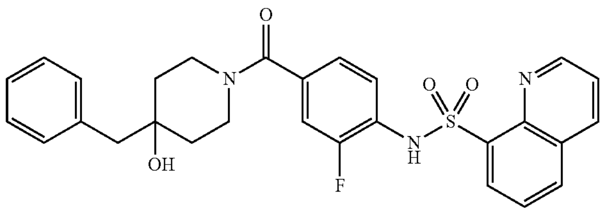 [SMILES: O=C(c1ccc(NS(=O)(=O)c2cccc3cccnc23)c(F)c1)N1CCC(O)(Cc2ccccc2)CC1] |
| 164 | 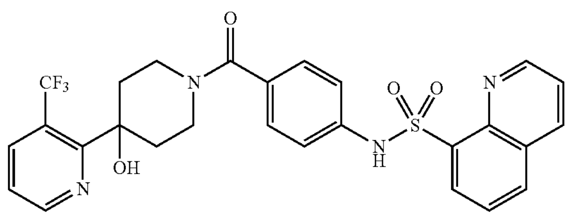 |
| 165 | 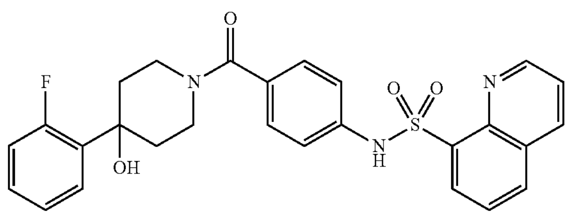 |
| 166 | 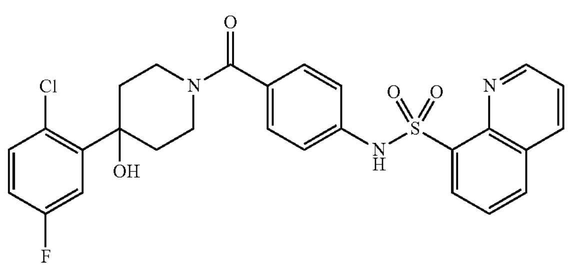 [SMILES: O=C(c1ccc(NS(=O)(=O)c2cccc3cccnc23)cc1)N1CCC(O)(c2cc(F)ccc2Cl)CC1] |
| 167 | 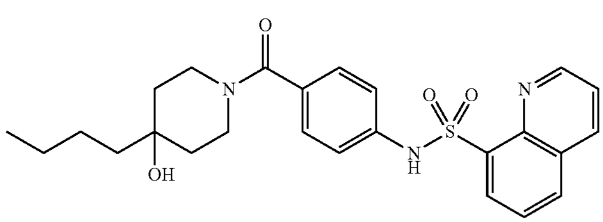 [SMILES: CCCCC1(O)CCN(C(=O)c2ccc(NS(=O)(=O)c3cccc4cccnc34)cc2)CC1] |
| 168 | 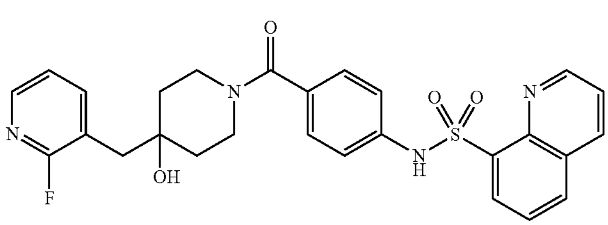 [SMILES: O=C(c1ccc(NS(=O)(=O)c2cccc3cccnc23)cc1)N1CCC(O)(Cc2cccnc2F)CC1] |

TABLE 1-continued

Exemplary Compounds of Formula I:

| Compound # | Structure |
|---|---|
| 169 | 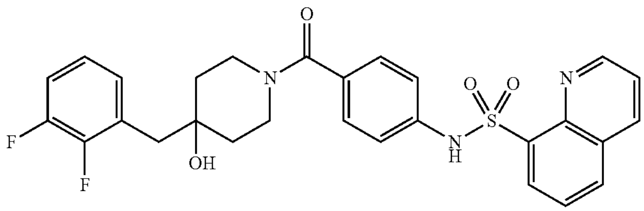 [SMILES: O=C(c1ccc(NS(=O)(=O)c2cccc3cccnc23)cc1)N1CCC(O)(Cc2cccc(F)c2F)CC1] |
| 170 | 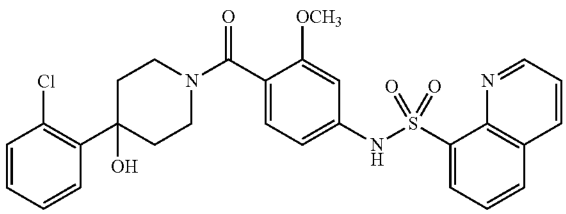 [SMILES: COc1cc(NS(=O)(=O)c2cccc3cccnc23)ccc1C(=O)N1CCC(O)(c2ccccc2Cl)CC1] |
| 171 | 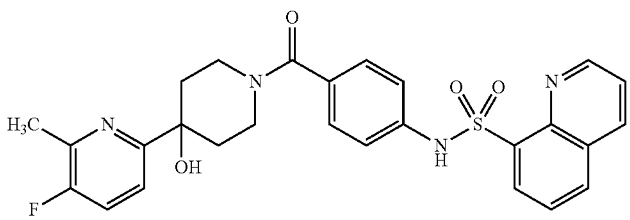 [SMILES: Cc1nc(C2(O)CCN(C(=O)c3ccc(NS(=O)(=O)c4cccc5cccnc45)cc3)CC2)ccc1F] |
| 172 | 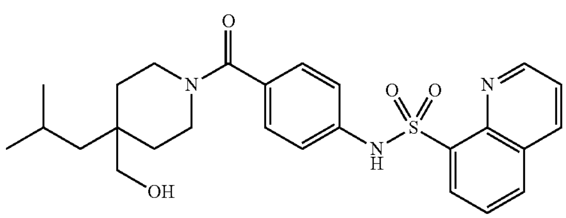 [SMILES: CC(C)CC1(CO)CCN(C(=O)c2ccc(NS(=O)(=O)c3cccc4cccnc34)cc2)CC1] |
| 173 | 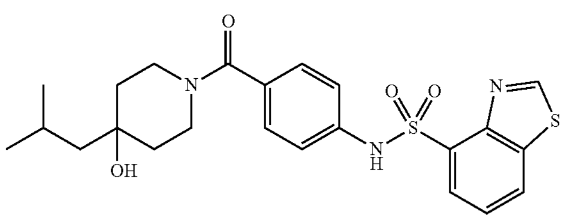 [SMILES: CC(C)CC1(O)CCN(C(=O)c2ccc(NS(=O)(=O)c3cccc4scnc34)cc2)CC1] |
| 174 | 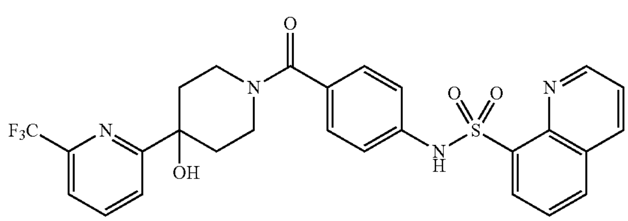 [SMILES: O=C(c1ccc(NS(=O)(=O)c2cccc3cccnc23)cc1)N1CCC(O)(c2cccc(C(F)(F)F)n2)CC1] |
| 175 | 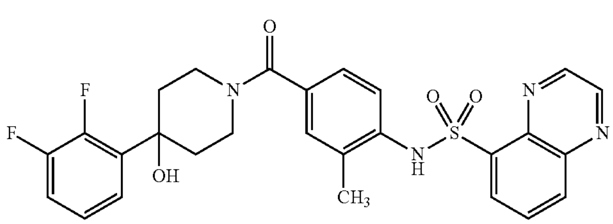 [SMILES: Cc1cc(C(=O)N2CCC(O)(c3cccc(F)c3F)CC2)ccc1NS(=O)(=O)c1cccc2nccnc12] |

TABLE 1-continued

Exemplary Compounds of Formula I:

| Compound # | Structure |
|---|---|
| 176 | 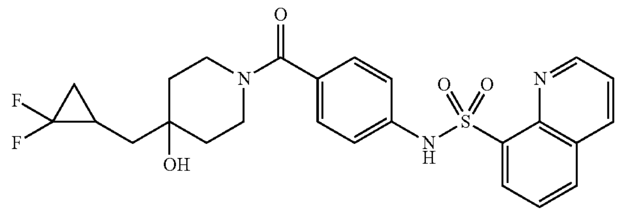 [SMILES: O=C(c1ccc(NS(=O)(=O)c2cccc3cccnc23)cc1)N1CCC(O)(CC2CC2(F)F)CC1] |
| 177 | 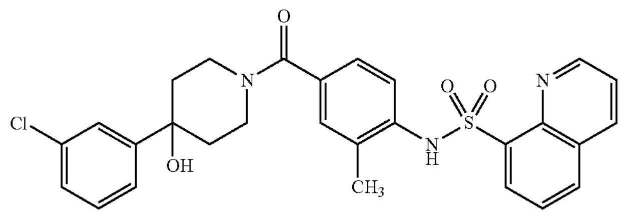 [SMILES: Cc1cc(C(=O)N2CCC(O)(c3cccc(Cl)c3)CC2)ccc1NS(=O)(=O)c1cccc2cccnc12] |
| 178 | 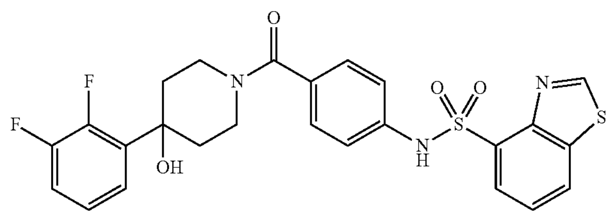 [SMILES: O=C(c1ccc(NS(=O)(=O)c2cccc3scnc23)cc1)N1CCC(O)(c2cccc(F)c2F)CC1] |
| 179 | 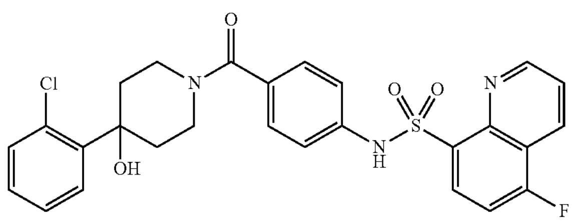 [SMILES: O=C(c1ccc(NS(=O)(=O)c2ccc(F)c3cccnc23)cc1)N1CCC(O)(c2ccccc2Cl)CC1] |
| 180 | 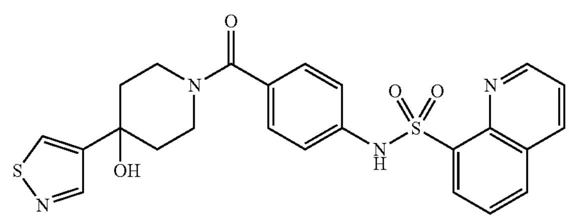 [SMILES: O=C(c1ccc(NS(=O)(=O)c2cccc3cccnc23)cc1)N1CCC(O)(c2cnsc2)CC1] |
| 181 | 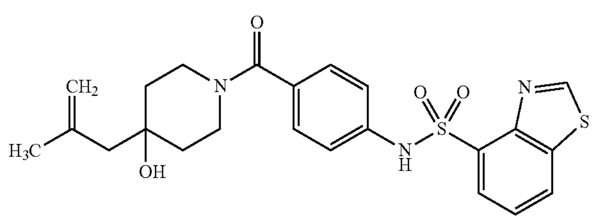 [SMILES: C=C(C)CC1(O)CCN(C(=O)c2ccc(NS(=O)(=O)c3cccc4scnc34)cc2)CC1] |
| 182 | 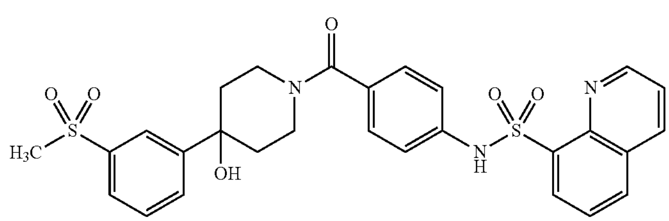 [SMILES: CS(=O)(=O)c1cccc(C2(O)CCN(C(=O)c3ccc(NS(=O)(=O)c4cccc5cccnc45)cc3)CC2)c1] |

TABLE 1-continued

Exemplary Compounds of Formula I:

| Compound # | Structure |
|---|---|
| 183 | 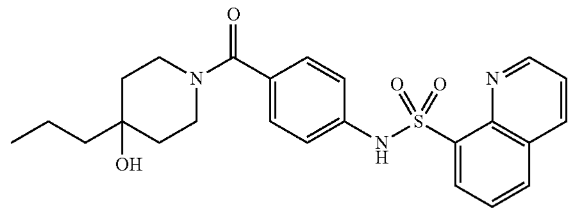 [SMILES: CCCC1(O)CCN(C(=O)c2ccc(NS(=O)(=O)c3cccc4cccnc34)cc2)CC1] |
| 184 | 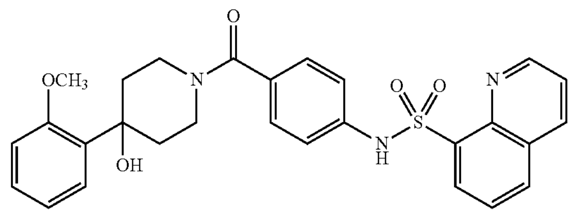 [SMILES: COc1ccccc1C1(O)CCN(C(=O)c2ccc(NS(=O)(=O)c3cccc4cccnc34)cc2)CC1] |
| 185 | 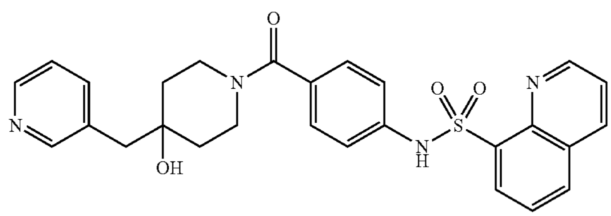 [SMILES: O=C(c1ccc(NS(=O)(=O)c2cccc3cccnc23)cc1)N1CCC(O)(Cc2cccnc2)CC1] |
| 186 | 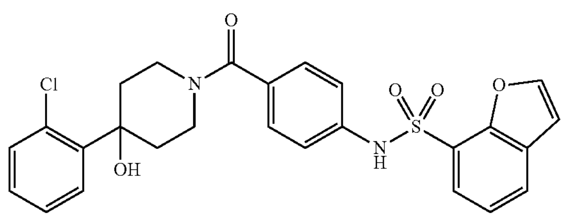 [SMILES: O=C(c1ccc(NS(=O)(=O)c2cccc3ccoc23)cc1)N1CCC(O)(c2ccccc2Cl)CC1] |
| 187 | 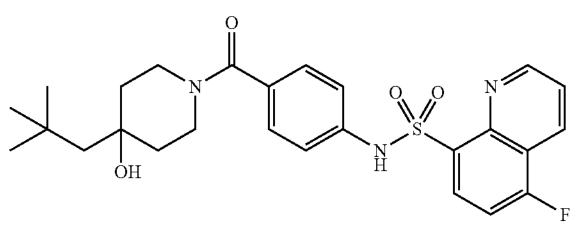 [SMILES: CC(C)(C)CC1(O)CCN(C(=O)c2ccc(NS(=O)(=O)c3ccc(F)c4cccnc34)cc2)CC1] |
| 188 | 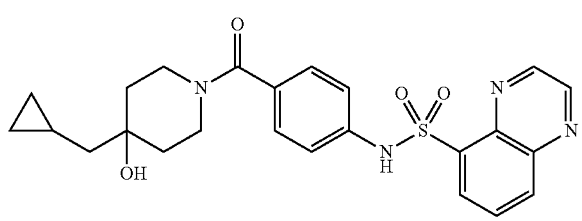 [SMILES: O=C(c1ccc(NS(=O)(=O)c2cccc3nccnc23)cc1)N1CCC(O)(CC2CC2)CC1] |
| 189 | 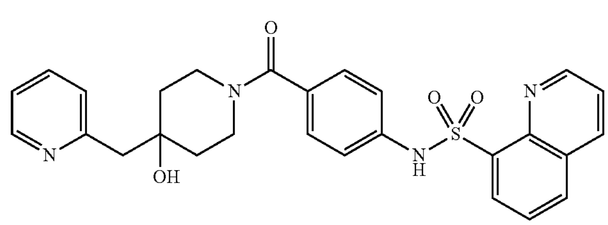 [SMILES: O=C(c1ccc(NS(=O)(=O)c2cccc3cccnc23)cc1)N1CCC(O)(Cc2ccccn2)CC1] |

TABLE 1-continued

Exemplary Compounds of Formula I:

| Compound # | Structure |
|---|---|
| 190 | 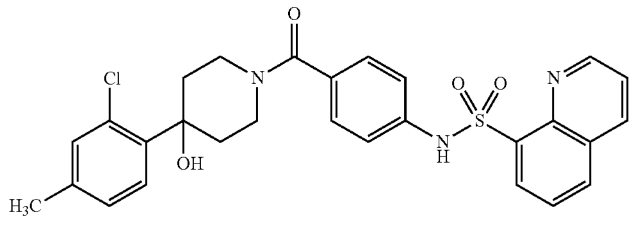 [SMILES: Cc1ccc(C2(O)CCN(C(=O)c3ccc(NS(=O)(=O)c4cccc5cccnc45)cc3)CC2)c(Cl)c1] |
| 191 | 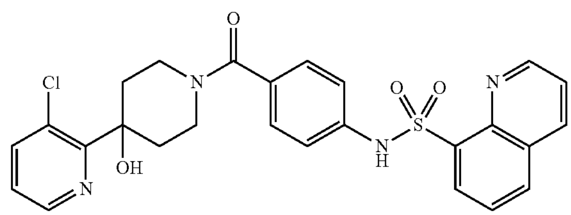 [SMILES: O=C(c1ccc(NS(=O)(=O)c2cccc3cccnc23)cc1)N1CCC(O)(c2ncccc2Cl)CC1] |
| 192 | 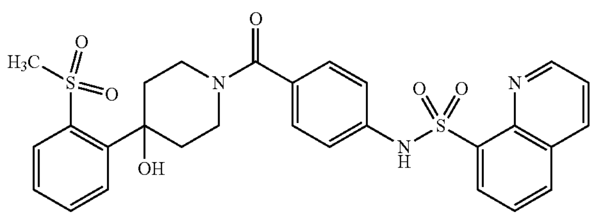 [SMILES: CS(=O)(=O)c1ccccc1C1(O)CCN(C(=O)c2ccc(NS(=O)(=O)c3cccc4cccnc34)cc2)CC1] |
| 193 | 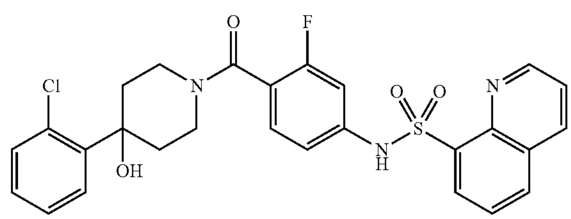 [SMILES: O=C(c1ccc(NS(=O)(=O)c2cccc3cccnc23)cc1F)N1CCC(O)(c2ccccc2Cl)CC1] |
| 194 | 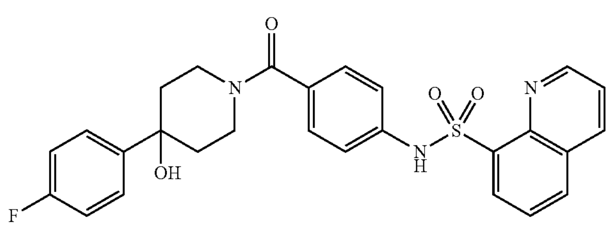 [SMILES: O=C(c1ccc(NS(=O)(=O)c2cccc3cccnc23)cc1)N1CCC(O)(c2ccc(F)cc2)CC1] |
| 195 | 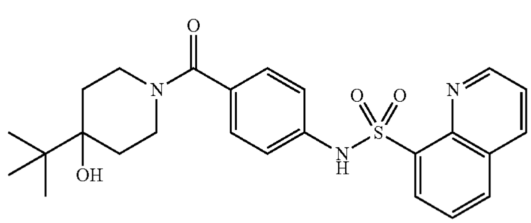 [SMILES: CC(C)(C)C1(O)CCN(C(=O)c2ccc(NS(=O)(=O)c3cccc4cccnc34)cc2)CC1] |

TABLE 1-continued

Exemplary Compounds of Formula I:

| Compound # | Structure |
|---|---|
| 196 | 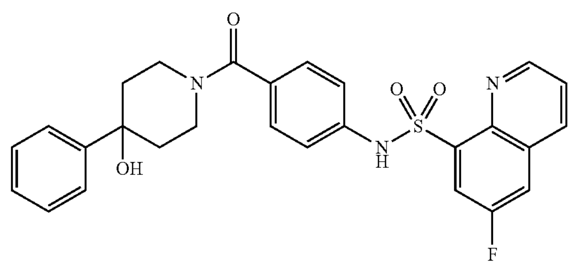 [SMILES: O=C(c1ccc(NS(=O)(=O)c2cc(F)cc3cccnc23)cc1)N1CCC(O)(c2ccccc2)CC1] |
| 197 | 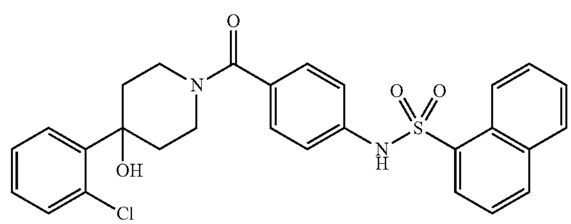 [SMILES: O=C(c1ccc(NS(=O)(=O)c2cccc3ccccc23)cc1)N1CCC(O)(c2ccccc2Cl)CC1] |
| 198 | 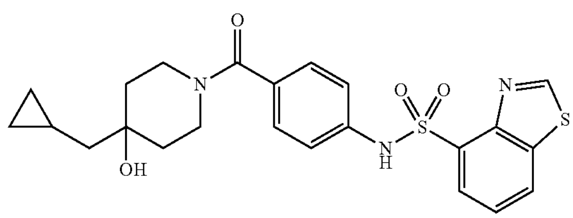 [SMILES: O=C(c1ccc(NS(=O)(=O)c2cccc3scnc23)cc1)N1CCC(O)(CC2CC2)CC1] |
| 199 | 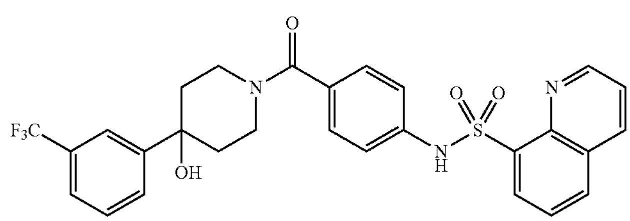 [SMILES: O=C(c1ccc(NS(=O)(=O)c2cccc3cccnc23)cc1)N1CCC(O)(c2cccc(C(F)(F)F)c2)CC1] |
| 200 | 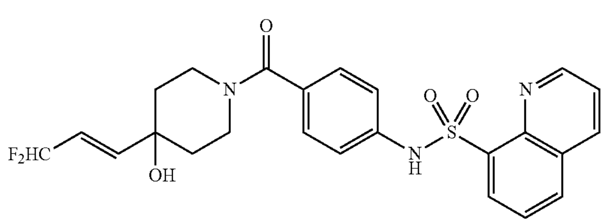 [SMILES: O=C(c1ccc(NS(=O)(=O)c2cccc3cccnc23)cc1)N1CCC(O)(/C=C/C(F)F)CC1] |
| 201 | 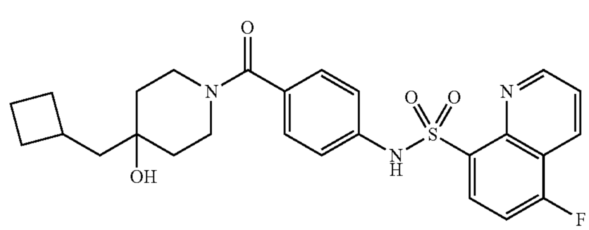 [SMILES: O=C(c1ccc(NS(=O)(=O)c2ccc(F)c3cccnc23)cc1)N1CCC(O)(CC2CCC2)CC1] |

TABLE 1-continued

Exemplary Compounds of Formula I:

| Compound # | Structure |
|---|---|
| 202 | *(structure: 4-isobutyl-4-hydroxypiperidine-1-carbonyl-phenyl-sulfonamide linked to 6-fluorobenzothiazole)* |
| 203 | *(structure: 4-isobutyl-4-hydroxypiperidine-1-carbonyl-phenyl-sulfonamide linked to 5-fluoroquinolin-8-yl)* |
| 204 | *(structure: 4-(3,3-difluoropropyl)-4-hydroxypiperidine-1-carbonyl-phenyl-sulfonamide linked to quinolin-8-yl)* |
| 205 | *(structure: 4-benzyl-4-hydroxypiperidine-1-carbonyl-phenyl-sulfonamide linked to benzo[1,2,5]thiadiazol-5-yl)* |
| 206 | *(structure: 4-(pyridin-4-yl)-4-hydroxypiperidine-1-carbonyl-phenyl-sulfonamide linked to quinolin-8-yl)* |
| 207 | *(structure: 4-((6-methylpyridin-2-yl)methyl)-4-hydroxypiperidine-1-carbonyl-phenyl-sulfonamide linked to quinolin-8-yl)* |

TABLE 1-continued

Exemplary Compounds of Formula I:

| Compound # | Structure |
|---|---|
| 208 | 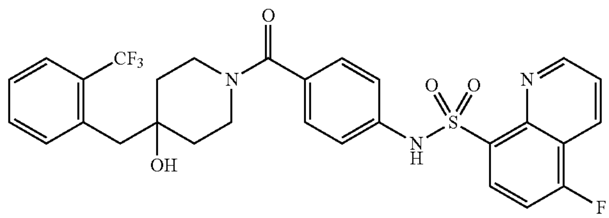 [SMILES: O=C(c1ccc(NS(=O)(=O)c2ccc(F)c3cccnc23)cc1)N1CCC(O)(Cc2ccccc2C(F)(F)F)CC1] |
| 209 | 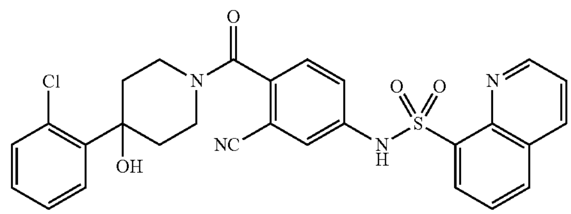 [SMILES: N#Cc1cc(NS(=O)(=O)c2cccc3cccnc23)ccc1C(=O)N1CCC(O)(c2ccccc2Cl)CC1] |
| 210 | 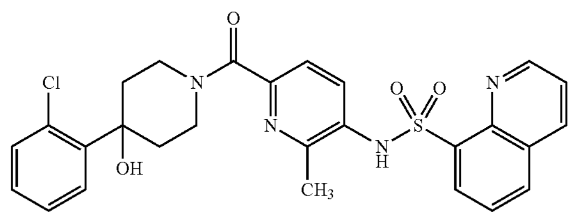 [SMILES: Cc1nc(C(=O)N2CCC(O)(c3ccccc3Cl)CC2)ccc1NS(=O)(=O)c1cccc2cccnc12] |
| 211 | 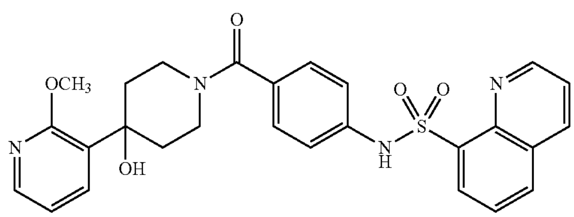 [SMILES: COc1ncccc1C1(O)CCN(C(=O)c2ccc(NS(=O)(=O)c3cccc4cccnc34)cc2)CC1] |
| 212 | 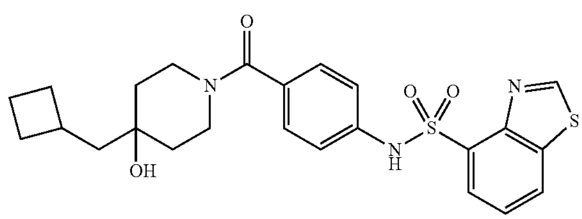 [SMILES: O=C(c1ccc(NS(=O)(=O)c2cccc3scnc23)cc1)N1CCC(O)(CC2CCC2)CC1] |
| 213 | 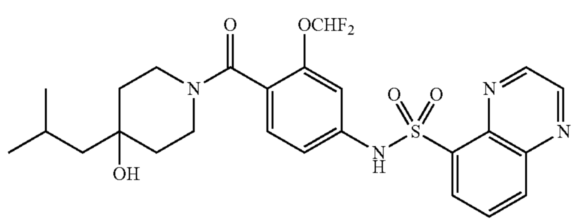 [SMILES: CC(C)CC1(O)CCN(C(=O)c2ccc(NS(=O)(=O)c3cccc4nccnc34)cc2OC(F)F)CC1] |
| 214 | 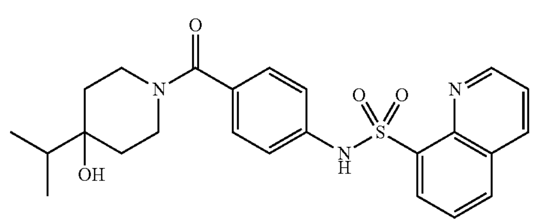 [SMILES: CC(C)C1(O)CCN(C(=O)c2ccc(NS(=O)(=O)c3cccc4cccnc34)cc2)CC1] |

TABLE 1-continued

Exemplary Compounds of Formula I:

| Compound # | Structure |
|---|---|
| 215 | 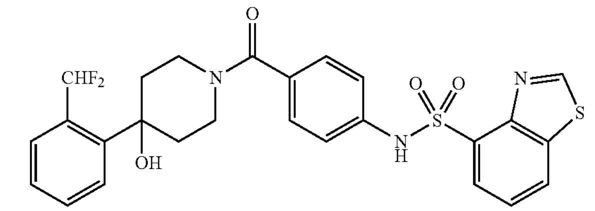 [SMILES: O=C(c1ccc(NS(=O)(=O)c2cccc3scnc23)cc1)N1CCC(O)(c2ccccc2C(F)F)CC1] |
| 216 | 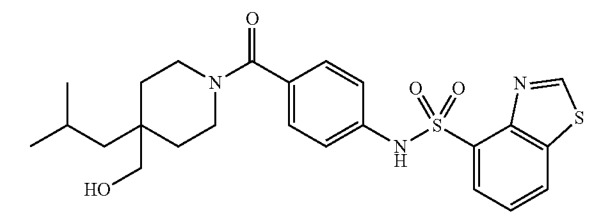 [SMILES: CC(C)CC1(CO)CCN(C(=O)c2ccc(NS(=O)(=O)c3cccc4scnc34)cc2)CC1] |
| 217 | 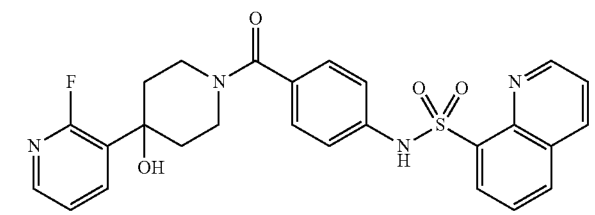 [SMILES: O=C(c1ccc(NS(=O)(=O)c2cccc3cccnc23)cc1)N1CCC(O)(c2cccnc2F)CC1] |
| 218 | 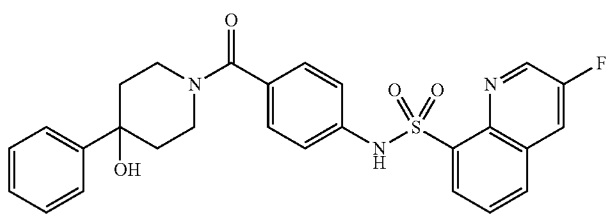 [SMILES: O=C(c1ccc(NS(=O)(=O)c2cccc3cc(F)cnc23)cc1)N1CCC(O)(c2ccccc2)CC1] |
| 219 | 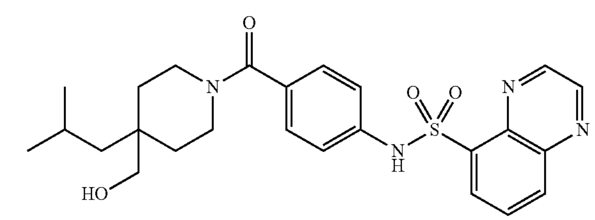 [SMILES: CC(C)CC1(CO)CCN(C(=O)c2ccc(NS(=O)(=O)c3cccc4nccnc34)cc2)CC1] |
| 220 | 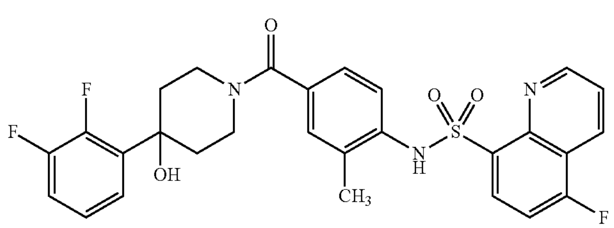 [SMILES: Cc1cc(C(=O)N2CCC(O)(c3cccc(F)c3F)CC2)ccc1NS(=O)(=O)c1ccc(F)c2cccnc12] |
| 221 | 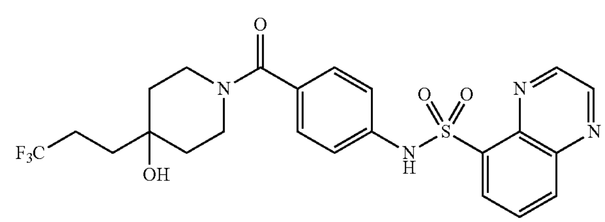 [SMILES: O=C(c1ccc(NS(=O)(=O)c2cccc3nccnc23)cc1)N1CCC(O)(CCC(F)(F)F)CC1] |

TABLE 1-continued

Exemplary Compounds of Formula I:

| Compound # | Structure |
|---|---|
| 222 | 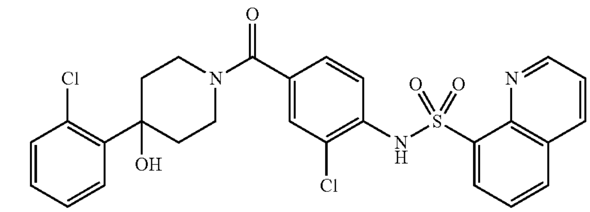 [SMILES: O=C(c1ccc(NS(=O)(=O)c2cccc3cccnc23)c(Cl)c1)N1CCC(O)(c2ccccc2Cl)CC1] |
| 223 | 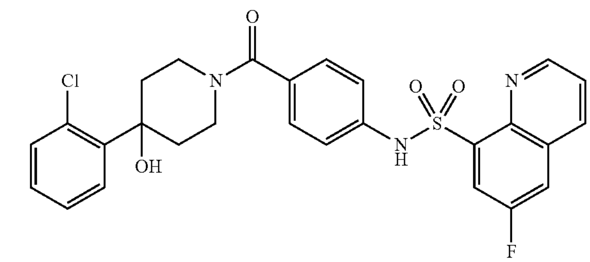 [SMILES: O=C(c1ccc(NS(=O)(=O)c2cc(F)cc3cccnc23)cc1)N1CCC(O)(c2ccccc2Cl)CC1] |
| 224 | 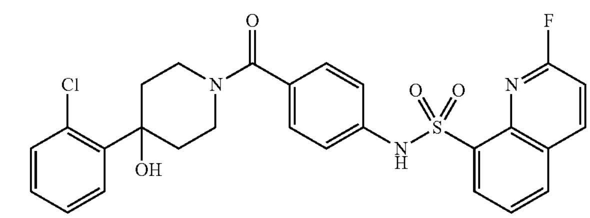 [SMILES: O=C(c1ccc(NS(=O)(=O)c2cccc3ccc(F)nc23)cc1)N1CCC(O)(c2ccccc2Cl)CC1] |
| 225 | 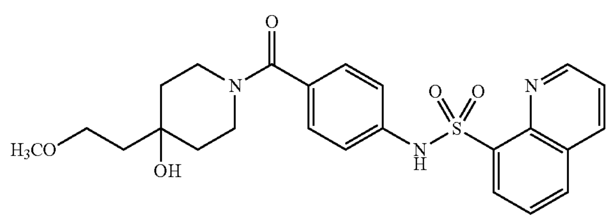 [SMILES: COCCC1(O)CCN(C(=O)c2ccc(NS(=O)(=O)c3cccc4cccnc34)cc2)CC1] |
| 226 | 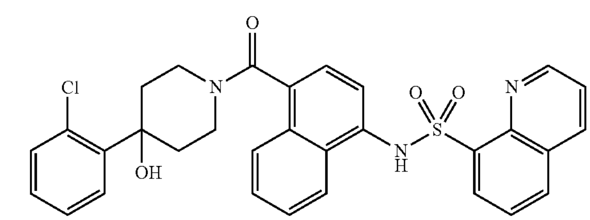 [SMILES: O=C(c1ccc(NS(=O)(=O)c2cccc3cccnc23)c2ccccc12)N1CCC(O)(c2ccccc2Cl)CC1] |
| 227 | 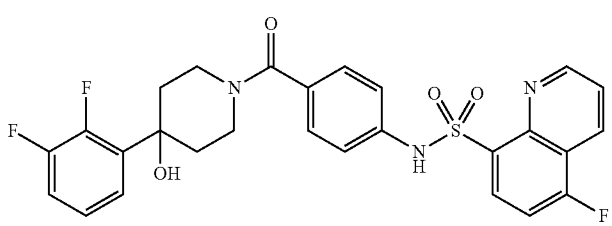 [SMILES: O=C(c1ccc(NS(=O)(=O)c2ccc(F)c3cccnc23)cc1)N1CCC(O)(c2cccc(F)c2F)CC1] |
| 228 | 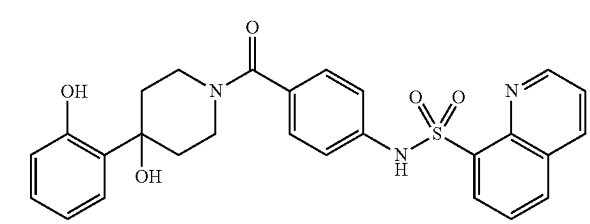 |

TABLE 1-continued

Exemplary Compounds of Formula I:

| Compound # | Structure |
|---|---|
| 229 | 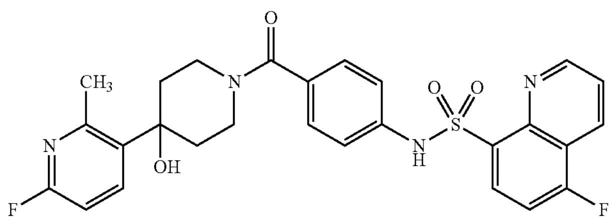 [SMILES: Cc1nc(F)ccc1C1(O)CCN(C(=O)c2ccc(NS(=O)(=O)c3ccc(F)c4cccnc34)cc2)CC1] |
| 230 | 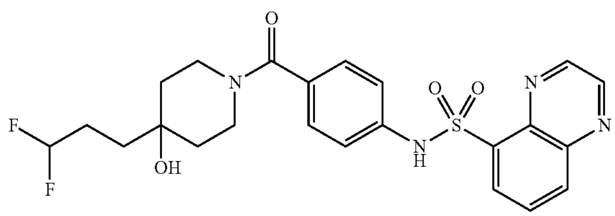 [SMILES: O=C(c1ccc(NS(=O)(=O)c2cccc3nccnc23)cc1)N1CCC(O)(CCC(F)F)CC1] |
| 231 | 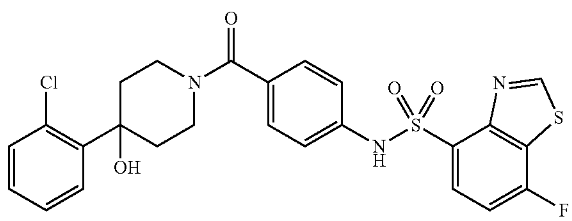 [SMILES: O=C(c1ccc(NS(=O)(=O)c2ccc(F)c3scnc23)cc1)N1CCC(O)(c2ccccc2Cl)CC1] |
| 232 | 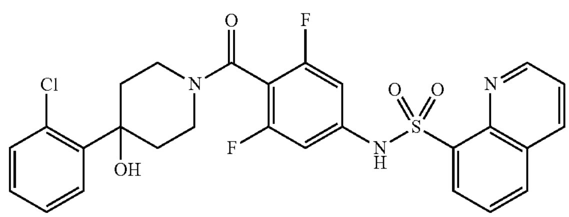 [SMILES: O=C(c1c(F)cc(NS(=O)(=O)c2cccc3cccnc23)cc1F)N1CCC(O)(c2ccccc2Cl)CC1] |
| 233 | 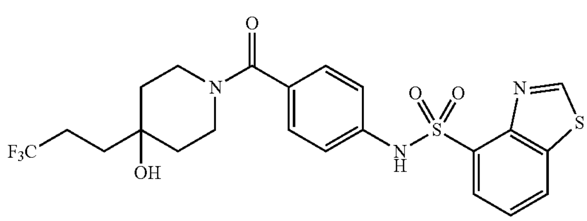 [SMILES: O=C(c1ccc(NS(=O)(=O)c2cccc3scnc23)cc1)N1CCC(O)(CCC(F)(F)F)CC1] |
| 234 | 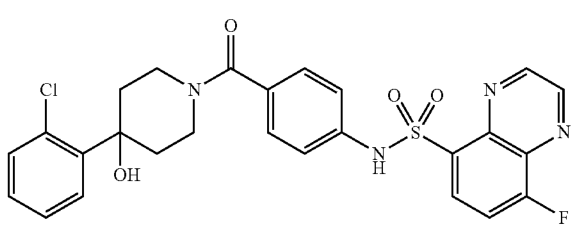 [SMILES: O=C(c1ccc(NS(=O)(=O)c2ccc(F)c3nccnc23)cc1)N1CCC(O)(c2ccccc2Cl)CC1] |
| 235 | 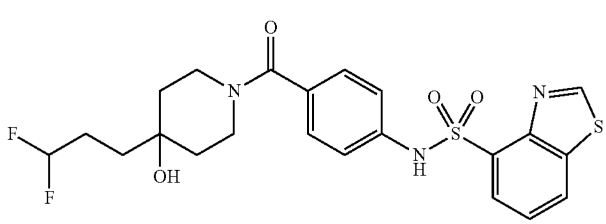 [SMILES: O=C(c1ccc(NS(=O)(=O)c2cccc3scnc23)cc1)N1CCC(O)(CCC(F)F)CC1] |

TABLE 1-continued

Exemplary Compounds of Formula I:

| Compound # | Structure |
|---|---|
| 237 | 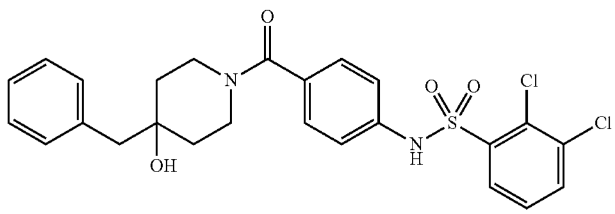 [SMILES: O=C(c1ccc(NS(=O)(=O)c2cccc(Cl)c2Cl)cc1)N1CCC(O)(Cc2ccccc2)CC1] |
| 238 | 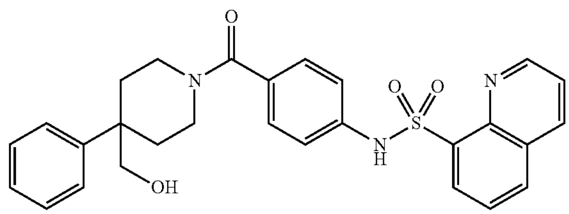 [SMILES: O=C(c1ccc(NS(=O)(=O)c2cccc3cccnc23)cc1)N1CCC(CO)(c2ccccc2)CC1] |
| 239 | 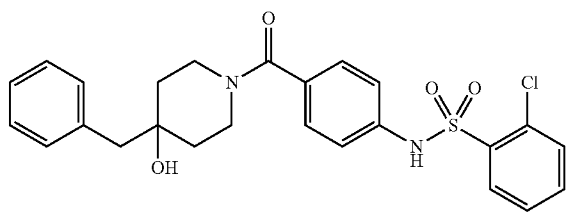 [SMILES: O=C(c1ccc(NS(=O)(=O)c2ccccc2Cl)cc1)N1CCC(O)(Cc2ccccc2)CC1] |
| 240 | 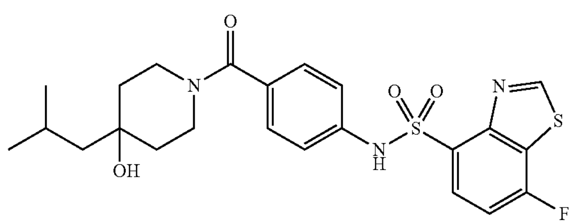 [SMILES: CC(C)CC1(O)CCN(C(=O)c2ccc(NS(=O)(=O)c3ccc(F)c4scnc34)cc2)CC1] |
| 241 | 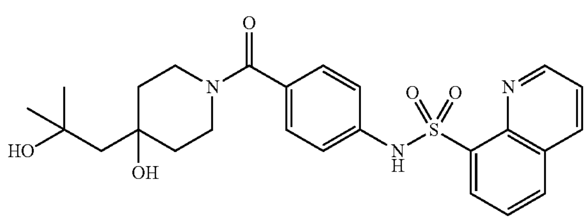 [SMILES: CC(C)(O)CC1(O)CCN(C(=O)c2ccc(NS(=O)(=O)c3cccc4cccnc34)cc2)CC1] |
| 242 | 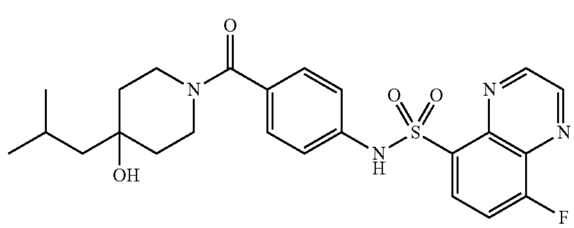 [SMILES: CC(C)CC1(O)CCN(C(=O)c2ccc(NS(=O)(=O)c3ccc(F)c4nccnc34)cc2)CC1] |
| 243 | 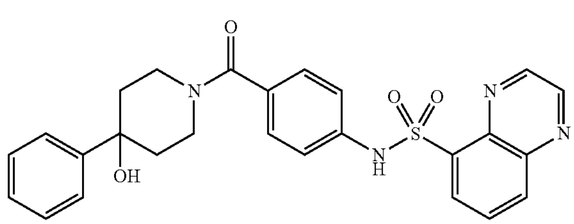 [SMILES: O=C(c1ccc(NS(=O)(=O)c2cccc3nccnc23)cc1)N1CCC(O)(c2ccccc2)CC1] |

TABLE 1-continued

Exemplary Compounds of Formula I:

| Compound # | Structure |
|---|---|
| 244 | 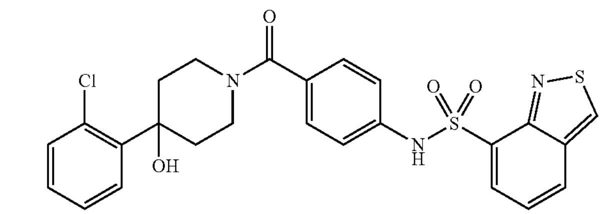 [SMILES: O=C(c1ccc(NS(=O)(=O)c2cccc3csnc23)cc1)N1CCC(O)(c2ccccc2Cl)CC1] |
| 245 | 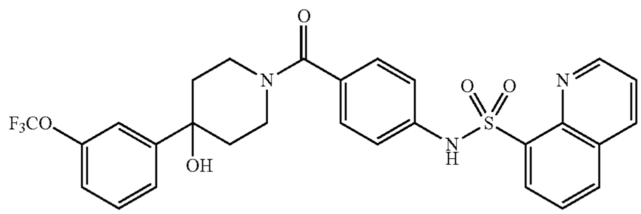 [SMILES: O=C(c1ccc(NS(=O)(=O)c2cccc3cccnc23)cc1)N1CCC(O)(c2cccc(OC(F)(F)F)c2)CC1] |
| 246 | 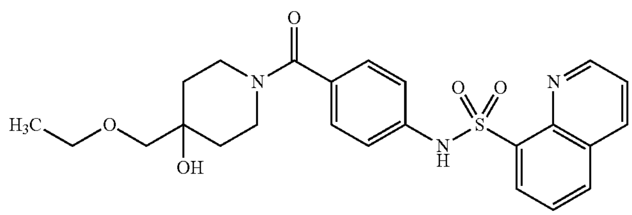 [SMILES: CCOCC1(O)CCN(C(=O)c2ccc(NS(=O)(=O)c3cccc4cccnc34)cc2)CC1] |
| 247 | 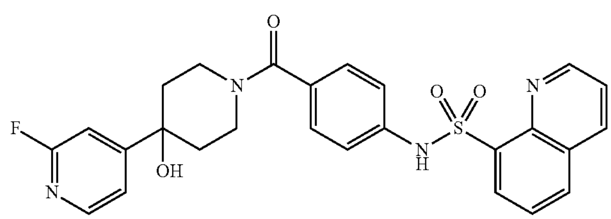 |
| 250 | 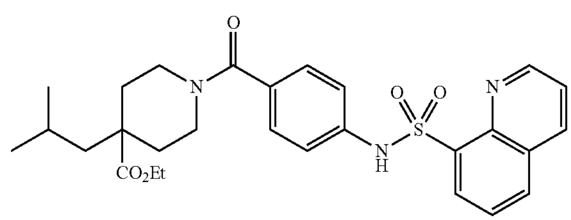 [SMILES: CCOC(=O)C1(CC(C)C)CCN(C(=O)c2ccc(NS(=O)(=O)c3cccc4cccnc34)cc2)CC1] |
| 251 | 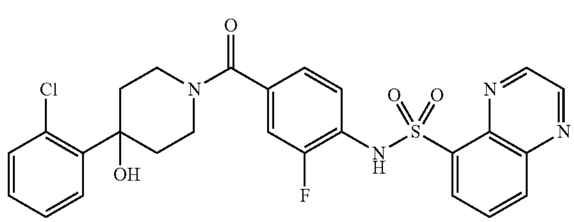 [SMILES: O=C(c1ccc(NS(=O)(=O)c2cccc3nccnc23)c(F)c1)N1CCC(O)(c2ccccc2Cl)CC1] |
| 253 | 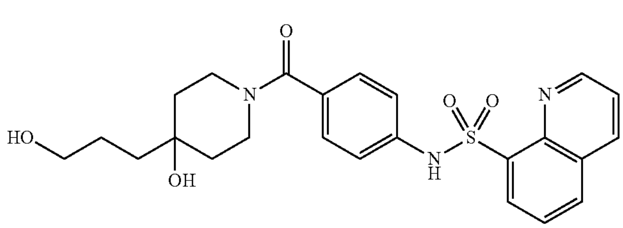 [SMILES: O=C(c1ccc(NS(=O)(=O)c2cccc3cccnc23)cc1)N1CCC(O)(CCCO)CC1] |

TABLE 1-continued

Exemplary Compounds of Formula I:

| Compound # | Structure |
|---|---|
| 254 | 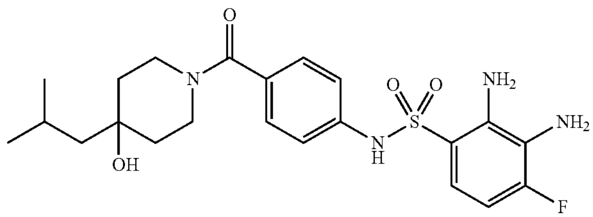 [SMILES: CC(C)CC1(O)CCN(C(=O)c2ccc(NS(=O)(=O)c3ccc(F)c(N)c3N)cc2)CC1] |
| 255 | 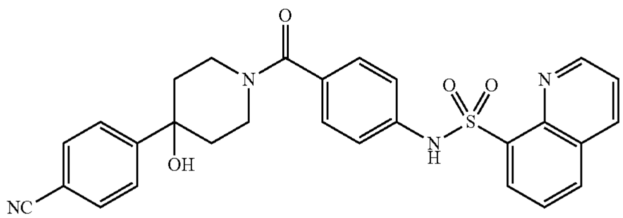 [SMILES: N#Cc1ccc(C2(O)CCN(C(=O)c3ccc(NS(=O)(=O)c4cccc5cccnc45)cc3)CC2)cc1] |
| 256 | 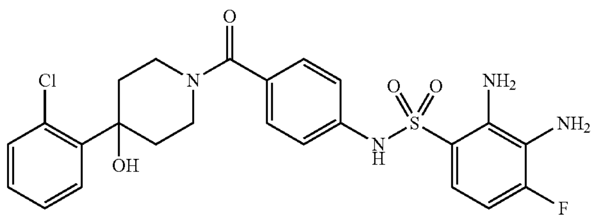 [SMILES: Nc1c(F)ccc(S(=O)(=O)Nc2ccc(C(=O)N3CCC(O)(c4ccccc4Cl)CC3)cc2)c1N] |
| 257 | 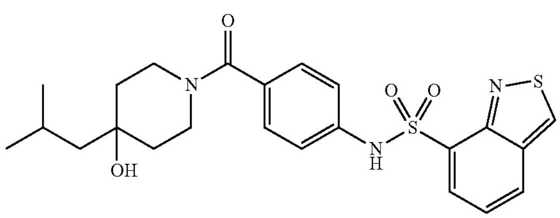 [SMILES: CC(C)CC1(O)CCN(C(=O)c2ccc(NS(=O)(=O)c3cccc4csnc34)cc2)CC1] |
| 258 | 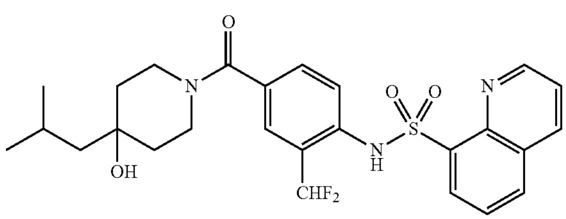 [SMILES: CC(C)CC1(O)CCN(C(=O)c2ccc(NS(=O)(=O)c3cccc4cccnc34)c(C(F)F)c2)CC1] |
| 259 | 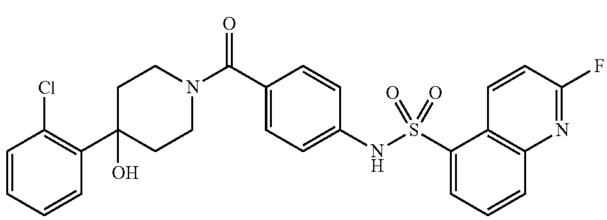 [SMILES: O=C(c1ccc(NS(=O)(=O)c2cccc3nc(F)ccc23)cc1)N1CCC(O)(c2ccccc2Cl)CC1] |
| 260 | 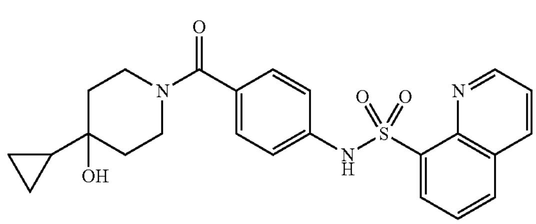 [SMILES: O=C(c1ccc(NS(=O)(=O)c2cccc3cccnc23)cc1)N1CCC(O)(C2CC2)CC1] |

TABLE 1-continued

Exemplary Compounds of Formula I:

| Compound # | Structure |
|---|---|
| 261 | 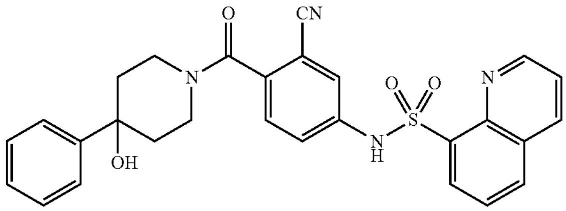 [SMILES: N#Cc1cc(NS(=O)(=O)c2cccc3cccnc23)ccc1C(=O)N1CCC(O)(c2ccccc2)CC1] |
| 262 | 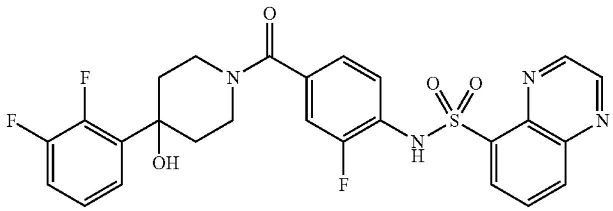 [SMILES: O=C(c1ccc(NS(=O)(=O)c2cccc3nccnc23)c(F)c1)N1CCC(O)(c2cccc(F)c2F)CC1] |
| 263 | 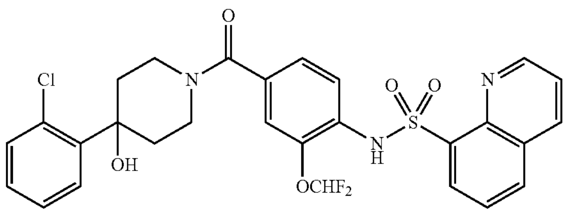 [SMILES: O=C(c1ccc(NS(=O)(=O)c2cccc3cccnc23)c(OC(F)F)c1)N1CCC(O)(c2ccccc2Cl)CC1] |
| 265 | 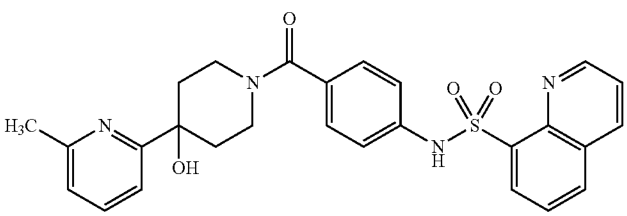 [SMILES: Cc1cccc(C2(O)CCN(C(=O)c3ccc(NS(=O)(=O)c4cccc5cccnc45)cc3)CC2)n1] |
| 266 | 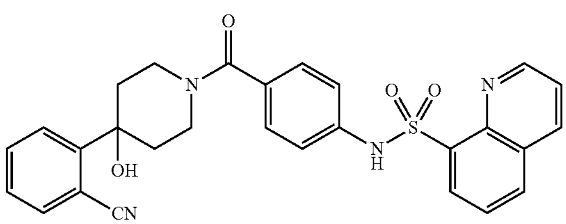 [SMILES: N#Cc1ccccc1C1(O)CCN(C(=O)c2ccc(NS(=O)(=O)c3cccc4cccnc34)cc2)CC1] |
| 267 | 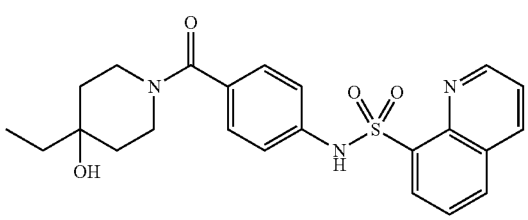 [SMILES: CCC1(O)CCN(C(=O)c2ccc(NS(=O)(=O)c3cccc4cccnc34)cc2)CC1] |
| 268 | 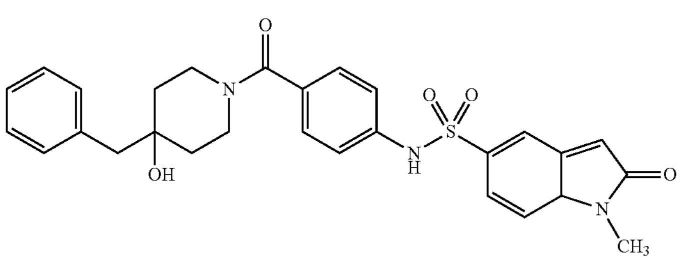 [SMILES: CN1C(=O)C=C2C=C(S(=O)(=O)Nc3ccc(C(=O)N4CCC(O)(Cc5ccccc5)CC4)cc3)C=CC21] |

TABLE 1-continued
Exemplary Compounds of Formula I:
| Compound # | Structure |
|---|---|
| 269 | 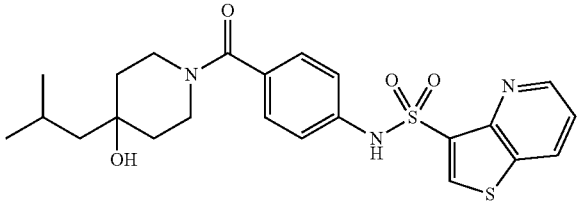 [SMILES: CC(C)CC1(O)CCN(C(=O)c2ccc(NS(=O)(=O)c3csc4cccnc34)cc2)CC1] |
| 270 | 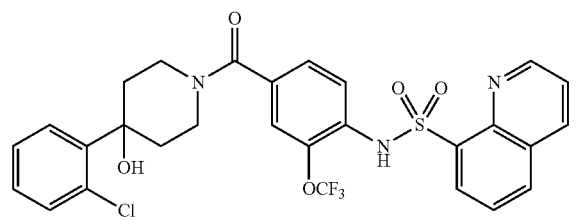 [SMILES: O=C(c1ccc(NS(=O)(=O)c2cccc3cccnc23)c(OC(F)(F)F)c1)N1CCC(O)(c2ccccc2Cl)CC1] |
| 271 | 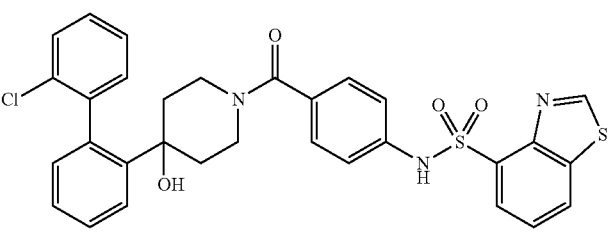 [SMILES: O=C(c1ccc(NS(=O)(=O)c2cccc3scnc23)cc1)N1CCC(O)(c2ccccc2-c2ccccc2Cl)CC1] |
| 272 | 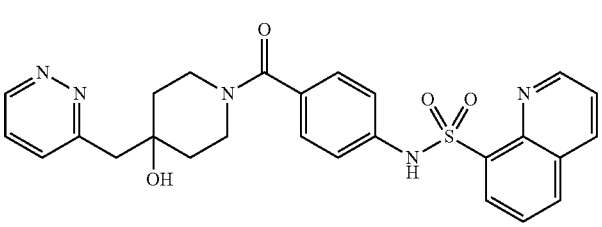 [SMILES: O=C(c1ccc(NS(=O)(=O)c2cccc3cccnc23)cc1)N1CCC(O)(Cc2cccnn2)CC1] |
| 273 | 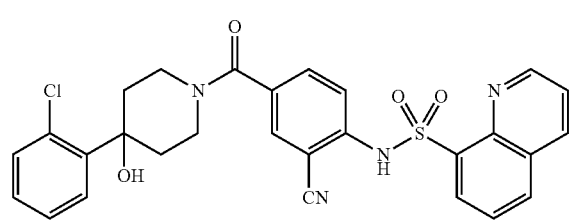 [SMILES: N#Cc1cc(C(=O)N2CCC(O)(c3ccccc3Cl)CC2)ccc1NS(=O)(=O)c1cccc2cccnc12] |
| 274 | 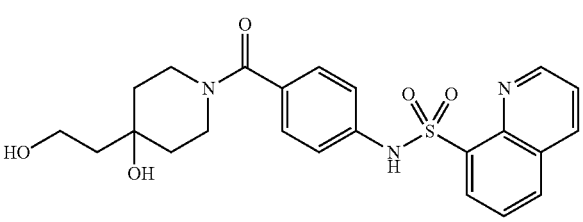 [SMILES: O=C(c1ccc(NS(=O)(=O)c2cccc3cccnc23)cc1)N1CCC(O)(CCO)CC1] |
| 275 | 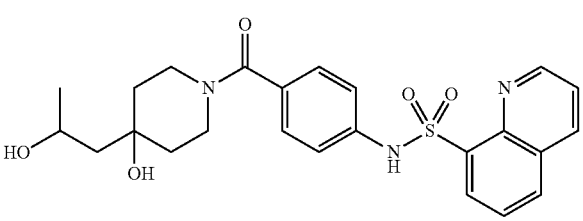 [SMILES: CC(O)CC1(O)CCN(C(=O)c2ccc(NS(=O)(=O)c3cccc4cccnc34)cc2)CC1] |

TABLE 1-continued

Exemplary Compounds of Formula I:

| Compound # | Structure |
| --- | --- |
| 276 | 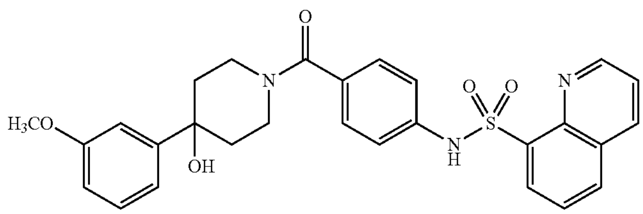 [SMILES: COc1cccc(C2(O)CCN(C(=O)c3ccc(NS(=O)(=O)c4cccc5cccnc45)cc3)CC2)c1] |
| 277 | 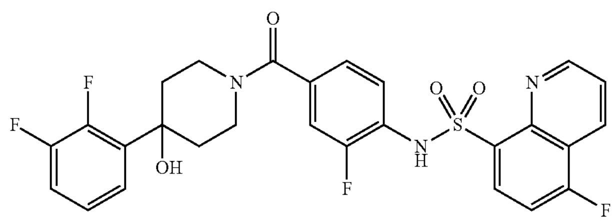 [SMILES: O=C(c1ccc(NS(=O)(=O)c2ccc(F)c3cccnc23)c(F)c1)N1CCC(O)(c2cccc(F)c2F)CC1] |
| 278 | 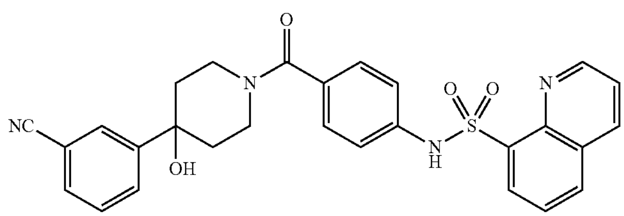 [SMILES: N#Cc1cccc(C2(O)CCN(C(=O)c3ccc(NS(=O)(=O)c4cccc5cccnc45)cc3)CC2)c1] |
| 280 | 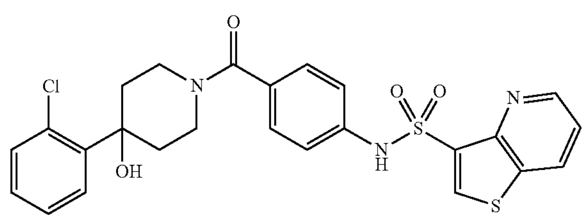 [SMILES: O=C(c1ccc(NS(=O)(=O)c2csc3cccnc23)cc1)N1CCC(O)(c2ccccc2Cl)CC1] |
| 281 | 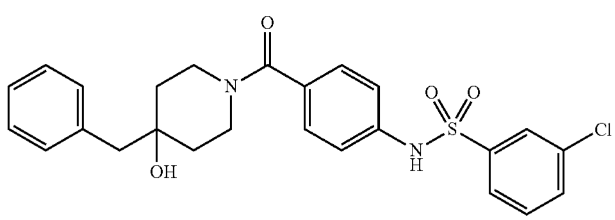 [SMILES: O=C(c1ccc(NS(=O)(=O)c2cccc(Cl)c2)cc1)N1CCC(O)(Cc2ccccc2)CC1] |
| 283 | 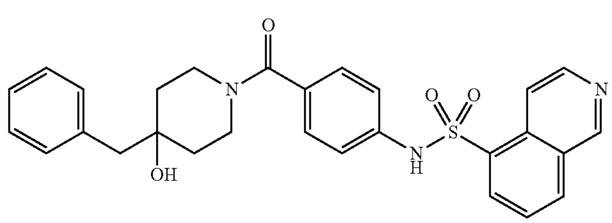 [SMILES: O=C(c1ccc(NS(=O)(=O)c2cccc3cnccc23)cc1)N1CCC(O)(Cc2ccccc2)CC1] |
| 284 | 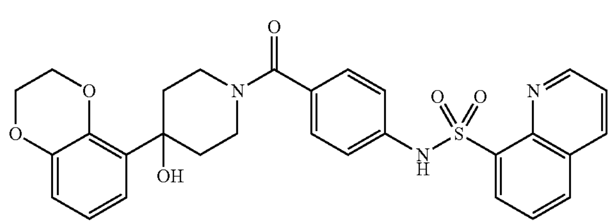 [SMILES: O=C(c1ccc(NS(=O)(=O)c2cccc3cccnc23)cc1)N1CCC(O)(c2cccc3c2OCCO3)CC1] |

TABLE 1-continued
Exemplary Compounds of Formula I:
| Compound # | Structure |
|---|---|
| 285 | 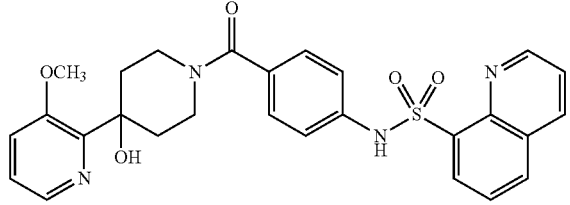 [SMILES: COc1cccnc1C1(O)CCN(C(=O)c2ccc(NS(=O)(=O)c3cccc4cccnc34)cc2)CC1] |
| 286 | 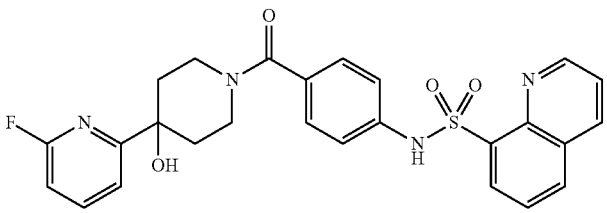 |
| 287 | 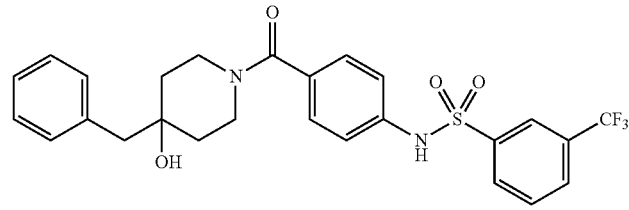 [SMILES: O=C(c1ccc(NS(=O)(=O)c2cccc(C(F)(F)F)c2)cc1)N1CCC(O)(Cc2ccccc2)CC1] |
| 288 | 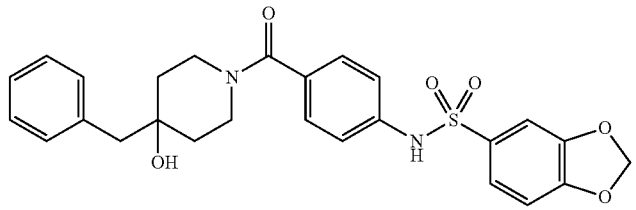 [SMILES: O=C(c1ccc(NS(=O)(=O)c2ccc3c(c2)OCO3)cc1)N1CCC(O)(Cc2ccccc2)CC1] |
| 289 | 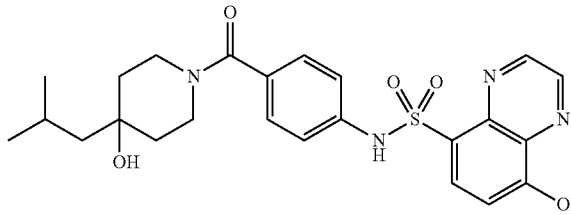 |
| 290 | 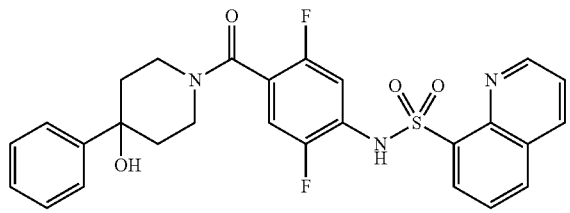 [SMILES: O=C(c1cc(F)c(NS(=O)(=O)c2cccc3cccnc23)cc1F)N1CCC(O)(c2ccccc2)CC1] |
| 292 | 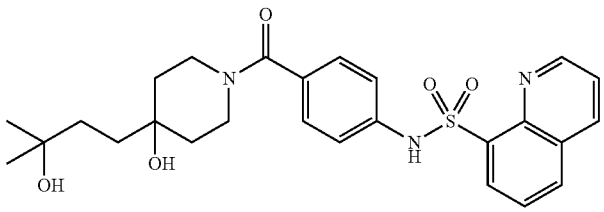 [SMILES: CC(C)(O)CCC1(O)CCN(C(=O)c2ccc(NS(=O)(=O)c3cccc4cccnc34)cc2)CC1] |

TABLE 1-continued

Exemplary Compounds of Formula I:

| Compound # | Structure |
|---|---|
| 293 | 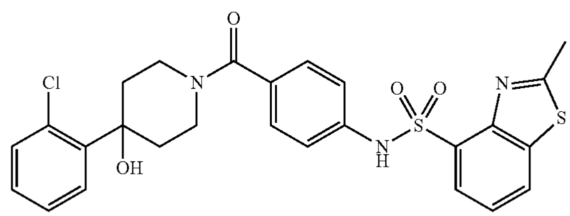 [SMILES: Cc1nc2c(S(=O)(=O)Nc3ccc(C(=O)N4CCC(O)(c5ccccc5Cl)CC4)cc3)cccc2s1] |
| 294 | 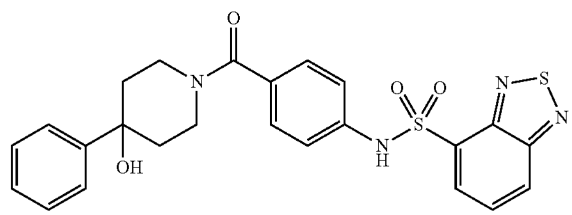 [SMILES: O=C(c1ccc(NS(=O)(=O)c2cccc3nsnc23)cc1)N1CCC(O)(c2ccccc2)CC1] |
| 296 | 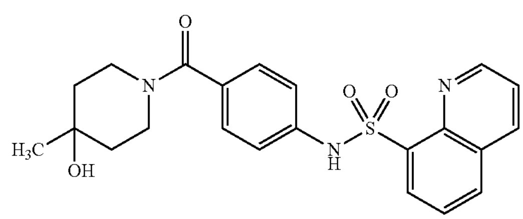 [SMILES: CC1(O)CCN(C(=O)c2ccc(NS(=O)(=O)c3cccc4cccnc34)cc2)CC1] |
| 297 | 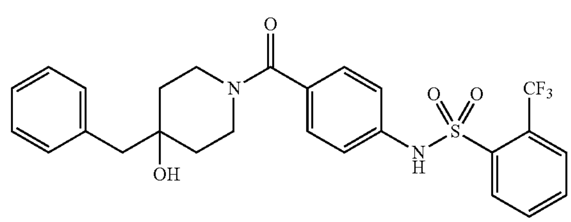 [SMILES: O=C(c1ccc(NS(=O)(=O)c2ccccc2C(F)(F)F)cc1)N1CCC(O)(Cc2ccccc2)CC1] |
| 298 | 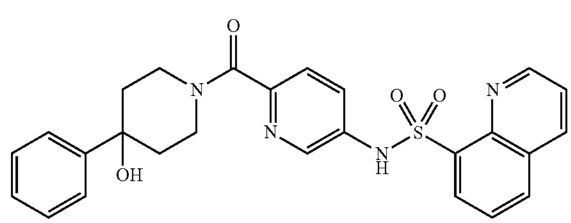 [SMILES: O=C(c1ccc(NS(=O)(=O)c2cccc3cccnc23)cn1)N1CCC(O)(c2ccccc2)CC1] |
| 299 | 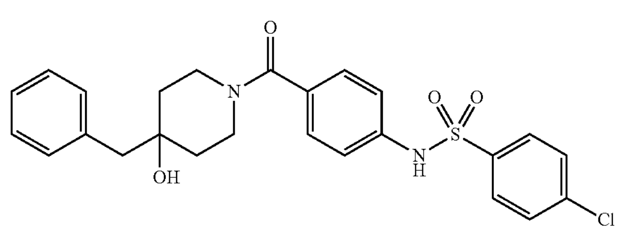 [SMILES: O=C(c1ccc(NS(=O)(=O)c2ccc(Cl)cc2)cc1)N1CCC(O)(Cc2ccccc2)CC1] |
| 300 | 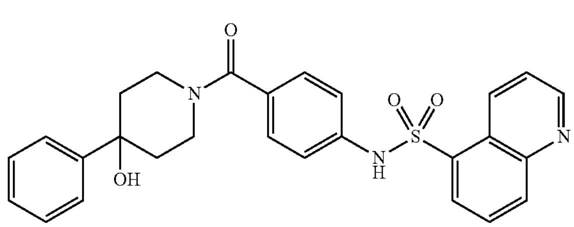 [SMILES: O=C(c1ccc(NS(=O)(=O)c2cccc3ncccc23)cc1)N1CCC(O)(c2ccccc2)CC1] |

TABLE 1-continued

Exemplary Compounds of Formula I:

| Compound # | Structure |
|---|---|
| 301 | 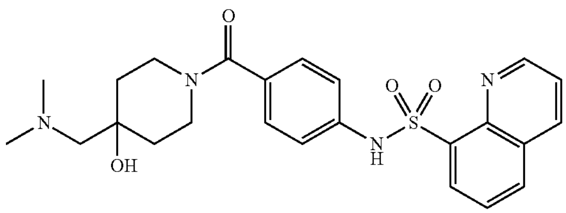 [SMILES: CN(C)CC1(O)CCN(C(=O)c2ccc(NS(=O)(=O)c3cccc4cccnc34)cc2)CC1] |
| 302 | 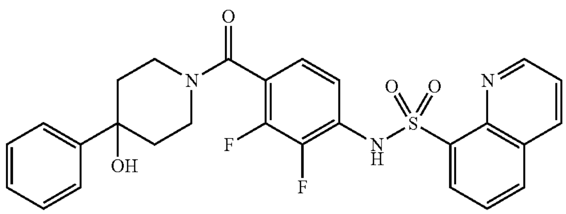 [SMILES: O=C(c1ccc(NS(=O)(=O)c2cccc3cccnc23)c(F)c1F)N1CCC(O)(c2ccccc2)CC1] |
| 303 | 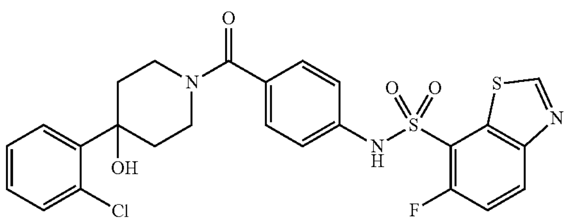 [SMILES: O=C(c1ccc(NS(=O)(=O)c2c(F)ccc3ncsc23)cc1)N1CCC(O)(c2ccccc2Cl)CC1] |
| 304 | 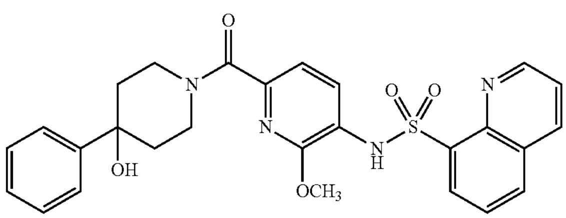 [SMILES: COc1nc(C(=O)N2CCC(O)(c3ccccc3)CC2)ccc1NS(=O)(=O)c1cccc2cccnc12] |
| 306 | 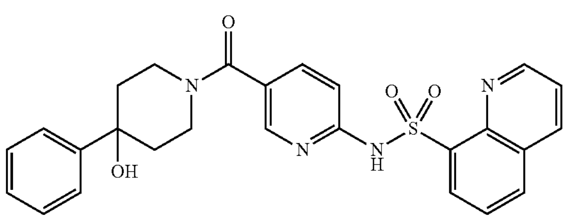 [SMILES: O=C(c1ccc(NS(=O)(=O)c2cccc3cccnc23)nc1)N1CCC(O)(c2ccccc2)CC1] |
| 307 | 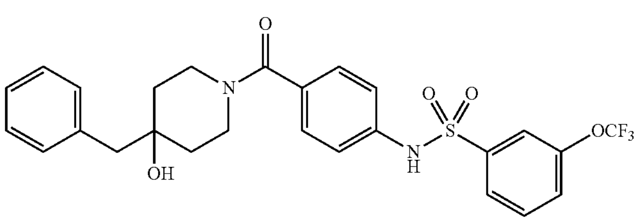 [SMILES: O=C(c1ccc(NS(=O)(=O)c2cccc(OC(F)(F)F)c2)cc1)N1CCC(O)(Cc2ccccc2)CC1] |
| 308 | 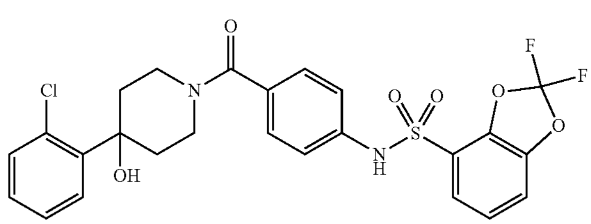 [SMILES: O=C(c1ccc(NS(=O)(=O)c2cccc3c2OC(F)(F)O3)cc1)N1CCC(O)(c2ccccc2Cl)CC1] |

TABLE 1-continued

Exemplary Compounds of Formula I:

| Compound # | Structure |
|---|---|
| 309 | 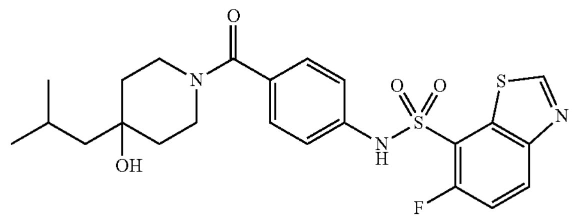 [SMILES: CC(C)CC1(O)CCN(C(=O)c2ccc(NS(=O)(=O)c3c(F)ccc4ncsc34)cc2)CC1] |
| 310 | 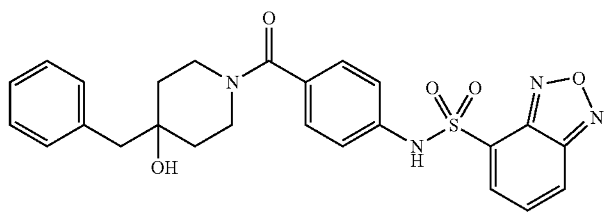 [SMILES: O=C(c1ccc(NS(=O)(=O)c2cccc3nonc23)cc1)N1CCC(O)(Cc2ccccc2)CC1] |
| 311 | 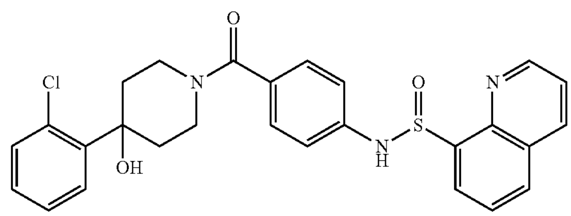 [SMILES: O=C(c1ccc(NS(=O)c2cccc3cccnc23)cc1)N1CCC(O)(c2ccccc2Cl)CC1] |
| 312 | 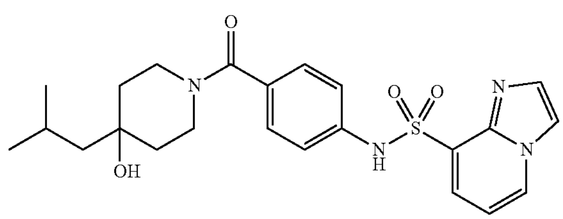 [SMILES: CC(C)CC1(O)CCN(C(=O)c2ccc(NS(=O)(=O)c3cccn4ccnc34)cc2)CC1] |
| 313 | 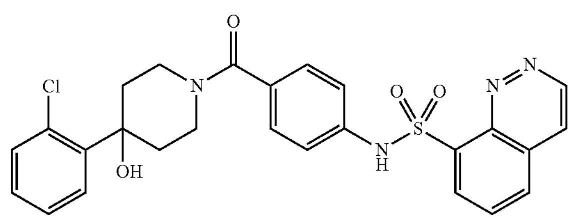 [SMILES: O=C(c1ccc(NS(=O)(=O)c2cccc3ccnnc23)cc1)N1CCC(O)(c2ccccc2Cl)CC1] |
| 314 | 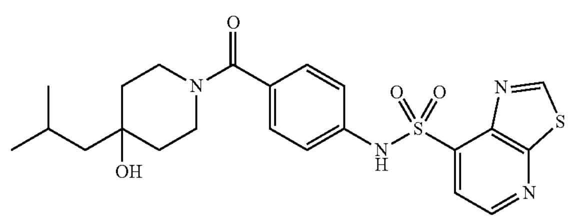 [SMILES: CC(C)CC1(O)CCN(C(=O)c2ccc(NS(=O)(=O)c3ccnc4scnc34)cc2)CC1] |
| 315 | 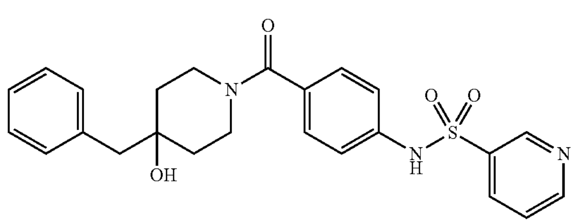 [SMILES: O=C(c1ccc(NS(=O)(=O)c2cccnc2)cc1)N1CCC(O)(Cc2ccccc2)CC1] |

TABLE 1-continued
Exemplary Compounds of Formula I:
| Compound # | Structure |
|---|---|
| 316 | 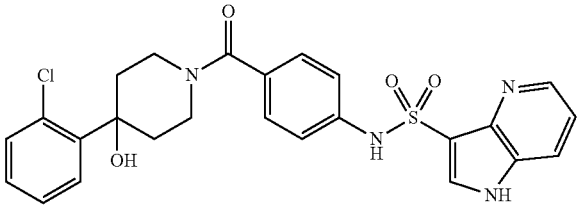 [SMILES: O=C(c1ccc(NS(=O)(=O)c2c[nH]c3cccnc23)cc1)N1CCC(O)(c2ccccc2Cl)CC1] |
| 317 | 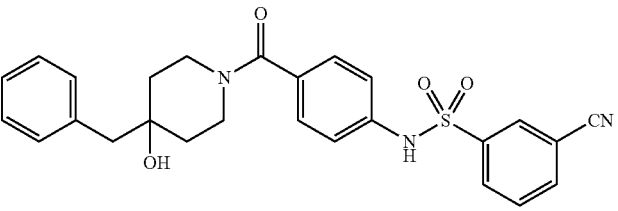 [SMILES: N#Cc1cccc(S(=O)(=O)Nc2ccc(C(=O)N3CCC(O)(Cc4ccccc4)CC3)cc2)c1] |
| 318 | 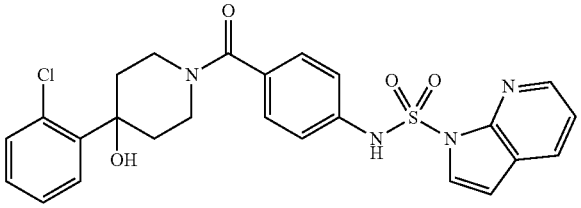 [SMILES: O=C(c1ccc(NS(=O)(=O)n2ccc3cccnc32)cc1)N1CCC(O)(c2ccccc2Cl)CC1] |
| 319 | 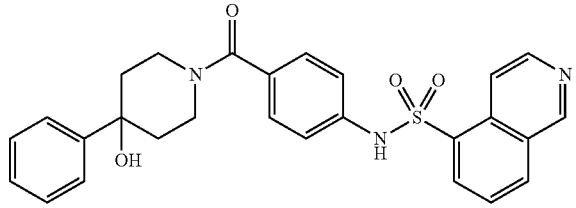 [SMILES: O=C(c1ccc(NS(=O)(=O)c2cccc3cnccc23)cc1)N1CCC(O)(c2ccccc2)CC1] |
| 320 | 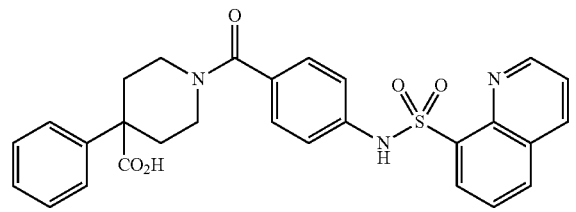 [SMILES: O=C(c1ccc(NS(=O)(=O)c2cccc3cccnc23)cc1)N1CCC(C(=O)O)(c2ccccc2)CC1] |
| 321 | 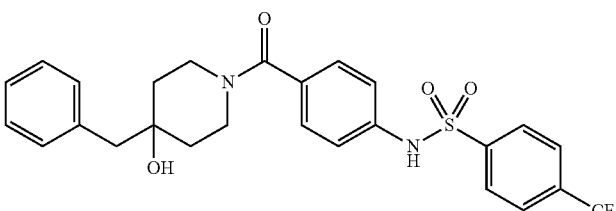 |
| 322 | 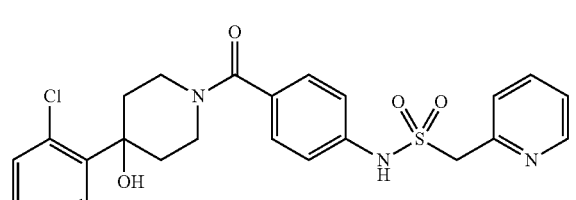 |

TABLE 1-continued

Exemplary Compounds of Formula I:

| Compound # | Structure |
|---|---|
| 323 | 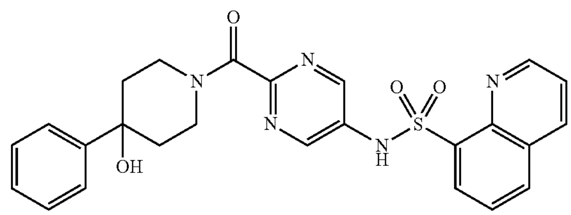 [SMILES: O=C(c1ncc(NS(=O)(=O)c2cccc3cccnc23)cn1)N1CCC(O)(c2ccccc2)CC1] |
| 324 | 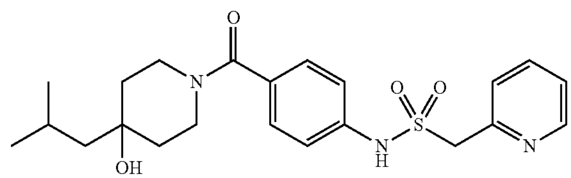 [SMILES: CC(C)CC1(O)CCN(C(=O)c2ccc(NS(=O)(=O)Cc3ccccn3)cc2)CC1] |
| 325 | 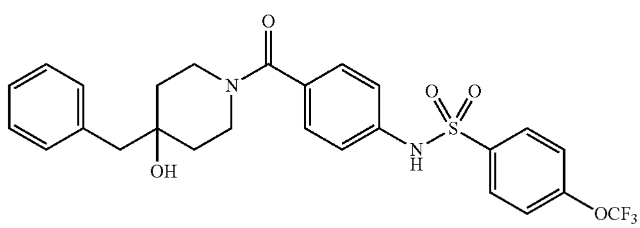 [SMILES: O=C(c1ccc(NS(=O)(=O)c2ccc(OC(F)(F)F)cc2)cc1)N1CCC(O)(Cc2ccccc2)CC1] |
| 326 | 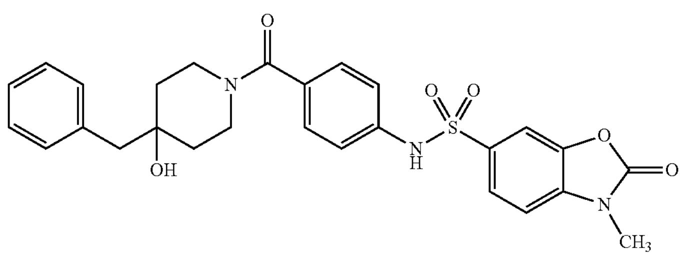 [SMILES: Cn1c(=O)oc2cc(S(=O)(=O)Nc3ccc(C(=O)N4CCC(O)(Cc5ccccc5)CC4)cc3)ccc21] |
| 327 | 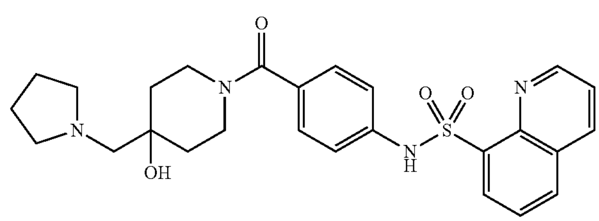 [SMILES: O=C(c1ccc(NS(=O)(=O)c2cccc3cccnc23)cc1)N1CCC(O)(CN2CCCC2)CC1] |
| 330 | 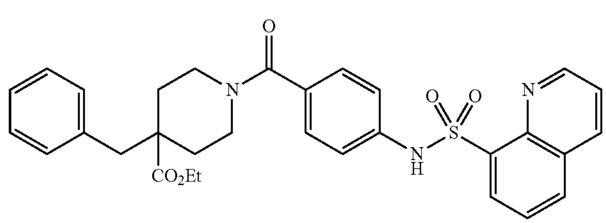 [SMILES: CCOC(=O)C1(Cc2ccccc2)CCN(C(=O)c2ccc(NS(=O)(=O)c3cccc4cccnc34)cc2)CC1] |
| 331 | 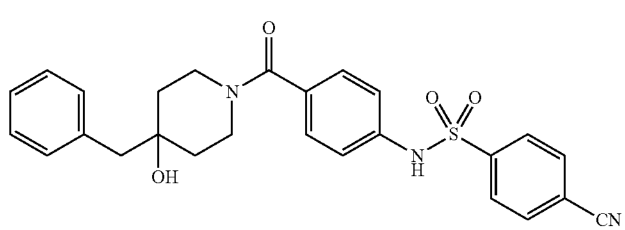 [SMILES: N#Cc1ccc(S(=O)(=O)Nc2ccc(C(=O)N3CCC(O)(Cc4ccccc4)CC3)cc2)cc1] |

TABLE 1-continued

Exemplary Compounds of Formula I:

| Compound # | Structure |
|---|---|
| 353 | 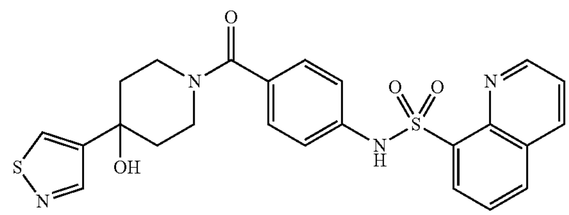 [SMILES: O=C(c1ccc(NS(=O)(=O)c2cccc3cccnc23)cc1)N1CCC(O)(c2cnsc2)CC1] |
| 368 | 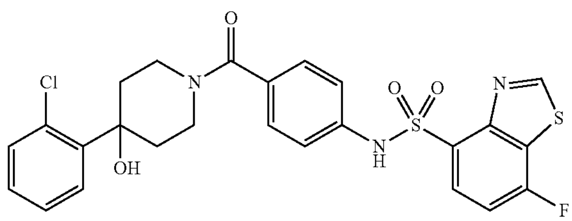 [SMILES: O=C(c1ccc(NS(=O)(=O)c2ccc(F)c3scnc23)cc1)N1CCC(O)(c2ccccc2Cl)CC1] |
| 372 | 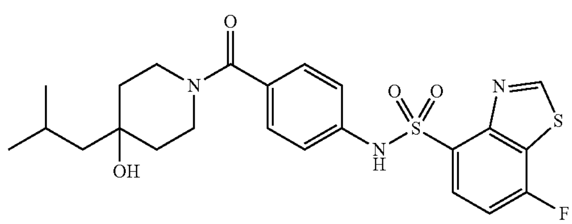 [SMILES: CC(C)CC1(O)CCN(C(=O)c2ccc(NS(=O)(=O)c3ccc(F)c4scnc34)cc2)CC1] |
| 376 | 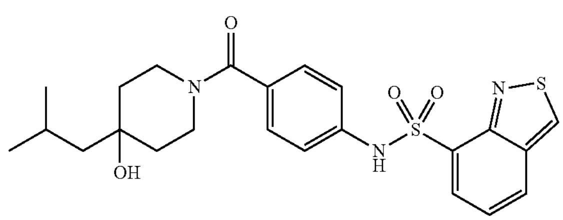 [SMILES: CC(C)CC1(O)CCN(C(=O)c2ccc(NS(=O)(=O)c3cccc4csnc34)cc2)CC1] |
| 377 | 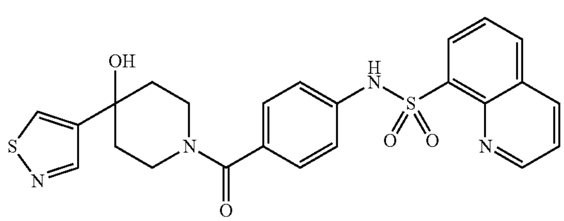 [SMILES: O=C(c1ccc(NS(=O)(=O)c2cccc3cccnc23)cc1)N1CCC(O)(c2cnsc2)CC1] |
| 378 | 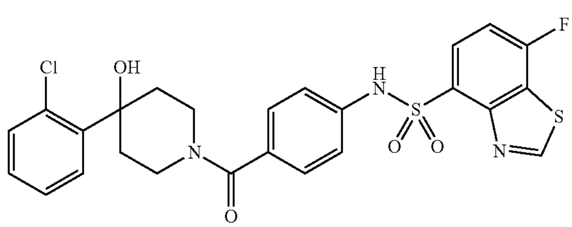 [SMILES: O=C(c1ccc(NS(=O)(=O)c2ccc(F)c3scnc23)cc1)N1CCC(O)(c2ccccc2Cl)CC1] |
| 379 | 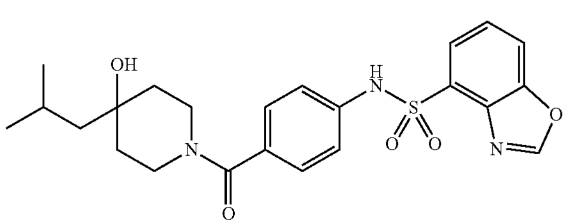 [SMILES: CC(C)CC1(O)CCN(C(=O)c2ccc(NS(=O)(=O)c3cccc4ocnc34)cc2)CC1] |

TABLE 1-continued
| Exemplary Compounds of Formula I: | |
|---|---|
| Compound # | Structure |
380
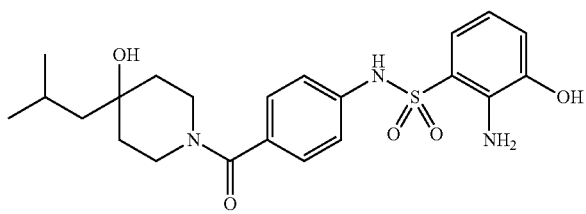 [SMILES: CC(C)CC1(O)CCN(C(=O)c2ccc(NS(=O)(=O)c3cccc(O)c3N)cc2)CC1]
381
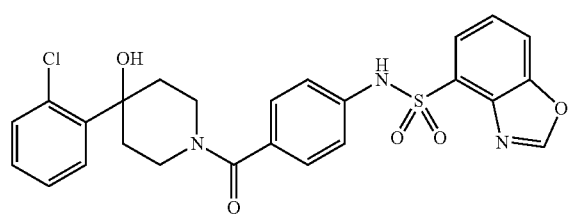 [SMILES: O=C(c1ccc(NS(=O)(=O)c2cccc3ocnc23)cc1)N1CCC(O)(c2ccccc2Cl)CC1]
382
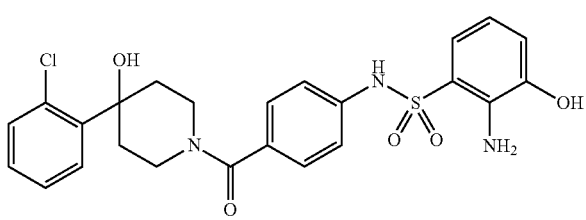 [SMILES: Nc1c(O)cccc1S(=O)(=O)Nc1ccc(C(=O)N2CCC(O)(c3ccccc3Cl)CC2)cc1]
383
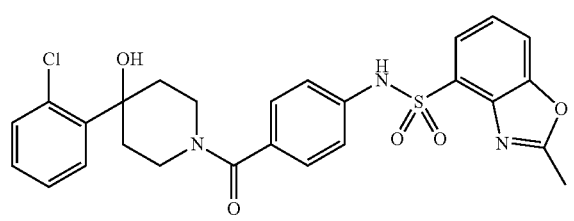 [SMILES: Cc1nc2c(S(=O)(=O)Nc3ccc(C(=O)N4CCC(O)(c5ccccc5Cl)CC4)cc3)cccc2o1]
384
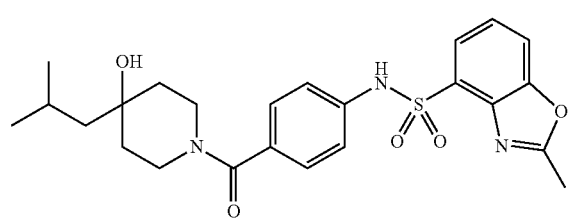 [SMILES: Cc1nc2c(S(=O)(=O)Nc3ccc(C(=O)N4CCC(O)(CC(C)C)CC4)cc3)cccc2o1]
385
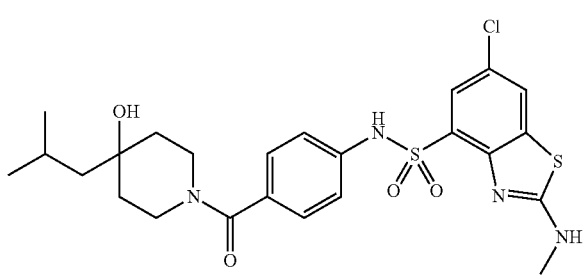 [SMILES: CNc1nc2c(S(=O)(=O)Nc3ccc(C(=O)N4CCC(O)(CC(C)C)CC4)cc3)cc(Cl)cc2s1]

TABLE 1-continued

Exemplary Compounds of Formula I:

| Compound # | Structure |
|---|---|
| 386 | 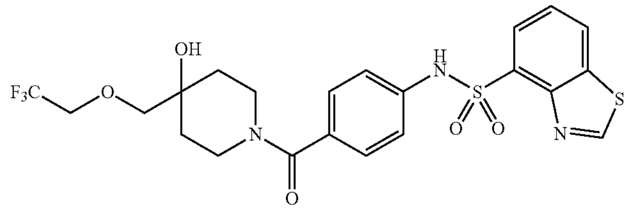 [SMILES: O=C(c1ccc(NS(=O)(=O)c2cccc3scnc23)cc1)N1CCC(O)(COCC(F)(F)F)CC1] |
| 387 | 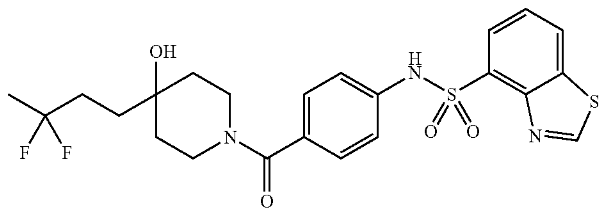 [SMILES: CC(F)(F)CCC1(O)CCN(C(=O)c2ccc(NS(=O)(=O)c3cccc4scnc34)cc2)CC1] |
| 388 | 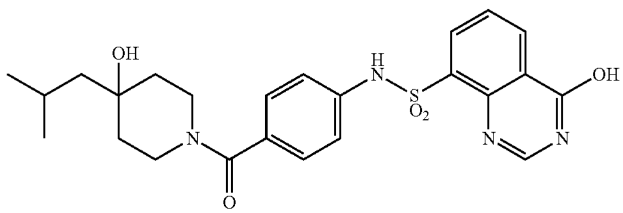 [SMILES: CC(C)CC1(O)CCN(C(=O)c2ccc(NS(=O)(=O)c3cccc4c(O)ncnc34)cc2)CC1] |
| 389 | 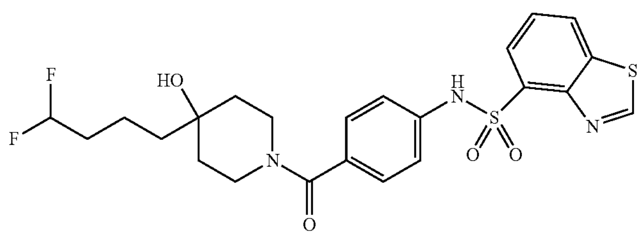 [SMILES: O=C(c1ccc(NS(=O)(=O)c2cccc3scnc23)cc1)N1CCC(O)(CCCC(F)F)CC1] |
| 390 | 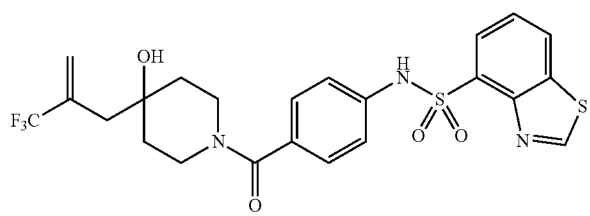 [SMILES: C=C(CC1(O)CCN(C(=O)c2ccc(NS(=O)(=O)c3cccc4scnc34)cc2)CC1)C(F)(F)F] |
| 391 | 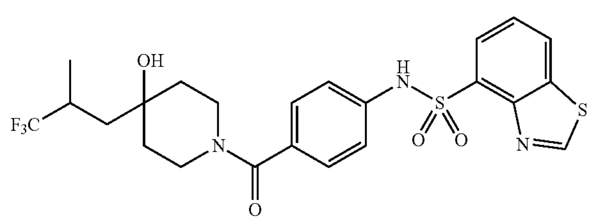 [SMILES: CC(CC1(O)CCN(C(=O)c2ccc(NS(=O)(=O)c3cccc4scnc34)cc2)CC1)C(F)(F)F] |
| 392 | 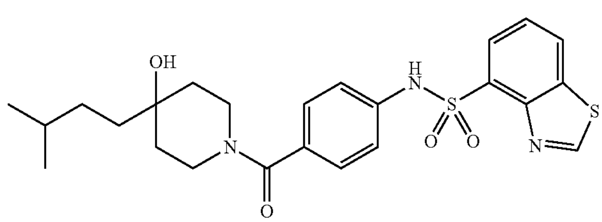 [SMILES: CC(C)CCC1(O)CCN(C(=O)c2ccc(NS(=O)(=O)c3cccc4scnc34)cc2)CC1] |

TABLE 1-continued

Exemplary Compounds of Formula I:

| Compound # | Structure |
|---|---|
| 393 | 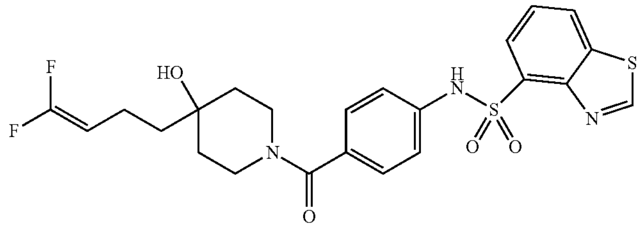 [SMILES: O=C(c1ccc(NS(=O)(=O)c2cccc3scnc23)cc1)N1CCC(O)(CCC=C(F)F)CC1] |
| 394 | 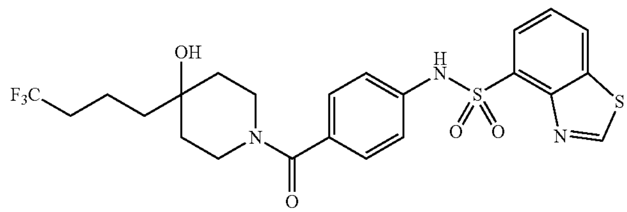 [SMILES: O=C(c1ccc(NS(=O)(=O)c2cccc3scnc23)cc1)N1CCC(O)(CCCC(F)(F)F)CC1] |
| 395 | 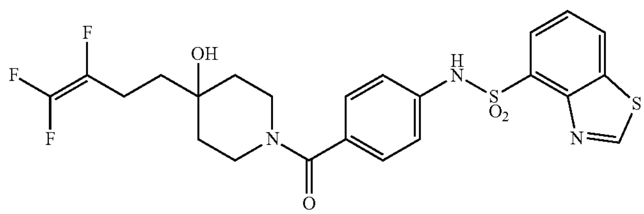 [SMILES: O=C(c1ccc(NS(=O)(=O)c2cccc3scnc23)cc1)N1CCC(O)(CCC(F)=C(F)F)CC1] |
| 396 | 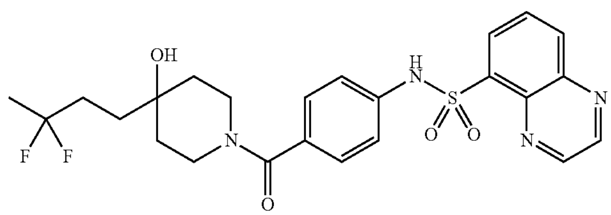 [SMILES: CC(F)(F)CCC1(O)CCN(C(=O)c2ccc(NS(=O)(=O)c3cccc4nccnc34)cc2)CC1] |
| 397 | 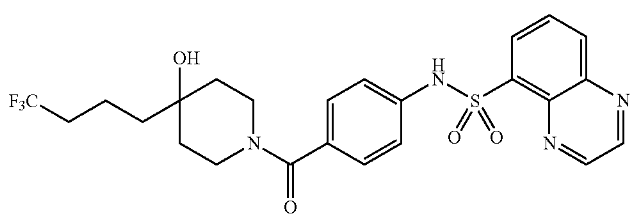 [SMILES: O=C(c1ccc(NS(=O)(=O)c2cccc3nccnc23)cc1)N1CCC(O)(CCCC(F)(F)F)CC1] |
| 398 | 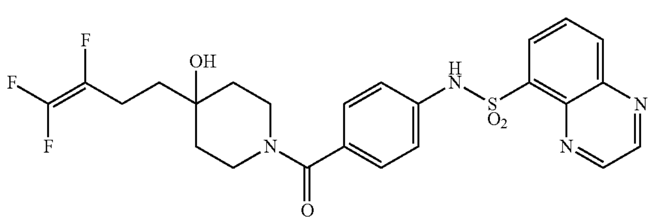 [SMILES: O=C(c1ccc(NS(=O)(=O)c2cccc3nccnc23)cc1)N1CCC(O)(CCC(F)=C(F)F)CC1] |
| 399 | 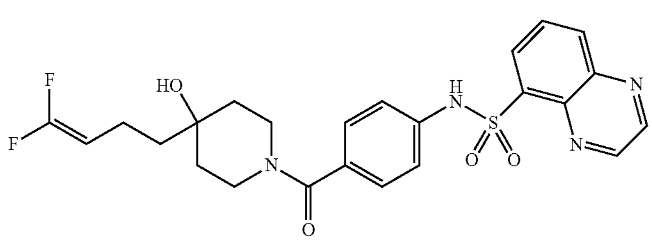 [SMILES: O=C(c1ccc(NS(=O)(=O)c2cccc3nccnc23)cc1)N1CCC(O)(CCC=C(F)F)CC1] |

TABLE 1-continued
Exemplary Compounds of Formula I:
| Compound # | Structure |
|---|---|
| 400 | 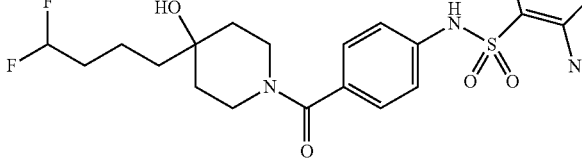 |
| 401 | 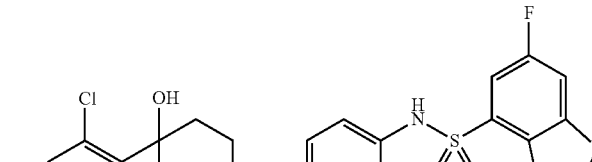 |
| 402 | 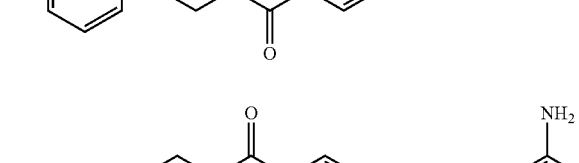 |
| 403 | 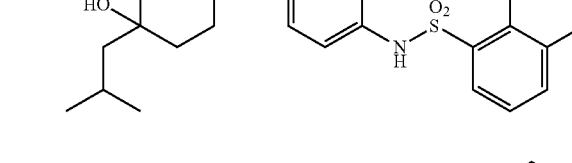 |
| 404 | 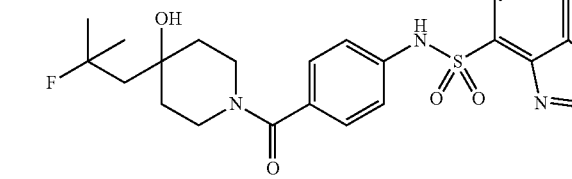 |
| 405 | 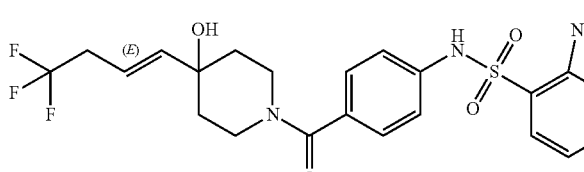 |

TABLE 1-continued

Exemplary Compounds of Formula I:

| Compound # | Structure |
|---|---|
| 406 | 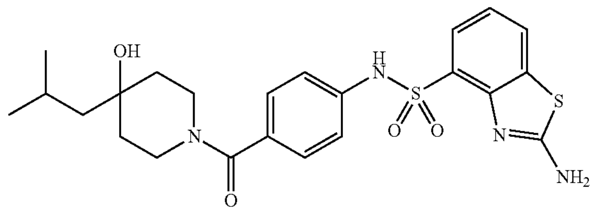 [SMILES: CC(C)CC1(O)CCN(C(=O)c2ccc(NS(=O)(=O)c3cccc4sc(N)nc34)cc2)CC1] |
| 407 | 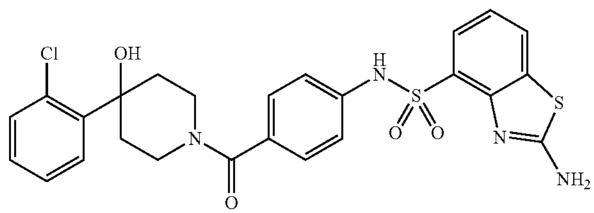 [SMILES: Nc1nc2c(S(=O)(=O)Nc3ccc(C(=O)N4CCC(O)(c5ccccc5Cl)CC4)cc3)cccc2s1] |
| 408 | 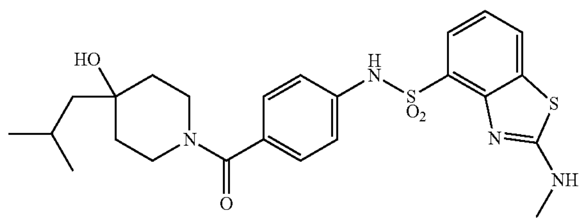 [SMILES: CNc1nc2c(S(=O)(=O)Nc3ccc(C(=O)N4CCC(O)(CC(C)C)CC4)cc3)cccc2s1] |
| 409 | 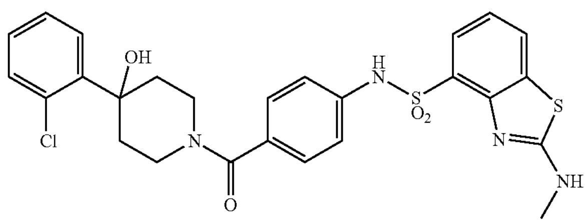 [SMILES: CNc1nc2c(S(=O)(=O)Nc3ccc(C(=O)N4CCC(O)(c5ccccc5Cl)CC4)cc3)cccc2s1] |
| 410 | 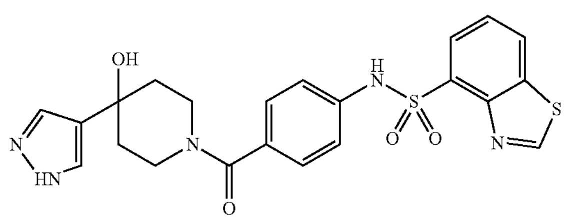 [SMILES: O=C(c1ccc(NS(=O)(=O)c2cccc3scnc23)cc1)N1CCC(O)(c2cn[nH]c2)CC1] |
| 411 | 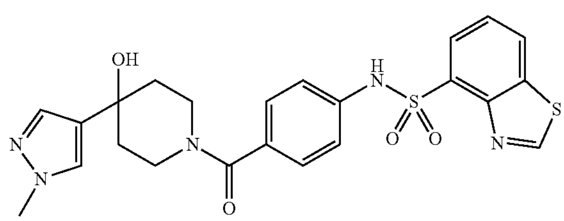 [SMILES: Cn1cc(C2(O)CCN(C(=O)c3ccc(NS(=O)(=O)c4cccc5scnc45)cc3)CC2)cn1] |
| 412 | 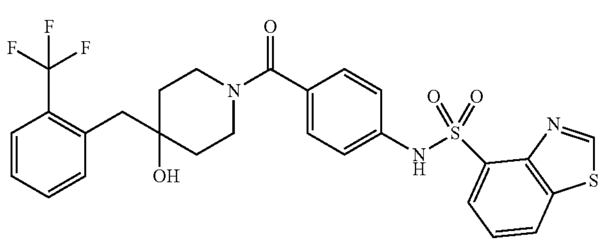 [SMILES: O=C(c1ccc(NS(=O)(=O)c2cccc3scnc23)cc1)N1CCC(O)(Cc2ccccc2C(F)(F)F)CC1] |

TABLE 1-continued

Exemplary Compounds of Formula I:

| Compound # | Structure |
|---|---|
| 413 | 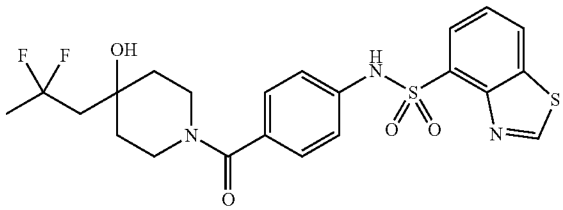 [SMILES: CC(F)(F)CC1(O)CCN(C(=O)c2ccc(NS(=O)(=O)c3cccc4scnc34)cc2)CC1] |
| 414 | 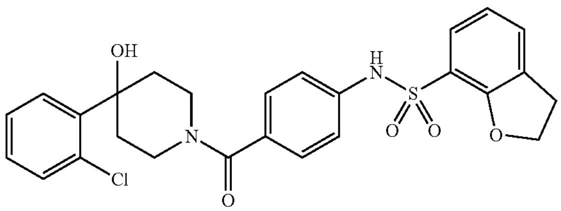 [SMILES: O=C(c1ccc(NS(=O)(=O)c2cccc3c2OCC3)cc1)N1CCC(O)(c2ccccc2Cl)CC1] |
| 415 | 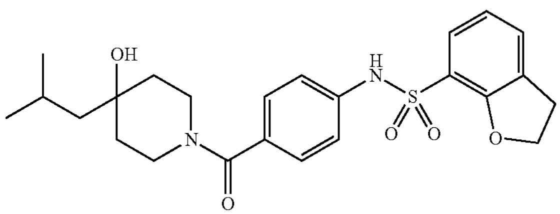 [SMILES: CC(C)CC1(O)CCN(C(=O)c2ccc(NS(=O)(=O)c3cccc4c3OCC4)cc2)CC1] |
| 416 | 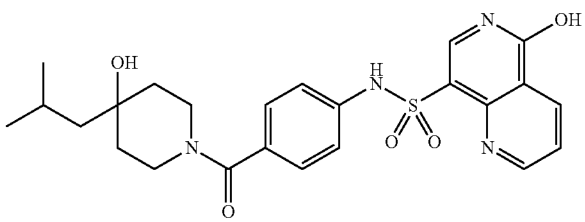 [SMILES: CC(C)CC1(O)CCN(C(=O)c2ccc(NS(=O)(=O)c3cnc(O)c4cccnc34)cc2)CC1] |
| 417 | 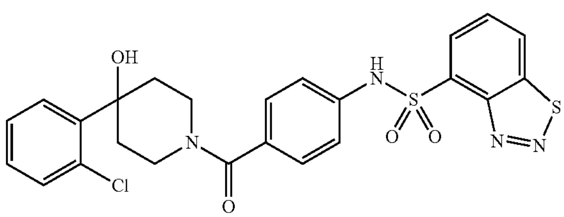 [SMILES: O=C(c1ccc(NS(=O)(=O)c2cccc3snnc23)cc1)N1CCC(O)(c2ccccc2Cl)CC1] |
| 418 | 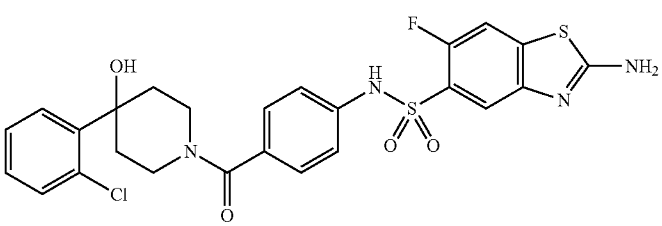 [SMILES: Nc1nc2cc(S(=O)(=O)Nc3ccc(C(=O)N4CCC(O)(c5ccccc5Cl)CC4)cc3)c(F)cc2s1] |
| 419 | 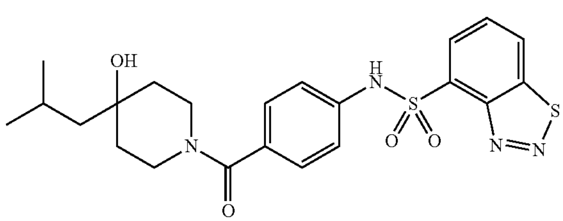 [SMILES: CC(C)CC1(O)CCN(C(=O)c2ccc(NS(=O)(=O)c3cccc4snnc34)cc2)CC1] |

TABLE 1-continued

Exemplary Compounds of Formula I:

| Compound # | Structure |
|---|---|
| 420 | 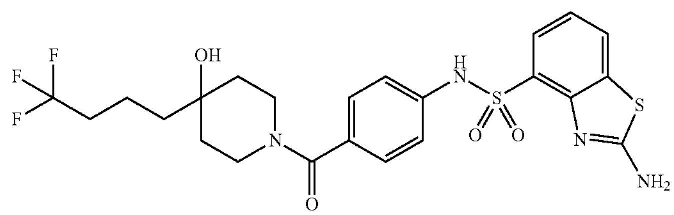 [SMILES: Nc1nc2c(S(=O)(=O)Nc3ccc(C(=O)N4CCC(O)(CCCC(F)(F)F)CC4)cc3)cccc2s1] |
| 421 | 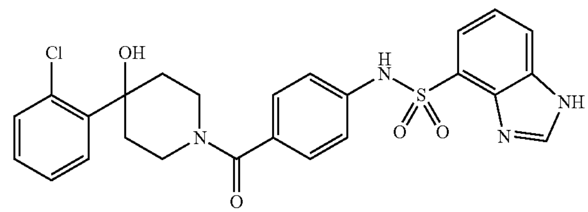 [SMILES: O=C(c1ccc(NS(=O)(=O)c2cccc3[nH]cnc23)cc1)N1CCC(O)(c2ccccc2Cl)CC1] |
| 422 | 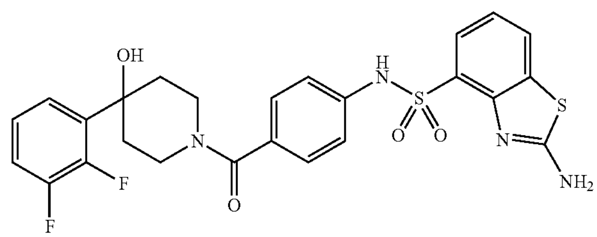 [SMILES: Nc1nc2c(S(=O)(=O)Nc3ccc(C(=O)N4CCC(O)(c5cccc(F)c5F)CC4)cc3)cccc2s1] |
| 423 | 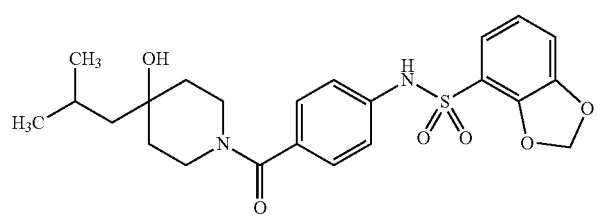 [SMILES: CC(C)CC1(O)CCN(C(=O)c2ccc(NS(=O)(=O)c3cccc4c3OCO4)cc2)CC1] |
| 424 | 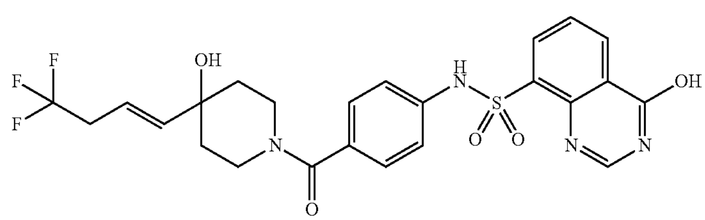 [SMILES: O=C(c1ccc(NS(=O)(=O)c2cccc3c(O)ncnc23)cc1)N1CCC(O)(/C=C/CC(F)(F)F)CC1] |
| 425 | 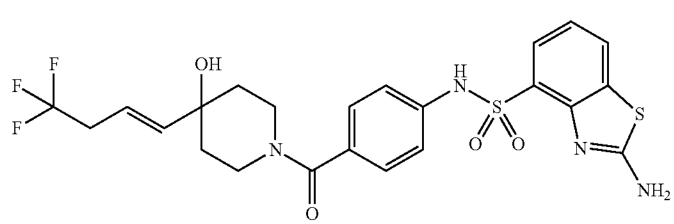 [SMILES: Nc1nc2c(S(=O)(=O)Nc3ccc(C(=O)N4CCC(O)(/C=C/CC(F)(F)F)CC4)cc3)cccc2s1] |
| 426 | 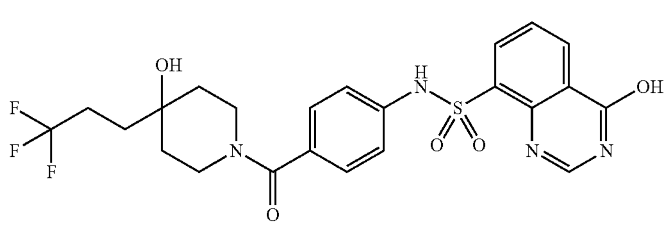 [SMILES: O=C(c1ccc(NS(=O)(=O)c2cccc3c(O)ncnc23)cc1)N1CCC(O)(CCC(F)(F)F)CC1] |

US 9,365,545 B2
TABLE 1-continued
Exemplary Compounds of Formula I:
| Compound # | Structure |
|---|---|
| 427 | 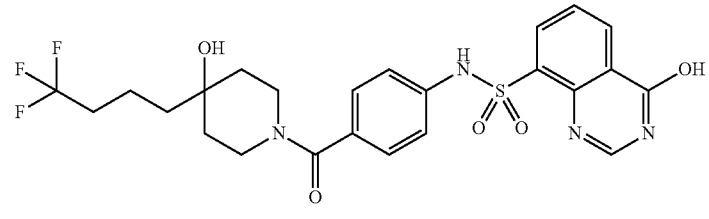 [SMILES: O=C(c1ccc(NS(=O)(=O)c2cccc3c(O)ncnc23)cc1)N1CCC(O)(CCCC(F)(F)F)CC1] |
| 428 | 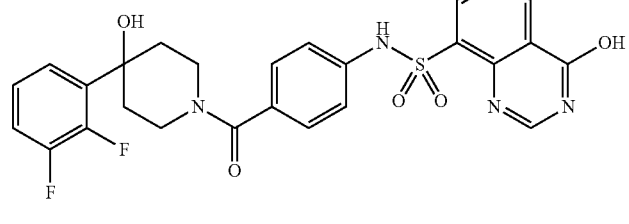 |
| 429 | 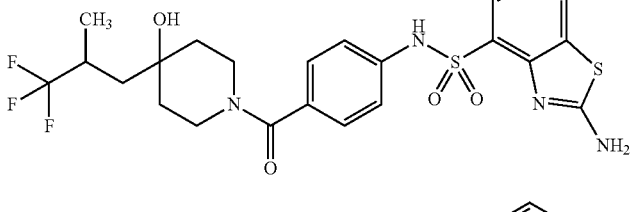 |
| 430 | 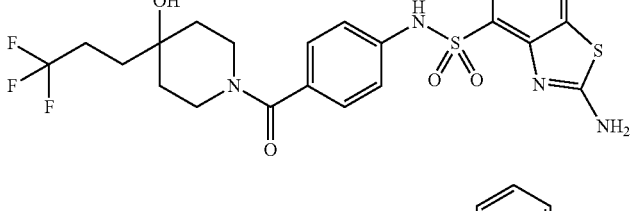 |
| 431 | 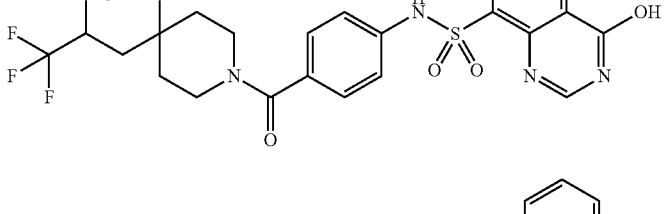 |
| 432 | 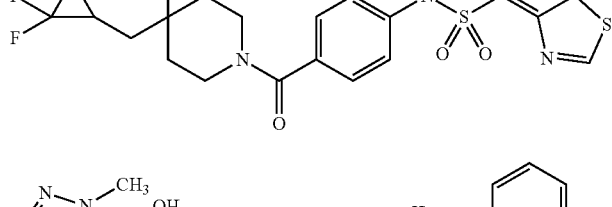 |
| 433 | 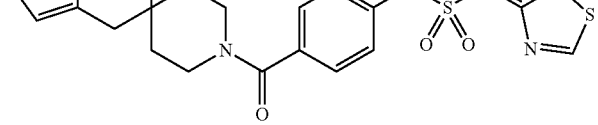 |

TABLE 1-continued
Exemplary Compounds of Formula I:
| Compound # | Structure |
|---|---|
| 434 | 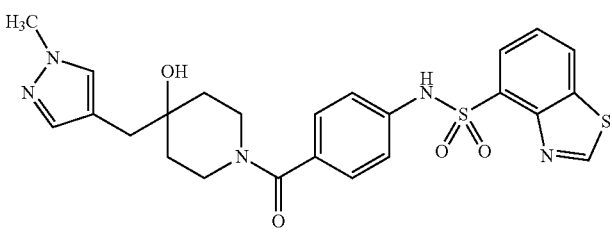 [SMILES: Cn1cc(CC2(O)CCN(C(=O)c3ccc(NS(=O)(=O)c4cccc5scnc45)cc3)CC2)cn1] |
| 435 | 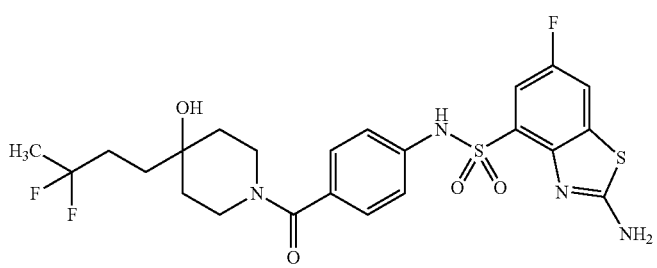 [SMILES: CC(F)(F)CCC1(O)CCN(C(=O)c2ccc(NS(=O)(=O)c3cc(F)cc4sc(N)nc34)cc2)CC1] |
| 436 | 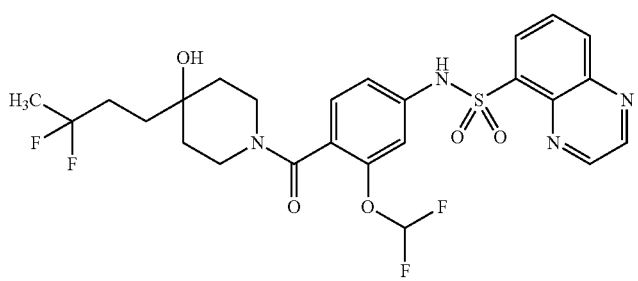 [SMILES: CC(F)(F)CCC1(O)CCN(C(=O)c2ccc(NS(=O)(=O)c3cccc4nccnc34)cc2OC(F)F)CC1] |
| 437 | 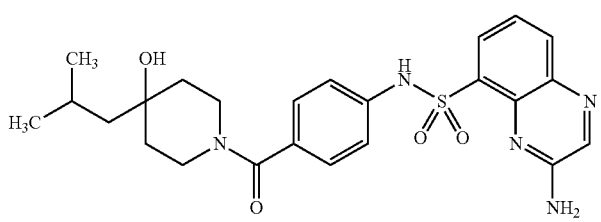 [SMILES: CC(C)CC1(O)CCN(C(=O)c2ccc(NS(=O)(=O)c3cccc4ncc(N)nc34)cc2)CC1] |
| 438 | 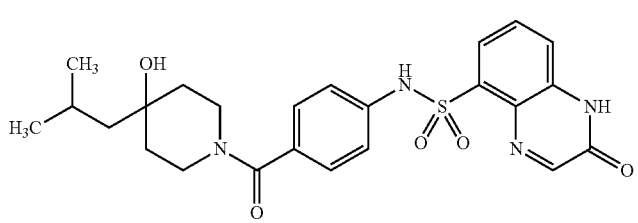 [SMILES: CC(C)CC1(O)CCN(C(=O)c2ccc(NS(=O)(=O)c3cccc4[nH]c(=O)cnc34)cc2)CC1] |
| 439 | 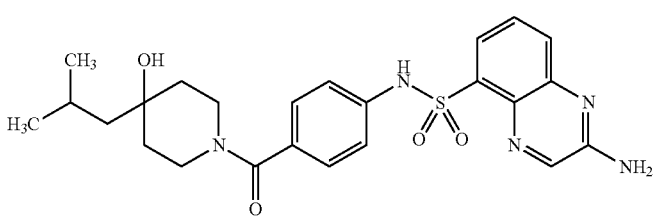 [SMILES: CC(C)CC1(O)CCN(C(=O)c2ccc(NS(=O)(=O)c3cccc4nc(N)cnc34)cc2)CC1] |

TABLE 1-continued

Exemplary Compounds of Formula I:

| Compound # | Structure |
|---|---|
| 440 | (structure) |
| 441 | (structure) |
| 442 | (structure) |
| 443 | (structure) |
| 444 | (structure) |

Compounds described herein are useful as activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Example 8. Compounds described herein are also useful as activators of wild type PKR.

In an embodiment, to increase the lifetime of the red blood cells, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibribrium to the R, or oxygenated state, thus producing a therapeutic inhibition of the intracellular polymerization that underlies sickling by increasing oxygen affinity due to the 2,3-DPG depletion, thereby stabilizing the more soluble oxy-hemoglobin. Accordingly, in one embodiment, compounds and pharmaceutical compositions described herein are useful as antisickling agents. In another embodiment, to regulate 2,3-diphosphoglycerate, a compound, composition or pharmaceutical composition described herein is added directly to whole blood or packed cells extracorporeally or be provided to the patient directly (e.g., by i.p., i.v., i.m., oral, inhalation (aerosolized delivery), transdermal, sublingual and other delivery routes).

A compound described herein may be an activator of a PKR, for example, a wild type (wt), mutated PKR (e.g., R510Q, or R532W). Activities of exemplary compounds against wt PKR (in an enzymatic or cell based assay) and mutant PKRs are shown in Table 2 as measured by assays in Examples 2-5 below. As shown in Table 2, AA refers to an $AC_{50}$ less than 100 nM, BB refers to an $AC_{50}$ from 101 nM to 1.00 μM, CC refers to an $AC_{50}$ from than 1.01 μM to 10.00 μM, DD refers to an $AC_{50}$ greater than 10.01 μM and EE refers to an AC50 that is not available.

TABLE 2

| Compound # | PKR R510Q AC50 (μM) | PKR R532W AC50 (μM) | PKR WT AC50 (μM) | PKR WT Cell Based AC50 (μM) |
|---|---|---|---|---|
| 100 | AA | AA | AA | AA |
| 101 | AA | AA | AA | AA |
| 102 | AA | AA | AA | AA |
| 103 | AA | AA | AA | AA |
| 104 | AA | AA | AA | AA |
| 105 | AA | AA | AA | AA |
| 106 | EE | AA | AA | AA |
| 108 | AA | AA | AA | AA |
| 109 | AA | AA | AA | AA |
| 110 | AA | AA | AA | AA |
| 111 | AA | AA | AA | AA |
| 112 | AA | AA | AA | BB |
| 113 | AA | AA | AA | AA |
| 114 | AA | AA | AA | AA |
| 115 | AA | AA | AA | AA |
| 116 | AA | AA | AA | AA |
| 117 | AA | AA | AA | AA |
| 118 | BB | AA | AA | AA |
| 119 | AA | AA | AA | AA |
| 120 | AA | AA | AA | AA |
| 121 | AA | AA | AA | AA |
| 122 | AA | AA | AA | AA |
| 123 | AA | AA | AA | AA |
| 124 | AA | AA | AA | AA |
| 125 | AA | AA | AA | AA |
| 126 | AA | AA | AA | AA |
| 127 | AA | AA | AA | AA |
| 128 | AA | AA | AA | AA |
| 129 | AA | AA | AA | AA |
| 130 | AA | AA | AA | AA |
| 131 | AA | AA | AA | AA |
| 132 | AA | AA | AA | EE |
| 133 | AA | AA | AA | AA |
| 134 | AA | AA | AA | AA |
| 135 | BB | AA | AA | AA |
| 136 | AA | AA | AA | AA |
| 137 | AA | AA | AA | AA |
| 138 | AA | AA | AA | AA |
| 140 | AA | AA | AA | AA |
| 141 | BB | AA | AA | AA |
| 142 | BB | AA | AA | AA |
| 143 | AA | AA | AA | AA |
| 144 | AA | AA | AA | AA |
| 145 | AA | AA | AA | AA |
| 146 | BB | AA | AA | AA |
| 147 | BB | AA | AA | AA |
| 148 | BB | AA | AA | BB |
| 149 | EE | AA | AA | AA |
| 150 | AA | AA | AA | BB |
| 151 | AA | AA | AA | AA |
| 152 | BB | AA | AA | BB |
| 153 | BB | AA | AA | AA |
| 154 | AA | AA | AA | AA |
| 155 | BB | AA | AA | AA |
| 156 | BB | AA | AA | AA |
| 157 | BB | AA | AA | AA |
| 158 | AA | AA | AA | EE |
| 159 | BB | AA | AA | AA |
| 160 | AA | AA | AA | AA |
| 161 | BB | AA | AA | AA |
| 162 | BB | AA | AA | AA |
| 163 | BB | AA | AA | AA |
| 164 | BB | AA | AA | AA |
| 165 | BB | AA | AA | AA |
| 166 | BB | AA | AA | AA |
| 167 | AA | AA | AA | AA |
| 168 | BB | AA | AA | AA |
| 169 | BB | AA | AA | AA |
| 170 | BB | AA | AA | BB |
| 171 | BB | AA | AA | BB |
| 172 | AA | AA | AA | AA |
| 173 | AA | AA | AA | AA |
| 174 | BB | AA | AA | AA |
| 175 | BB | AA | AA | AA |
| 176 | BB | AA | AA | AA |
| 177 | BB | AA | AA | AA |
| 178 | BB | AA | AA | AA |
| 179 | BB | AA | AA | AA |
| 180 | BB | AA | AA | AA |
| 181 | BB | AA | AA | EE |
| 182 | CC | EE | AA | AA |
| 183 | BB | AA | AA | AA |
| 184 | BB | AA | AA | BB |
| 185 | BB | AA | AA | BB |
| 186 | BB | AA | AA | BB |
| 187 | AA | AA | AA | AA |
| 188 | BB | AA | AA | EE |
| 189 | BB | AA | AA | BB |
| 190 | BB | AA | AA | BB |
| 191 | BB | AA | AA | AA |
| 192 | CC | AA | AA | AA |
| 193 | BB | AA | AA | AA |
| 194 | BB | AA | AA | AA |
| 195 | BB | AA | AA | AA |
| 196 | BB | AA | AA | BB |
| 197 | BB | AA | AA | BB |
| 198 | BB | AA | AA | EE |
| 199 | BB | AA | AA | AA |
| 200 | BB | BB | AA | EE |
| 201 | BB | AA | AA | EE |
| 202 | BB | AA | AA | EE |
| 203 | BB | AA | AA | AA |
| 204 | BB | AA | AA | AA |
| 205 | BB | AA | AA | BB |
| 206 | CC | AA | AA | AA |
| 207 | BB | AA | AA | BB |
| 208 | BB | AA | AA | EE |
| 209 | BB | AA | AA | AA |
| 210 | BB | AA | AA | BB |
| 211 | BB | AA | AA | BB |
| 212 | BB | AA | AA | AA |
| 213 | BB | AA | AA | AA |
| 214 | BB | AA | AA | AA |
| 215 | BB | AA | AA | BB |
| 216 | BB | AA | AA | EE |
| 217 | BB | BB | AA | BB |
| 218 | BB | AA | AA | AA |
| 219 | BB | AA | AA | EE |
| 220 | BB | AA | AA | CC |

TABLE 2-continued

| Compound # | PKR R510Q AC50 (μM) | PKR R532W AC50 (μM) | PKR WT AC50 (μM) | PKR WT Cell Based AC50 (μM) |
|---|---|---|---|---|
| 221 | BB | AA | AA | EE |
| 222 | BB | AA | AA | AA |
| 223 | BB | AA | AA | BB |
| 224 | CC | AA | AA | BB |
| 225 | BB | BB | AA | BB |
| 226 | BB | AA | AA | BB |
| 227 | BB | BB | BB | EE |
| 228 | CC | AA | BB | AA |
| 229 | BB | BB | BB | BB |
| 230 | BB | BB | BB | EE |
| 231 | CC | BB | BB | EE |
| 232 | BB | BB | BB | EE |
| 233 | BB | BB | BB | EE |
| 234 | BB | BB | BB | EE |
| 235 | BB | BB | BB | EE |
| 237 | BB | BB | BB | BB |
| 238 | CC | BB | BB | EE |
| 239 | BB | BB | BB | EE |
| 240 | BB | BB | BB | EE |
| 241 | CC | BB | BB | BB |
| 242 | BB | BB | BB | EE |
| 243 | CC | BB | BB | AA |
| 244 | CC | BB | BB | EE |
| 245 | CC | BB | BB | CC |
| 246 | CC | AA | BB | EE |
| 247 | CC | BB | BB | EE |
| 250 | CC | BB | BB | CC |
| 251 | BB | BB | BB | EE |
| 253 | CC | BB | BB | EE |
| 254 | BB | BB | BB | EE |
| 255 | CC | BB | BB | EE |
| 256 | CC | BB | BB | EE |
| 257 | CC | BB | BB | EE |
| 258 | BB | BB | BB | EE |
| 259 | CC | BB | BB | EE |
| 260 | CC | BB | BB | CC |
| 261 | BB | BB | BB | EE |
| 262 | BB | BB | BB | EE |
| 263 | BB | BB | BB | EE |
| 265 | CC | BB | BB | EE |
| 266 | CC | BB | BB | EE |
| 267 | CC | BB | BB | EE |
| 268 | CC | BB | BB | EE |
| 269 | CC | BB | BB | EE |
| 270 | CC | BB | BB | EE |
| 271 | CC | BB | BB | EE |
| 272 | CC | BB | BB | EE |
| 273 | CC | BB | BB | EE |
| 274 | CC | BB | BB | EE |
| 275 | CC | BB | BB | EE |
| 276 | CC | BB | BB | EE |
| 277 | CC | BB | BB | EE |
| 278 | CC | BB | BB | EE |
| 280 | CC | BB | BB | EE |
| 281 | EE | BB | BB | EE |
| 283 | CC | BB | BB | EE |
| 284 | CC | BB | BB | EE |
| 285 | DD | BB | BB | EE |
| 286 | CC | BB | BB | EE |
| 287 | EE | CC | BB | EE |
| 288 | EE | CC | BB | EE |
| 289 | CC | BB | BB | EE |
| 290 | CC | BB | BB | EE |
| 292 | CC | CC | BB | EE |
| 293 | CC | BB | BB | EE |
| 294 | DD | CC | CC | EE |
| 296 | DD | CC | CC | EE |
| 297 | CC | CC | CC | EE |
| 298 | DD | CC | CC | EE |
| 299 | EE | EE | CC | EE |
| 300 | DD | CC | CC | EE |
| 301 | EE | CC | CC | EE |
| 302 | DD | CC | CC | EE |
| 303 | DD | CC | CC | EE |
| 304 | DD | CC | CC | EE |
| 306 | DD | CC | CC | EE |
| 307 | DD | CC | CC | EE |
| 308 | DD | CC | CC | EE |
| 309 | DD | CC | CC | EE |
| 310 | EE | CC | CC | EE |
| 311 | DD | CC | CC | EE |
| 312 | DD | CC | CC | EE |
| 313 | DD | DD | CC | EE |
| 314 | DD | DD | CC | EE |
| 315 | EE | DD | CC | EE |
| 316 | DD | DD | DD | EE |
| 317 | EE | EE | DD | EE |
| 318 | DD | DD | DD | EE |
| 319 | EE | DD | DD | EE |
| 320 | DD | DD | DD | EE |
| 321 | EE | DD | DD | EE |
| 322 | DD | DD | DD | EE |
| 323 | EE | EE | DD | EE |
| 324 | DD | DD | DD | EE |
| 325 | EE | EE | EE | EE |
| 326 | EE | EE | EE | EE |
| 327 | EE | CC | EE | EE |
| 330 | CC | BB | EE | EE |
| 331 | EE | EE | EE | EE |
| 353 | BB | AA | AA | AA |
| 368 | CC | BB | BB | EE |
| 372 | BB | BB | BB | EE |
| 373 | BB | BB | BB | EE |
| 376 | CC | BB | BB | EE |
| 377 | BB | AA | AA | AA |
| 378 | CC | BB | BB | EE |
| 379 | BB | BB | BB | BB |
| 380 | BB | BB | AA | AA |
| 381 | BB | BB | AA | EE |
| 382 | BB | BB | AA | AA |
| 383 | BB | AA | AA | AA |
| 384 | BB | BB | BB | EE |
| 385 | AA | AA | AA | AA |
| 386 | BB | BB | BB | EE |
| 387 | BB | AA | AA | BB |
| 388 | AA | AA | AA | AA |
| 389 | AA | AA | AA | AA |
| 390 | AA | AA | AA | AA |
| 391 | AA | AA | AA | AA |
| 392 | AA | AA | AA | AA |
| 393 | BB | AA | AA | AA |
| 394 | BB | AA | AA | AA |
| 395 | BB | AA | AA | BB |
| 396 | BB | BB | AA | AA |
| 397 | AA | AA | AA | AA |
| 398 | BB | AA | AA | AA |
| 399 | AA | AA | AA | AA |
| 400 | BB | AA | AA | AA |
| 401 | BB | AA | AA | BB |
| 402 | AA | AA | AA | AA |
| 403 | BB | AA | AA | AA |
| 404 | AA | AA | AA | BB |
| 405 | BB | BB | BB | BB |
| 406 | AA | AA | AA | AA |
| 407 | AA | AA | AA | AA |
| 408 | AA | AA | AA | AA |
| 409 | AA | AA | AA | EE |
| 410 | DD | BB | BB | EE |
| 411 | BB | AA | BB | AA |
| 412 | BB | AA | AA | BB |
| 413 | BB | BB | BB | EE |
| 414 | DD | CC | CC | EE |
| 415 | CC | CC | CC | EE |
| 416 |  | DD | CC | EE |
| 417 | DD | CC | CC | EE |
| 418 | DD | DD | CC | EE |
| 419 |  | DD | DD | EE |
| 420 | AA | AA | AA | AA |

TABLE 2-continued

| Compound # | PKR R510Q AC50 (μM) | PKR R532W AC50 (μM) | PKR WT AC50 (μM) | PKR WT Cell Based AC50 (μM) |
|---|---|---|---|---|
| 421 | DD | CC | CC | EE |
| 422 | AA | AA | AA | AA |
| 423 | BB | AA | AA | AA |
| 424 | AA | BB | AA | BB |
| 425 | AA | BB | AA | AA |
| 426 | BB | BB | BB | BB |
| 427 | AA | AA | AA | AA |
| 428 | BB | AA | AA | AA |
| 429 | AA | AA | AA | AA |
| 430 | BB | AA | AA | BB |
| 431 | AA | AA | AA | BB |
| 432 | BB | AA | AA | BB |
| 433 | BB | AA | BB | BB |
| 434 | BB | AA | BB | BB |
| 435 | AA | AA | AA | BB |
| 436 | BB | AA | BB | BB |
| 437 | AA | AA | AA | AA |
| 438 | CC | CC | CC | EE |
| 439 | AA | AA | AA | AA |
| 440 | BB | BB | | |
| 441 | CC | BB | | |

The compounds described herein can be made using a variety of synthetic techniques, general and specific examples of which are set forth in Example section.

As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds provided herein may contain one or more asymmetric centers and thus occur as racemates and racemic mixtures, single enantiomers, individual diastereomers and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds) or substituents that can restrict bond rotation, e.g., restriction resulting from the presence of a ring or double bond. Accordingly, all cis/trans and E/Z isomers are expressly included.

The compounds provided herein (e.g., of Formula I) may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like. The compounds provided herein may also be represented in multiple tautomeric forms, in such instances, expressly includes all tautomeric forms of the compounds described herein, even though only a single tautomeric form may be represented (e.g., alkylation of a ring system may result in alkylation at multiple sites; all such reaction products are expressly included). All such isomeric forms of such compounds are expressly included. All crystal forms of the compounds described herein are expressly included.

The compounds provided herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

The compounds provided herein may be modified by appending appropriate functionalities to enhance selected biological properties, e.g., targeting to a particular tissue. Such modifications are known in the art and include those which increase biological penetration into a given biological compartment (e.g., blood, lymphatic system, central nervous system), increase oral availability, increase solubility to allow administration by injection, alter metabolism and alter rate of excretion.

In an alternate embodiment, the compounds described herein may be used as platforms or scaffolds that may be utilized in combinatorial chemistry techniques for preparation of derivatives and/or chemical libraries of compounds. Such derivatives and libraries of compounds have biological activity and are useful for identifying and designing compounds possessing a particular activity. Combinatorial techniques suitable for utilizing the compounds described herein are known in the art as exemplified by Obrecht, D. and Villalgrodo, J. M., *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, A. W., *Curr. Opin. Chem. Bio.*, (1997) 1, 60. Thus, one embodiment relates to a method of using the compounds described herein for generating derivatives or chemical libraries comprising: 1) providing a body comprising a plurality of wells; 2) providing one or more compounds identified by methods described herein in each well; 3) providing an additional one or more chemicals in each well; 4) isolating the resulting one or more products from each well. An alternate embodiment relates to a method of using the compounds described herein for generating derivatives or chemical libraries comprising: 1) providing one or more compounds described herein attached to a solid support; 2) treating the one or more compounds identified by methods described herein attached to a solid support with one or more additional chemicals; 3) isolating the resulting one or more products from the solid support. In the methods described above, "tags" or identifier or labeling moieties may be attached to and/or detached from the compounds described herein or their derivatives, to facilitate tracking, identification or isolation of the desired products or their intermediates. Such moieties are known in the art. The chemicals used in the aforementioned methods may include, for example, solvents, reagents, catalysts, protecting group and deprotecting group reagents and the like. Examples of such chemicals are those that appear in the various synthetic and protecting group chemistry texts and treatises referenced herein.

Methods of Evaluating Compounds

The compounds described herein can be evaluated for ability to modulate PKM2 (e.g., activate PKM2) by methods known in the art. In some embodiments, compounds described herein are evaluated for ability to modulate PKM2 (e.g., activate PKM2) in serine deficient conditions. In some embodiments, exemplary methods include contacting the compound with a cell-based assay which allows assessment of the ability to modulate (e.g., activate) PKM2. E.g., the candidate compound can be contacted with a cell and measuring the consumption of oxygen or production of lactate. A change in cellular phosphoenolpyruvate, a change in glycerol-phosphate, a change in ribose or deoxyribose, a change in lipid synthesis, or a change in glucose conversion to lipid or nucleic acids or amino acids or protein can also be used to evaluate a compound for its ability to modulate PKM2 (e.g., activate PKM2). The evaluation could also include measuring a change in pyruvate or a determination of an alteration in mitochondrial membrane potential, e.g., as measured by fluorescent potentiometric dyes.

PKM1 and PKM2 for use in the screening/testing method may be produced by any method known in the art for expression of recombinant proteins. For example, nucleic acids that encode the desired polypeptide may be introduced into various cell types or cell-free systems for expression. Eukaryotic (e.g., COS, HEK293T, CHO, and NIH cell lines) and prokaryotic (e.g., E. coli) expression systems may be generated in which a PKM sequence is introduced into a plasmid or other vector, which is then used to transform living cells. Constructs in which the PKM cDNA contains the entire open reading frame, or biologically active fragment thereof, are inserted in the correct orientation into an expression plasmid and may be used for protein expression. Prokaryotic and eukaryotic expression systems allow for the expression and recovery of fusion proteins in which the PKM protein is covalently linked to a tag molecule on either the amino terminal or carboxy terminal side, which facilitates identification and/or purification. Examples of tags that can be used include hexahistidine, HA, FLAG, and c-myc epitope tags. An enzymatic or chemical cleavage site can be engineered between the PKM protein and the tag molecule so that the tag can be removed following purification.

The activity of the PKM enzyme measured in the screening/testing assay may be measured by, e.g., monitoring the concentration of a substrate (e.g., ATP or NADH) present in the reaction mixture. Pyruvate, produced by the enzymatic activity of pyruvate kinase, is converted into lactate by lactate dehydrogenase, which requires the consumption of NADH (NADH→NAD+). Thus, the activity of PKM2 can be indirectly measured by monitoring the consumption of NADH through, e.g., fluorescence assays. Additionally, the activity of the PKM2 enzyme can be directly monitored by measuring the production of ATP, as ATP is produced when phosphoenolpyruvate is converted to pyruvate. Methods for monitoring the amount of substrate in a reaction mixture include, e.g., absorbance, fluorescence, Raman scattering, phosphorescence, luminescence, luciferase assays, and radioactivity.

The screening procedure requires the presence of specific components in the reaction mixture. Components utilized in the assay include, e.g., a nucleoside diphosphate (e.g., ADP), phosphoenolpyruvate, NADH, lactate dehydrogenase, FBP, a reducing agent (e.g., dithiothreitol), a detergent (e.g., Brij 35), glycerol, and a solvent (e.g., DMSO). Exemplary reaction conditions are found in Table 3.

TABLE 3

| Component of Reaction Condition | Amount in Activation Assay |
|---|---|
| ADP | 0.1-5.0 mM |
| Phosphoenolpyruvate | 0.1-5.0 mM |
| NADH | 10-1000 µM |
| Lactate dehydrogenase | 0.1-10 units |
| Fructose-1,6-bisphosphate | 0 |
| DTT | 0.1-50 mM |
| Brij 35 | 0.01-1% |
| Glycerol | 0.1-10% |
| Pyruvate Kinase M2 (used for screen) | 1-100 pg |
| DMSO | 1-10% |

Compounds useful as PKM2 activators are those that demonstrate specificity and activation of PKM2 enzyme in the absence of FBP to a level greater than that of 10, 15, 20, 25, 30, 35, 40, 45, 50, 55, 60, 65, 70, 75, 80, 85, 90, 95, 99, or 100% in the presence of FBP. Furthermore, compounds can be evaluated in the presence or absence of a phosphotyrosine peptide. Phosphotyrosine peptide binding to PKM2 leads to a dissociation of FBP from PKM2 and conformational changes of PKM2 from an active, tetrameric form to an inactive form. Compounds that bind to PKM2 and lock the enzyme in the active confirmation even in the presence of a phosphotyrosine peptide will lead to the loss of allosteric control of PKM2 needed for shunting the biochemical intermediates from glycolysis into biosynthesis of other intermediates. This, in turn, will lead to inhibition of growth of cancer cells, activated immune cells and fat cells.

Methods of Treatment

In one embodiment, provided is a method for treating or preventing a disease, condition or disorder as described herein (e.g., treating) comprising administering a compound, a pharmaceutically acceptable salt of a compound or pharmaceutical composition comprising a compound described herein (e.g., a compound of formula (I), (Ia), (II), (IIa) or in Table 1).

The compounds and compositions described herein can be administered to cells in culture, e.g., in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a disorder (e.g., a disorder as described herein), a symptom of a disorder, with the purpose to cure, heal, alleviate, relieve, alter, remedy, ameliorate, improve or affect the disorder, or one or more symptoms of the disorder.

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "prevent" is defined as the application or administration of a compound, alone or in combination with, a second therapeutic agent to a subject, e.g., a patient, or application or administration of the compound to an isolated tissue or cell, e.g., cell line, from a subject, e.g., a patient, who has a predisposition toward a disorder, with the purpose to prevent the occurrence of at least one symptom of the disorder or to delay onset of at least one symptom of the disorder).

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Blood Related Conditions

A compound or composition described herein can be used to treat a blood related condition. In one embodiment, provided is a method for increasing lifetime of the red blood cells (RBCs) in need thereof comprising contacting blood with an effective amount of (1) a compound disclosed herein or a pharmaceutically acceptable salt, solvate or hydrate thereof; (2) a composition comprising a compound disclosed herein or a salt, solvate or hydrate thereof and a carrier; or (3) a pharmaceutical composition comprising a compound disclosed herein or a pharmaceutically acceptable salt, solvate or hydrate thereof, and a pharmaceutically acceptable carrier.

In another embodiment, provided is a method for regulating 2,3-diphosphoglycerate levels in blood in need thereof comprising contacting blood with an effective amount of (1) a compound disclosed herein or a pharmaceutically acceptable salt, solvate or hydrate thereof; (2) a composition comprising a compound disclosed herein or a salt, solvate or hydrate thereof and a carrier; or (3) a pharmaceutical composition comprising a compound disclosed herein or a pharmaceutically acceptable salt, solvate or hydrate thereof, and a pharmaceutically acceptable carrier.

In another embodiment, provided is a method for treating hereditary non-spherocytic haemolytic anemia comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating sickle cell anemia (e.g., by activating wild type PKR) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating hemolytic anemia (e.g., chronic hemolytic anemia caused by phosphoglycerate kinase deficiency, Blood Cells Mol Dis, 2011; 46(3):206) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating thalassemia (e.g., beta-thalassemia), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

In another embodiment, provided is a method for treating diseases or conditions that are associated with increased 2,3-diphosphoglycerate levels (e.g., liver diseases (Am J Gastroenterol, 1987; 82(12):1283) and Parkinson's (J. Neurol, Neurosurg, and Psychiatry 1976, 39:952) comprising administering to a subject in need thereof a therapeutically effective amount of (1) a compound disclosed herein or a pharmaceutically acceptable salt, solvate or hydrate thereof; (2) a pharmaceutical composition comprising a compound disclosed herein or a pharmaceutically acceptable salt, solvate or hydrate thereof, and a pharmaceutically acceptable carrier.

Compounds and compositions described herein are activators of PKR mutants having lower activities compared to the wild type, thus are useful for methods of the present invention. Such mutations in PKR can affect enzyme activity (catalytic efficiency), regulatory properties (modulation by fructose bisphosphate (FBP)/ATP), and/or thermostability of the enzyme. Examples of such mutations are described in Valentini et al, JBC 2002. Some examples of the mutants that are activated by the compounds described herein include G332S, G364D, T384M, G37E, R479H, R479K, R486W, R532W, R510Q, and R490W. Without being bound by theory, compounds described herein affect the activities of PKR mutants by activating FBP non-responsive PKR mutants, restoring thermostability to mutants with decreased stability, or restoring catalytic efficiency to impaired mutants. The activating activity of the present compounds against PKR mutants may be tested following a method described in Examples 2-5. Compounds described herein are also activators of wild type PKR.

In an embodiment, to increase the lifetime of the red blood cells, a compound, composition or pharmaceutical composition described herein is added directly to whole blood or packed cells extracorporeally or be provided to the subject (e.g., the patient) directly (e.g., by i.p., i.v., i.m., oral, inhalation (aerosolized delivery), transdermal, sublingual and other delivery routes). Without being bound by theory, compounds described herein increase the lifetime of the RBCs, thus counteract aging of stored blood, by impacting the rate of release of 2,3-DPG from the blood. A decrease in the level of 2,3-DPG concentration induces a leftward shift of the oxygen-hemoglobin dissociation curve and shifts the allosteric equilibrium to the R, or oxygenated state, thus producing a therapeutic inhibition of the intracellular polymerization that underlies sickling by increasing oxygen affinity due to the 2,3-DPG depletion, thereby stabilizing the more soluble oxyhemoglobin. Accordingly, in one embodiment, compounds and pharmaceutical compositions described herein are useful as antisickling agents.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Without being bound by theory, applicants believe that altered PKM2 levels characterize a subset of all types of cancers, without regard to their cellular nature or location in the body. Thus, the compounds and methods disclosed herein are useful to treat any type of cancer that is characterized by altered PKM2 levels.

Cancer Combination Therapies

In some embodiments, a compound described herein is administered together with one or more additional cancer treatments. Exemplary cancer treatments include, for example: chemotherapy, targeted therapies such as antibody therapies, immunotherapy, and hormonal therapy. Examples of each of these treatments are provided below.

Chemotherapy

In some embodiments, a compound described herein is administered with one or morechemotherapies. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Satraplatin, Streptozocin, Talaporfin, Tegafur-uracil, Temoporfin, Temozolomide, Teniposide, Tesetaxel, Testolactone, Tetranitrate, Thiotepa, Tiazofurin, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted Therapy

In some embodiments, a compound described herein is administered with one or more targeted therapies. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary anbibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound described herein is administered with one or more immunotherapies. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with one or more hormonal therapies. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Obesity and Fat Disorders

A compound or composition described herein can be used to treat or prevent obesity, e.g., in a human subject, e.g., a child or adult subject. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Overweight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with a compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

A compound or composition described herein can be administered to treat obesity associated with Prader-Willi Syndrome (PWS). PWS is a genetic disorder associated with obesity (e.g., morbid obesity).

A compound or composition described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Compositions and Routes of Administration

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound provided herewith, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions provided herewith may be administered orally, parenterally, by inhalation spray, topically, rectally, nasally, buccally, vaginally or via an implanted reservoir, preferably by oral administration or administration by injection. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions provided herewith may also be administered in the form of suppositories for rectal administration. These compositions can be prepared by mixing a compound provided herewith with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions provided herewith is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds provided herewith include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions provided herewith may also be topically applied to the lower intestinal tract by rectal suppository formulation or in a suitable enema formulation. Topically-transdermal patches are also included.

The pharmaceutical compositions provided herewith may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions provided herewith comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds provided herewith. Alternatively, those agents may be part of a single dosage form, mixed together with the compounds provided herewith in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Patient Selection and Monitoring

The compounds described herein can modulate PKM2. Accordingly, a patient and/or subject can be selected for treatment using a compound described herein by first evaluating the patient and/or subject to determine whether the subject is in need of modulation of PKM2, and if the subject is determined to be in need of modulation of PKM2, then administering to the subject a compound described herein.

A subject can be evaluated as being in need of modulation of PKM2 using methods known in the art, e.g., by measuring the presence and/or activity of PKM2 in the patient. In some embodiments, the activity and/or level of PKM2 is evaluated in the cancer.

A patient receiving a compound described herein can be monitored, for example, for improvement in the condition and/or adverse effects. Improvement of a patient's condition can be evaluated, for example, by monitoring the growth, absence of growth, or regression of the cancer (e.g., a tumor).

In some embodiments, the patient is evaluated using a radiological assay or evaluation of hemolytic parameters.

The compounds described herein can activate mutant PKRs. Accordingly, a patient and/or subject can be selected for treatment using a compound described herein by first evaluating the patient and/or subject to determine whether the subject carries a mutation in PKR (for examples, one of the mutations as described herein), and if the subject is determined to be carrying a mutation in PKR thus is in need of activation of the activity of the mutant PKR, then optionally administering to the subject a compound described herein. A subject can be evaluated as carrying a mutation in PKR using methods known in the art.

EXAMPLES

In the following examples, the reagents (chemicals) were purchased from commercial sources (such as Alfa, Acros, Sigma Aldrich, TCI and Shanghai Chemical Reagent Company), and used without further purification. Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were given with electrospray ionization (ESI) from a Waters LCT TOF Mass Spectrometer (Waters, USA). Microwave reactions were run on an Initiator 2.5 Microwave Synthesizer (Biotage, Sweden).

ABBREVIATIONS LIST

General anhy. anhydrous
aq. aqueous
Min minute(s)
hr Hour (s)
mL milliliter
mmol millimole(s)
mol mole(s)
s.m. starting material
MS mass spectrometry
NMR nuclear magnetic resonance
r.t. (rt) room temperature
TLC thin layer chromatography
HPLC high-performance liquid chromatography

Spectrum

Hz hertz
δ chemical shift
J coupling constant
s singlet
d doublet
t triplet
q quartet
m multiplet
br broad
qd quartet of doublets
dquin doublet of quintets
dd doublet of doublets
dt doublet of triplets

Solvents and Reagents $CHCl_3$ chloroform
DCM dichloromethane
DMF dimethylformamide
$Et_2O$ diethyl ether
EtOH ethyl alcohol
EtOAc ethyl acetate
MeOH methyl alcohol
MeCN acetonitrile
PE petroleum ether
THF tetrahydrofuran
AcOH acetic acid
HCl hydrochloric acid
$H_2SO_4$ sulfuric acid
$NH_4Cl$ ammonium chloride
KOH potassium hydroxide
NaOH sodium hydroxide
$K_2CO_3$ potassium carbonate
$Na_2CO_3$ sodium carbonate
TFA trifluoroacetic acid
$Na_2SO_4$ sodium sulfate
$NaBH_4$ sodium borohydride
$NaHCO_3$ sodium bicarbonate
LiHMDS lithium hexamethyldisilylamide
NaHMDS sodium hexamethyldisilylamide
LAH lithium aluminum hydride
$NaBH_4$ sodium borohydride
LDA lithium diisopropylamide
$Et_3N$ triethylamine
Py pyridine
DMAP 4-(dimethylamino)pyridine
DIPEA N,N-diisopropylethylamine
$NH_4OH$ ammonium hydroxide
EDCI 1-ethyl-3-(3-dimethylaminopropyl)carbodiimide
HOBt 1-hydroxybenzotriazole
HBTU 2-(1H-Benzotriazole-1-yl)-1,1,3,3-tetramethyluronium hexafluorophosphate
HATU O-(7-azabenzotriazol-1-yl)-N,N,N',N'-tetramethyluronium
Xphos 2-Dicyclohexylphosphino-2',4',6'-triisopropylbiphenyl
BINAP 2,2'-bis(diphenylphosphanyl)-1,1'-binaphthyl
Togni 3,3-Dimethyl-1-(trifluoromethyl)-1,2-benziodoxole reagent
BOMCl (chloromethoxy)methyl)benzene

Example 1

PKM2 Assay

Procedure:
PKM2 stock enzyme solution was diluted in Reaction Buffer
2 μL of compound was added into each well first, and then 180 μL of the Reaction Mix was added.
Reaction mixture with compound (without ADP) were incubated for 30 minutes at 4° C.
Plates were re-equilibrated to room temperature prior to adding 20 μL ADP to initiate the reaction.
Reaction progress was measured as changes in absorbance at 340 nm wavelength at room temperature (25° C.)
Reaction Mix:
PKM2 (50 ng/well), ADP (0.7 mM), PEP (0.15 mM), NADH (180 μM), LDH (2 units) in Reaction Buffer
Reaction Buffer:
100 mM KCl, 50 mM Tris pH 7.5, 5 mM MgCl2, 1 mM DTT, 0.03% BSA.

Example 2 PKR Mutant Assay

Procedure

PKR or PKR mutant enzyme solution was diluted in assay buffer.
2 μL of test compound was added into wells first, and then 180 μL reaction mix was added.

Reactions mixture with test compound was assembled except for ADP, and plates were stored for 60 minutes at room temperature.

20 μL ADP was added to start reaction at room temperature and reaction progress was measured as changes in absorbance at 340 nm wavelength at room temperature.

Test Compound Preparation:

Test compound stock was made at 100× concentration in 100% DMSO (10 mM)

1 to 3 dilutions were made for 11 points (i.e. 50 μl of first concentration added to 100 μl 100% DMSO to yield 3.33 mM, 50 μl of this added to 100 μl DMSO to yield 1.11 mM, and so forth)

1 to 100 dilution into assay (2 μl in 200 μl) yielded starting concentration of 100 μM, decreasing 3 fold for 11 points.

Assay Buffer:

100 mM KCl, 50 mM Tris 7.5, 5 mM $MgCl_2$, 1 mM DTT, 0.03% BSA

Reaction Mixture:

PKR mutant enzyme: 80-400 ng/well; ADP: 0.22-1.65 mM; PEP: 0.1-0.5 mM; NADH:180 uM; LDH: 0.5 units (Sigma#59023); DTT: 1 mM; BSA: 0.03%.

Example 3

PKR WT Single Point Percent Activation Assay

A compound described herein was diluted with DMSO and tested at 1 μM concentration. The enzyme was diluted in 1× Buffer: (100 mM KCl, 50 mM Tris 7.5, 5 mM $MgCl_2$, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:

PKR wt (100 ng/well), Tris pH 7.5 (50 mM), KCl (100 mM), $MgCl_2$ (5 mM), ADP (0.48 mM), PEP (0.15 mM), NADH (180 μM), LDH (0.5 units, Sigma 59023), DTT (1 mM) and BSA (0.03%).

Example 4

PKR R510Q Single Point Percent Activation Assay

A compound described herein was diluted with DMSO and tested at 1 μM concentration. The enzyme was diluted in 1× Buffer: (100 mM KCl, 50 mM Tris 7.5, 5 mM $MgCl_2$, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:

PKR R510Q (40 ng/well), Tris pH 7.5 (50 mM), KCl (100 mM), $MgCl_2$ (5 mM), ADP (0.2 mM), PEP (0.11 mM), NADH (180 μM), LDH (0.5 units, Sigma 59023), DTT (1 mM) and BSA (0.03%).

Example 5

PKR R532W Single Point Percent Activation Assay

A compound described herein was diluted with DMSO and tested at 1 μM concentration. The enzyme was diluted in 1× Buffer: (100 mM KCl, 50 mM Tris 7.5, 5 mM $MgCl_2$, 1 mM DTT, 0.03% BSA). 2 μL of compound solution was first added into wells, and then 180 μL of enzyme solution was added. Assays were assembled except for ADP, and plates were stored for 60 minutes at RT. 20 μL ADP was added to start the assay and assay output was evaluated using OD340 at SpectraMax. The assay was run at room temperature.

Final Concentration:

PKR R532W (100 ng/well), Tris pH 7.5 (50 mM), KCl (100 mM), $MgCl_2$ (5 mM), ADP (0.36 mM), PEP (0.1 mM), NADH (180 μM), LDH (0.5 units, Sigma 59023), DTT (1 mM) and BSA (0.03%).

Example 6

General Procedure 1:1A

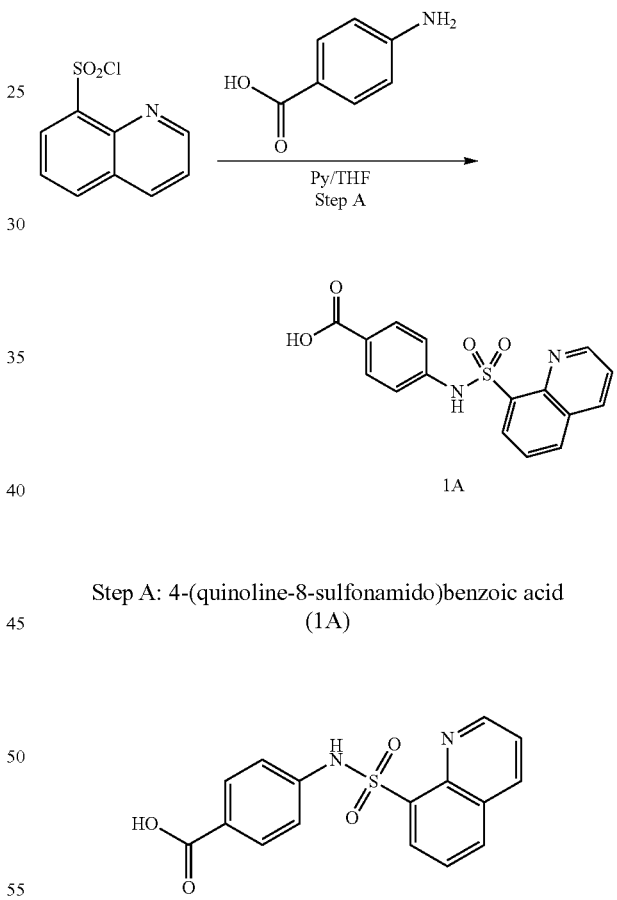

Step A: 4-(quinoline-8-sulfonamido)benzoic acid (1A)

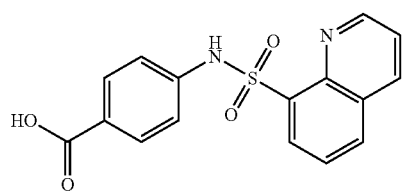 [SMILES: O=C(O)c1ccc(NS(=O)(=O)c2cccc3cccnc23)cc1]

To a solution of 4-aminobenzoic acid (10 g, 73 mmol) in 100 mL of anhydrous THF was added pyridine (1.15 g, 146 mmol), and quinoline-8-sulfonyl chloride (20 g, 88 mmol) at 0° C. The resulting mixture was stirred at 70° C. overnight. After filtration, the residue was washed with EtOH and 14 g of title compound was obtained as pure product.

$^1$H NMR (DMSO-$d_6$) δ: 10.71 (s, 1H), 9.12 (dd, J=4.2, 1.7 Hz, 1H), 8.47 (dd, J=7.5, 1.3 Hz, 1H), 8.51 (dd, J=8.3, 1.9 Hz, 1H), 8.29 (dd, J=8.2, 1.2 Hz, 1H), 7.62-7.79 (m, 4H), 7.14-7.22 (m, 2H). LC-MS: m/z 329.3 (M+H)[+]

General Procedure 2:

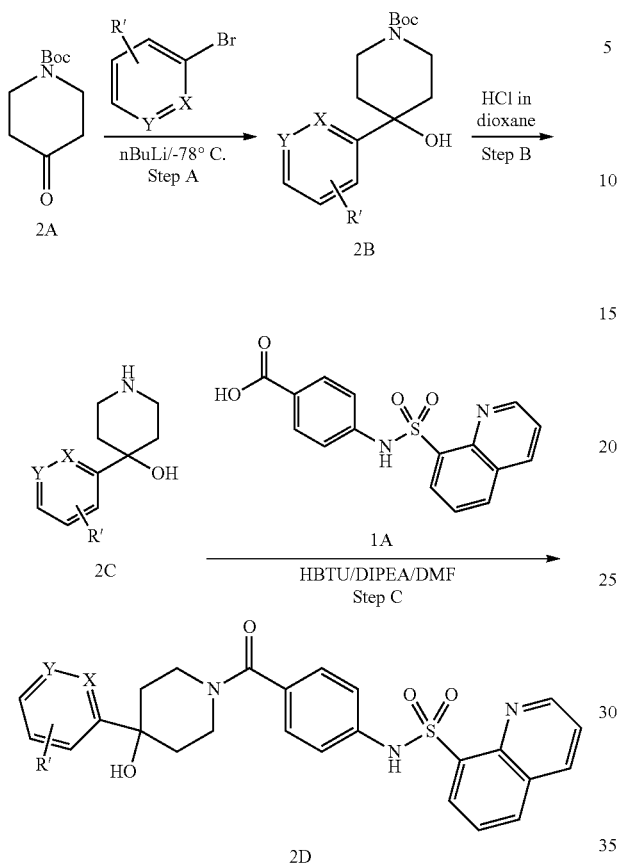

Step A:

To a solution of the corresponding Aryl Bromide (1.0 eq.) in anhydrous THF was added a solution of n-BuLi in THF (1.05 eq.) dropwise at −78° C. After the addition, the mixture was stirred at −78° C. for about 0.5 hour. Then a solution of Boc-4-piperidone in THF was added dropwise via a syringe at −78° C. After the addition, the resulting mixture was stirred at −78° C. under $N_2$ for 2 h, then allowed to warm to r.t. The reaction mixture was quenched by satd. $NH_4Cl$ solution, the resulting mixture was extracted with EtOAc (50 mL, 30 mL). The combined organic phase was washed with brine, dried over anhydrous $Na_2SO_4$ and concentrated in vacuo. The residue was purified by column chromatography (PE/EtOAc) to afford compound 2B.

Step B:

To a solution of compound 2 (1 eq.) in dioxane, was added a solution of HCl in dioxane (3 eq.), the reaction mixture was stirred at room temperature for about 2 hours, when LCMS detected no s.m. The reaction mixture was concentrated to afford the desired product 2C.

Step C:

To a round-bottomed flask was added compound 2C (1 eq.), DMF (5 mL), DIPEA (3.0 eq.), HBTU (1.2 eq.), and 1A (1 eq.) sequentially. The reaction mixture was stirred at room temperature overnight or until TLC indicated that s.m. was consumed. The mixture was diluted with brine, extracted with ethyl acetate, the organic layer was dried with anhydrous $Na_2SO_4$, filtered, and filtrate was concentrated. The desired product 2D was purified by a standard method.

Compound 142 (General Procedure 2, Step C)

N-(4-(4-(3-fluorophenyl)-4-hydroxypiperidine-1-carbonyl)phenyl)quinoline-8-sulfonamide

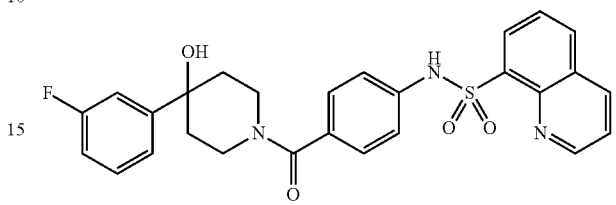

$^1$H NMR (CHLOROFORM-d) δ 9.17 (dd, J=4.3, 1.7 Hz, 1H), 8.56 (s, 1H), 8.38 (dd, J=7.3, 1.4 Hz, 1H), 8.32 (dd, J=8.4, 1.7 Hz, 1H), 8.06 (dd, J=8.2, 1.3 Hz, 1H), 7.69-7.57 (m, 2H), 7.34 (td, J=8.1, 6.2 Hz, 1H), 7.25-7.15 (m, 4H), 7.14-7.07 (m, 2H), 6.99 (tdd, J=8.2, 2.5, 0.8 Hz, 1H), 4.60 (s, 1H), 3.60 (s, 1H), 3.47 (s, 1H), 3.26 (s, 1H), 2.06 (s, 1H), 1.82 (s, 2H), 1.68 (d, J=9.1 Hz, 2H). LC-MS: m/z 506.6 (M+H)$^+$.

Compound 126 (General Procedure 2, Step C)

N-(4-(4-hydroxy-4-(2-(trifluoromethyl)phenyl)piperidine-1-carbonyl)phenyl)quinoline-8-sulfonamide

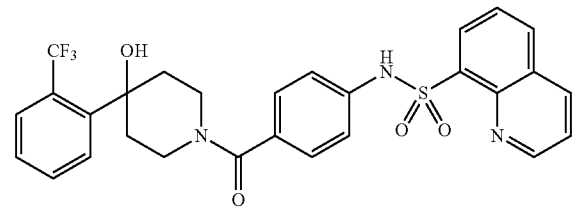 [SMILES: O=C(c1ccc(NS(=O)(=O)c2cccc3cccnc23)cc1)N1CCC(O)(c2ccccc2C(F)(F)F)CC1]

$^1$H NMR (CHLOROFORM-d) δ 9.17 (dd, J=1.8, 4.1 Hz, 1H), 8.57 (br. s., 1H), 8.42-8.30 (m, 2H), 8.06 (dd, J=1.2, 8.2 Hz, 1H), 7.80 (d, J=7.9 Hz, 1H), 7.67-7.47 (m, 4H), 7.47-7.36 (m, 1H), 7.16-7.07 (m, 4H), 4.61 (br. s., 1H), 3.58-3.50 (m, 4H), 2.30-1.85 (m, 4H). LC-MS: m/z 556.5 (M+H)$^+$

Compound 127 (General Procedure 2, Step C)

N-(4-(4-(2-ethylphenyl)-4-hydroxypiperidine-1-carbonyl)phenyl)quinoline-8-sulfonamide

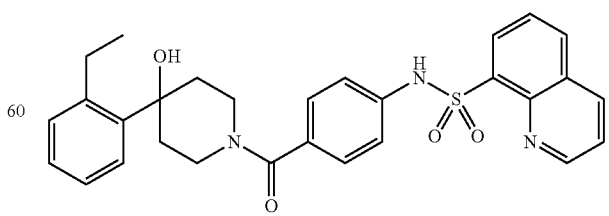

$^1$H NMR (CHLOROFORM-d) δ 9.18 (dd, J=4.3 Hz, J=1.6 Hz, 1H), 8.63 (br. s., 1H), 8.31-8.43 (m, 2H), 8.07 (dd, J=8.4

Hz, J=1.3 Hz, 1H), 7.60-7.69 (m, 2H), 7.30-7.33 (m, 2H), 7.23-7.27 (m, 1H), 7.14-7.23 (m, 3H), 7.07-7.13 (m, 2H), 4.58 (br. s., 1H), 3.58 (br. s., 2H), 3.33 (br. s., 1H), 3.01 (q, J=7.6 Hz, 2H), 2.03 (d, J=5.9 Hz, 1H), 1.93 (br. s., 2H), 1.69 (br. s., 2H), 1.25 (t, J=7.5 Hz, 3H). LC-MS: m/z 516.1 (M+H)+

Compound 138 (General Procedure 2, Step C)

N-(4-(4-(4-fluoro-2-methylphenyl)-4-hydroxypiperidine-1-carbonyl)phenyl)quinoline-8-sulfonamide

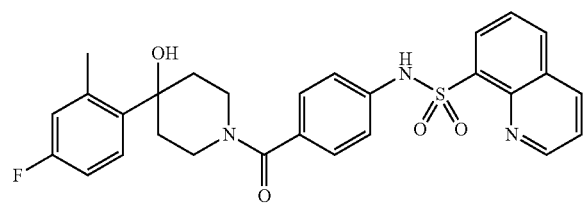 [SMILES: Cc1cc(F)ccc1C1(O)CCN(C(=O)c2ccc(NS(=O)(=O)c3cccc4cccnc34)cc2)CC1]

¹H NMR (CHLOROFORM-d) δ 9.14 (dd, J=1.6, 4.3 Hz, 1H), 8.62 (br. s., 1H), 8.39-8.24 (m, 2H), 8.04 (dd, J=1.3, 8.4 Hz, 1H), 7.66-7.52 (m, 2H), 7.25-7.02 (m, 5H), 6.86-6.70 (m, 2H), 4.45 (br. s., 1H), 3.50 (br. s., 2H), 3.33-3.20 (m, 1H), 2.52 (s, 3H), 2.05 (d, J=9.1 Hz, 1H), 1.96 (br. s., 2H), 1.84 (br. s., 2H). LC-MS: m/z 520.6 (M+H)+

Compound 150 (General Procedure 2, Step C)

N-(4-(4-hydroxy-4-(2-(trifluoromethoxy)phenyl)piperidine-1-carbonyl)phenyl)quinoline-8-sulfonamide

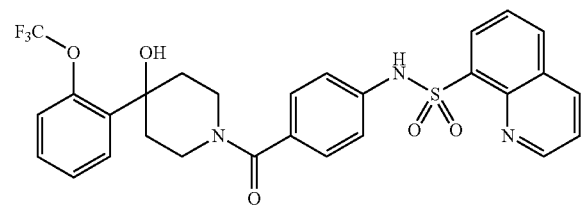 [SMILES: O=C(c1ccc(NS(=O)(=O)c2cccc3cccnc23)cc1)N1CCC(O)(c2ccccc2OC(F)(F)F)CC1]

¹H NMR (CHLOROFORM-d) δ 9.16 (dd, J=1.6, 4.3 Hz, 1H), 8.61 (br. s., 1H), 8.42-8.26 (m, 2H), 8.05 (dd, J=1.2, 8.2 Hz, 1H), 7.67-7.49 (m, 3H), 7.36-7.06 (m, 7H), 4.55 (br. s., 1H), 3.54 (br. s., 1H), 3.48 (s, 2H), 3.24 (br. s., 1H), 1.83 (br. s., 2H), 1.76 (br. s., 2H). LC-MS: m/z 572.6 (M+H)+

Compound 199 (General Procedure 2, Step C)

N-(4-(4-hydroxy-4-(3-(trifluoromethyl)phenyl)piperidine-1-carbonyl)phenyl)quinoline-8-sulfonamide

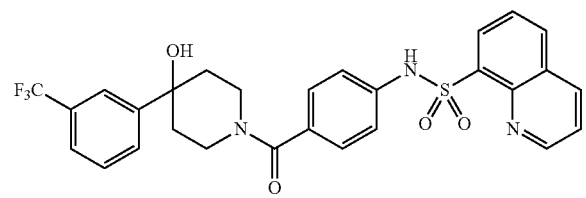 [SMILES: O=C(c1ccc(NS(=O)(=O)c2cccc3cccnc23)cc1)N1CCC(O)(c2cccc(C(F)(F)F)c2)CC1]

¹H NMR (CHLOROFORM-d) δ 9.15 (dd, J=1.6, 4.3 Hz, 1H), 8.62 (br. s., 1H), 8.41-8.27 (m, 2H), 8.10-8.01 (m, 1H), 7.72 (s, 1H), 7.68-7.41 (m, 5H), 7.23-7.15 (m, 2H), 7.15-7.02

(m, 2H), 4.54 (br. s., 1H), 3.57 (br. s., 1H), 3.47 (s, 1H), 3.23 (br. s., 1H), 2.12-1.91 (m, 2H), 1.80 (br. s., 2H), 1.68 (br. s., 1H). LC-MS: m/z 556.6 (M+H)+

Compound 177 (General Procedure 2, Step C)

N-(4-(4-(3-chlorophenyl)-4-hydroxypiperidine-1-carbonyl)phenyl)quinoline-8-sulfonamide

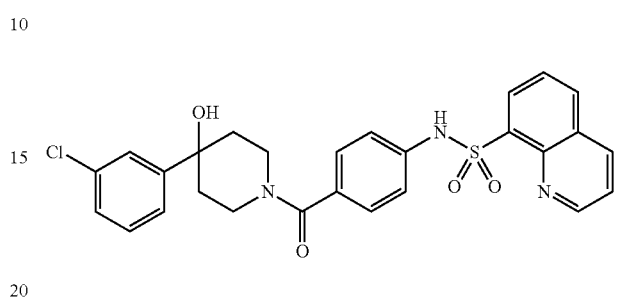

¹H NMR (CHLOROFORM-d) δ 9.13 (dd, J=1.6, 4.3 Hz, 1H), 8.63 (br. s., 1H), 8.31 (dd, J=1.5, 10.6 Hz, 1H), 8.37-8.23 (m, 1H), 8.03 (dd, J=1.2, 8.2 Hz, 1H), 7.65-7.51 (m, 2H), 7.44-7.35 (m, 1H), 7.27-7.10 (m, 5H), 7.10-7.01 (m, 2H), 4.45 (br. s., 1H), 3.59-3.29 (m, 2H), 3.17 (br. s., 1H), 1.98-1.61 (br. s., 5H). LC-MS: m/z 522.5 (M+H)+

Compound 194 (General Procedure 2, Step C)

N-(4-(4-(4-fluorophenyl)-4-hydroxypiperidine-1-carbonyl)phenyl)quinoline-8-sulfonamide

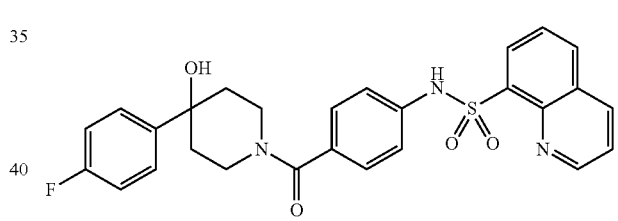

¹H NMR (CHLOROFORM-d) δ 9.16 (dd, J=1.8, 4.1 Hz, 1H), 8.58 (br. s., 1H), 8.42-8.24 (m, 2H), 8.06 (dd, J=1.5, 8.2 Hz, 1H), 7.68-7.55 (m, 2H), 7.47-7.36 (m, 2H), 7.24-7.16 (m, 2H), 7.13-6.97 (m, 4H), 3.50 (s, 3H), 3.19 (s, 1H), 2.06 (s, 1H), 1.79 (br. s., 3H). LC-MS: m/z 506.6 (M+H)+

Compound 245 (General Procedure 2, Step C)

N-(4-(4-hydroxy-4-(3-(trifluoromethoxy)phenyl)piperidine-1-carbonyl)phenyl)quinoline-8-sulfonamide

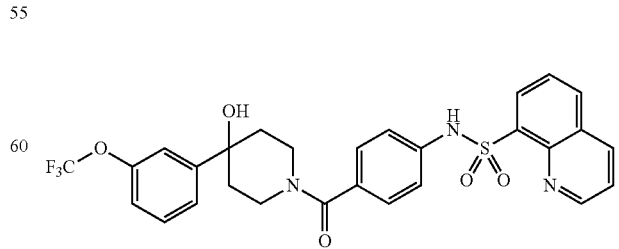

¹H NMR (CHLOROFORM-d) δ 9.16 (dd, J=1.8, 4.4 Hz, 1H), 8.67 (br. s., 1H), 8.42-8.24 (m, 2H), 8.10-8.00 (m, 1H), 7.68-7.53 (m, 2H), 7.42-7.29 (m, 3H), 7.24-7.03 (m, 5H), 4.55 (br. s., 1H), 3.57-3.23 (br. s., 3H), 2.02-1.80 (br. s., 5H). LC-MS: m/z 572.6 (M+H)⁺

Compound 122 (General Procedure 2, Step C)

N-(4-(4-(2-chlorophenyl)-4-hydroxypiperidine-1-carbonyl)phenyl)quinoline-8-sulfonamide

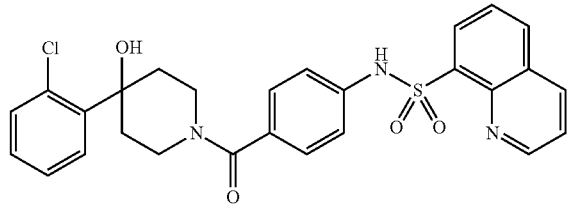 [SMILES: O=C(c1ccc(NS(=O)(=O)c2cccc3cccnc23)cc1)N1CCC(O)(c2ccccc2Cl)CC1]

¹H NMR (CHLOROFORM-d) δ: 9.15-9.21 (m, 1H), 8.58 (br. s., 1H), 8.39 (dd, J=7.3, 1.3 Hz, 1H), 8.32 (dd, J=8.3, 1.6 Hz, 1H), 8.06 (dd, J=8.2, 1.2 Hz, 1H), 7.59-7.68 (m, 2H), 7.48-7.54 (m, 1H), 7.39 (dd, J=7.5, 1.6 Hz, 1H), 7.24-7.29 (m, 2H), 7.18-7.23 (m, 2H), 7.07-7.14 (m, 2H), 3.58-3.29 (br. s., 4H), 2.34-1.97 (br. m., 4H). LC-MS: m/z 523.1 (M+H)⁺

Compound 165 (General Procedure 2, Step C)

N-(4-(4-(2-fluorophenyl)-4-hydroxypiperidine-1-carbonyl)phenyl)quinoline-8-sulfonamide

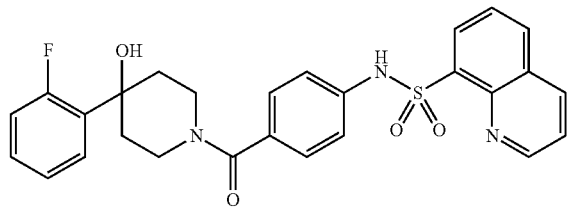

¹H NMR (CHLOROFORM-d) δ: 9.16 (dd, J=4.3, 1.8 Hz, 1H), 8.59 (br. s., 1H), 8.37 (dd, J=7.4, 1.4 Hz, 1H), 8.31 (dd, J=8.4, 1.6 Hz, 1H), 8.05 (dd, J=8.3, 1.3 Hz, 1H), 7.56-7.67 (m, 2H), 7.45 (td, J=8.0, 1.8 Hz, 1H), 7.24-7.32 (m, 1H), 7.17-7.23 (m, 2H), 7.00-7.17 (m, 4H), 4.56 (br. s., 1H), 3.54 (br. s., 2H), 3.25 (br. s., 1H), 2.44 (br. s., 1H), 2.25 (br. s., 1H), 2.1 (s, 1H), 1.85 (s, 1H). LC-MS: m/z 506.6 (M+H)⁺

Compound 184 (General Procedure 2, Step C)

N-(4-(4-hydroxy-4-(2-methoxyphenyl)piperidine-1-carbonyl)phenyl)quinoline-8-sulfonamide

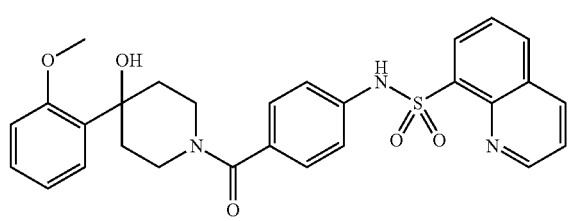 [SMILES: COc1ccccc1C1(O)CCN(C(=O)c2ccc(NS(=O)(=O)c3cccc4cccnc34)cc2)CC1]

¹H NMR (CHLOROFORM-d) δ: 9.16 (br. s., 1H), 8.59 (br. s., 1H), 8.25-8.42 (m, 2H), 8.05 (d, J=7.9 Hz, 1H), 7.53-7.69 (m, 2H), 7.04-7.33 (m, 6H), 6.89-7.02 (m, 2H), 4.54 (br. s., 1H), 3.91 (s, 3H), 3.55 (br. s., 2H), 3.32 (br. s., 1H), 2.20-1.90 (m, 4H). LC-MS: m/z 518.6 (M+H)⁺

Compound 100 (General Procedure 2, Step C)

N-[4-[4-(2,3-difluorophenyl)-4-hydroxy-piperidine-1-carbonyl]phenyl]quinoline-8-sulfonamide

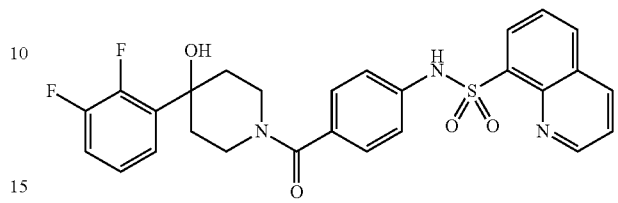

¹H NMR (CHLOROFORM-d) δ: 9.15 (d, J=3.0 Hz, 1H), 8.61 (br. s., 1H), 8.31 (d, J=8.3 Hz, 1H), 8.36 (d, J=7.3 Hz, 1H), 8.05 (d, J=8.1 Hz, 1H), 7.55-7.66 (m, 2H), 7.23 (t, J=7.1 Hz, 1H), 7.18 (d, J=8.3 Hz, 2H), 7.02-7.12 (m, 4H), 4.52 (br. s., 1H), 3.51 (br. s., 2H), 3.22 (br. s., 1H), 2.65 (br. s., 1H), 2.14-2.29 (m, 1H), 2.09 (br. s., 1H), 1.79 (br. s., 1H). LC-MS: m/z 523.6 (M+H)⁺

Compound 113 (General Procedure 2, Step C)

N-[4-[4-[2-(difluoromethyl)phenyl]-4-hydroxy-piperidine-1-carbonyl]phenyl]quinoline-8-sulfonamide

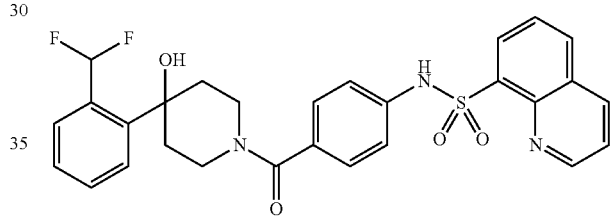

¹H NMR (CHLOROFORM-d) δ: 9.02-9.07 (m, 2H), 8.51 (d, J=7.3 Hz, 1H), 8.38 (d, J=8.3 Hz, 1H), 7.89 (t, J=7.9 Hz, 1H), 7.76 (s, 1H), 7.50-7.54 (m, 1H), 7.39 (dd, J=7.5, 1.3 Hz, 1H), 7.29-7.32 (m, 1H), 7.22-7.28 (m, 2H), 7.16 (s, 1H), 7.06 (d, J=8.1 Hz, 1H), 4.60 (br. s., 1H), 3.61 (br. s., 1H), 3.55 (br. s., 1H), 3.31 (d, J=11.3 Hz, 1H), 2.35 (d, J=7.5 Hz, 1H), 2.20 (d, J=14.8 Hz, 1H), 2.01-2.12 (m, 2H), 1.97 (br. s., 2H). LC-MS: m/z 537.6 (M+H)⁺

Compound 266 (General Procedure 2, Step C)

N-(4-(4-(2-cyanophenyl)-4-hydroxypiperidine-1-carbonyl)phenyl)quinoline-8-sulfonamide

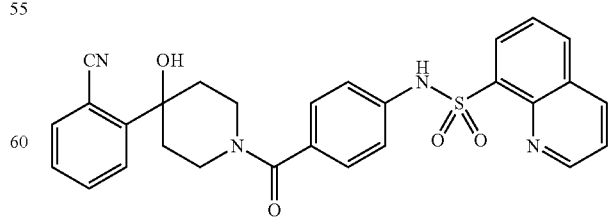

¹H NMR (CHLOROFORM-d) δ: 9.17 (dd, J=4.2, 1.7 Hz, 1H), 8.39 (dd, J=7.3, 1.3 Hz, 1H), 8.33 (dd, J=8.3, 1.6 Hz, 1H), 8.07 (dd, J=8.2, 1.2 Hz, 1H), 7.92 (d, J=7.5 Hz, 1H), 7.71

(s, 1H), 7.54-7.67 (m, 3H), 7.38 (d, J=7.5 Hz, 1H), 7.26 (d, J=8.9 Hz, 2H), 7.13 (d, J=8.3 Hz, 2H), 4.66-4.84 (m, 1H), 3.70-3.90 (m, 1H), 3.46-3.64 (m, 1H), 3.21-3.39 (m, 1H), 2.23 (s, 2H), 1.71-1.88 (m, 2H). LC-MS: m/z 514.7 (M+H)⁺

Compound 255 (General Procedure 2, Step C)

N-[4-[4-(4-cyanophenyl)-4-hydroxy-piperidine-1-carbonyl]phenyl]quinoline-8-sulfonamide

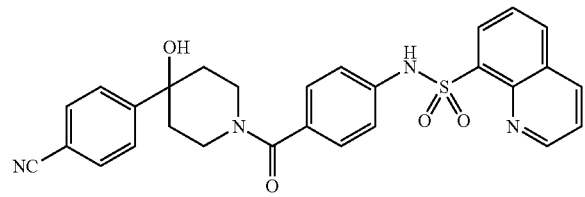 [SMILES: N#Cc1ccc(C2(O)CCN(C(=O)c3ccc(NS(=O)(=O)c4cccc5cccnc45)cc3)CC2)cc1]

¹H NMR (CHLOROFORM-d) δ: 9.42 (br. s., 1H), 9.29 (d, J=4.3 Hz, 1H), 8.50 (d, J=8.1 Hz, 2H), 8.14 (d, J=8.1 Hz, 1H), 7.68-7.81 (m, 4H), 7.60 (d, J=7.5 Hz, 1H), 7.50 (t, J=7.8 Hz, 1H), 7.18-7.26 (m, 4H), 4.64 (t, J=17.2 Hz, 1H), 3.53-3.81 (m, 1H), 3.51 (s, 1H), 3.32 (s, 1H), 2.07 (br. s., 2H), 2.00 (br. s. 2H). LC-MS: m/z 512.6 (M+H)⁺

Compound 166 (General Procedure 2, Step C)

N-(4-(4-(2-chloro-5-fluorophenyl)-4-hydroxypiperidine-1-carbonyl)phenyl)naphthalene-1-sulfonamide

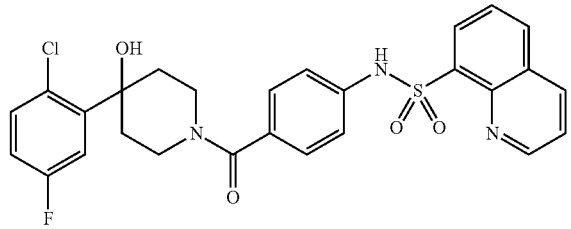 [SMILES: O=C(c1ccc(NS(=O)(=O)c2cccc3cccnc23)cc1)N1CCC(O)(c2cc(F)ccc2Cl)CC1]

¹H NMR (CHLOROFORM-d) δ: 9.18 (d, J=3.0 Hz, 1H), 8.61 (br. s., 1H), 8.30-8.42 (m, 2H), 8.07 (d, J=8.3 Hz, 1H), 7.58-7.68 (m, 2H), 7.49 (dd, J=7.0, 2.7 Hz, 1H), 7.30-7.37 (m, 1H), 7.19-7.26 (m, 2H), 7.11 (d, J=8.3 Hz, 2H), 6.95-7.04 (m, 1H), 4.61 (br. s., 1H), 3.60 (br. s., 1H), 3.50 (br. s., 1H), 3.23 (br. s., 1H), 2.16-2.31 (m, 1H), 2.09 (br. s., 1H), 1.82 (br. s., 2H). LC-MS: m/z 541.1 (M+H)⁺

Compound 190 (General Procedure 2, Step C)

N-[4-[4-(2-chloro-4-methyl-phenyl)-4-hydroxy-piperidine-1-carbonyl]phenyl]quinoline-8-sulfonamide

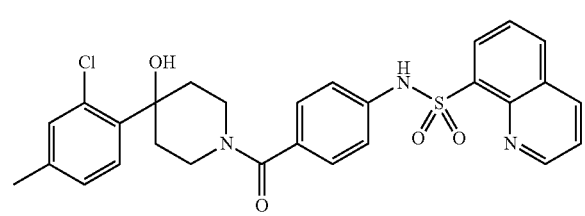 [SMILES: Cc1ccc(C2(O)CCN(C(=O)c3ccc(NS(=O)(=O)c4cccc5cccnc45)cc3)CC2)c(Cl)c1]

¹H NMR (CHLOROFORM-d) δ: 1.79 (br. s., 1H), 1.94 (br. s., 1H), 2.05 (br. s., 1H), 2.13 (br. s., 1H), 2.32 (s, 3H), 2.98 (br. s., 1H), 3.27 (br. s., 1H), 3.56 (br. s., 2H), 4.58 (br. s., 1H), 7.07-7.11 (m, 3H), 7.18-7.22 (m, 3H), 7.37 (d, J=8.03 Hz, 1H), 7.59-7.66 (m, 2H), 8.06 (dd, J=8.16, 1.13 Hz, 1H) 8.32 (dd, J=8.28, 1.51 Hz, 1H), 8.38 (dd, J=7.28, 1.25 Hz, 1H), 8.60 (br. s., 1H), 9.17 (dd, J=4.27, 1.51 Hz, 1H). LC-MS: m/z 537.0 (M+H)⁺

Compound 111 (General Procedure 2, Step C)

N-[4-[4-(2-chloro-4-fluoro-phenyl)-4-hydroxy-piperidine-1-carbonyl]phenyl]quinoline-8-sulfonamide

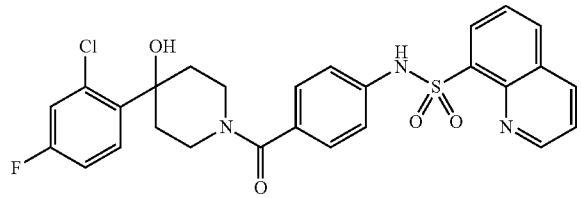 [SMILES: O=C(c1ccc(NS(=O)(=O)c2cccc3cccnc23)cc1)N1CCC(O)(c2ccc(F)cc2Cl)CC1]

¹H NMR (CHLOROFORM-d) δ: 1.57-1.76 (m, 4H), 2.04 (br. s., 1H), 2.13 (br. s., 1H), 3.57 (br. s., 2H), 4.57 (br. s., 1H), 6.97-7.04 (m, 1H), 7.10 (d, J=8.06 Hz, 2H), 7.19-7.23 (m, 4H), 7.59-7.67 (m, 2H), 8.06 (d, J=8.06 Hz, 1H), 8.32 (d, J=8.33 Hz, 1H), 8.39 (d, J=7.52 Hz, 1H), 8.59 (br. s., 1H), 9.17 (d, J=4.03 Hz, 1H).
LC-MS: m/z 540.6 (M+H)⁺

Compound 123 (General Procedure 2, Step C)

N-[4-[4-(2-chloro-3-fluoro-phenyl)-4-hydroxy-piperidine-1-carbonyl]phenyl]quinoline-8-sulfonamide

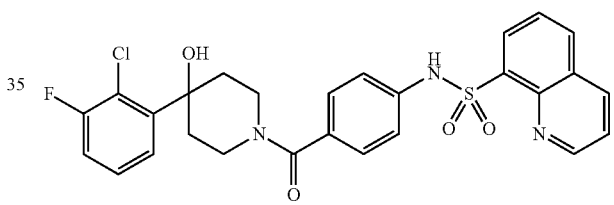

¹H NMR (CHLOROFORM-d) δ: 1.70-1.90 (m, 4H), 3.28 (br. s., 1H), 3.51 (s, 2H), 3.60 (br. s., 1H), 4.61 (br. s., 1H), 7.09-7.15 (m, 3H), 7.22 (d, J=8.33 Hz, 2H), 7.34-7.44 (m, 3H), 7.59-7.70 (m, 2H), 8.08 (d, J=8.33 Hz, 1H), 8.36 (d, J=8.06 Hz, 1H), 8.41 (d, J=7.25 Hz, 1H), 8.77 (br. s., 1H), 9.20 (d, J=3.76 Hz, 1H). LC-MS: m/z 540.6 (M+H)⁺

Compound 182 (General Procedure 2, Step C)

N-(4-(4-hydroxy-4-(3-(methylsulfonyl)phenyl)piperidine-1-carbonyl)phenyl)quinoline-8-sulfonamide

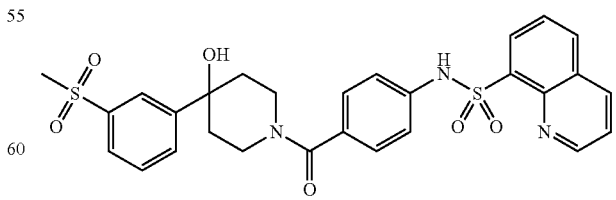

¹H NMR (CHLOROFORM-d) δ: 9.18 (dd, J=4.3, 1.3 Hz, 1H), 8.63 (br. s., 1H), 8.37 (dd, J=10.6, 1.2 Hz, 1H), 8.32-8.43 (m, 1H), 8.07 (dd, J=8.3, 1.1 Hz, 1H), 7.89-7.96 (m, 2H), 7.57-7.74 (m, 5H), 7.14-7.19 (m, J=8.6 Hz, 2H), 7.06-7.12

(m, J=8.6 Hz, 2H), 4.36 (br. s., 1H), 3.87 (br. s., 1H), 3.37-3.57 (m, 2H), 3.24-3.33 (m, 2H), 3.20 (br. s., 1H), 1.79 (br. s., 2H), 1.64 (br. s., 2H). LC-MS: m/z 566.7 (M+H)+

Compound 192 (General Procedure 2, Step C)

N-[4-[4-hydroxy-4-(2-methylsulfonylphenyl)piperidine-1-carbonyl]phenyl]quinoline-8-sulfonamide

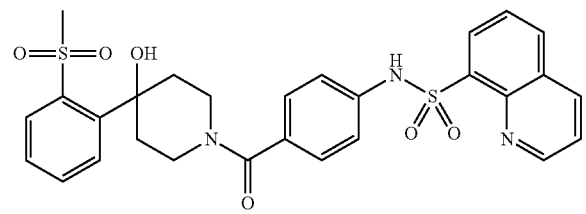 [SMILES: CS(=O)(=O)c1ccccc1C1(O)CCN(C(=O)c2ccc(NS(=O)(=O)c3cccc4cccnc34)cc2)CC1]

¹H NMR (CHLOROFORM-d) δ: 1.95 (d, J=12.89 Hz, 3H), 1.99-2.11 (m, 2H), 3.27 (br. s., 3H), 3.48 (br. s., 2H), 3.87 (br. s., 1H), 4.38 (br. s., 1H), 7.10 (m, J=8.60 Hz, 2H), 7.17 (m, J=8.60 Hz, 2H), 7.61-7.65 (m, 3H), 7.69-7.74 (m, 1H), 7.93 (d, J=8.60 Hz, 2H), 8.07 (d, J=8.33 Hz, 1H), 8.34 (d, J=8.33 Hz, 1H), 8.39 (d, J=7.25 Hz, 1H), 8.64 (br. s., 1H), 9.18 (d, J=3.49 Hz, 1H). LC-MS: m/z 566.7 (M+H)+

Compound 228 (General Procedure 2, Step C)

N-[4-[4-hydroxy-4-(2-hydroxyphenyl)piperidine-1-carbonyl]phenyl]quinoline-8-sulfonamide

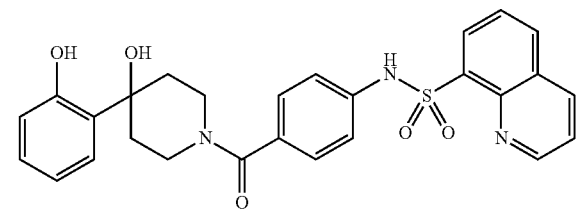 [SMILES: O=C(c1ccc(NS(=O)(=O)c2cccc3cccnc23)cc1)N1CCC(O)(c2ccccc2O)CC1]

¹H NMR (CHLOROFORM-d) δ: 1.94-2.09 (m, 4H), 2.21-2.27 (m, 1H), 2.50 (br. s., 1H), 3.30 (br. s., 1H), 3.50 (br. s., 1H), 3.62 (br. s., 1H), 4.63 (br. s., 1H), 6.89 (t, J=8.06 Hz, 2H), 7.05-7.12 (m, 3H), 7.17-7.24 (m, 3H), 7.60-7.67 (m, 2H), 8.07 (d, J=8.06 Hz, 1H), 8.32 (d, J=6.72 Hz, 1H), 8.39 (d, J=7.25 Hz, 1H), 8.59 (br. s., 1H), 9.17 (d, J=5.91 Hz, 1H). LC-MS: m/z 504.6 (M+H)+

Compound 156

N-(4-(4-hydroxy-4-phenylpiperidine-1-carbonyl)phenyl)quinoline-8-sulfonamide

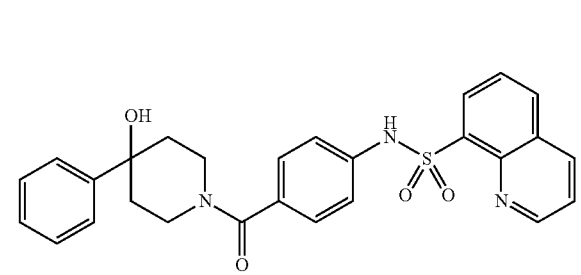 [SMILES: O=C(c1ccc(NS(=O)(=O)c2cccc3cccnc23)cc1)N1CCC(O)(c2ccccc2)CC1]

¹H NMR (DMSO-d₆) δ: 9.05 (1H), 8.5 (m, 1H), 8.4 (m, 1H), 8.2 (m, 1H), 7.7 (m, 2H), 7.4 (m, 2H), 7.4-7.05 (m, 7H), 4.2 (br, 2H), 3.2 (br, 2H), 1.85 (br, 2H), 1.6 (br, 2H). LC-MS: m/z 488.6 (M+H)+

Compound 103

N-(4-(4-hydroxy-4-(o-tolyl)piperidine-1-carbonyl)phenyl)quinoline-8-sulfonamide

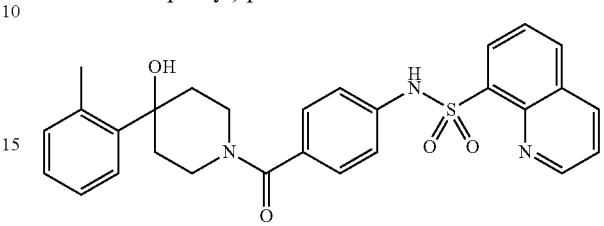

¹H NMR (CD₃OD) δ: 9.1 (1H), 8.4 (m, 2H), 8.2 (m, 1H), 7.6 (m, 2H), 7.4 (m, 1H), 7.2-7.05 (m, 7H), 4, 4 (br, 1H), 3.5 (br, 2H), 2.5 (s, 3H), 2.2-1.8 (m, 4H), 1.4 (br, 2H). LC-MS: m/z 502.6 (M+H)+

Compound 247 (General Procedure 2, Step C)

N-[4-[4-(2-fluoropyridin-4-yl)-4-hydroxy-piperidine-1-carbonyl]phenyl]quinoline-8-sulfonamide

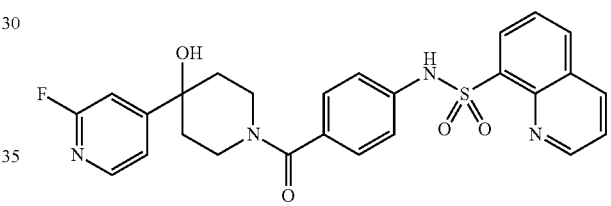

¹H NMR (CHLOROFORM-d) δ: 2.08 (br. s., 1H), 2.14-2.37 (m, 2H), 2.75 (br. s., 1H), 3.22 (br. s., 1H), 3.49 (br. s., 2H), 3.56 (br. s., 1H), 4.55 (br. s., 1H), 7.09 (d, J=8.60 Hz, 2H), 7.19 (d, J=8.60 Hz, 3H), 7.56-7.66 (m, 2H), 7.94 (t, J=8.19 Hz, 1H), 8.05 (d, J=8.06 Hz, 1H), 8.12 (d, J=4.57 Hz, 1H), 8.31 (d, J=8.33 Hz, 1H), 8.37 (d, J=7.25 Hz, 1H), 8.62 (br. s., 1H), 9.16 (d, J=5.91 Hz, 1H). LC-MS: m/z 507.6 (M+H)+

Compound 265 (General Procedure 2, Step C)

N-[4-[4-hydroxy-4-(6-methylpyridin-2-yl)piperidine-1-carbonyl]phenyl]quinoline-8-sulfonamide

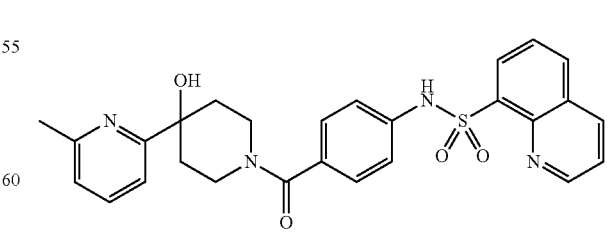

¹H NMR (CHLOROFORM-d) δ: 1.70 (br. s., 2H), 1.80 (br. s., 2H), 2.02 (br. s., 1H), 2.56 (s, 3H), 3.29 (br. s., 1H), 3.63 (br. s., 2H), 4.65 (br. s., 1H), 7.07-7.12 (m, 4H), 7.24 (d, J=8.60 Hz, 2H), 7.58-7.66 (m, 3H), 8.05 (d, J=8.33 Hz, 1H), 8.31 (d, J=6.72 Hz, 1H), 8.38 (d, J=7.25 Hz, 1H), 8.58 (br. s., 1H), 9.16 (d, J=5.91 Hz, 1H). LC-MS: m/z 503.6 (M+H)+

Compound 174 (General Procedure 2, Step C)

N-[4-[4-hydroxy-4-[6-(trifluoromethyl)pyridin-2-yl]piperidine-1-carbonyl]phenyl]quinoline-8-sulfonamide

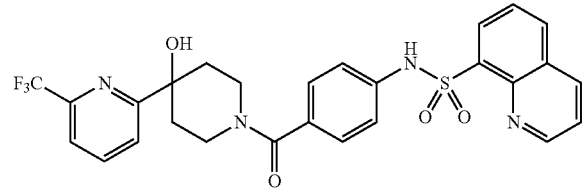 [SMILES: O=C(c1ccc(NS(=O)(=O)c2cccc3cccnc23)cc1)N1CCC(O)(c2cccc(C(F)(F)F)n2)CC1]

$^1$H NMR (CHLOROFORM-d) δ: 9.16 (dd, J=4.3, 1.6 Hz, 1H), 8.63 (br. s., 1H), 8.37 (dd, J=7.3, 1.3 Hz, 1H), 8.31 (dd, J=8.3, 1.6 Hz, 1H), 8.02-8.08 (m, 1H), 7.92 (t, J=7.9 Hz, 1H), 7.55-7.66 (m, 4H), 7.20-7.25 (m, J=8.6 Hz, 2H), 7.07-7.13 (m, J=8.3 Hz, 2H), 4.50-4.71 (m, 2H), 3.60-3.71 (m, 1H), 3.50-3.60 (m, 1H), 1.80-1.97 (m, 2H), 1.74 (br. s., 2H). LC-MS: m/z 556.6 (M+H)+

Compound 211 (General Procedure 2, Step C)

N-(4-(4-hydroxy-4-(2-methoxypyridin-3-yl)piperidine-1-carbonyl)phenyl)quinoline-8-sulfonamide

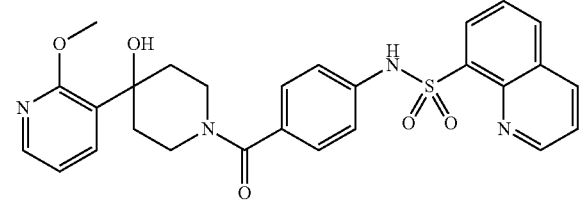 [SMILES: COc1ncccc1C1(O)CCN(C(=O)c2ccc(NS(=O)(=O)c3cccc4cccnc34)cc2)CC1]

$^1$H NMR (CHLOROFORM-d) δ: 9.12-9.19 (m, 1H), 8.61 (br. s., 1H), 8.37 (dd, J=7.3, 1.2 Hz, 1H), 8.30 (dd, J=8.4, 1.3 Hz, 1H), 8.09 (dd, J=5.0, 1.5 Hz, 1H), 8.02-8.07 (m, 1H), 7.56-7.66 (m, 2H), 7.50 (dd, J=7.3, 1.8 Hz, 1H), 7.19 (d, J=8.5 Hz, 2H), 7.09 (d, J=8.5 Hz, 2H), 6.91 (dd, J=7.3, 5.0 Hz, 1H), 4.57 (br. s., 1H), 4.02 (s, 3H), 3.89 (br. s., 1H), 3.56 (br. s., 2H), 3.29 (br. s., 1H), 2.05-1.89 (m, 4H). LC-MS: m/z 519.6 (M+H)+

Compound 129 (General Procedure 2, Step C)

N-(4-(4-(6-fluoro-2-methylpyridin-3-yl)-4-hydroxypiperidine-1-carbonyl)phenyl)quinoline-8-sulfonamide

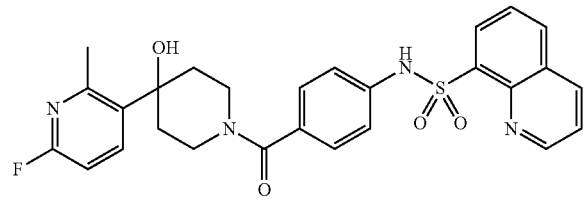 [SMILES: Cc1nc(F)ccc1C1(O)CCN(C(=O)c2ccc(NS(=O)(=O)c3cccc4cccnc34)cc2)CC1]

$^1$H NMR (CHLOROFORM-d) δ: 9.16 (dd, J=4.3, 1.6 Hz, 1H), 8.60 (br. s., 1H), 8.33 (dd, J=19.9, 1.3 Hz, 1H), 8.35 (dd, J=18.9, 1.5 Hz, 1H), 8.02-8.10 (m, 1H), 7.70 (t, J=8.2 Hz, 1H), 7.56-7.66 (m, 2H), 7.17 (d, J=8.3 Hz, 2H), 7.08 (d, J=8.3 Hz, 2H), 6.68 (dd, J=8.6, 3.5 Hz, 1H), 4.55 (br. s., 1H), 3.56 (br. s., 2H), 3.28 (br. s., 1H), 2.70 (s, 3H), 1.92-2.08 (m, 4H). LC-MS: m/z 519.6 (M+H)+

Compound 171 (General Procedure 2, Step C)

N-(4-(4-(5-fluoro-6-methylpyridin-2-yl)-4-hydroxypiperidine-1-carbonyl)phenyl)quinoline-8-sulfonamide

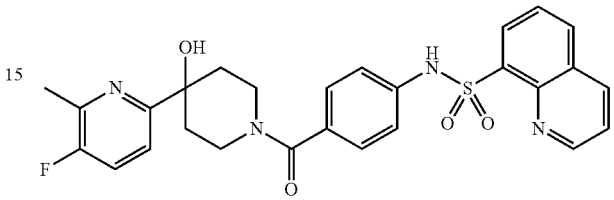

$^1$H NMR (CHLOROFORM-d) δ: 9.15 (dd, J=4.3, 1.9 Hz, 1H), 8.64 (br. s., 1H), 8.36 (dd, J=7.4, 1.2 Hz, 1H), 8.31 (dd, J=8.3, 1.6 Hz, 1H), 8.20 (d, J=5.1 Hz, 1H), 8.05 (dd, J=8.2, 1.2 Hz, 1H), 7.55-7.67 (m, 2H), 7.26-7.32 (m, 1H), 7.18 (d, J=8.6 Hz, 2H), 7.09 (d, J=8.6 Hz, 2H), 4.53 (br. s., 1H), 3.53 (br. s., 2H), 3.19 (br. s., 2H), 2.50 (d, J=3.5 Hz, 3H), 2.04-2.23 (m, 2H), 1.61-1.73 (m, 2H). LC-MS: m/z 519.6 (M+H)+

Compound 148 (General Procedure 2, Step C)

N-(4-(4-(3-fluoropyridin-2-yl)-4-hydroxypiperidine-1-carbonyl)phenyl)quinoline-8-sulfonamide

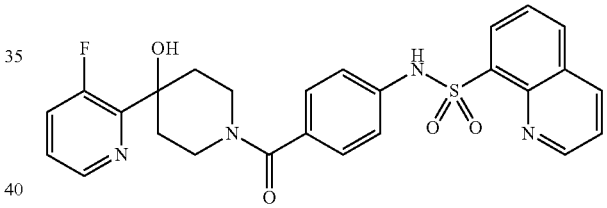

$^1$H NMR (CHLOROFORM-d) δ: 9.17 (dd, J=4.3, 1.6 Hz, 1H), 8.60 (br. s., 1H), 8.41-8.46 (m, 2H), 8.39 (dd, J=7.3, 1.5 Hz, 1H), 8.33 (dd, J=8.4, 1.6 Hz, 1H), 8.07 (dd, J=8.2, 1.2 Hz, 1H), 7.58-7.68 (m, 2H), 7.51 (dd, J=6.7, 5.3 Hz, 1H), 7.22 (d, J=8.5 Hz, 2H), 7.11 (d, J=8.5 Hz, 2H), 4.63 (br. s., 1H), 3.60-3.23 (m, 3H), 2.32-1.86 (br. m., 4H). LC-MS: m/z 507.5 (M+H)+

Compound 166

N-(4-(4-(2-chloro-5-fluorophenyl)-4-hydroxypiperidine-1-carbonyl)phenyl)naphthalene-1-sulfonamide

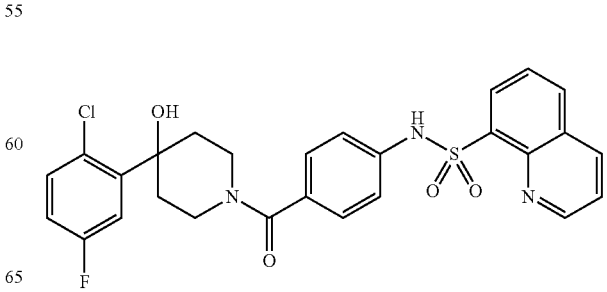

¹H NMR (CHLOROFORM-d) δ: 9.18 (d, J=3.0 Hz, 1H), 8.61 (br. s., 1H), 8.30-8.42 (m, 2H), 8.07 (d, J=8.3 Hz, 1H), 7.58-7.68 (m, 2H), 7.49 (dd, J=7.0, 2.7 Hz, 1H), 7.30-7.37 (m, 1H), 7.19-7.26 (m, 2H), 7.11 (d, J=8.3 Hz, 2H), 6.95-7.04 (m, 1H), 4.61 (br. s., 1H), 3.60 (br. s., 1H), 3.50 (br. s., 1H), 3.23 (br. s., 1H), 2.16-2.31 (m, 1H), 2.09 (br. s., 1H), 1.82 (br. s., 2H). LC-MS: m/z 541.0 (M+H)⁺

Compound 133 (General Procedure 2, Step C)

N-(4-(4-(6-bromo-5-fluoropyridin-2-yl)-4-hydroxypiperidine-1-carbonyl)phenyl)quinoline-8-sulfonamide

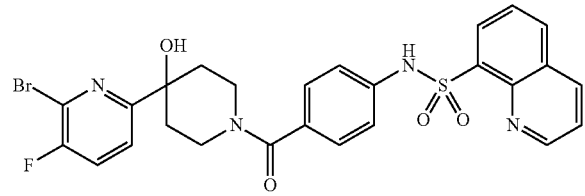

¹H NMR (CHLOROFORM-d) δ: 9.17 (dd, J=4.4, 1.8 Hz, 1H), 8.66 (br. s., 1H), 8.28-8.43 (m, 2H), 8.13 (d, J=5.0 Hz, 1H), 8.07 (dd, J=8.2, 1.2 Hz, 1H), 7.57-7.70 (m, 2H), 7.44 (t, J=5.3 Hz, 1H), 7.19 (d, J=8.5 Hz, 2H), 7.10 (d, J=8.5 Hz, 2H), 4.55 (br. s., 1H), 3.18-3.56 (m, 3H), 2.04-2.34 (m, 2H), 1.63-1.65 (m, 2H). LC-MS: m/z 586.4 (M+H)⁺

Compound 147 (General Procedure 2, Step C)

N-(4-(4-hydroxy-4-(2-methylpyridin-3-yl)piperidine-1-carbonyl)phenyl)quinoline-8-sulfonamide

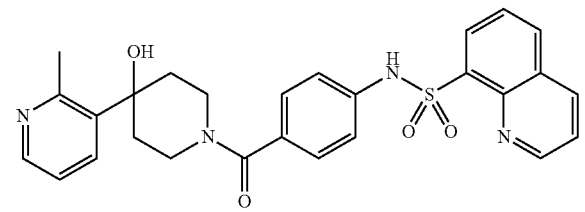 [SMILES: Cc1ncccc1C1(O)CCN(C(=O)c2ccc(NS(=O)(=O)c3cccc4cccnc34)cc2)CC1]

¹H NMR (CHLOROFORM-d) δ: 9.13 (dd, J=1.6, 4.3 Hz, 1H), 8.66 (br. s., 1H), 8.38-8.26 (m, 2H), 8.22 (d, J=4.7 Hz, 1H), 8.04 (dd, J=1.2, 8.2 Hz, 1H), 7.66-7.51 (m, 3H), 7.18-7.10 (m, 2H), 7.10-6.97 (m, 3H), 4.47 (br. s., 1H), 3.53 (br. s., 1H), 3.47-3.32 (m, 1H), 3.26 (br. s., 1H), 2.70 (s, 3H), 2.09-1.71 (m, 5H). LC-MS: m/z 503.6 (M+H)⁺

Compound 164 (General Procedure 2, Step C)

N-(4-(4-hydroxy-4-(3-(trifluoromethyl)pyridin-2-yl)piperidine-1-carbonyl)phenyl)quinoline-8-sulfonamide

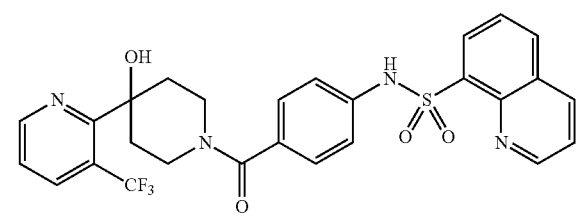 [SMILES: O=C(c1ccc(NS(=O)(=O)c2cccc3cccnc23)cc1)N1CCC(O)(c2ncccc2C(F)(F)F)CC1]

¹H NMR (CHLOROFORM-d) δ: 9.20 (dd, J=4.3, 1.6 Hz, 1H), 8.75 (d, J=3.5 Hz, 1H), 8.71 (s, 1H), 8.45-8.38 (m, 1H), 8.35 (d, J=8.4 Hz, 1H), 8.12 (d, J=6.9 Hz, 1H), 8.08 (dd, J=8.2, 1.3 Hz, 1H), 7.71-7.59 (m, 2H), 7.43 (dd, J=7.8, 4.9 Hz, 1H), 7.23 (d, J=8.6 Hz, 2H), 7.12 (d, J=8.6 Hz, 2H), 4.64 (s, 1H), 3.61 (s, 2H), 3.30 (s, 1H), 2.37 (s, 2H), 1.68 (d, J=11.9 Hz, 3H). LC-MS: m/z 577.7 (M+H)⁺

Compound 191 (General Procedure 2, Step C)

N-(4-(4-(3-chloropyridin-2-yl)-4-hydroxypiperidine-1-carbonyl)phenyl)quinoline-8-sulfonamide

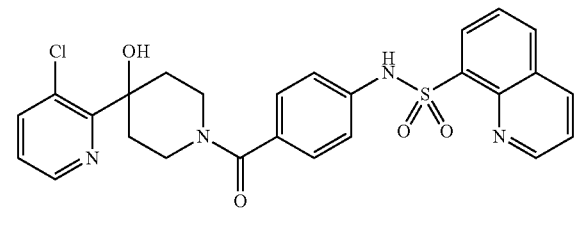 [SMILES: O=C(c1ccc(NS(=O)(=O)c2cccc3cccnc23)cc1)N1CCC(O)(c2ncccc2Cl)CC1]

¹H NMR (CHLOROFORM-d) δ: 9.19 (dd, J=4.3, 1.7 Hz, 1H), 8.68 (s, 1H), 8.50 (dd, J=4.6, 1.3 Hz, 1H), 8.40 (dd, J=7.3, 1.3 Hz, 1H), 8.35 (dd, J=8.3, 1.7 Hz, 1H), 8.08 (dd, J=8.2, 1.3 Hz, 1H), 7.78 (dd, J=8.0, 1.3 Hz, 1H), 7.65 (ddd, J=13.7, 7.9, 4.4 Hz, 2H), 7.32-7.29 (m, 1H), 7.28-7.21 (m, 2H), 7.18-7.09 (m, 2H), 4.68 (d, J=12.4 Hz, 1H), 3.60 (d, J=24.5 Hz, 2H), 3.31 (t, J=13.6 Hz, 1H), 2.75 (d, J=49.9 Hz, 2H), 1.52 (d, J=9.9 Hz, 2H). LC-MS: m/z 523.6 (M+H)⁺

Compound 153 (General Procedure 2, Step C)

N-(4-(4-hydroxy-4-(3-methylpyridin-2-yl)piperidine-1-carbonyl)phenyl)quinoline-8-sulfonamide

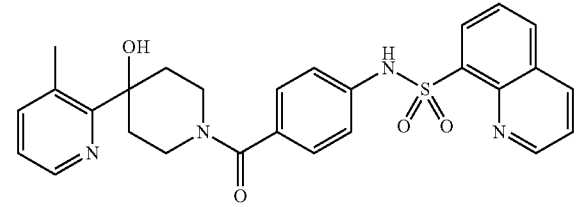 [SMILES: Cc1cccnc1C1(O)CCN(C(=O)c2ccc(NS(=O)(=O)c3cccc4cccnc34)cc2)CC1]

¹H NMR (CHLOROFORM-d) δ: 9.18 (dd, J=4.3, 1.7 Hz, 1H), 8.56 (s, 1H), 8.43-8.36 (m, 2H), 8.33 (dd, J=8.4, 1.8 Hz, 1H), 8.07 (dd, J=8.3, 1.3 Hz, 1H), 7.69-7.59 (m, 2H), 7.53 (d, J=7.1 Hz, 1H), 7.26-7.18 (m, 3H), 7.14-7.08 (m, 2H), 6.71 (s, 1H), 4.65 (s, 1H), 3.64 (s, 2H), 3.35 (s, 1H), 2.51 (s, 3H), 2.39 (s, 1H), 2.24 (dd, J=10.2, 4.5 Hz, 1H), 1.56 (m, 2H). LC-MS: m/z 503.6 (M+H)⁺

Compound 159 (General Procedure 2, Step C)

N-(4-(4-hydroxy-4-(2-(trifluoromethyl)pyridin-3-yl)piperidine-1-carbonyl)phenyl)quinoline-8-sulfonamide

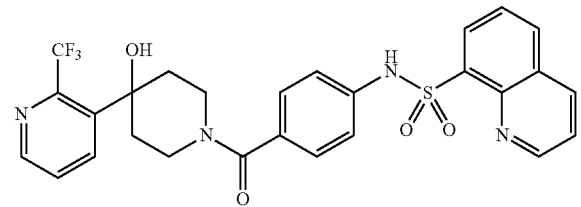 [SMILES: O=C(c1ccc(NS(=O)(=O)c2cccc3cccnc23)cc1)N1CCC(O)(c2cccnc2C(F)(F)F)CC1]

¹H NMR (CHLOROFORM-d) δ: 9.15 (dd, J=1.3, 4.3 Hz, 1H), 8.62 (d, J=4.4 Hz, 1H), 8.42-8.26 (m, 2H), 8.11-7.92 (m,

2H), 7.69-7.55 (m, 2H), 7.47 (dd, J=4.4, 8.2 Hz, 1H), 7.22-7.06 (m, 4H), 3.61-3.40 (m, 6H), 3.40-3.17 (m, 2H), 2.07 (br. s., 1H), 2.04-1.74 (m, 5H). LC-MS: m/z 557.6 (M+H)$^+$

Compound 217 (General Procedure 2, Step C)

N-(4-(4-(2-fluoropyridin-3-yl)-4-hydroxypiperidine-1-carbonyl)phenyl)quinoline-8-sulfonamide

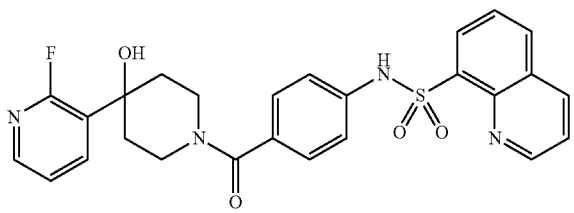 [SMILES: O=C(c1ccc(NS(=O)(=O)c2cccc3cccnc23)cc1)N1CCC(O)(c2cccnc2F)CC1]

$^1$H NMR (CHLOROFORM-d) δ: 9.17 (dd, J=1.8, 4.4 Hz, 1H), 8.64 (br. s., 1H), 8.42-8.27 (m, 2H), 8.13 (td, J=1.6, 4.7 Hz, 1H), 8.06 (dd, J=1.3, 8.4 Hz, 1H), 7.94 (ddd, J=1.9, 7.7, 10.1 Hz, 1H), 7.69-7.55 (m, 2H), 7.26-7.16 (m, 3H), 7.14-7.05 (m, 2H), 4.58 (br. s., 1H), 3.67-3.38 (m, 2H), 3.23 (br. s., 1H), 2.22-2.09 (br. s., 5H). LC-MS: m/z 507.5 (M+H)$^+$ Compound 206

N-(4-(4-hydroxy-4-(pyridin-4-yl)piperidine-1-carbonyl)phenyl)quinoline-8-sulfonamide

$^1$H NMR (CHLOROFORM-d) δ: 9.19-9.14 (m, 1H), 8.62 (s, 2H), 8.39 (d, J=7.3 Hz, 1H), 8.32 (d, J=8.3 Hz, 1H), 8.07 (d, J=3.9 Hz, 2H), 7.68-7.58 (m, 2H), 7.44 (s, 2H), 7.23 (d, J=8.5 Hz, 2H), 7.12 (d, J=8.5 Hz, 2H), 4.66 (s, 1H), 3.68 (s, 1H), 3.49 (s, 1H), 3.28 (s, 1H), 1.87-1.64 (m, 4H). LC-MS: m/z 489.4 (M+H)$^+$

Compound 161

N-(4-(4-(3-chloropyridin-4-yl)-4-hydroxypiperidine-1-carbonyl)phenyl)quinoline-8-sulfonamide

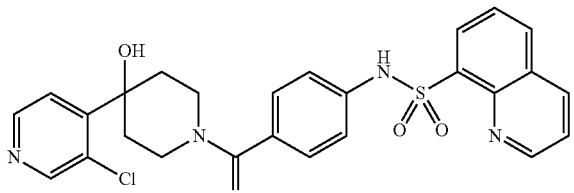

$^1$H NMR (CHLOROFORM-d) δ: 9.17 (dd, J=4.2, 1.5 Hz, 1H), 8.62 (s, 1H), 8.55 (s, 1H), 8.50 (s, 1H), 8.38 (dd, J=7.3, 1.1 Hz, 1H), 8.32 (dd, J=8.3, 1.5 Hz, 1H), 8.07 (d, J=8.2 Hz, 1H), 7.68-7.58 (m, 2H), 7.54 (d, J=4.9 Hz, 1H), 7.21 (d, J=8.5 Hz, 2H), 7.11 (d, J=8.5 Hz, 2H), 4.61 (s, 1H), 3.65 (d, J=19.1 Hz, 1H), 3.25 (s, 2H), 2.83 (s, 1H), 2.41 (d, J=57.6 Hz, 2H), 1.84 (s, 1H). LC-MS: m/z 523.6 (M+H)$^+$

Compound 377 (General Procedure 2, Step C)

(4-hydroxy-4-(isothiazol-4-yl)piperidin-1-yl)(4-((quinolin-8-ylsulfonyl)methyl)phenyl)methanone

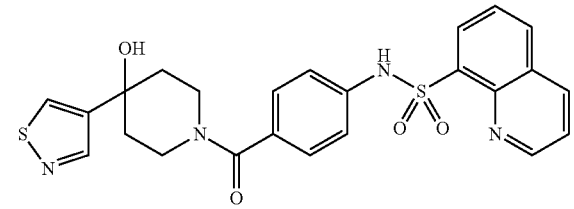 [SMILES: O=C(c1ccc(NS(=O)(=O)c2cccc3cccnc23)cc1)N1CCC(O)(c2cnsc2)CC1]

$^1$H NMR (CHLOROFORM-d) δ: 9.15 (d, J=2.7 Hz, 1H), 8.39-8.46 (m, 2H), 8.38 (s, 1H), 8.18 (d, J=8.3 Hz, 1H), 7.62-7.71 (m, 2H), 7.17-7.25 (m, 5H), 4.45 (br. s., 1H), 3.49 (br. s., 2H), 2.00 (br. s., 3H), 1.81 (br. s., 1H), 1.31 (br. s., 1H). LC-MS: m/z 495.6 (M+H)$^+$

General Procedure 3:

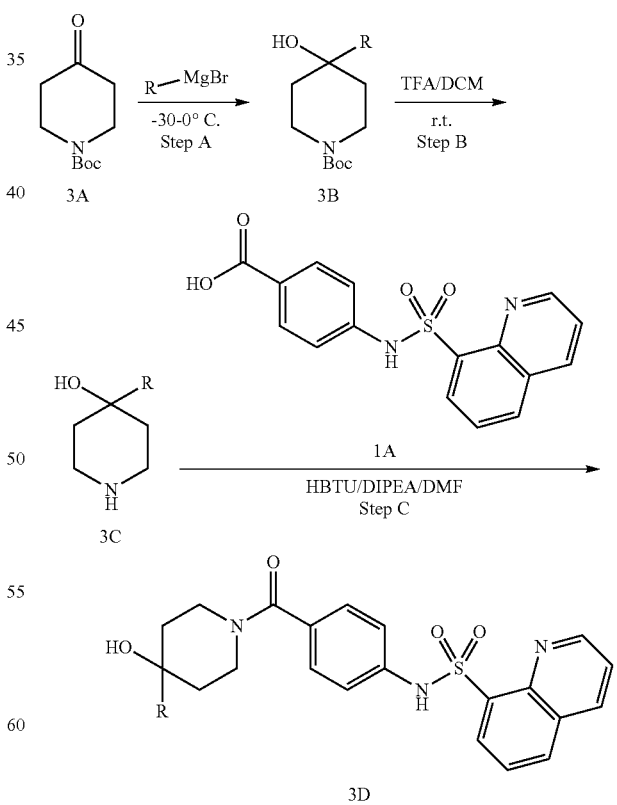

Step A:
To a solution of tert-butyl 4-oxopiperidine-1-carboxylate (1 eq.) in THF was added dropwise the corresponding RMgBr solution in THF (4 eq.) via a syringe at −30° C. After the addition, the resulting mixture was stirred at −30° C. under N$_2$ for 2 h, then allowed to warm to r.t. The reaction mixture was quenched by satd. NH$_4$Cl solution, and the resulting mixture was extracted with EtOAc (50 mL, 30 mL). The combined organic phase was washed with brine, dried over anhydrous Na$_2$SO$_4$ and concentrated in vacuo. The residue was purified by column chromatography (PE/EtOAc) to give the desired compound 3B.

Step B:

To a solution of compound 3B (1 eq.) in DCM, was added TFA (10 eq.), the reaction mixture was stirred at room temperature for about 2 hours, when LCMS detected no s.m. The reaction mixture was concentrated to afford the desired product 3C. The crude product was used for the next step directly without further purification.

Step C:

To a round-bottomed flask was added compound 3C (1 eq.), DMF (5 mL), DIPEA (3.0 eq.), HBTU (1.2 eq.), and 1A (1 eq.) sequentially. The reaction mixture was stirred at room temperature overnight or until TLC indicated that s.m. was consumed. The mixture was diluted with brine, extracted with ethyl acetate, the organic layer was dried with anhydrous Na$_2$SO$_4$, filtered, and filtrate was concentrated. The desired product was purified by a standard method.

Compound 214 (General procedure 3, Step C)

N-(4-(4-hydroxy-4-isopropylpiperidine-1-carbonyl)phenyl)quinoline-8-sulfonamide

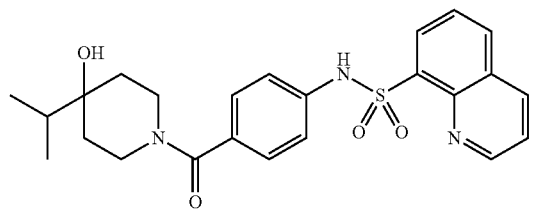 [SMILES: CC(C)C1(O)CCN(C(=O)c2ccc(NS(=O)(=O)c3cccc4cccnc34)cc2)CC1]

$^1$H NMR (CHLOROFORM-d) δ: 9.23 (s, 1H), 8.96 (s, 1H), 8.48-8.34 (m, 2H), 8.10 (d, J=8.1 Hz, 1H), 7.76-7.61 (m, 2H), 7.18 (d, J=8.4 Hz, 2H), 7.13 (d, J=8.5 Hz, 2H), 4.48 (s, 1H), 3.50 (s, 1H), 3.33 (s, 1H), 3.11 (s, 1H), 1.65-1.56 (m, 1H), 1.41 (d, J=53.9 Hz, 4H), 0.92 (d, J=6.9 Hz, 6H). LC-MS: m/z 454.6 (M+H)$^+$

Compound 260 (General procedure 3, Step C)

N-(4-(4-cyclopropyl-4-hydroxypiperidine-1-carbonyl)phenyl)quinoline-8-sulfonamide

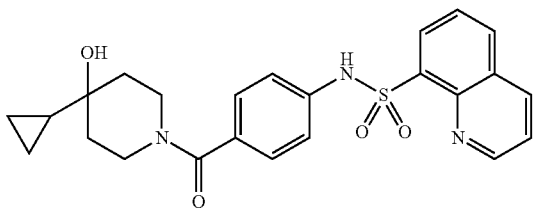 [SMILES: O=C(c1ccc(NS(=O)(=O)c2cccc3cccnc23)cc1)N1CCC(O)(C2CC2)CC1]

$^1$H NMR (CHLOROFORM-d) δ: 9.17 (dd, J=4.3, 1.7 Hz, 1H), 8.58 (s, 1H), 8.39 (dd, J=7.3, 1.3 Hz, 1H), 8.33 (dd, J=8.4, 1.7 Hz, 1H), 8.07 (dd, J=8.2, 1.3 Hz, 1H), 7.69-7.59 (m, 2H), 7.19 (d, J=8.6 Hz, 2H), 7.10 (d, J=8.6 Hz, 2H), 5.28 (t, J=7.0 Hz, 1H), 3.65 (t, J=6.4 Hz, 4H), 3.32 (s, 2H), 2.40-2.22 (m, 4H), 2.14 (dd, J=23.1, 12.0 Hz, 2H). LC-MS: m/z 452.6 (M+H)$^+$

Compound 183 (General procedure 3, Step C)

N-(4-(4-hydroxy-4-propylpiperidine-1-carbonyl)phenyl)quinoline-8-sulfonamide

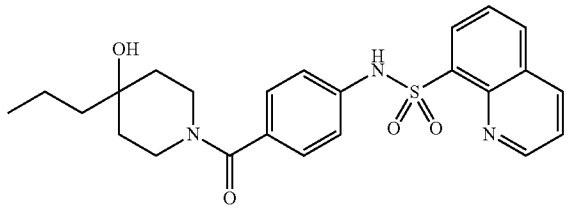 [SMILES: CCCC1(O)CCN(C(=O)c2ccc(NS(=O)(=O)c3cccc4cccnc34)cc2)CC1]

$^1$H NMR (CHLOROFORM-d) δ: 9.17 (dd, J=4.3, 1.7 Hz, 1H), 8.55 (s, 1H), 8.38 (dd, J=7.3, 1.3 Hz, 1H), 8.32 (dd, J=8.4, 1.7 Hz, 1H), 8.06 (dd, J=8.2, 1.3 Hz, 1H), 7.68-7.58 (m, 2H), 7.17 (d, J=8.6 Hz, 2H), 7.08 (d, J=8.6 Hz, 2H), 4.34 (s, 1H), 3.52-3.10 (m, 3H), 1.46 (dd, J=10.2, 4.6 Hz, 4H), 1.33 (ddd, J=26.6, 11.0, 7.3 Hz, 4H), 0.95 (t, J=7.0 Hz, 3H). LC-MS: m/z 454.6 (M+H)$^+$ Compound 140 (General procedure 3, Step C)

N-(4-(4-hydroxy-4-isobutylpiperidine-1-carbonyl)phenyl)quinoline-8-sulfonamide

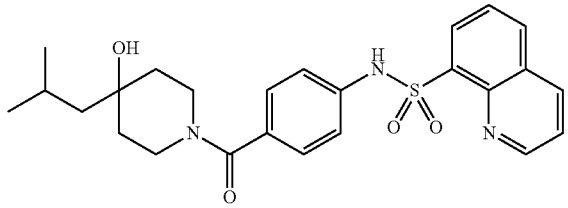 [SMILES: CC(C)CC1(O)CCN(C(=O)c2ccc(NS(=O)(=O)c3cccc4cccnc34)cc2)CC1]

$^1$H NMR (CHLOROFORM-d) δ: 9.17 (dd, J=4.3, 1.7 Hz, 1H), 8.56 (s, 1H), 8.38 (dd, J=7.3, 1.3 Hz, 1H), 8.32 (dd, J=8.4, 1.6 Hz, 1H), 8.06 (dd, J=8.2, 1.3 Hz, 1H), 7.68-7.58 (m, 2H), 7.17 (d, J=8.5 Hz, 2H), 7.09 (d, J=8.6 Hz, 2H), 4.34 (s, 1H), 3.43 (s, 1H), 3.35 (s, 1H), 3.20 (s, 1H), 1.83 (tt, J=13.0, 6.5 Hz, 1H), 1.49 (s, 2H), 1.41 (d, J=6.0 Hz, 2H), 1.31 (d, J=23.9 Hz, 2H), 0.98 (d, J=6.6 Hz, 6H). LC-MS: m/z 468.6 (M+H)$^+$

Compound 195 (General procedure 3, Step C)

N-(4-(4-(tert-butyl)-4-hydroxypiperidine-1-carbonyl)phenyl)quinoline-8-sulfonamide

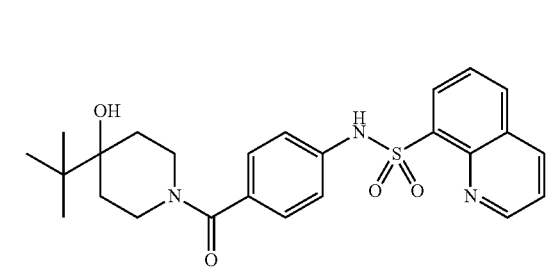 [SMILES: CC(C)(C)C1(O)CCN(C(=O)c2ccc(NS(=O)(=O)c3cccc4cccnc34)cc2)CC1]

$^1$H NMR (CHLOROFORM-d) δ: 9.19 (dd, J=4.3, 1.5 Hz, 1H), 8.71 (s, 1H), 8.40 (dd, J=7.3, 1.3 Hz, 1H), 8.35 (dd,

J=8.3, 1.4 Hz, 1H), 8.08 (dd, J=8.2, 1.2 Hz, 1H), 7.70-7.60 (m, 2H), 7.18 (d, J=8.5 Hz, 2H), 7.10 (d, J=8.5 Hz, 2H), 4.52 (s, 1H), 3.54 (s, 1H), 3.32 (s, 1H), 3.04 (s, 1H), 1.71 (s, 4H), 0.93 (s, 9H). LC-MS: m/z 468.6 (M+H)$^+$

Compound 124 (General procedure 3, Step C)

N-(4-(4-(cyclobutylmethyl)-4-hydroxypiperidine-1-carbonyl)phenyl)quinoline-8-sulfonamide

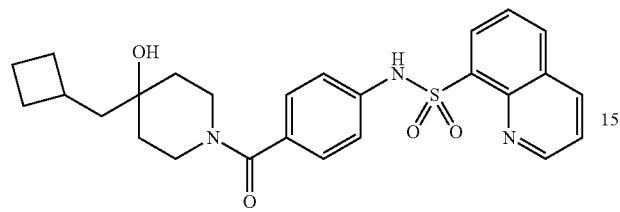

$^1$H NMR (CHLOROFORM-d) δ: 9.17 (dd, J=4.2, 1.5 Hz, 1H), 8.56 (s, 1H), 8.38 (dd, J=7.3, 1.3 Hz, 1H), 8.32 (dd, J=8.3, 1.5 Hz, 1H), 8.06 (dd, J=8.2, 1.2 Hz, 1H), 7.68-7.58 (m, 2H), 7.17 (d, J=8.5 Hz, 2H), 7.08 (d, J=8.5 Hz, 2H), 4.33 (s, 1H), 3.51-3.08 (m, 3H), 2.57-2.43 (m, 1H), 2.14-2.01 (m, 2H), 1.91 (dd, J=18.4, 9.5 Hz, 1H), 1.79 (dd, J=10.5, 8.5 Hz, 1H), 1.76-1.64 (m, 4H), 1.61 (s, 2H), 1.43-1.35 (m, 2H). LC-MS: m/z 480.6 (M+H)$^+$

General Procedure 4:

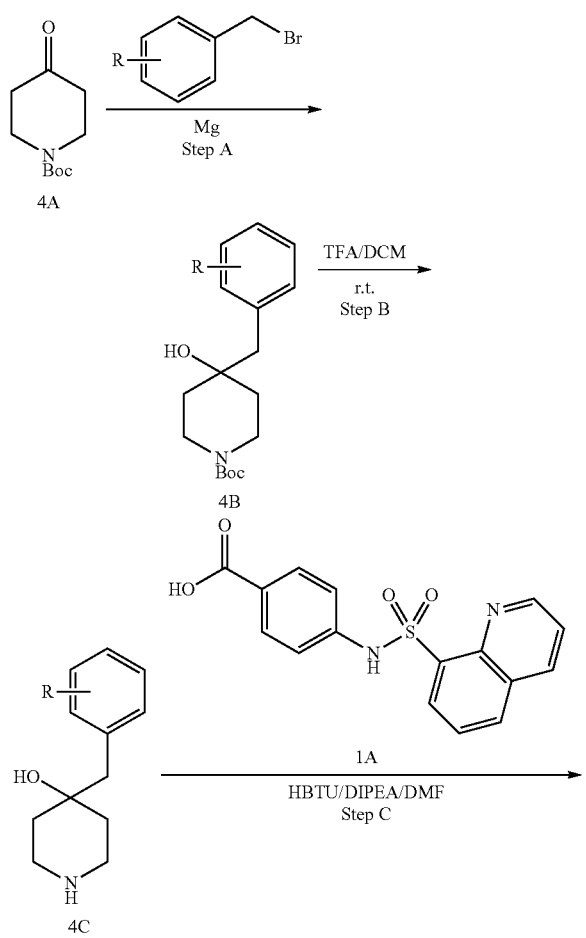

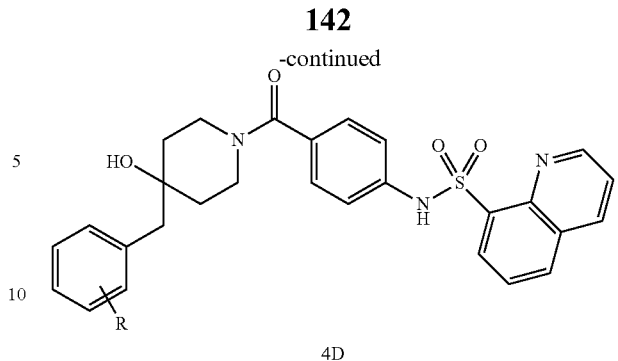

4D

Step A:

To a solution of diethyl ether (freshly distilled from sodium/benzophenone) containing a catalytic amount of 1,2-dibromoethane was added magnesium turnings (6.6 eq.) under argon and the resulting mixture was stirred at room temperature for 30 min A solution of substituted benzyl bromide/chloride (5 eq.) in dry diethyl ether was then added slowly to the reaction mixture over a period of 2 h and stirring was continued at room temperature for additional 2 h. The reaction mixture was then cooled to 0° C., when compound 4A (1 eq.) taken in a solution of dry diethyl ether was slowly added to the reaction mixture under argon atmosphere. The resulting reaction mixture was allowed to stir at room temperature for another 4 hrs. The progress of the reaction was monitored by TLC. Upon completion of the reaction, the mixture was quenched with satd. NH$_4$Cl solution, and extracted with EtOAc. The combined organic layers were washed with water, dried over Na$_2$SO$_4$ and concentrated under reduced pressure to give the crude product. The crude product was then purified by column chromatography using silica gel (100-200 mesh) and 20% EtOAc in hexane to afford desired compound 4B.

Step B:

Compound 4B (1 eq.) was dissolved in DCM and cooled to 0° C., when TFA (10 eq.) was added at 0° C. The reaction mixture was allowed to warm to r.t. and stirred for 3-4 hrs at r.t. until LCMS and TLC confirmed completion of reaction. The reaction mixture was concentrated to get the crude product which was triturated 3 to 4 times with DCM and n-pentane to afford compound 4C.

Step C:

To a solution of compound 4C (1.2 eq.) in DMF, 1A (1 eq.) was added followed by addition of DIPEA (2 eq.), HATU (1.2 eq.) and DMAP (0.1 eq.) at room temperature under nitrogen atmosphere. The reaction mixture was allowed to stir at room temperature for 16 hrs. The progress of the reaction was monitored by TLC and upon completion of reaction the crude mixture was diluted with EtOAc and washed sequentially with water and saturated sodium bicarbonate solution. The resulting organic layer was then separated, dried over Na$_2$SO$_4$ and concentrated under reduced pressure to give the crude product which was purified by a standard method to afford desired compound 4D.

Compound 110 (General procedure 4, Step C)

N-(4-(4-(2-fluorobenzyl)-4-hydroxypiperidine-1-carbonyl)phenyl)quinoline-8-sulfonamide

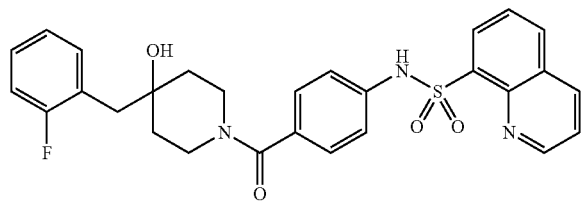 [SMILES: O=C(c1ccc(NS(=O)(=O)c2cccc3cccnc23)cc1)N1CCC(O)(Cc2ccccc2F)CC1]

$^1$H NMR (CHLOROFORM-d) δ: 9.14 (s, 1H), 8.51 (bs, 1H), 8.32 (dd, 2H, J=6.8 Hz & J=7.6 Hz), 8.03 (d, 1H, J=8 Hz), 7.61-7.57 (m, 2H), 7.18-7.05 (m, 8H), 4.36 (bs, 1H), 3.44 (m, 1H), 3.27 (m, 1H), 3.13 (m, 1H), 2.96-2.88 (m, 2H), 2.80 (s, 2H), 1.33-1.25 (m, 3H). LC-MS: m/z 520.2 (M+H)$^+$

Compound 105 (General procedure 4, Step C)

N-(4-(4-(3-fluorobenzyl)-4-hydroxypiperidine-1-carbonyl)phenyl)quinoline-8-sulfonamide

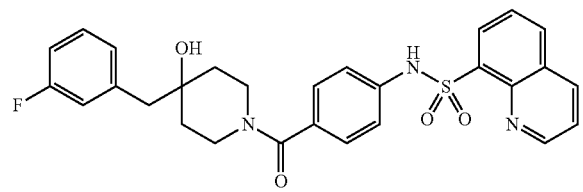 [SMILES: O=C(c1ccc(NS(=O)(=O)c2cccc3cccnc23)cc1)N1CCC(O)(Cc2cccc(F)c2)CC1]

$^1$H NMR (DMSO-d$_6$) δ: 10.40 (s, 1H), 9.13-9.12 (m, 1H), 8.45 (dd, 2H, J=8.4 Hz & J=7.2 Hz), 8.27 (d, 1H, J=8 Hz), 7.74-7.69 (m, 2H), 7.29-7.25 (m, 1H), 7.18-6.98 (m, 7H), 4.49 (s, 1H), 4.06 (m, 1H), 3.62-3.61 (m, 1H), 3.18-3.12 (m, 2H), 2.68 (s, 2H), 1.38-1.33 (m, 4H). LC-MS: m/z 520.2 (M+H)$^+$

Compound 118 (General procedure 4, Step C)

N-(4-(4-hydroxy-4-(3-methylbenzyl)piperidine-1-carbonyl)phenyl)quinoline-8-sulfonamide

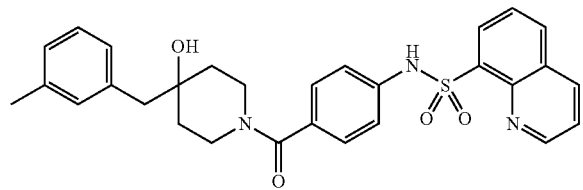 [SMILES: Cc1cccc(CC2(O)CCN(C(=O)c3ccc(NS(=O)(=O)c4cccc5cccnc45)cc3)CC2)c1]

$^1$H NMR (CHLOROFORM-d) δ: 9.15-9.13 (m, 1H), 8.52 (bs, 1H), 8.36-8.28 (m, 2H), 8.03 (d, 1H, J=7.6 Hz), 7.63-7.57 (m, 2H), 7.22-7.05 (m, 5H), 6.99-6.93 (m, 2H), 4.37 (bs, 1H), 3.90-3.45 (m, 2H), 3.27-2.98 (m, 2H), 2.70 (s, 2H), 2.33 (s, 2H), 1.51-132 (m, 4H). LC-MS: m/z 516.2 (M+H)$^+$

Compound 108 (General procedure 4, Step C)

N-(4-(4-hydroxy-4-(2-methylbenzyl)piperidine-1-carbonyl)phenyl)quinoline-8-sulfonamide

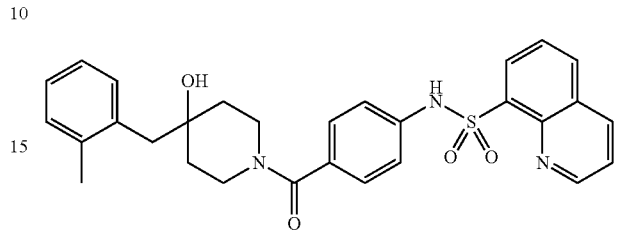

$^1$H NMR (CHLOROFORM-d) δ: 9.14-9.13 (m, 1H), 8.52 (bs, 1H), 8.36-8.28 (m, 2H), 8.03 (d, 1H, J=8.4 Hz), 7.63-7.57 (m, 2H), 7.18-7.05 (m, 8H), 4.35-4.48 (m, 1H), 3.60-2.95 (m, 3H), 2.80-2.79 (m, 3H), 2.33 (s, 3H), 1.52-1.39 (m, 4H). LC-MS: m/z 516.2 (M+H)$^+$

Compound 116 (General procedure 4, Step C)

N-(4-(4-hydroxy-4-(2-methoxybenzyl)piperidine-1-carbonyl)phenyl)quinoline-8-sulfonamide

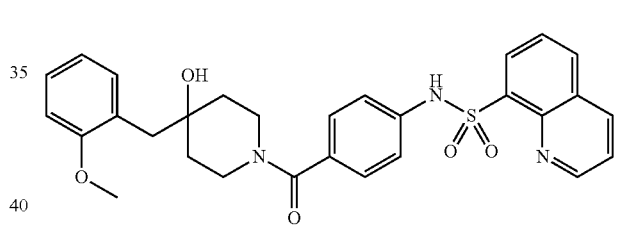

$^1$H NMR (DMSO-d$_6$) δ: 9.15-9.14 (m, 1H), 8.51 (bs, 1H), 8.36-8.28 (dd, 2H, J=4.2 Hz & J=8 Hz), 8.03 (d, 1H, J=8 Hz), 7.63-7.57 (m, 2H), 7.24-6.98 (m, 6H), 6.94-6.89 (m, 2H), 4.33 (bs, 1H), 3.83 (s, 3H), 3.41-3.12 (m, 3H), 2.85-2.83 (m, 3H), 1.57-1.29 (m, 4H). LC-MS: m/z 532.6 (M+H)$^+$

Compound 135 (General procedure 4, Step C)

N-(4-(4-hydroxy-4-(3-methoxybenzyl)piperidine-1-carbonyl)phenyl)quinoline-8-sulfonamide

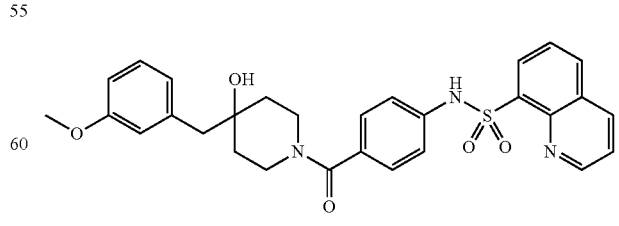

$^1$H NMR (CHLOROFORM-d) δ: 9.15-9.14 (m, 1H), 8.51 (s, 1H), 8.32 (dd, 2H, J=7.2 Hz & J=8 Hz), 8.03 (d, 1H, J=8 Hz), 7.63-7.57 (m, 2H), 7.23-7.05 (m, 5H), 6.90-6.68 (m,

3H), 4.38 (m, 1H), 3.79 (s, 3H), 3.60-2.98 (m, 4H), 2.71 (s, 2H), 1.54-1.40 (m, 4H). LC-MS: m/z 532.6 (M+H)⁺

Compound 152 (General procedure 4, Step C)

N-(4-(4-hydroxy-4-(3-(trifluoromethyl)benzyl)piperidine-1-carbonyl)phenyl)quinoline-8-sulfonamide

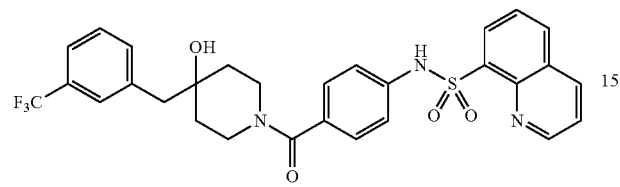

¹H NMR (CHLOROFORM-d) δ: 9.14-9.13 (m, 1H), 8.53 (bs, 1H), 8.32 (dd, 2H, J=6.8 Hz, J=8.4 Hz), 8.03 (d, 1H, J=8 Hz), 7.63-7.50 (m, 3H), 7.45-7.33 (m, 3H), 7.16-7.00 (m, 4H), 4.38 (m, 1H), 3.50-3.45 (m, 1H), 3.28-2.91 (m, 2H), 2.90-2.79 (m, 3H), 1.58-1.33 (m, 4H). LC-MS: m/z 570.2 (M+H)⁺

General Procedure 5:

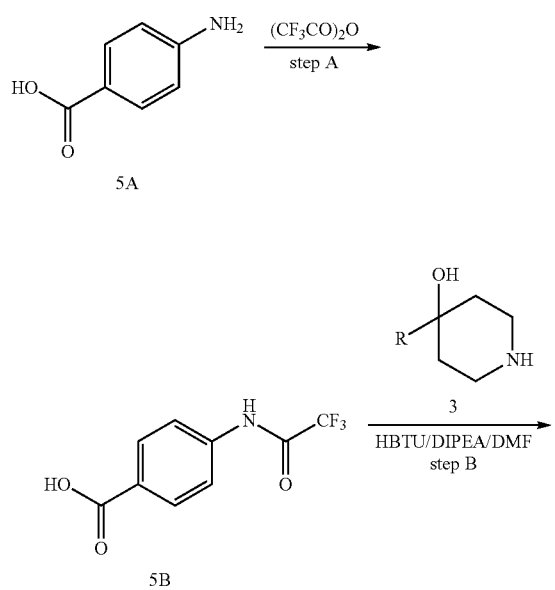

5C-1, R = 2-ClPh
5C-2, R = iBu
5C-3, R = 2,3-diFPh
5C-4, R = Bn

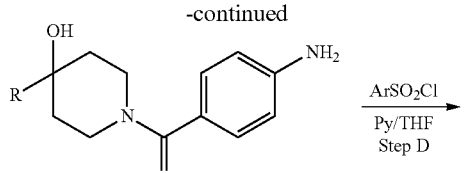

1B, R = 2-ClPh
1C, R = iBu
1D, R = 2,3-diFPh
1E, R = Bn

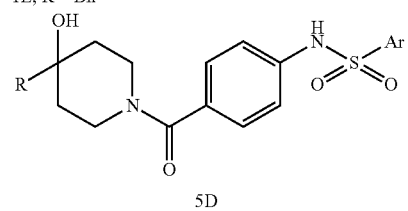

5D

Step A: 4-(2,2,2-trifluoroacetamido)benzoic acid (5B)

To a mixture of 4-aminobenzoic acid (44 g, 0.32 mmol) in TFA (300 mL) was added trifluoroacetic anhydride (100 mL) dropwise, keeping the temperature below 10° C. After the addition, the mixture was stirred at room temperature overnight. The mixture was then poured into crushed ice, the precipitate that formed was filtered, and was dried in vacuo overnight to give the title compound (2, 72 g). ¹H NMR (DMSO-d₆) δ: 11.52 (s, 1H), 7.93-8.07 (m, 2H), 7.76-7.86 (m, 2H). LC-MS: m/z 234.1 (M+H)⁺

Step B:

To a round-bottomed flask was added the corresponding compound 3 (21 mmol, 1 eq.), DMF (50 mL), DIPEA (3.0 eq.), HBTU (1.2 eq.), and intermediate 2 (5 g, 21 mmol, 1 eq.) sequentially. The reaction mixture was stirred at room temperature overnight or until TLC indicated that s.m. was consumed. The mixture was diluted with brine, extracted with ethyl acetate, the organic layer was dried with anhydrous Na₂SO₄, filtered, and the filtrate was concentrated. The desired product was purified by silica gel chromatography. 5C-1, LC-MS: m/z 427.8 (M+H)⁺; 5C-2, LC-MS: m/z 373.4 (M+H)⁺; 5C-3, LC-MS: m/z 429.4 (M+H)⁺; 5C-4, LC-MS: m/z 407.4 (M+H)⁺

Step C:

To a mixture of the corresponding compound 5C (1 eq.) in methanol, was added K₂CO₃ (2 eq.). The mixture was stirred at room temperature overnight, when TLC indicated consumption of s.m. and product formation. The mixture was then concentrated in vacuo, partitioned between brine and EtOAc, the organic layer was separated and concentrated to give the crude product. Further purification was done by a standard method.

1B: 4-aminophenyl)(4-(2-chlorophenyl)-4-hydroxypiperidin-1-yl)methanone

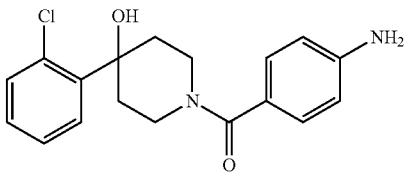 [SMILES: Nc1ccc(C(=O)N2CCC(O)(c3ccccc3Cl)CC2)cc1]

¹H NMR (CHLOROFORM-d) δ: 7.55 (dd, J=7.9, 1.7 Hz, 1H), 7.41 (dd, J=7.8, 1.3 Hz, 1H), 7.29-7.34 (m, 3H), 7.23-7.28 (m, 1H), 6.66-6.71 (m, 2H), 4.59 (br. s., 1H), 3.88 (br. s., 2H), 3.50 (br. s., 2H), 2.97 (br. s., 1H), 2.33 (br. s., 2H), 2.20-2.29 (m, 1H), 1.97-2.16 (m, 2H). LC-MS: m/z 331.8 (M+H)⁺

1C: (4-aminophenyl)(4-hydroxy-4-isobutylpiperidin-1-yl)methanone

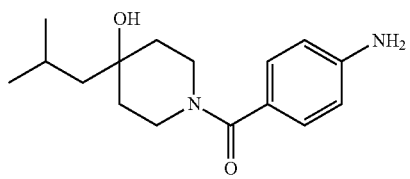 [SMILES: CC(C)CC1(O)CCN(C(=O)c2ccc(N)cc2)CC1]

¹H NMR (CHLOROFORM-d) δ: 7.21-7.33 (m, 2H), 6.63-6.72 (m, 2H), 3.35 (br. s., 2H), 1.87 (dt, J=12.9, 6.4 Hz, 1H), 1.62 (br. s., 4H), 1.44 (d, J=5.9 Hz, 2H), 1.00 (d, J=6.7 Hz, 6H). LC-MS: m/z 277.4 (M+H)⁺

1D: (4-aminophenyl)(4-(2,3-difluorophenyl)-4-hydroxypiperidin-1-yl)methanone

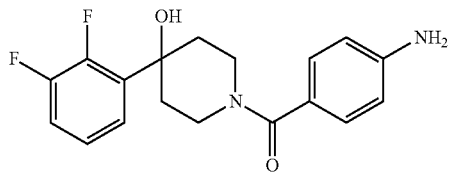 [SMILES: Nc1ccc(C(=O)N2CCC(O)(c3cccc(F)c3F)CC2)cc1]

LC-MS: m/z 333.3 (M+H)⁺

1E: (4-aminophenyl)(4-benzyl-4-hydroxypiperidin-1-yl)methanone

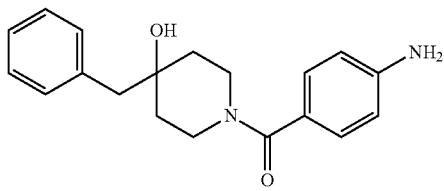 [SMILES: Nc1ccc(C(=O)N2CCC(O)(Cc3ccccc3)CC2)cc1]

¹H NMR (DMSO-d₆) δ: 7.44 (d, 2H, J=8 Hz), 7.32-7.16 (m, 5H), 6.66 (d, 2H, J=8.4 Hz), 4.80 (m, 2H), 4.37 (m, 2H), 2.29 (s, 2H). LC-MS: m/z 311.4 (M+H)⁺

Step D:

To a suspension of the 1B-1E (0.5 mmol) and sulfonyl chloride (80 mg, 0.55 mmol) in 30 mL of anhydrous THF, was added pyridine (1.0 mmol) at room temperature. The resulting mixture was heated and stirred at reflux for 6 h. The reaction mixture was cooled to room temperature, then extracted with EtOAc (100 mL×2). The combined organic phase was washed with brine, dried over anhy. Na₂SO₄ and concentrated in vacuo. The title compound was obtained by a standard purification method.

Compound 155 (General procedure 5, Step D)

N-(4-(4-(2-chlorophenyl)-4-hydroxypiperidine-1-carbonyl)phenyl)benzo[d]thiazole-4-sulfonamide

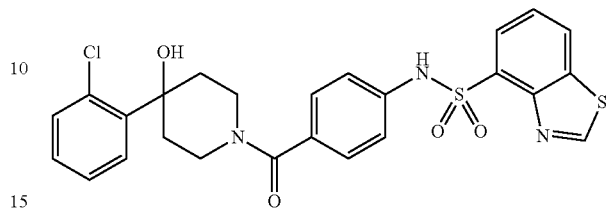

¹H NMR (CHLOROFORM-d) δ: 9.31 (s, 1H), 8.19 (d, J=8.1 Hz, 1H), 8.10 (d, J=7.5 Hz, 1H), 7.94 (s, 1H), 7.54 (dd, J=15.3, 7.6 Hz, 2H), 7.40 (dd, J=7.6, 1.3 Hz, 1H), 7.32 (d, J=6.5 Hz, 1H), 7.27 (d, J=9.2 Hz, 1H), 7.24 (d, J=8.2 Hz, 2H), 7.13 (d, J=7.9 Hz, 2H), 4.61 (s, 1H), 3.58 (s, 2H), 3.32 (s, 1H), 2.42-1.96 (m, 4H). LC-MS: m/z 528.6 (M+H)⁺

Compound 179 (General procedure 5, Step D)

N-(4-(4-(2-chlorophenyl)-4-hydroxypiperidine-1-carbonyl)phenyl)-5-fluoroquinoline-8-sulfonamide

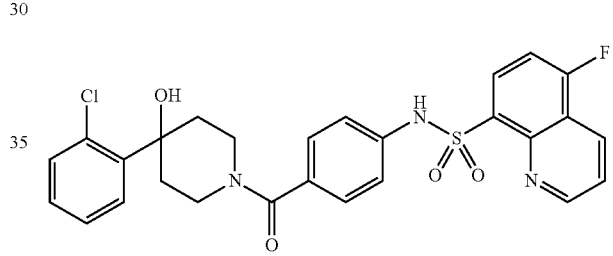

¹H NMR (CHLOROFORM-d) δ: 1.72 (br. s., 2H), 1.96 (br. s., 1H), 2.18 (br. s., 1H), 2.33 (br. s., 1H), 2.96 (br. s., 1H), 3.28 (br. s., 1H), 3.57 (br. s., 2H), 4.61 (br. s., 1H), 7.08 (d, J=8.60 Hz, 2H), 7.21 (d, J=8.33 Hz, 2H), 7.23-7.28 (m, 2H), 7.29-7.32 (m, 1H), 7.38 (dd, J=7.52, 1.34 Hz, 1H), 7.51 (dd, J=7.66, 1.48 Hz, 1H), 7.70 (dd, J=8.33, 4.30 Hz, 1H), 8.34-8.43 (m, 2H), 8.57 (dd, J=8.46, 1.48 Hz, 1H), 9.19-9.24 (m, 1H). LC-MS: m/z 540.1 (M+H)⁺

Compound 259

N-(4-(4-(2-chlorophenyl)-4-hydroxypiperidine-1-carbonyl)phenyl)-2-fluoroquinoline-5-sulfonamide

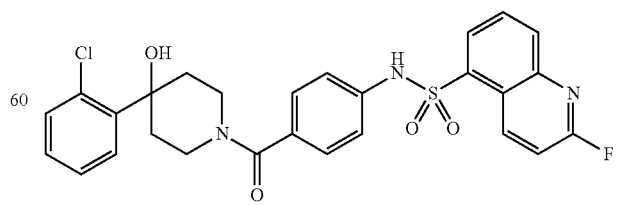

¹H NMR (CHLOROFORM-d) δ: 9.22 (t, J=8.0 Hz, 1H), 8.98 (br. s., 1H), 8.21 (d, J=8.0 Hz, 1H), 8.12 (d, J=8.0 Hz,

1H), 7.72 (t, J=8.0 Hz, 1H), 7.53 (d, J=8.0 Hz, 1H), 7.38 (d, J=8.0 Hz, 1H), 7.28-7.13 (m, 5H), 6.94 (d, J=8.0 Hz, 2H), 4.64 (br. s., 1H), 3.55 (br. s., 2H), 3.35 (br. s., 1H), 3.17 (br. s., 1H), 2.42 (br. s., 1H), 2.21 (s, 1H), 2.08 (s, 1H), 1.95 (s, 1H). LC-MS: m/z 541.1 (M+H)⁺

Compound 244 (General procedure 5, Step D)

N-(4-(4-(2-chlorophenyl)-4-hydroxypiperidine-1-carbonyl)phenyl)benzo[c]isothiazole-7-sulfonamide

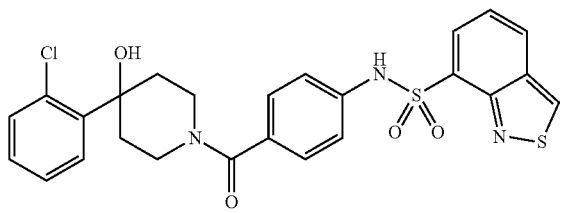 [SMILES: O=C(c1ccc(NS(=O)(=O)c2cccc3csnc23)cc1)N1CCC(O)(c2ccccc2Cl)CC1]

¹H NMR (CHLOROFORM-d) δ: 9.45 (s, 1H), 8.12 (d, J=6.2 Hz, 1H), 8.03 (d, J=8.6 Hz, 1H), 7.89 (s, 1H), 7.51 (dd, J=7.7, 1.5 Hz, 1H), 7.40 (dd, J=7.7, 1.5 Hz, 1H), 7.30-7.35 (m, 2H), 7.26 (dd, J=7.5, 1.6 Hz, 1H), 7.22 (d, J=8.6 Hz, 2H), 7.11 (d, J=8.3 Hz, 2H), 4.59 (br. s., 1H), 3.57 (br. s., 2H), 3.34 (br. s., 2H), 2.26 (br. s., 2H), 2.04 (br. s., 3H). LC-MS: m/z 529.1 (M+H)⁺

Compound 173 (General procedure 5, Step D)

N-(4-(4-hydroxy-4-isobutylpiperidine-1-carbonyl)phenyl)benzo[d]thiazole-4-sulfonamide

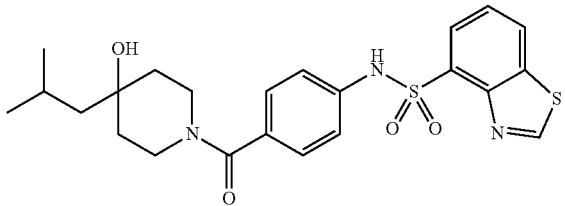

¹H NMR (CHLOROFORM-d) δ: 9.31 (s, 1H), 8.19 (d, J=8.1 Hz, 1H), 8.10 (d, J=7.5 Hz, 1H), 7.93 (s, 1H), 7.54 (t, J=7.9 Hz, 1H), 7.20 (d, J=8.3 Hz, 2H), 7.11 (d, J=8.4 Hz, 2H), 3.28 (s, 2H), 1.83 (dt, J=12.8, 6.5 Hz, 1H), 1.56 (s, 7H), 1.42 (d, J=6.0 Hz, 2H), 0.98 (d, J=6.6 Hz, 6H). LC-MS: m/z 474.6 (M+H)⁺

Compound 378 (General procedure 5, Step D)

N-(4-(4-(2-chlorophenyl)-4-hydroxypiperidine-1-carbonyl)phenyl)-7-fluorobenzo[d]thiazole-4-sulfonamide

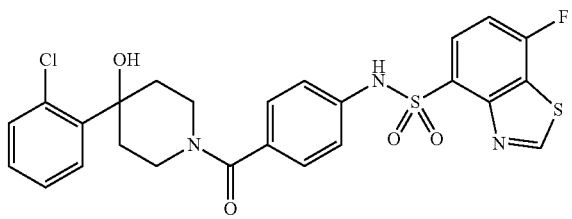 [SMILES: O=C(c1ccc(NS(=O)(=O)c2ccc(F)c3scnc23)cc1)N1CCC(O)(c2ccccc2Cl)CC1]

¹H NMR (DMSO-d₆) δ: 10.87 (s, 1H), 9.73 (s, 1H), 8.19 (dd, J=8.6, 5.1 Hz, 1H), 7.80 (dd, J=7.9, 1.5 Hz, 1H), 7.57 (t, J=8.7 Hz, 1H), 7.32-7.40 (m, 2H), 7.24-7.29 (m, 1H), 7.19-7.23 (m, J=8.6 Hz, 2H), 7.10-7.16 (m, J=8.6 Hz, 2H), 5.41 (s, 1H), 4.30 (br. s., 1H), 3.43 (br. s., 1H), 2.46 (br. s., 2H). LC-MS: m/z 529.1 (M+H)⁺

Compound 203 (General procedure 5, Step D)

5-fluoro-N-(4-(4-hydroxy-4-isobutylpiperidine-1-carbonyl)phenyl)quinoline-8-sulfonamide

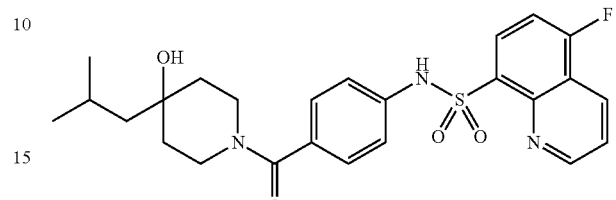

¹H NMR (CHLOROFORM-d) δ: 9.22 (d, J=2.8 Hz, 1H), 8.58 (dd, J=8.5, 1.3 Hz, 1H), 8.44-8.32 (m, 2H), 7.71 (dd, J=8.5, 4.3 Hz, 1H), 7.18 (d, J=8.3 Hz, 2H), 7.08 (d, J=8.3 Hz, 2H), 4.33 (s, 1H), 3.31 (s, 3H), 1.83 (dt, J=12.8, 6.3 Hz, 1H), 1.57 (s, 4H), 1.41 (d, J=6.0 Hz, 2H), 0.98 (d, J=6.6 Hz, 6H). LC-MS: m/z 486.7 (M+H)⁺

Compound 240 (General procedure 5, Step D)

7-fluoro-N-(4-(4-hydroxy-4-isobutylpiperidine-1-carbonyl)phenyl)benzo[d]thiazole-4-sulfonamide

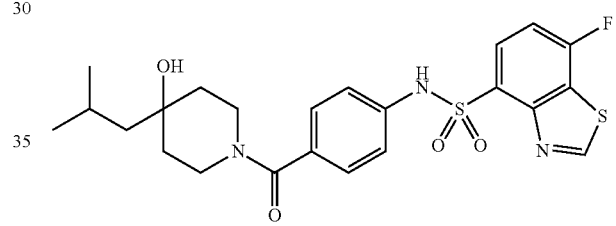

¹H NMR (CHLOROFORM-d) δ: 9.32 (s, 1H), 8.12 (dd, J=8.3, 4.8 Hz, 1H), 7.84 (s, 1H), 7.22-7.27 (m, 1H), 7.20 (d, J=8.6 Hz, 2H), 7.09 (d, J=8.6 Hz, 2H), 4.25-4.46 (m, 1H), 3.42 (br. s., 2H), 3.20 (br. s., 1H), 1.83 (dt, J=12.9, 6.4 Hz, 1H), 1.55-1.70 (m, 3H), 1.51 (br. s., 1H), 1.42 (d, J=6.2 Hz, 2H), 0.98 (d, J=6.4 Hz, 6H). LC-MS: m/z 492.6 (M+H)⁺

Compound 145 (General procedure 5, Step D)

2-amino-6-fluoro-N-(4-(4-hydroxy-4-isobutylpiperidine-1-carbonyl)phenyl)benzo[d]thiazole-4-sulfonamide

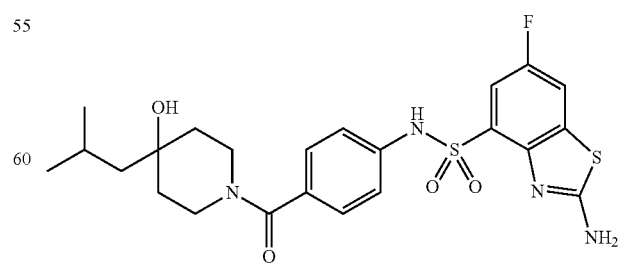

¹H NMR (CHLOROFORM-d) δ: 8.09 (s, 1H), 7.59 (dd, J=8.2, 2.5 Hz, 1H), 7.49 (dd, J=7.5, 2.5 Hz, 1H), 7.25 (d,

J=8.5 Hz, 2H), 7.13 (d, J=8.5 Hz, 2H), 5.98 (d, J=15.1 Hz, 2H), 4.37 (s, 1H), 3.43 (d, J=30.3 Hz, 2H), 3.22 (s, 1H), 1.85 (dt, J=12.9, 6.4 Hz, 1H), 1.49 (d, J=28.9 Hz, 4H), 1.43 (d, J=6.0 Hz, 2H), 0.99 (d, J=6.6 Hz, 6H). LC-MS: m/z 507.78 (M+H)$^+$

Compound 379 (General procedure 5, Step D)

N-(4-(4-hydroxy-4-isobutylpiperidine-1-carbonyl) phenyl)benzo[d]oxazole-4-sulfonamide

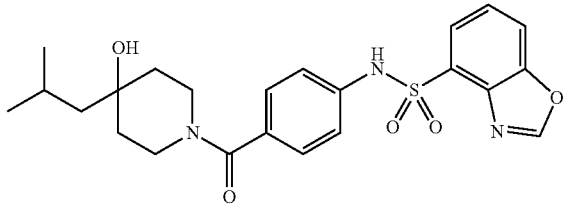 [SMILES: CC(C)CC1(O)CCN(C(=O)c2ccc(NS(=O)(=O)c3cccc4ocnc34)cc2)CC1]

$^1$H NMR (CHLOROFORM-d) δ: 8.33 (s, 1H), 7.92 (d, J=7.7 Hz, 1H), 7.83 (d, J=8.2 Hz, 1H), 7.61 (s, 1H), 7.49 (t, J=8.0 Hz, 1H), 7.22 (d, J=8.4 Hz, 2H), 7.15 (d, J=8.4 Hz, 2H), 4.35 (s, 1H), 3.40 (d, J=25.4 Hz, 2H), 3.21 (s, 1H), 1.89-1.77 (m, 1H), 1.65 (s, 4H), 1.42 (d, J=6.0 Hz, 2H), 0.98 (d, J=6.6 Hz, 6H). LC-MS: m/z 458.72 (M+H)$^+$

Compound 380 (General procedure 5, Step D)

2-amino-3-hydroxy-N-(4-(4-hydroxy-4-isobutylpiperidine-1-carbonyl)phenyl)benzenesulfonamide

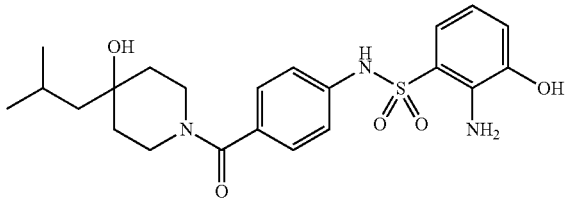 [SMILES: CC(C)CC1(O)CCN(C(=O)c2ccc(NS(=O)(=O)c3cccc(O)c3N)cc2)CC1]

$^1$H NMR (CHLOROFORM-d) δ: 10.54 (s, 1H), 9.95 (s, 1H), 7.24 (d, J=8.6 Hz, 2H), 7.10-7.03 (m, 3H), 6.81 (dd, J=7.7, 1.2 Hz, 1H), 6.45 (t, J=8.0 Hz, 1H), 5.47 (s, 2H), 4.18 (s, 1H), 4.08 (s, 1H), 3.33-2.95 (m, 3H), 1.80 (dp, J=12.7, 6.4 Hz, 1H), 1.44 (d, J=48.4 Hz, 4H), 1.29 (d, J=5.7 Hz, 2H), 0.90 (d, J=6.6 Hz, 6H). LC-MS: m/z 448.69 (M+H)$^+$

Compound 381 (General procedure 5, Step D)

N-(4-(4-(2-chlorophenyl)-4-hydroxypiperidine-1-carbonyl)phenyl)benzo[d]oxazole-4-sulfonamide

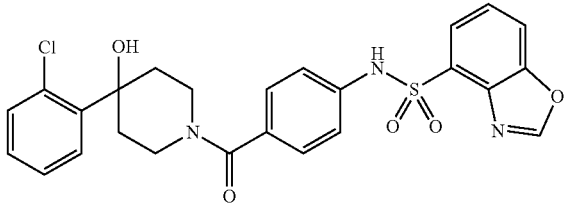 [SMILES: O=C(c1ccc(NS(=O)(=O)c2cccc3ocnc23)cc1)N1CCC(O)(c2ccccc2Cl)CC1]

$^1$H NMR (CHLOROFORM-d) δ: 8.33 (s, 1H), 7.93 (d, J=7.7 Hz, 1H), 7.83 (d, J=8.2 Hz, 1H), 7.70 (s, 1H), 7.56-7.46 (m, 2H), 7.40 (dd, J=7.6, 1.3 Hz, 1H), 7.35-7.30 (m, 1H), 7.26 (d, J=8.5 Hz, 3H), 7.17 (d, J=8.4 Hz, 2H), 4.63 (s, 1H), 3.60 (s, 2H), 3.31 (s, 1H), 2.94 (s, 1H), 2.36 (s, 1H), 2.20 (s, 1H), 2.10 (s, 1H), 1.99 (s, 1H). LC-MS: m/z 512.67 (M+H)$^+$

Compound 382 (General procedure 5, Step D)

2-amino-N-(4-(4-(2-chlorophenyl)-4-hydroxypiperidine-1-carbonyl)phenyl)-3-hydroxybenzenesulfonamide

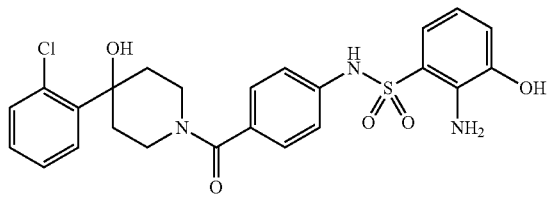 [SMILES: Nc1c(O)cccc1S(=O)(=O)Nc1ccc(C(=O)N2CCC(O)(c3ccccc3Cl)CC2)cc1]

$^1$H NMR (CHLOROFORM-d) δ: 10.57 (s, 1H), 9.94 (d, J=3.7 Hz, 1H), 7.81 (dd, J=7.9, 1.6 Hz, 1H), 7.44-7.32 (m, 2H), 7.32-7.23 (m, 3H), 7.15-7.03 (m, 3H), 6.81 (d, J=7.7 Hz, 1H), 6.45 (t, J=7.9 Hz, 1H), 5.48 (s, 2H), 5.42 (s, 1H), 4.36 (s, 1H), 3.48 (s, 2H), 3.11 (s, 1H), 2.41 (s, 1H), 1.53 (d, J=38.6 Hz, 3H). LC-MS: m/z 502.66 (M+H)$^+$

Compound 383 (General procedure 5, Step D)

N-(4-(4-(2-chlorophenyl)-4-hydroxypiperidine-1-carbonyl)phenyl)-2-methylbenzo[d]oxazole-4-sulfonamide

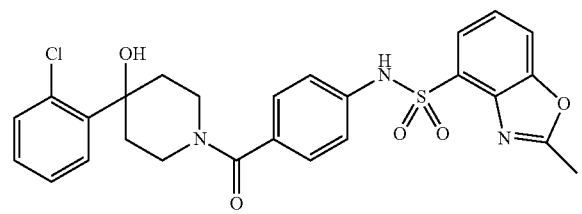 [SMILES: Cc1nc2c(S(=O)(=O)Nc3ccc(C(=O)N4CCC(O)(c5ccccc5Cl)CC4)cc3)cccc2o1]

$^1$H NMR (CHLOROFORM-d) δ: 7.83 (d, J=7.8 Hz, 1H), 7.78 (s, 1H), 7.68 (d, J=8.2 Hz, 1H), 7.53 (d, J=6.6 Hz, 1H), 7.37 (dd, J=13.5, 7.1 Hz, 2H), 7.32-7.21 (m, 4H), 7.16 (d, J=8.4 Hz, 2H), 4.61 (s, 1H), 3.60 (s, 2H), 3.31 (s, 1H), 3.04 (s, 1H), 2.76 (s, 3H), 2.38 (s, 1H), 2.19 (s, 1H), 2.02 (d, J=45.1 Hz, 2H). LC-MS: m/z 526.70 (M+H)$^+$

Compound 384 (General procedure 5, Step D)

N-(4-(4-hydroxy-4-isobutylpiperidine-1-carbonyl) phenyl)-2-methylbenzo[d]oxazole-4-sulfonamide

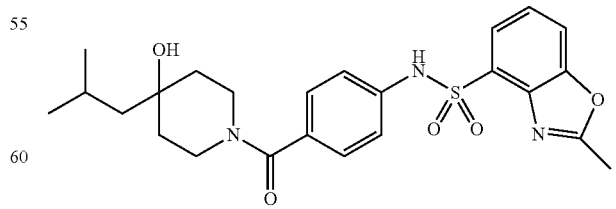

$^1$H NMR (CHLOROFORM-d) δ: 7.83 (dd, J=7.8, 0.7 Hz, 1H), 7.68 (d, J=8.1 Hz, 1H), 7.59 (s, 1H), 7.37 (t, J=8.0 Hz, 1H), 7.23 (d, J=8.5 Hz, 2H), 7.14 (d, J=8.5 Hz, 2H), 4.35 (s, 1H), 3.39 (dd, J=73.0, 45.6 Hz, 3H), 2.77 (s, 3H), 1.84 (dp,

J=12.9, 6.5 Hz, 1H), 1.65 (s, 3H), 1.52 (s, 1H), 1.42 (d, J=6.0 Hz, 2H), 0.99 (d, J=6.6 Hz, 6H). LC-MS: m/z 472.70 (M+H)+

Compound 385 (General procedure 5, Step D)

6-chloro-N-(4-(4-hydroxy-4-isobutylpiperidine-1-carbonyl)phenyl)-2-(methylamino)benzo[d]thiazole-4-sulfonamide

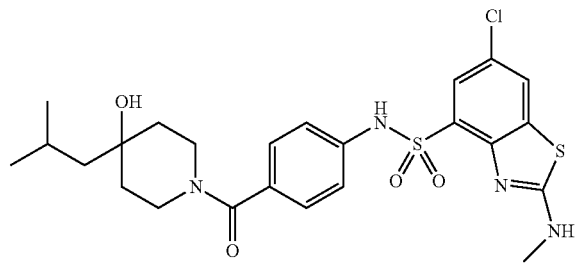 [SMILES: CNc1nc2c(S(=O)(=O)Nc3ccc(C(=O)N4CCC(O)(CC(C)C)CC4)cc3)cc(Cl)cc2s1]

¹H NMR (CHLOROFORM-d) δ: 7.98 (br. s., 1H), 7.78 (d, J=1.9 Hz, 1H), 7.71 (d, J=1.9 Hz, 1H), 7.26 (d, J=8.6 Hz, 2H), 7.10-7.14 (m, 2H), 3.44 (br. s., 1H), 3.22 (d, J=3.2 Hz, 3H), 1.82-1.87 (m, 1H), 1.64-1.66 (m, 2H), 1.42-1.44 (m, 2H), 0.99 (d, J=6.7 Hz, 6H). LC-MS: m/z 538.1 (M+H)+

Compound 154 (General procedure 5, Step D)

2-amino-N-(4-(4-(2-chlorophenyl)-4-hydroxypiperidine-1-carbonyl)phenyl)-6-fluorobenzo[d]thiazole-4-sulfonamide

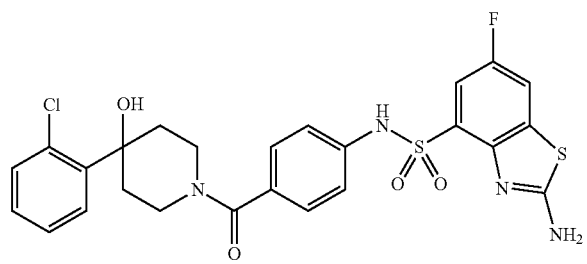 [SMILES: Nc1nc2c(S(=O)(=O)Nc3ccc(C(=O)N4CCC(O)(c5ccccc5Cl)CC4)cc3)cc(F)cc2s1]

¹H NMR (CHLOROFORM-d) δ: 8.01 (s, 1H), 7.59 (dd, J=8.2, 2.5 Hz, 1H), 7.53 (dd, J=7.9, 1.8 Hz, 1H), 7.49 (dd, J=7.5, 2.6 Hz, 1H), 7.41 (dd, J=7.7, 1.5 Hz, 1H), 7.32 (dd, J=7.5, 1.5 Hz, 1H), 7.30 (d, J=3.8 Hz, 2H), 7.25 (dd, J=7.5, 1.7 Hz, 1H), 7.15 (d, J=8.5 Hz, 2H), 5.83 (s, 2H), 4.64 (s, 1H), 3.62 (s, 2H), 3.34 (s, 1H), 2.37 (s, 1H), 2.26-2.17 (m, 1H), 2.08 (d, J=10.1 Hz, 1H), 2.03 (s, 1H). LC-MS: m/z 561.71 (M+H)+

Compound 173 (General procedure 5, Step D)

N-(4-(4-hydroxy-4-isobutylpiperidine-1-carbonyl)phenyl)benzo[d]thiazole-4-sulfonamide

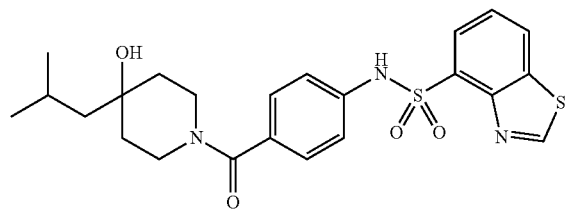

¹H NMR (CHLOROFORM-d) δ: 9.31 (s, 1H), 8.19 (d, J=8.1 Hz, 1H), 8.10 (d, J=7.5 Hz, 1H), 7.93 (s, 1H), 7.54 (t, J=7.9 Hz, 1H), 7.20 (d, J=8.3 Hz, 2H), 7.11 (d, J=8.4 Hz, 2H), 3.28 (s, 2H), 1.83 (dt, J=12.8, 6.5 Hz, 1H), 1.56 (s, 7H), 1.42 (d, J=6.0 Hz, 2H), 0.98 (d, J=6.6 Hz, 6H). LC-MS: m/z 474.6 (M+H)+

Compound 203 (General procedure 5, Step D)

5-fluoro-N-(4-(4-hydroxy-4-isobutylpiperidine-1-carbonyl)phenyl)quinoline-8-sulfonamide

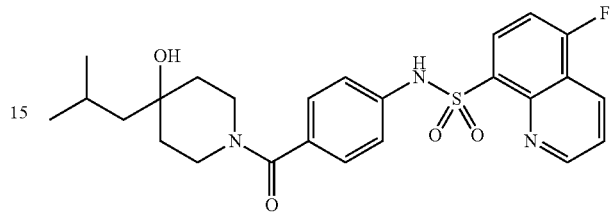

¹H NMR (CHLOROFORM-d) δ: 9.22 (d, J=2.8 Hz, 1H), 8.58 (dd, J=8.5, 1.3 Hz, 1H), 8.44-8.32 (m, 2H), 7.71 (dd, J=8.5, 4.3 Hz, 1H), 7.18 (d, J=8.3 Hz, 2H), 7.08 (d, J=8.3 Hz, 2H), 4.33 (s, 1H), 3.31 (s, 3H), 1.83 (dt, J=12.8, 6.3 Hz, 1H), 1.57 (s, 4H), 1.41 (d, J=6.0 Hz, 2H), 0.98 (d, J=6.6 Hz, 6H). LC-MS: m/z 486.7 (M+H)+

Compound 227 (General procedure 5, Step D)

N-(4-(4-(2,3-difluorophenyl)-4-hydroxypiperidine-1-carbonyl)phenyl)-5-fluoroquinoline-8-sulfonamide

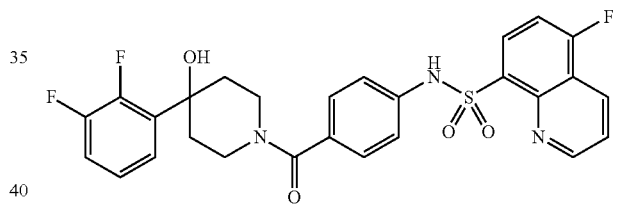

¹H NMR (CHLOROFORM-d) δ: 9.24 (br. s., 1H), 8.59 (d, J=7.8 Hz, 1H), 8.47 (br. s., 1H), 8.36-8.42 (m, 1H), 7.68-7.76 (m, 1H), 7.18-7.28 (m, 4H), 7.10 (d, m, 4H), 4.58 (br. s., 1H), 3.52 (br. s., 2H), 3.25 (br. s., 1H), 1.99-2.29 (m, 4H). LC-MS: m/z 543.6 (M+H)+

Compound 205 (General procedure 5, Step D)

N-(4-(4-benzyl-4-hydroxypiperidine-1-carbonyl)phenyl)benzo[c][1,2,5]thiadiazole-4-sulfonamide

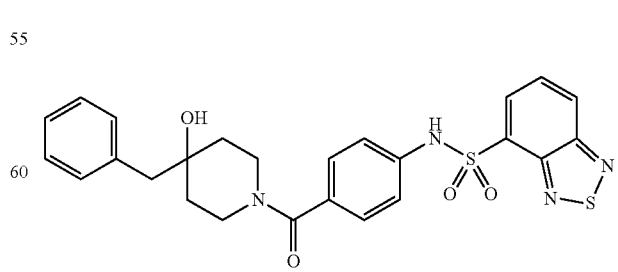

¹H NMR (DMSO-d6) δ: 10.98 (bs, 1H), 8.33 (dd, 2H, J=8.8 Hz, J=6.8 Hz), 7.86-7.81 (m, 1H), 7.25-7.12 (m, 7H), 7.07 (d, 2H, J=8.4 Hz), 4.42 (s, 1H), 4.25-3.90 (m, 1H), 3.21-2.98 (m, 3H), 2.65 (s, 2H), 1.54-1.42 (m, 4H). LC-MS: m/z 543.6 (M+H)+

Compound 106 (General procedure 5, Step D)

N-(4-(4-benzyl-4-hydroxypiperidine-1-carbonyl) phenyl)-2,3,4a,8a-tetrahydrobenzo[b][1,4]dioxine-5-sulfonamide

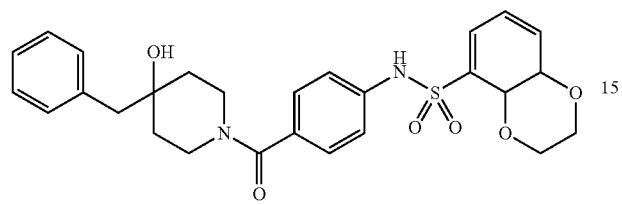

1H NMR (DMSO-d6) δ: 10.31 (s, 1H), 7.38-7.16 (m, 8H), 7.15-7.00 (m, 3H), 6.90 (t, 1H, J=8 Hz), 4.44 (bs, 1H), 4.28 (d, 4H, J=8.4 Hz), 4.19-4.10 (m, 1H), 3.51-3.25 (m, 3H), 2.68 (s, 2H), 1.61-1.30 (m, 4H). LC-MS: m/z 511.6 (M+H)+

Compound 239 (General procedure 5, Step D)

N-(4-(4-benzyl-4-hydroxypiperidine-1-carbonyl) phenyl)-6-chlorocyclohexa-1,3-diene-1-sulfonamide

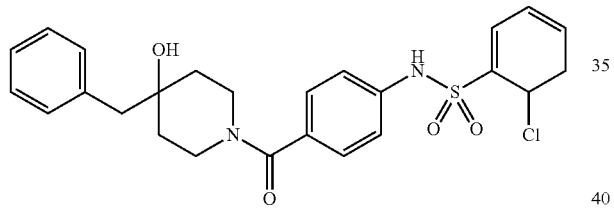 [SMILES: O=C(c1ccc(NS(=O)(=O)C2=CC=CC3OCCOC23)cc1)N1CCC(O)(Cc2ccccc2)CC1]

1H NMR (DMSO-d6) δ: 10.87 (bs, 1H), 8.07 (d, 1H, J=8 Hz), 7.70-7.45 (m, 3H), 7.37-6.96 (m, 9H), 4.43 (s, 1H), 4.25-3.98 (m, 1H), 3.40-2.88 (m, 3H), 2.66 (s, 2H), 1.60-1.29 (m, 4H). LC-MS: m/z 488.0 (M+H)+

Compound 237 (General procedure 5, Step D)

N-(4-(4-benzyl-4-hydroxypiperidine-1-carbonyl) phenyl)-2,3-dichlorobenzenesulfonamide

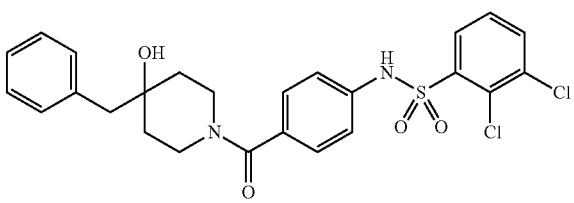 [SMILES: O=C(c1ccc(NS(=O)(=O)c2cccc(Cl)c2Cl)cc1)N1CCC(O)(Cc2ccccc2)CC1]

1H NMR (DMSO-d6) δ: 11.03 (bs, 1H), 8.05 (d, 1H, J=7.6 Hz), 7.89 (d, 1H, J=8 Hz), 7.54 (d, 1H, J=8 Hz), 7.31-7.11 (m, 7H), 7.07 (d, 2H, J=8.8 Hz), 4.43 (s, 1H), 4.23-3.90 (m, 1H), 3.41-2.90 (m, 3H), 2.27 (s, 2H), 1.58-1.30 (m, 4H). LC-MS: m/z 520.4 (M+H)+

General Procedure 6:

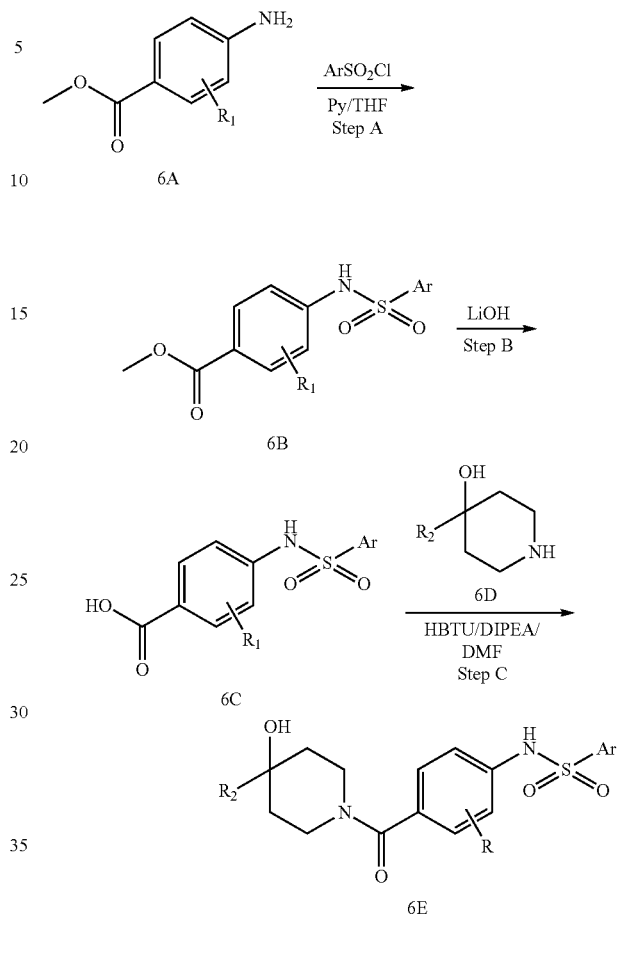

Step A:

To a solution of compound 6A (1 eq.) in THF was added pyridine (5 eq.), then aryl-sulfonyl chloride (1.2 eq.). The resulting mixture was heated at 70° C. under microwave irradiation for 20 minutes, when LC-MS showed that the reaction was complete. The mixture was then concentrated and purified by reverse phase chromatography (0-100% MeOH/H2O) to afford compound 6B.

Step B:

To a mixture of the corresponding compound 6B (1 eq.) in THF, was added LiOH (10 eq.), and the mixture was stirred at room temperature overnight. The reaction mixture was concentrated, the residue diluted with water, and extracted with DCM. The aqueous layer was neutralized with 1N HCl, then extracted with DCM. The organic layer was separated, concentrated to get the crude product, which was purified by silica gel chromatography to obtain compound 6C.

Step C:

To a round-bottomed flask was added the corresponding compound 6C (1 eq.), DMF (5 mL), DIPEA (3.0 eq.), HBTU (1.2 eq.), and compound 6D (1.0 eq.) sequentially. The reaction mixture was stirred at room temperature overnight or until TLC showed that s.m. was consumed. The mixture was diluted with brine, extracted with ethyl acetate, the organic layer was dried with anhydrous Na2SO4, filtered, and the filtrate was concentrated in vacuo. The desired product was purified by a standard method.

Compound 185 (General procedure 6, Step C)

N-(4-(4-hydroxy-4-(pyridin-3-ylmethyl)piperidine-1-carbonyl)phenyl)quinoline-8-sulfonamide

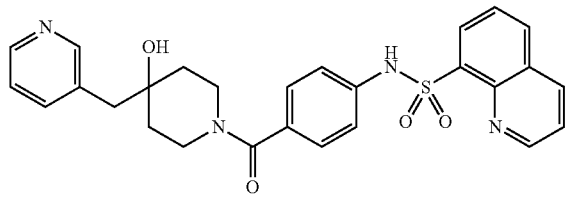 [SMILES: O=C(c1ccc(NS(=O)(=O)c2cccc3cccnc23)cc1)N1CCC(O)(Cc2cccnc2)CC1]

¹H NMR (DMSO-d₆) δ: 10.41 (bs, 1H), 9.12 (m, 1H), 8.52-8.26 (m, 5H), 7.74-7.57 (m, 3H), 7.27-7.24 (m, 1H), 7.11-7.09 (m, 4H), 4.54 (s, 1H), 4.06-3.99 (m, 1H), 3.18-2.99 (m, 3H), 2.33 (s, 2H), 1.37-1.34 (m, 4H). LC-MS: m/z 503.6 (M+H)⁺

Compound 189 (General procedure 6, Step C)

N-(4-(4-hydroxy-4-(pyridin-2-ylmethyl)piperidine-1-carbonyl)phenyl)quinoline-8-sulfonamide

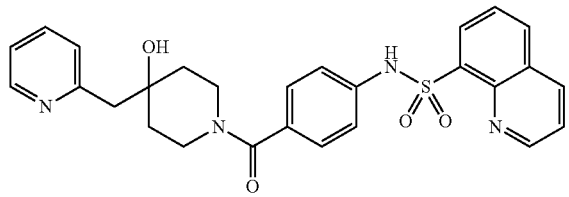 [SMILES: O=C(c1ccc(NS(=O)(=O)c2cccc3cccnc23)cc1)N1CCC(O)(Cc2ccccn2)CC1]

¹H NMR (CHLOROFORM-d) δ: 9.14-9.12 (m, 1H), 8.48-8.47 (m, 2H), 8.31 (dd, 2H, J=8.4 Hz & J=7.2 Hz), 8.02 (d, 1H, J=7.2 Hz), 7.65-7.56 (m, 3H), 7.25-7.03 (m, 6H), 4.13 (bs, 1H), 3.39-3.23 (m, 4H), 2.87 (s, 2H), 1.53-1.28 (m, 4H). LC-MS: m/z 503.6 (M+H)⁺

Compound 207 (General procedure 6, Step C)

N-(4-(4-hydroxy-4-((6-methylpyridin-2-yl)methyl)piperidine-1-carbonyl)phenyl)quinoline-8-sulfonamide

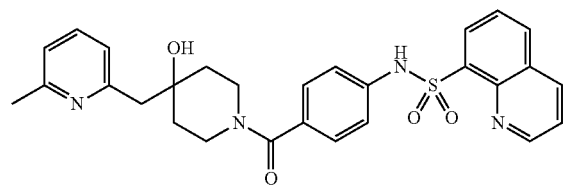 [SMILES: Cc1cccc(CC2(O)CCN(C(=O)c3ccc(NS(=O)(=O)c4cccc5cccnc45)cc3)CC2)n1]

¹H NMR (CHLOROFORM-d) δ: 9.14-9.13 (m, 1H), 8.50 (bs, 1H), 8.31 (dd, 2H, J=7.2 & J=8 Hz), 8.03 (d, 1H, J=8 Hz), 7.62-7.49 (m, 3H), 7.14 (d, 2H, J=8.4 Hz), 7.09-7.03 (m, 3H), 6.88 (d, 1H, J=7.6 Hz), 5.29 (s, 1H), 4.32-4.30 (m, 1H), 3.48-3.21 (m, 3H), 2.82 (s, 2H), 2.50 (s, 3H), 1.45-1.33 (m, 4H). LC-MS: m/z 517.6 (M+H)⁺

Compound 146 (General procedure 6, Step C)

N-(4-(4-((6-fluoropyridin-2-yl)methyl)-4-hydroxypiperidine-1-carbonyl)phenyl)quinoline-8-sulfonamide

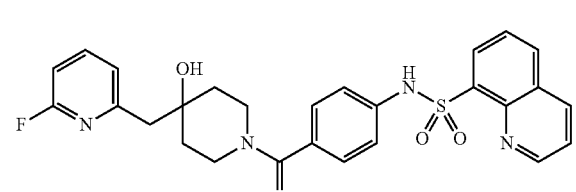

¹H NMR (CHLOROFORM-d) δ: 9.14-9.13 (m, 1H), 8.511 (bs, 1H), 8.32 (dd, 2H, J=7.2 Hz & J=7.2), 8.03 (d, 1H, J=8 Hz), 7.76-7.59 (m, 3H), 7.14 (d, 2H, J=8.4 Hz), 7.04 (d, 2H, J=8.4 Hz), 7.00-6.98 (m, 1H), 6.83-6.80 (m, 1H), 4.61 (s, 1H), 4.34-4.32 (m, 1H), 3.40-3.19 (m, 3H), 2.86 (s, 2H), 1.58-1.43 (m, 4H). LC-MS: m/z 521.6 (M+H)⁺

Compound 168 (General procedure 6, Step C)

N-(4-(4-((2-fluoropyridin-3-yl)methyl)-4-hydroxypiperidine-1-carbonyl)phenyl)quinoline-8-sulfonamide

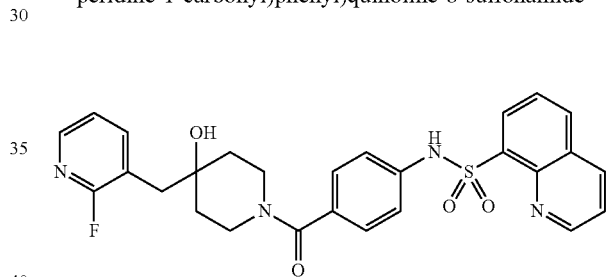

¹H NMR (400 MHz, CDCl₃) δ: 9.15 (dd, J=4.4, 1.6 Hz, 1H), 8.54 (s, 1H), 8.36 (dd, J=7.2, 1.2 Hz, 1H), 8.30 (dd, J=8.4, 1.6 Hz, 1H), 8.12 (d, J=4.4 Hz, 1H), 8.04 (d, J=7.2 Hz, 1H), 7.66-7.56 (m, 3H), 7.18-7.11 (m, 3H), 7.06 (d, J=8.5 Hz, 2H), 4.36 (s, 1H), 3.49 (s, 1H), 3.29-3.21 (m, 1H), 3.21-3.07 (m, 1H), 2.80 (s, 2H), 2.17 (s, 1H), 1.74-1.60 (m, 2H), 1.40-1.29 (m, 2H). LC-MS: m/z 521.6 (M+H)⁺

Compound 143 (General procedure 6, Step C)

N-(4-(4-(2-chlorophenyl)-4-hydroxypiperidine-1-carbonyl)-2-fluorophenyl)quinoline-8-sulfonamide

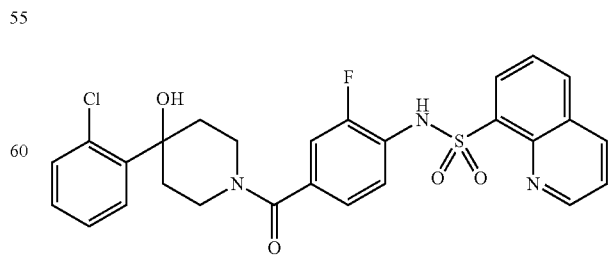

¹H NMR (CHLOROFORM-d) δ: 9.16 (dd, J=4.3, 1.6 Hz, 1H), 8.42 (dd, J=7.3, 1.3 Hz, 1H), 8.33 (dd, J=8.3, 1.6 Hz,

1H), 8.06-8.12 (m, 1H), 7.60-7.68 (m, 2H), 7.50 (dd, J=7.8, 1.6 Hz, 1H), 7.39 (dd, J=7.7, 1.5 Hz, 1H), 7.29-7.32 (m, 1H), 7.22-7.27 (m, 1H), 7.14 (t, J=7.8 Hz, 1H), 6.99 (d, J=9.7 Hz, 1H), 6.82 (d, J=8.1 Hz, 1H), 4.65 (d, J=13.2 Hz, 1H), 3.58 (br. s., 1H), 3.40 (d, J=11.3 Hz, 1H), 3.22-3.35 (m, 1H), 2.93 (br. s., 1H), 2.32 (td, J=13.3, 4.6 Hz, 1H), 2.20 (s, 3H), 2.11 (d, J=12.6 Hz, 1H), 1.98 (d, J=13.4 Hz, 1H). LC-MS: m/z 540.6 (M+H)$^+$

Compound 193 (General procedure 6, Step C)

N-(4-(4-(2-chlorophenyl)-4-hydroxypiperidine-1-carbonyl)-3-fluorophenyl)quinoline-8-sulfonamide

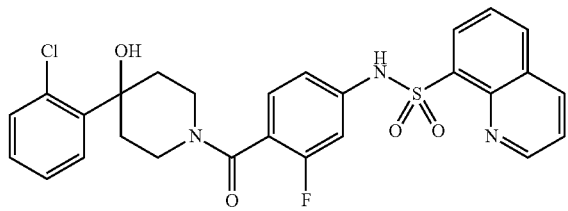

$^1$H NMR (CHLOROFORM-d) δ: 9.16 (dd, J=4.3, 1.6 Hz, 1H), 8.42 (dd, J=7.3, 1.3 Hz, 1H), 8.33 (dd, J=8.3, 1.6 Hz, 1H), 8.06-8.12 (m, 1H), 7.60-7.68 (m, 2H), 7.50 (dd, J=7.8, 1.6 Hz, 1H), 7.39 (dd, J=7.7, 1.5 Hz, 1H), 7.29-7.32 (m, 1H), 7.22-7.27 (m, 1H), 7.14 (t, J=7.8 Hz, 1H), 6.99 (d, J=9.7 Hz, 1H), 6.82 (d, J=8.1 Hz, 1H), 4.65 (d, J=13.2 Hz, 1H), 3.58 (br. s., 1H), 3.40 (d, J=11.3 Hz, 1H), 3.22-3.35 (m, 1H), 2.93 (br. s., 1H), 2.32 (td, J=13.3, 4.6 Hz, 1H), 2.20 (s, 3H), 2.11 (d, J=12.6 Hz, 1H), 1.98 (d, J=13.4 Hz, 1H). LC-MS: m/z 540.6 (M+H)$^+$

Compound 104 (General procedure 6, Step C)

N-(4-(4-(2-chlorophenyl)-4-hydroxypiperidine-1-carbonyl)-2-methylphenyl)quinoline-8-sulfonamide

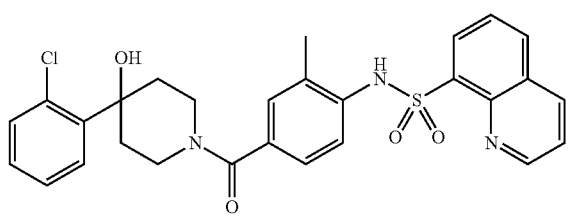 [SMILES: O=C(c1ccc(NS(=O)(=O)c2cccc3cccnc23)c(F)c1)N1CCC(O)(c2ccccc2Cl)CC1]

$^1$H NMR (CHLOROFORM-d) δ: 9.11 (dd, J=4.3, 1.6 Hz, 1H), 8.43 (dd, J=7.3, 1.1 Hz, 1H), 8.31 (dd, J=8.3, 1.6 Hz, 1H), 8.04-8.10 (m, 1H), 7.59-7.66 (m, 2H), 7.52 (dd, J=7.8, 1.9 Hz, 1H), 7.36 (dd, J=7.5, 1.6 Hz, 1H), 7.20-7.30 (m, 3H), 7.13 (s, 1H), 7.03 (dd, J=8.3, 1.6 Hz, 1H), 4.56 (br. s., 1H), 3.61 (br. s., 1H), 3.52 (br. s., 1H), 3.26 (br. s., 1H), 2.29-2.43 (m, 1H), 2.11-2.27 (m, 4H), 1.96-2.07 (m, 3H), 1.90 (d, J=7.8 Hz, 1H). LC-MS: m/z 536.3 (M+H)$^+$

Compound 141 (General procedure 6, Step C)

N-(4-(4-(2-chlorophenyl)-4-hydroxypiperidine-1-carbonyl)-3-methylphenyl)quinoline-8-sulfonamide

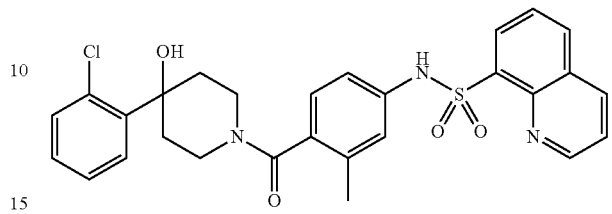

$^1$H NMR (CHLOROFORM-d) δ: 9.13-9.19 (m, 1H), 8.48 (br. s., 1H), 8.28-8.41 (m, 2H), 8.07 (d, J=8.1 Hz, 1H), 7.57-7.67 (m, 2H), 7.52 (d, J=7.3 Hz, 1H), 7.38 (d, J=7.5 Hz, 1H), 7.22-7.27 (m, 1H), 6.92-7.01 (m, 1H), 6.88 (d, J=8.1 Hz, 2H), 4.69 (d, J=13.7 Hz, 1H), 3.48 (br. s., 1H), 3.22-3.36 (m, 2H), 2.37 (br. s., 1H), 2.21 (br. s., 1H), 2.15 (br. s., 2H), 2.02-2.11 (m, 2H), 1.99 (br. s., 1H). LC-MS: m/z 536.3 (M+H)$^+$

Compound 170 (General procedure 6, Step C)

N-(4-(4-(2-chlorophenyl)-4-hydroxypiperidine-1-carbonyl)-3-methoxyphenyl)quinoline-8-sulfonamide

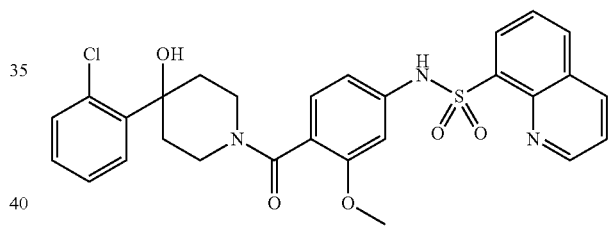

$^1$H NMR (CHLOROFORM-d) δ: 9.16 (d, J=4.0 Hz, 1H), 8.30-8.42 (m, 2H), 8.04-8.12 (m, 1H), 7.59-7.67 (m, 2H), 7.35-7.57 (m, 2H), 7.23-7.34 (m, 3H), 6.83-6.99 (m, 2H), 6.36-6.49 (m, 1H), 3.64-3.78 (m, 3H), 3.18-3.35 (m, 1H), 3.04 (s, 1H), 2.76 (s, 1H), 2.27-2.40 (m, 1H), 1.90-2.14 (m, 4H). LC-MS: m/z 552.3 (M+H)$^+$

Compound 209 (General procedure 6, Step C)

N—(N-(4-(4-(2-chlorophenyl)-4-hydroxypiperidine-1-carbonyl)-3-cyanophenyl)quinoline-8-sulfonamide

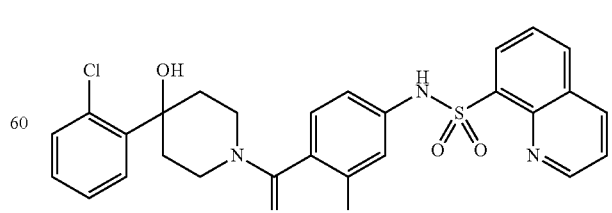

$^1$H NMR (CHLOROFORM-d) δ: 9.17 (dd, J=4.3, 1.6 Hz, 1H), 8.33-8.44 (m, 2H), 8.08-8.14 (m, 1H), 7.63-7.70 (m,

2H), 7.49 (dd, J=7.8, 1.6 Hz, 1H), 7.36-7.44 (m, 3H), 4.66 (d, J=13.2 Hz, 1H), 3.65 (t, J=12.0 Hz, 2H), 3.29-3.41 (m, 2H), 3.21 (br. s., 1H), 2.64 (br. s., 1H), 2.20-2.40 (m, 3H), 2.15 (d, J=12.6 Hz, 1H), 2.06 (d, J=7.3 Hz, 1H). LC-MS: m/z 547.7 (M+H)⁺.

Compound 263 (General procedure 6, Step C)

N-(4-(4-(2-chlorophenyl)-4-hydroxypiperidine-1-carbonyl)-2-(difluoromethoxy)phenyl)quinoline-8-sulfonamide

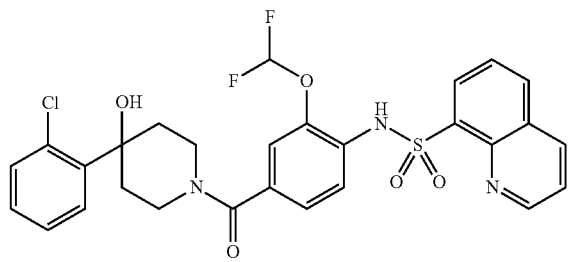 [SMILES: O=C(c1ccc(NS(=O)(=O)c2cccc3cccnc23)c(OC(F)F)c1)N1CCC(O)(c2ccccc2Cl)CC1]

¹H NMR (CHLOROFORM-d) δ: 2.09 (br. s., 4H) 2.35 (br. s., 2H), 3.30 (br. s., 1H), 3.61 (br. s., 2H), 4.60 (br. s., 1H), 6.21 (t, J=72 Hz1H), 7.04 (s, 1H), 7.17 (dd, J=8.46, 1.75 Hz, 1H), 7.25-7.28 (m, 1H), 7.30-7.33 (m, 1H), 7.40 (dd, J=7.79, 1.61 Hz, 1H), 7.51 (dd, J=7.66, 1.75 Hz, 1H), 7.61 (dd, J=4.57, 3.76 Hz, 1H), 7.63-7.66 (m, 1H), 7.84 (d, J=8.33 Hz, 1H), 8.08 (dd, J=8.33, 1.34 Hz, 1H), 8.30 (dd, J=8.33, 1.61 Hz, 1H), 8.43 (dd, J=7.39, 1.48 Hz, 1H), 8.97 (br. s., 1H), 9.14 (dd, J=4.30, 1.88 Hz, 1H). LC-MS: m/z 589.0 (M+H)⁺

Compound 151 (General procedure 6, Step C)

N-(4-(4-(2-chlorophenyl)-4-hydroxypiperidine-1-carbonyl)-3-(difluoromethoxy)phenyl)quinoline-8-sulfonamide

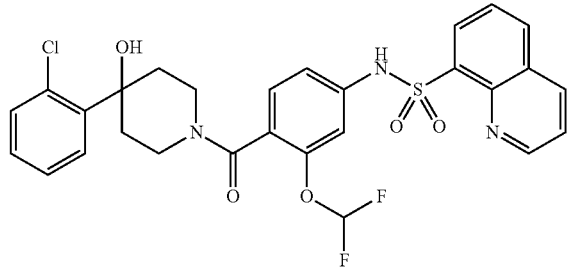 [SMILES: O=C(c1ccc(NS(=O)(=O)c2cccc3cccnc23)cc1OC(F)F)N1CCC(O)(c2ccccc2Cl)CC1]

¹H NMR (CHLOROFORM-d) δ: 9.21 (br. s., 1H), 8.89 (br. s., 1H), 8.38-8.50 (m, 2H), 8.13 (d, J=7.8 Hz, 1H), 7.66-7.75 (m, 2H), 7.50 (br. s., 1H), 7.39 (d, J=7.5 Hz, 1H), 7.29-7.33 (m, 1H), 7.21-7.27 (m, 1H), 7.07-7.16 (m, 1H), 6.94-7.06 (m, 2H), 6.37 (s, 1H), 4.66 (d, J=14.5 Hz, 1H), 3.50 (br. s., 1H), 3.31 (d, J=13.4 Hz, 2H), 2.29 (br. s., 2H), 2.11 (br. s., 2H). LC-MS: m/z 589.0 (M+H)⁺

Compound 136

N-(4-(4-(2-chlorophenyl)-4-hydroxypiperidine-1-carbonyl)-3-(trifluoromethoxy)phenyl)quinoline-8-sulfonamide

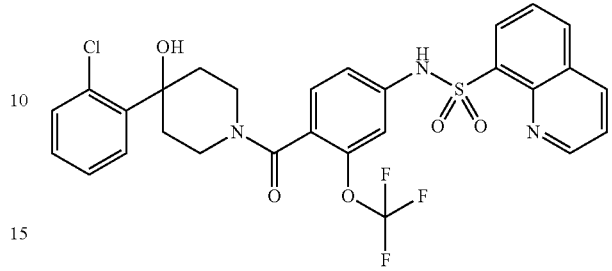

¹H NMR (CHLOROFORM-d) δ: 9.15 (dd, J=4.3, 1.3 Hz, 1H), 8.67 (br. s., 1H), 8.41 (dd, J=7.4, 1.2 Hz, 1H), 8.33 (dd, J=8.3, 1.3 Hz, 1H), 8.05-8.13 (m, 1H), 7.60-7.69 (m, 2H), 7.45-7.54 (m, 1H), 7.38 (d, J=7.5 Hz, 1H), 7.31 (br. s., 1H), 7.20-7.27 (m, 1H), 7.09-7.20 (m, 2H), 6.96-7.09 (m, 1H), 4.65 (d, J=13.2 Hz, 1H), 3.43-3.64 (m, 1H), 3.28 (d, J=9.7 Hz, 2H), 3.01 (br. s., 1H), 2.18-2.39 (m, 1H), 2.02-2.18 (m, 2H), 1.88-2.02 (m, 1H). LC-MS: m/z 607.1 (M+H)⁺

Compound 218 (General procedure 6, Step C)

3-fluoro-N-(4-(4-hydroxy-4-phenylpiperidine-1-carbonyl)phenyl)quinoline-8-sulfonamide

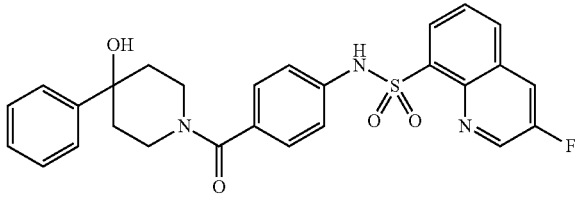 [SMILES: O=C(c1ccc(NS(=O)(=O)c2cccc3cc(F)cnc23)cc1)N1CCC(O)(c2ccccc2)CC1]

¹H NMR (CHLOROFORM-d) δ: 9.06 (d, J=2.6 Hz, 1H), 8.36 (dd, J=1.0, 7.2 Hz, 1H), 8.24 (s, 1H), 8.07-8.02 (m, 1H), 7.96-7.89 (m, 1H), 7.65 (t, J=7.8 Hz, 1H), 7.51-7.30 (m, 5H), 7.25-7.19 (m, J=8.2 Hz, 2H), 7.14-7.04 (m, J=8.5 Hz, 2H), 4.59 (br. s., 1H), 3.71-3.42 (m, 2H), 3.33 (br. s., 1H), 1.90-1.84 (m, 5H). LC-MS: m/z 506.6 (M+H)⁺

Compound 128 (General procedure 6, Step C)

N-(4-(4-benzyl-4-hydroxypiperidine-1-carbonyl)phenyl)-3-fluoroquinoline-8-sulfonamide

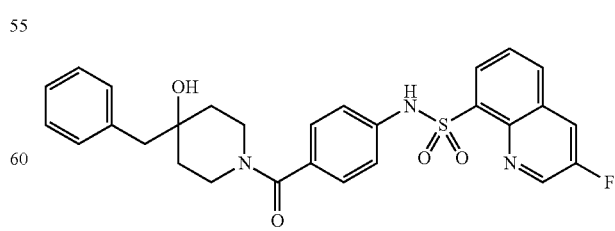

¹H NMR (CHLOROFORM-d) δ: 9.04 (d, J=3.0 Hz, 1H), 8.28-8.40 (m, 2H), 8.02 (dd, J=8.3, 1.1 Hz, 1H), 7.92 (dd, J=8.2, 2.8 Hz, 1H), 7.63 (t, J=7.8 Hz, 1H), 7.22-7.36 (m, 3H), 7.12-7.21 (m, 4H), 7.02-7.12 (m, 2H), 4.36 (br. s., 1H), 3.27-3.09 (m, 3H), 2.74 (s, 2H), 1.76 (br. s., 3H), 1.59 (br. s., 2H). LC-MS: m/z 520.6 (M+H)⁺

Compound 196 (General procedure 6, Step C)

6-fluoro-N-(4-(4-hydroxy-4-phenylpiperidine-1-carbonyl)phenyl)quinoline-8-sulfonamide

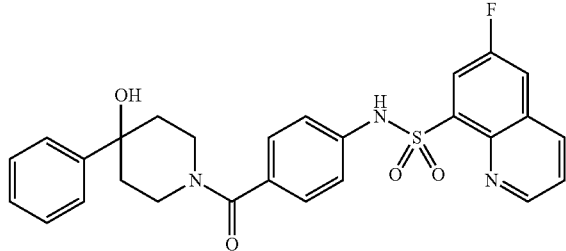 [SMILES: O=C(c1ccc(NS(=O)(=O)c2cc(F)cc3cccnc23)cc1)N1CCC(O)(c2ccccc2)CC1]

¹H NMR (CHLOROFORM-d) δ: 9.08-9.19 (m, 1H), 8.56 (br. s., 1H), 8.28 (dd, J=8.4, 1.3 Hz, 1H), 8.18 (dd, J=7.6, 2.9 Hz, 1H), 7.61-7.73 (m, 2H), 7.44-7.49 (m, 2H), 7.39 (t, J=7.6 Hz, 2H), 7.29-7.34 (m, 1H), 7.21-7.27 (m, J=8.5 Hz, 2H), 7.07-7.13 (m, J=8.5 Hz, 2H), 4.58 (br. s., 1H), 3.58 (br. s., 1H), 3.51 (br. s., 1H), 3.30 (br. s., 1H), 1.95-2.20 (m, 2H), 1.86 (br. s., 3H). LC-MS: m/z 506.6 (M+H)⁺

Compound 223 (General procedure 6, Step C)N-(4-(4-(2-chlorophenyl)-4-hydroxypiperidine-1-carbonyl)phenyl)-6-fluoroquinoline-8-sulfonamide

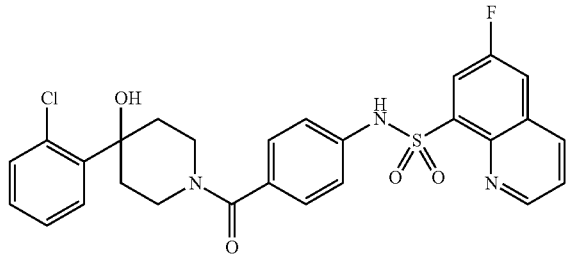 [SMILES: O=C(c1ccc(NS(=O)(=O)c2cc(F)cc3cccnc23)cc1)N1CCC(O)(c2ccccc2Cl)CC1]

¹H NMR (CHLOROFORM-d) δ: 8.94-9.05 (m, 1H), 8.33 (dd, J=8.3, 1.6 Hz, 1H), 8.20 (dd, J=8.6, 3.0 Hz, 1H), 7.76-7.83 (m, 1H), 7.67-7.74 (m, 1H), 7.57 (dd, J=8.3, 4.3 Hz, 1H), 7.26-7.39 (m, 2H), 7.18-7.26 (m, 1H), 7.09-7.18 (m, J=8.6 Hz, 2H), 6.96-7.09 (m, J=8.6 Hz, 2H), 4.45 (br. s., 1H), 2.71 (br. s., 2H), 1.47-1.68 (m, 6H). LC-MS: m/z 540.6 (M+H)⁺

Compound 220 (General procedure 6, Step C)

N-(4-(4-(2,3-difluorophenyl)-4-hydroxypiperidine-1-carbonyl)-2-methylphenyl)-5-fluoroquinoline-8-sulfonamide

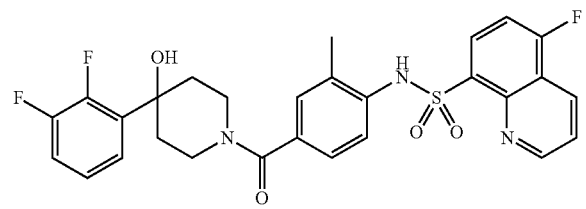 [SMILES: Cc1cc(C(=O)N2CCC(O)(c3cccc(F)c3F)CC2)ccc1NS(=O)(=O)c1ccc(F)c2cccnc12]

¹H NMR (CHLOROFORM-d) δ: 9.19 (dd, J=4.3, 1.6 Hz, 1H), 8.63 (dd, J=8.5, 1.7 Hz, 1H), 8.36 (dd, J=8.3, 5.9 Hz, 1H), 7.78 (dd, J=8.6, 4.3 Hz, 1H), 7.34-7.46 (m, 2H), 7.09-

7.20 (m, 4H), 7.04 (dd, J=8.3, 1.6 Hz, 1H), 4.58 (br. s., 1H), 4.48 (d, J=10.2 Hz, 1H), 3.52 (br. s., 3H), 2.06-2.36 (m, 7H). LC-MS: m/z 556.7 (M+H)⁺

Compound 232 (General procedure 6, Step C)

N-(4-(4-(2-chlorophenyl)-4-hydroxypiperidine-1-carbonyl)-3,5-difluorophenyl)quinoline-8-sulfonamide

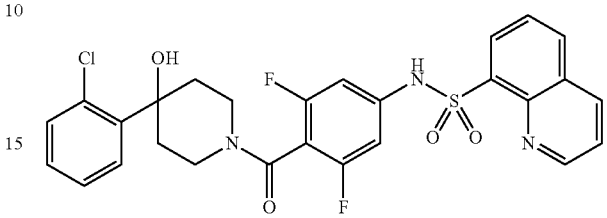

¹H NMR (CHLOROFORM-d) δ: 9.15 (dd, J=4.3, 1.6 Hz, 1H), 8.75 (br. s., 1H), 8.45 (dd, J=7.4, 1.2 Hz, 1H), 8.36 (dd, J=8.3, 1.3 Hz, 1H), 8.13 (d, J=8.1 Hz, 1H), 7.63-7.72 (m, 2H), 7.50 (dd, J=7.8, 1.6 Hz, 1H), 7.39 (dd, J=7.7, 1.5 Hz, 1H), 7.31 (d, J=7.5 Hz, 1H), 7.25 (td, J=7.5, 1.6 Hz, 1H), 6.69-6.80 (m, 2H), 4.67 (d, J=10.7 Hz, 1H), 3.53-3.68 (m, 1H), 3.26-3.46 (m, 2H), 2.94 (br. s., 1H), 2.32-2.00 (m, 4H). LC-MS: m/z 558.1 (M+H)⁺

Compound 246 (General procedure 6, Step C)

N-(4-(4-(ethoxymethyl)-4-hydroxypiperidine-1-carbonyl)phenyl)quinoline-8-sulfonamide

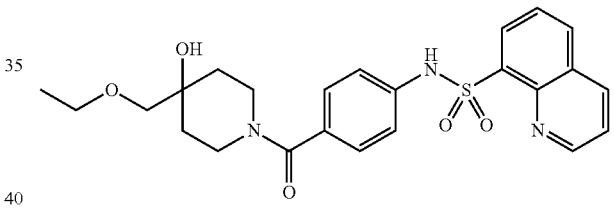

¹H NMR (CHLOROFORM-d) δ: 9.10-9.20 (m, 1H), 8.55 (br. s., 1H), 8.26-8.43 (m, 2H), 8.05 (d, J=8.2 Hz, 1H), 7.55-7.70 (m, 2H), 7.12-7.20 (m, J=8.5 Hz, 2H), 7.03-7.12 (m, J=8.5 Hz, 2H), 4.37 (br. s., 1H), 3.53 (q, J=6.9 Hz, 2H), 3.45 (br. s., 1H), 3.36 (br. s., 1H), 3.26 (s, 3H), 2.29-2.41 (m, 1H), 1.65 (br. s., 3H), 1.55 (br. s., 1H), 1.20 (td, J=7.0, 2.2 Hz, 3H). LC-MS: m/z 470.6 (M+H)⁺

Compound 225 (General procedure 6, Step C)

N-[4-[4-hydroxy-4-(2-methoxyethyl)piperidine-1-carbonyl]phenyl]quinoline-8-sulfonamide

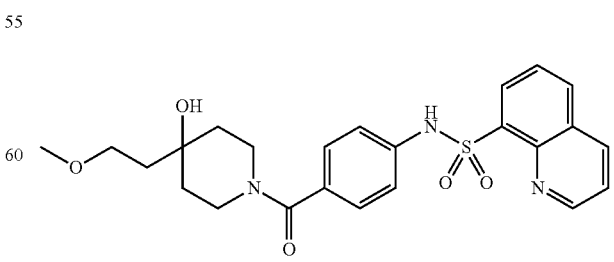

¹H NMR (CHLOROFORM-d) δ: 1.28 (br. s., 3H), 1.58 (br. s., 2H), 1.73-1.79 (m, 4H), 2.04 (d, J=4.99 Hz, 1H), 3.25 (br.

s., 1H), 3.45 (br. s., 2H), 3.65 (br. s., 2H), 4.38 (br. s., 1H), 7.11 (m, J=8.22 Hz, 2H), 7.18 (m, J=8.51 Hz, 2H), 7.61-7.72 (m, 2H), 8.09 (d, J=8.22 Hz, 1H), 8.36-8.44 (m, 2H), 8.86 (br. s., 1H), 9.19-9.24 (m, 1H). LC-MS: m/z 470.6 (M+H)$^+$

Compound 144 (General procedure 6, Step C)

N-(4-(4-(cyclopropylmethyl)-4-hydroxypiperidine-1-carbonyl)phenyl)quinoline-8-sulfonamide

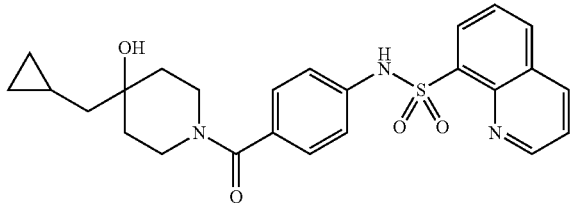 [SMILES: O=C(c1ccc(NS(=O)(=O)c2cccc3cccnc23)cc1)N1CCC(O)(CC2CC2)CC1]

$^1$H NMR (CHLOROFORM-d) δ: 9.19 (d, J=2.8 Hz, 1H), 8.67 (s, 1H), 8.40 (dd, J=7.3, 1.3 Hz, 1H), 8.35 (d, J=7.2 Hz, 1H), 8.07 (dd, J=8.2, 1.2 Hz, 1H), 7.70-7.58 (m, 2H), 7.18 (d, J=8.5 Hz, 2H), 7.10 (d, J=8.5 Hz, 2H), 4.37 (s, 1H), 3.42 (d, J=38.4 Hz, 2H), 3.20 (s, 1H), 1.62 (d, J=56.1 Hz, 4H), 1.42 (s, 2H), 0.80-0.66 (m, 1H), 0.59-0.46 (m, 2H), 0.10 (q, J=4.9 Hz, 2H). LC-MS: m/z 466.6 (M+H)$^+$

Compound 176 (General procedure 6, Step C)

N-(4-(4-((2,2-difluorocyclopropyl)methyl)-4-hydroxypiperidine-1-carbonyl)phenyl)quinoline-8-sulfonamide

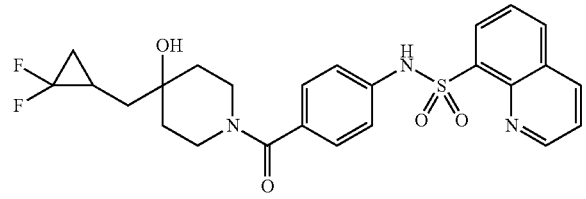 [SMILES: O=C(c1ccc(NS(=O)(=O)c2cccc3cccnc23)cc1)N1CCC(O)(CC2CC2(F)F)CC1]

$^1$H NMR (CHLOROFORM-d) δ: 9.17 (dd, J=4.3, 1.6 Hz, 1H), 8.64 (br. s., 1H), 8.28-8.43 (m, 2H), 8.07 (dd, J=8.1, 1.3 Hz, 1H), 7.54-7.71 (m, 2H), 7.13-7.21 (m, 2H), 7.06-7.13 (m, 2H), 4.23-4.51 (m, 1H), 3.49 (d, J=13.2 Hz, 1H), 3.34 (br. s., 1H), 3.23 (br. s., 1H), 1.58 (br. s., 2H), 1.38-1.56 (m, 5H), 0.77-1.02 (m, 3H). LC-MS: m/z 502.6 (M+H)$^+$

Compound 210 (General procedure 6, Step C)

N-(6-(4-(2-chlorophenyl)-4-hydroxypiperidine-1-carbonyl)-2-methylpyridin-3-yl)quinoline-8-sulfonamide

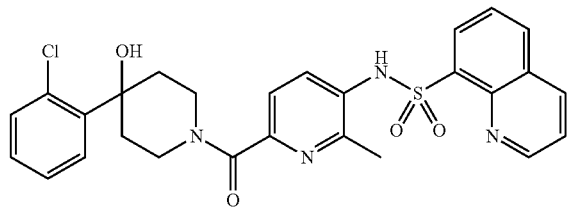 [SMILES: Cc1nc(C(=O)N2CCC(O)(c3ccccc3Cl)CC2)ccc1NS(=O)(=O)c1cccc2cccnc12]

$^1$H NMR (CHLOROFORM-d) δ: 9.14 (dd, J=4.4, 1.6 Hz, 1H), 8.46 (dd, J=7.3, 1.3 Hz, 1H), 8.34 (dd, J=8.3, 1.5 Hz, 1H), 8.09-8.14 (m, 1H), 7.78 (d, J=8.3 Hz, 1H), 7.61-7.71 (m, 2H), 7.50 (dd, J=7.8, 1.5 Hz, 1H), 7.39 (dd, J=7.7, 1.4 Hz, 1H), 7.31 (s, 1H), 7.22-7.28 (m, 1H), 4.63 (d, J=13.1 Hz, 1H), 3.84 (d, J=13.6 Hz, 1H), 3.54-3.64 (m, 1H), 3.33 (td, J=12.9, 2.6 Hz, 1H), 2.46 (s, 3H), 2.24-2.38 (m, 2H), 1.97-2.16 (m, 2H), 1.60-1.75 (m, 2H). LC-MS: m/z 537.7 (M+H)$^+$

Compound 261 (General procedure 6, Step C)

N-(3-cyano-4-(4-hydroxy-4-phenylpiperidine-1-carbonyl)phenyl)quinoline-8-sulfonamide

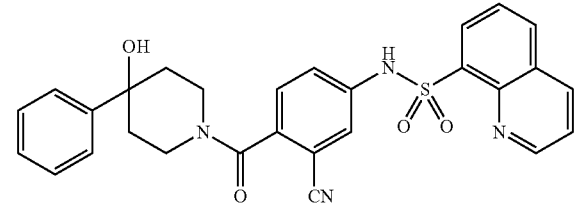 [SMILES: N#Cc1cc(NS(=O)(=O)c2cccc3cccnc23)ccc1C(=O)N1CCC(O)(c2ccccc2)CC1]

$^1$H NMR (CHLOROFORM-d) δ: 9.20 (dd, J=4.3, 1.6 Hz, 1H), 8.43 (dd, J=12.5, 7.8 Hz, 1H), 8.43 (dd, J=15.6, 7.9 Hz, 1H), 8.14 (dd, J=8.2, 1.2 Hz, 1H), 7.66-7.74 (m, 2H), 7.45-7.49 (m, 4H), 7.39 (d, J=7.6 Hz, 4H), 4.64 (d, J=13.5 Hz, 2H), 3.74 (d, J=7.0 Hz, 2H), 3.27 (br. s., 1H), 3.13 (br. s., 1H), 2.02 (dd, J=14.2, 4.0 Hz, 4H). LC-MS: m/z 512.6 (M+H)$^+$

Compound 197 (General procedure 6, Step C)

N-(4-(4-(2-chlorophenyl)-4-hydroxypiperidine-1-carbonyl)phenyl)naphthalene-1-sulfonamide

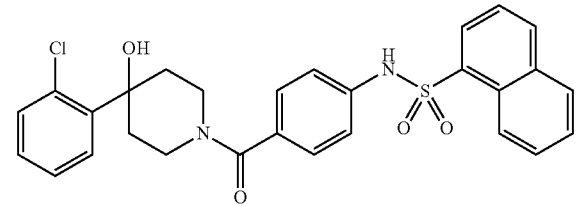

$^1$H NMR (CHLOROFORM-d) δ: 8.70 (d, J=8.3 Hz, 1H), 8.25 (d, J=7.0 Hz, 1H), 8.05 (d, J=8.1 Hz, 1H), 7.94 (d, J=7.8 Hz, 1H), 7.57-7.70 (m, 3H), 7.46-7.55 (m, 2H), 7.36-7.43 (m, 1H), 7.19-7.27 (m, 3H), 7.00 (d, J=8.6 Hz, 2H), 4.64 (br. s., 1H), 3.56 (br. s., 1H), 3.51 (s, 1H), 3.31 (br. s., 1H), 2.36 (br. s., 1H), 2.15-2.23 (m, 1H), 1.91-2.13 (m, 3H). LC-MS: m/z 521.0 (M+H)$^+$

Compound 102 (General procedure 6, Step C)

N-(4-(4-(2-chlorophenyl)-4-hydroxypiperidine-1-carbonyl)phenyl)chroman-8-sulfonamide

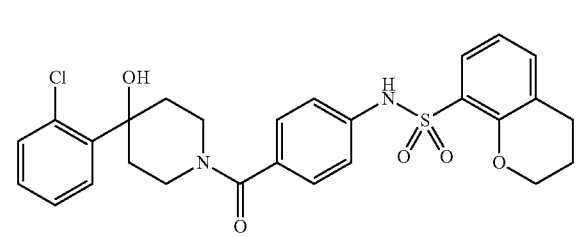 [SMILES: O=C(c1ccc(NS(=O)(=O)c2cccc3c2OCCC3)cc1)N1CCC(O)(c2ccccc2Cl)CC1]

$^1$H NMR (CHLOROFORM-d) δ: 7.68 (d, J=7.8 Hz, 1H), 7.54 (dd, J=7.8, 1.6 Hz, 1H), 7.39 (dd, J=7.7, 1.5 Hz, 1H), 7.29-7.33 (m, 2H), 7.19-7.28 (m, 2H), 7.17 (d, J=8.6 Hz, 2H), 6.87 (t, J=7.8 Hz, 1H), 4.63 (br. s., 1H), 4.36-4.47 (m, 2H), 3.61 (br. s., 2H), 3.31 (br. s., 1H), 2.81 (t, J=6.3 Hz, 2H), 2.39 (br. s., 1H), 2.14-2.32 (m, 1H), 2.01-2.12 (m, 3H), 1.87-2.01 (m, 1H), 1.71 (d, J=14.2 Hz, 1H). LC-MS: m/z 527.7 (M+H)+

Compound 186 (General procedure 6, Step C)

N-(4-(4-(2-chlorophenyl)-4-hydroxypiperidine-1-carbonyl)phenyl)benzofuran-7-sulfonamide

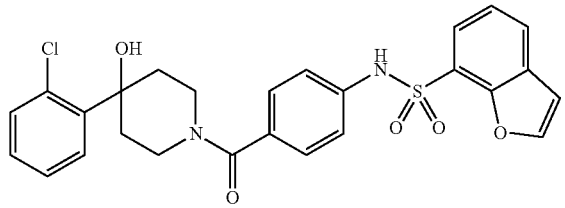 [SMILES: O=C(c1ccc(NS(=O)(=O)c2cccc3ccoc23)cc1)N1CCC(O)(c2ccccc2Cl)CC1]

¹H NMR (CHLOROFORM-d) δ: 7.75-7.88 (m, 3H), 7.52 (dd, J=7.9, 1.5 Hz, 1H), 7.40 (dd, J=7.5, 1.3 Hz, 1H), 7.30-7.35 (m, 2H), 7.21-7.28 (m, 3H), 7.10 (d, J=8.6 Hz, 2H), 6.90 (d, J=2.1 Hz, 1H), 4.64 (br. s., 1H), 3.59 (br. s., 1H), 3.51 (s, 1H), 3.31 (br. s., 1H), 2.91 (s, 1H), 2.14-2.31 (m, 1H), 2.09 (br. s., 1H), 1.86-2.07 (m, 2H). LC-MS: m/z 511.0 (M+H)+

Compound 157 (General procedure 6, Step C)

N-(3-chloro-4-(4-(2-chlorophenyl)-4-hydroxypiperidine-1-carbonyl)phenyl)quinoline-8-sulfonamide

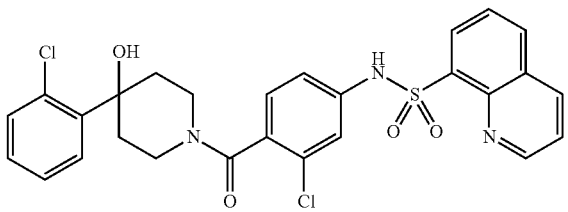 [SMILES: O=C(c1ccc(NS(=O)(=O)c2cccc3cccnc23)cc1Cl)N1CCC(O)(c2ccccc2Cl)CC1]

¹H NMR (CHLOROFORM-d) δ: 9.16 (d, J=4.0 Hz, 1H), 8.42 (d, J=7.3 Hz, 1H), 8.35 (d, J=8.1 Hz, 1H), 8.10 (d, J=8.3 Hz, 1H), 8.03 (d, J=5.4 Hz, 1H), 7.61-7.69 (m, 2H), 7.47-7.55 (m, 1H), 7.39 (d, J=7.5 Hz, 1H), 7.19-7.25 (m, 1H), 7.16 (s, 1H), 6.95-7.13 (m, 3H), 4.63-4.73 (m, 1H), 3.61 (d, J=11.0 Hz, 1H), 3.21-3.35 (m, 2H), 2.35 (td, J=13.2, 4.6 Hz, 2H), 2.10 (t, J=11.3 Hz, 2H). LC-MS: m/z 556.5 (M+H)+

Compound 222 (General procedure 6, Step C)

N-(2-chloro-4-(4-(2-chlorophenyl)-4-hydroxypiperidine-1-carbonyl)phenyl)quinoline-8-sulfonamide

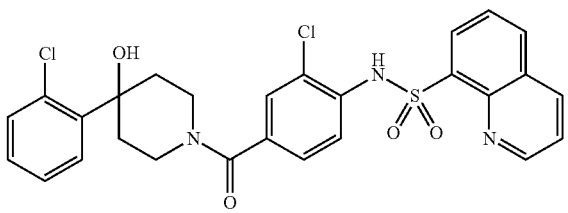

¹H NMR (CHLOROFORM-d) δ: 9.13 (dd, J=4.3, 1.6 Hz, 1H), 8.92 (br. s., 1H), 8.48 (dd, J=7.4, 1.2 Hz, 1H), 8.29 (dd, J=8.3, 1.6 Hz, 1H), 8.05-8.12 (m, 1H), 7.84 (d, J=8.6 Hz, 1H), 7.58-7.68 (m, 2H), 7.51 (d, J=7.8, 1.6 Hz, 1H), 7.40 (dd, J=7.7, 1.5 Hz, 1H), 7.30-7.34 (m, 1H), 7.23-7.27 (m, 1H), 7.19 (dd, J=8.6, 1.9 Hz, 1H), 4.60 (br. s., 1H), 3.61 (br. s., 2H), 3.31 (br. s., 1H), 2.91 (br. s., 1H), 2.14-2.27 (m, 1H), 1.91-2.14 (m, 3H). LC-MS: m/z 556.5 (M+H)+

Compound 253 (General procedure 6, Step C)

N-(4-(4-hydroxy-4-(3-hydroxypropyl)piperidine-1-carbonyl)phenyl)quinoline-8-sulfonamide

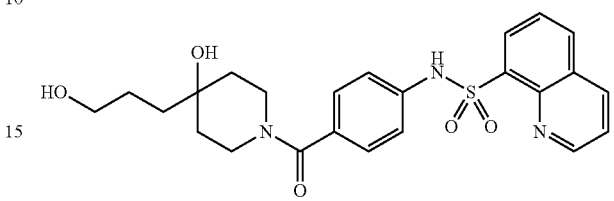

¹H NMR (DMSO-d₆) δ: 10.40 (s, 1H), 9.13 (dd, J=4.1, 1.8 Hz, 1H), 8.52 (dd, J=8.5, 1.8 Hz, 1H), 8.42 (dd, J=7.3, 1.2 Hz, 1H), 8.29 (dd, J=8.2, 1.5 Hz, 1H), 7.63-7.85 (m, 2H), 7.01-7.16 (m, 4H), 4.39 (br. s., 1H), 4.25 (s, 1H), 3.17 (br. s., 2H), 3.07 (br. s., 1H), 1.39-1.51 (m, 3H), 1.34 (dd, J=9.4, 5.6 Hz, 5H). LC-MS: m/z 470.2 (M+H)+

Compound 224 (General procedure 6, Step C)

N-(4-(4-(2-chlorophenyl)-4-hydroxypiperidine-1-carbonyl)phenyl)-2-fluoroquinoline-8-sulfonamide

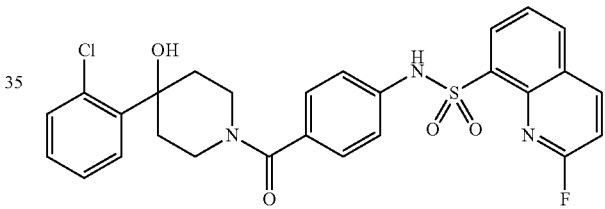

¹H NMR (CHLOROFORM-d) δ: 8.33-8.48 (m, 2H), 8.02-8.07 (m, 2H), 7.60 (t, J=7.8 Hz, 1H), 7.49 (dd, J=7.8, 1.3 Hz, 1H), 7.37 (dd, J=7.7, 1.5 Hz, 1H), 7.28 (br. s., 1H), 7.21-7.25 (m, 2H), 7.20 (s, 1H), 7.11-7.16 (m, 2H), 3.56 (br. s., 3H), 2.18-2.38 (m, 2H), 1.64 (br. s., 4H). LC-MS: m/z 540.6 (M+H)+

Compound 229 (General procedure 6, Step C)

5-fluoro-N-(4-(4-(6-fluoro-2-methylpyridin-3-yl)-4-hydroxypiperidine-1-carbonyl)phenyl)quinoline-8-sulfonamide

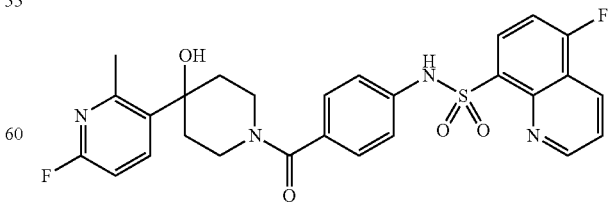

¹H NMR (CHLOROFORM-d) δ: 9.21 (dd, J=4.3, 1.6 Hz, 1H), 8.57 (dd, J=8.6, 1.6 Hz, 1H), 8.34-8.45 (m, 2H), 7.68-7.74 (m, 2H), 7.27 (s, 1H), 7.17-7.22 (m, J=8.3 Hz, 2H), 7.05-7.11 (m, J=8.3 Hz, 2H), 6.70 (dd, J=8.5, 3.6 Hz, 1H), 3.46-3.65 (m, 2H), 1.91-2.08 (m, 4H), 1.62-1.82 (m, 4H). LC-MS: m/z 539.7 (M+H)⁺

Compound 115 (General procedure 6, Step C)

N-(4-(4-benzyl-4-hydroxypiperidine-1-carbonyl)-3-fluorophenyl)quinoline-8-sulfonamide

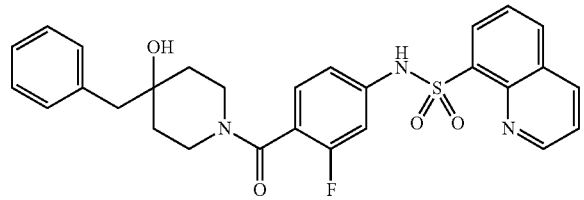 [SMILES: O=C(c1ccc(NS(=O)(=O)c2cccc3cccnc23)cc1F)N1CCC(O)(Cc2ccccc2)CC1]

¹H NMR (DMSO-d₆) δ: 10.67 (s, 1H), 9.119-9.110 (m, 1H), 8.48 (dd, 2H, J=8 Hz & J=7.2 Hz), 8.29 (d, 1H, J=8.4 Hz), 7.77-7.69 (m, 2H), 7.25-7.06 (m, 6H), 6.94-6.90 (m, 2H), 4.45 (s, 1H), 4.12-4.09 (m, 1H), 3.17-2.98 (m, 3H), 2.68 (s, 2H), 1.39-1.23 (m, 4H). LC-MS: m/z 520.6 (M+H)⁺

Compound 163 (General procedure 6, Step C)

N-(4-(4-benzyl-4-hydroxypiperidine-1-carbonyl)-2-fluorophenyl)quinoline-8-sulfonamide

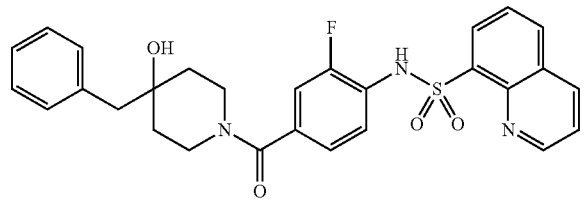 [SMILES: Cc1cc(C(=O)N2CCC(O)(Cc3ccccc3)CC2)ccc1NS(=O)(=O)c1cccc2cccnc12]

¹H NMR (DMSO-d₆) δ: 9.88 (bs, 1H), 9.08-9.06 (m, 1H), 8.57-8.54 (m, 1H), 8.29 (t, 2H, J=8.4 Hz), 7.31-7.17 (m, 6H), 7.08-7.03 (m, 2H), 4.44 (s, 1H), 4.09-4.01 (m, 1H), 3.21-3.02 (m, 3H), 2.65 (s, 2H), 1.41-1.23 (m, 4H). LC-MS: m/z 520.6 (M+H)⁺

Compound 101 (General procedure 6, Step C)

N-(4-(4-benzyl-4-hydroxypiperidine-1-carbonyl)-2-methylphenyl)quinoline-8-sulfonamide

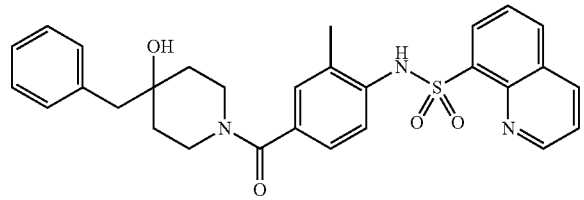

¹H NMR (DMSO-d₆) δ: 9.35 (s, 1H), 9.3-9.12 (m, 1H), 8.57 (d, 1H, J=8.4 Hz), 8.28 (dd, 2H, J=8.8 Hz & J=7.2 Hz), 7.77-7.68 (m, 2H), 7.25-7.17 (m, 5H), 7.04-6.95 (m, 3H), 4.08 (bs, 1H), 3.39-3.37 (m, 1H), 3.22-3.01 (m, 3H), 2.65 (s, 2H), 2.04 (s, 3H), 1.40-1.24 (m, 4H). LC-MS: m/z 516.6 (M+H)⁺

Compound 112 (General procedure 6, Step C)

N-(4-(4-benzyl-4-hydroxypiperidine-1-carbonyl)-3-methoxyphenyl)quinoline-8-sulfonamide

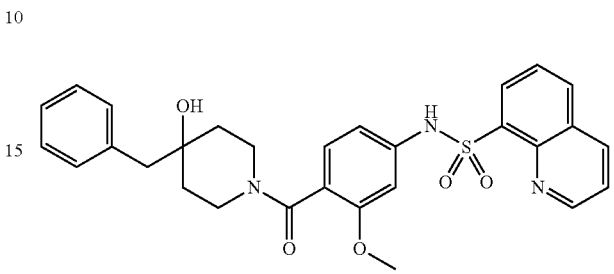

¹H NMR (DMSO-d₆) δ: 10.26 (bs, 1H), 9.13 (bs, 1H), 8.49-8.21 (m, 2H), 7.71-7.69 (m, 2H), 7.23-7.17 (m, 5H), 6.80-6.61 (m, 3H), 4.08-4.07 (m, 1H), 3.54 (s, 3H), 3.18 (s, 2H), 2.92-2.84 (m, 2H), 2.66-2.62 (m, 2H), 1.45-1.34 (m, 4H). LC-MS: m/z 532.6 (M+H)⁺

Compound 131 (General procedure 6, Step C)

N-(4-(4-benzyl-4-hydroxypiperidine-1-carbonyl)phenyl)quinoline-8-sulfonamide

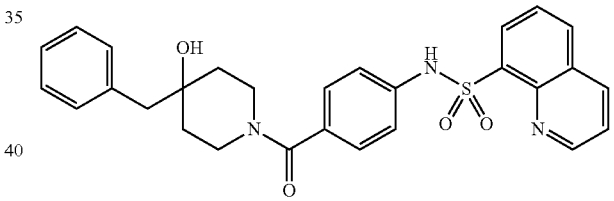

¹H NMR (CHLOROFORM-d) δ: 9.14-9.13 (m, 1H), 8.36-8.27 (m, 2H), 8.04-8.02 (m, 1H), 7.62-7.56 (m, 2H), 7.33-7.27 (m, 2H), 7.16-7.15 (m, 3H), 7.14-7.13 (m, 2H), 4.36 (bs, 1H), 3.72-3.66 (m, 1H), 3.44-3.42 (m, 2H), 3.18-3.12 (m, 1H), 2.74 (s, 2H), 1.48-1.42 (m, 4H). LC-MS: m/z 502.6 (M+H)⁺

Compound 226 (General procedure 6, Step C)

N-(4-(4-(2-chlorophenyl)-4-hydroxypiperidine-1-carbonyl)naphthalen-1-yl)quinoline-8-sulfonamide

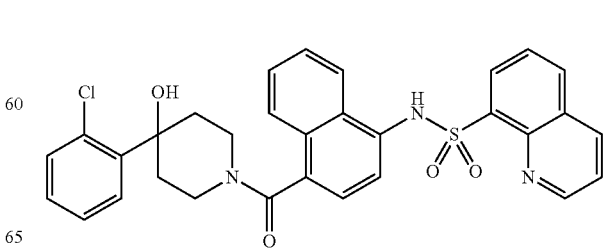

¹H NMR (CHLOROFORM-d) δ: 9.27 (d, J=4.3 Hz, 2H), 8.39-8.48 (m, 2H), 8.29-8.38 (m, 1H), 8.12 (dd, J=7.5, 4.3 Hz, 1H), 7.83-7.92 (m, 1H), 7.65-7.76 (m, 2H), 7.48-7.57 (m, 3H), 7.39 (d, J=7.5 Hz, 1H), 7.20-7.27 (m, 2H), 7.16 (d, J=2.4 Hz, 1H), 4.88 (br. s., 1H), 3.33-3.59 (m, 2H), 3.17-3.33 (m, 2H), 2.56 (d, J=5.1 Hz, 1H), 2.45 (d, J=4.8 Hz, 1H), 1.85 (d, J=11.0 Hz, 1H), 1.73 (d, J=16.1 Hz, 1H). LC-MS: m/z 573.1 (M+H)⁺

Compound 169 (General procedure 6, Step C)

N-(4-(4-(2,3-difluorobenzyl)-4-hydroxypiperidine-1-carbonyl)phenyl)quinoline-8-sulfonamide

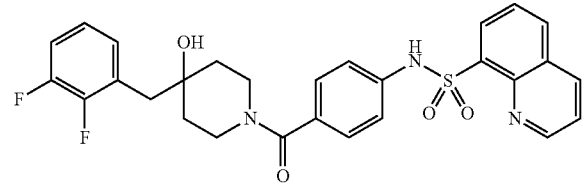 [SMILES: O=C(c1ccc(NS(=O)(=O)c2cccc3cccnc23)cc1)N1CCC(O)(Cc2cccc(F)c2F)CC1]

¹H NMR (400 MHz, CDCl₃) δ: 9.16 (dd, J=4.2, 1.4 Hz, 1H), 8.38 (d, J=7.3 Hz, 1H), 8.31 (d, J=8.4 Hz, 1H), 8.06 (d, J=8.2 Hz, 1H), 7.69-7.57 (m, 2H), 7.17-7.13 (m, 2H), 7.13-7.05 (m, 3H), 7.04-6.92 (m, 2H), 6.73 (s, 1H), 4.39 (s, 1H), 3.87 (s, 1H), 3.40 (s, 1H), 3.23 (s, 1H), 2.84-2.74 (m, 2H), 1.74-1.60 (m, 2H), 1.71-1.59 (m, 4H). LC-MS: m/z 538.6 (M+H)⁺

Compound 158 (General procedure 6, Step C)

5-fluoro-N-(4-(4-(2-fluorobenzyl)-4-hydroxypiperidine-1-carbonyl)phenyl)quinoline-8-sulfonamide

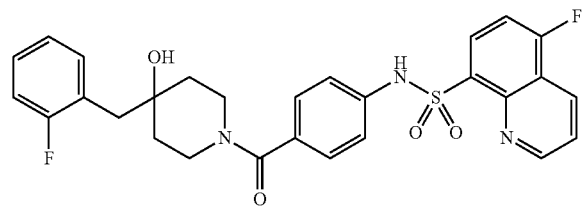 [SMILES: O=C(c1ccc(NS(=O)(=O)c2ccc(F)c3cccnc23)cc1)N1CCC(O)(Cc2ccccc2F)CC1]

¹H NMR (CHLOROFORM-d) δ: 9.19 (s, 1H), 8.53 (s, 1H), 8.41-8.33 (m, 1H), 7.66 (s, 1H), 7.24 (dd, J=13.3, 6.0 Hz, 2H), 7.17 (dd, J=14.0, 7.9 Hz, 3H), 7.13-7.08 (m, 2H), 7.05 (d, J=7.6 Hz, 3H), 4.37 (s, 1H), 3.49-3.05 (m, 3H), 2.82 (s, 2H), 1.78-1.50 (m, 4H). LC-MS: m/z 538.1 (M+H)⁺

Compound 120 (General procedure 6, Step C)

N-(4-(4-(2,6-difluorobenzyl)-4-hydroxypiperidine-1-carbonyl)phenyl)quinoline-8-sulfonamide

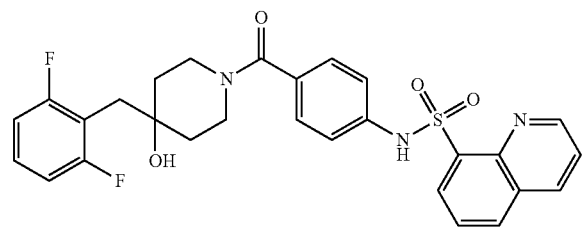 [SMILES: O=C(c1ccc(NS(=O)(=O)c2cccc3cccnc23)cc1)N1CCC(O)(Cc2c(F)cccc2F)CC1]

¹H NMR (CHLOROFORM-d) δ: 9.16 (dd, J=4.3, 1.9 Hz, 1H), 8.58 (br. s., 1H), 8.35 (dd, J=18.0, 7.8 Hz, 1H), 8.35 (dd, J=17.9, 7.9 Hz, 1H), 8.06 (dd, J=8.3, 1.3 Hz, 1H), 7.57-7.69 (m, 2H), 7.19-7.27 (m, 1H), 7.14-7.19 (m, 2H), 7.05-7.11 (m, 2H), 6.86-6.94 (m, 2H), 4.35-4.45 (m, 1H), 3.41-3.53 (m, 1H), 3.31 (br. s., 1H), 3.08-3.20 (m, 1H), 2.88-2.92 (m, 1H), 2.82 (s, 1H), 1.70 (br. s., 1H), 1.64 (dd, J=11.1, 6.9 Hz, 2H), 1.43-1.58 (m, 2H). LC-MS: m/z 538.7 (M+H)

Compound 109 (General procedure 6, Step C)

N-(4-(4-hydroxy-4-(2-(trifluoromethyl)benzyl)piperidine-1-carbonyl)phenyl)quinoline-8-sulfonamide

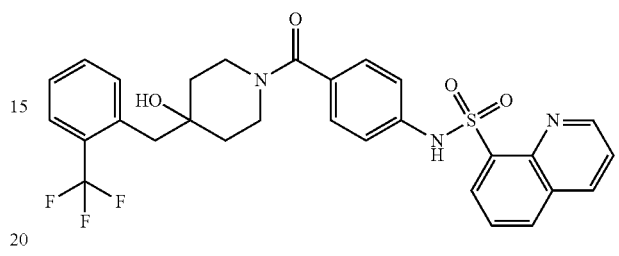

¹H NMR (CHLOROFORM-d) δ: 9.15 (dd, J=4.3, 1.6 Hz, 1H), 8.60 (br. s., 1H), 8.27-8.40 (m, 2H), 8.04 (dd, J=8.2, 1.2 Hz, 1H), 7.55-7.71 (m, 3H), 7.43-7.54 (m, 2H), 7.31-7.40 (m, 1H), 7.12-7.21 (m, J=8.6 Hz, 2H), 7.01-7.12 (m, J=8.6 Hz, 2H), 4.41 (br. s., 1H), 3.46 (d, J=9.1 Hz, 1H), 3.27 (br. s., 1H), 3.05 (br. s., 1H), 2.98 (s, 2H), 1.83 (br. s., 1H), 1.66 (br. s., 2H), 1.56 (br. s., 2H), 1.45 (br. s., 1H). LC-MS: m/z 570.7 (M+H)⁺

Compound 117 (General procedure 6, Step C)

N-(4-(4-hydroxy-4-neopentylpiperidine-1-carbonyl)phenyl)quinoline-8-sulfonamide

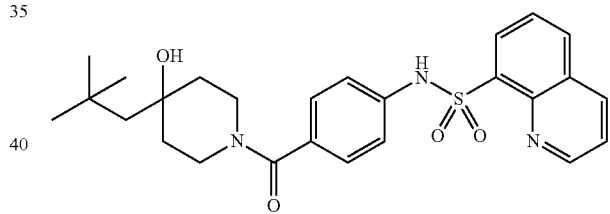

¹H NMR (CHLOROFORM-d) δ: 9.20 (d, J=2.9 Hz, 1H), 8.73 (s, 1H), 8.41 (dd, J=7.3, 1.2 Hz, 1H), 8.36 (d, J=7.3 Hz, 1H), 8.08 (dd, J=8.2, 1.2 Hz, 1H), 7.70-7.60 (m, 2H), 7.18 (d, J=8.5 Hz, 2H), 7.10 (d, J=8.5 Hz, 2H), 4.36 (s, 1H), 3.39 (d, J=33.4 Hz, 2H), 3.16 (s, 1H), 1.75-1.57 (m, 4H), 1.49 (s, 2H), 1.05 (s, 9H). LC-MS: m/z 482.7 (M+H)⁺

Compound 178 (General procedure 6, Step C)

N-(4-(4-(2,3-difluorophenyl)-4-hydroxypiperidine-1-carbonyl)phenyl)benzo[d]thiazole-4-sulfonamide

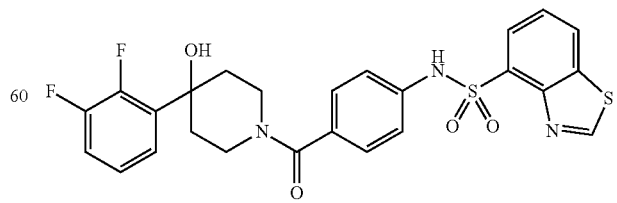

¹H NMR (DMSO-d₆) δ: 10.79 (s, 1H), 9.66 (s, 1H), 8.50 (d, J=8.1 Hz, 1H), 8.12 (d, J=7.5 Hz, 1H), 7.65 (t, J=7.8 Hz, 1H), 7.41 (t, J=7.4 Hz, 1H), 7.33 (q, J=8.2 Hz, 1H), 7.16-7.24 (m, 3H), 7.11-7.15 (m, 2H), 4.31 (br. s., 1H), 3.32-3.13 (br. s., 3H), 2.00 (d, J=7.3 Hz, 2H), 1.63 (br. s., 2H). LC-MS: m/z 530.6 (M+H)⁺

Compound 215 (General procedure 6, Step C)

N-(4-(4-(2-(difluoromethyl)phenyl)-4-hydroxypiperidine-1-carbonyl)phenyl)benzo[d]thiazole-4-sulfonamide

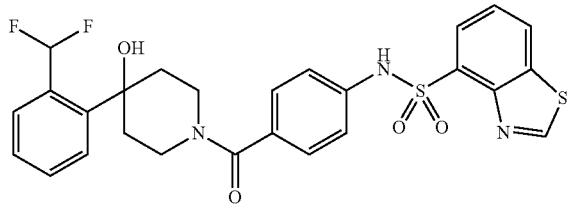 [SMILES: O=C(c1ccc(NS(=O)(=O)c2cccc3scnc23)cc1)N1CCC(O)(c2ccccc2C(F)F)CC1]

¹H NMR (CHLOROFORM-d) δ: 9.31 (br. s., 1H), 8.19 (d, J=7.8 Hz, 1H), 8.08-8.14 (m, 1H), 7.93-8.03 (m, 1H), 7.84 (d, J=4.8 Hz, 1H), 7.48-7.60 (m, 2H), 7.44 (br. s., 1H), 7.37 (br. s., 1H), 7.23 (d, J=8.3 Hz, 2H), 7.10-7.18 (m, 2H), 4.91-5.06 (m, 1H), 4.54-4.73 (m, 1H), 3.80 (br. s., 2H), 3.72 (br. s., 1H), 3.45-3.65 (m, 2H), 2.32-2.61 (m, 2H). LC-MS: m/z 544.7 (M+H)⁺

Compound 241 (General procedure 6, Step C)

N-(4-(4-hydroxy-4-(2-hydroxy-2-methylpropyl)piperidine-1-carbonyl)phenyl)quinoline-8-sulfonamide

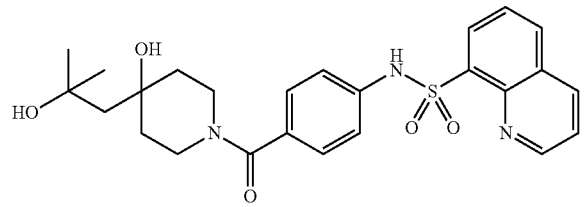 [SMILES: CC(C)(O)CC1(O)CCN(C(=O)c2ccc(NS(=O)(=O)c3cccc4cccnc34)cc2)CC1]

¹H NMR (CHLOROFORM-d) δ: 9.16 (dd, J=4.3, 1.8 Hz, 1H), 8.56 (br. s., 1H), 8.38 (dd, J=7.3, 1.3 Hz, 1H), 8.31 (dd, J=8.4, 1.6 Hz, 1H), 8.06 (dd, J=8.3, 1.1 Hz, 1H), 7.57-7.67 (m, 2H), 7.17 (d, J=8.5 Hz, 2H), 7.08 (d, J=8.5 Hz, 2H), 4.31 (br. s., 1H), 3.40 (br. s., 2H), 3.21 (br. s., 1H), 1.86-1.65 (br.m, 6H), 1.36 (s, 6H). LC-MS: m/z 484.6 (M+H)⁺

Compound 167 (General procedure 6, Step C)

N-(4-(4-butyl-4-hydroxypiperidine-1-carbonyl)phenyl)quinoline-8-sulfonamide

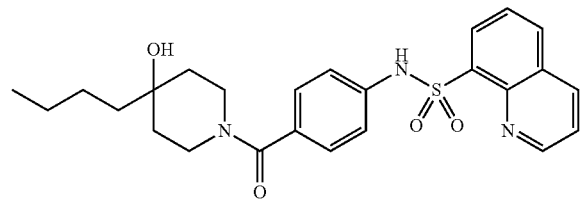 [SMILES: CCCCC1(O)CCN(C(=O)c2ccc(NS(=O)(=O)c3cccc4cccnc34)cc2)CC1]

¹H NMR (CHLOROFORM-d) δ: 9.16 (d, J=2.6 Hz, 1H), 8.59 (br. s., 1H), 8.25-8.42 (m, 2H), 8.06 (d, J=7.9 Hz, 1H), 7.55-7.68 (m, 2H), 7.17 (d, J=8.2 Hz, 2H), 7.08 (d, J=8.2 Hz, 2H), 4.33 (br. s., 1H), 3.42 (br. s., 1H), 3.34 (br. s., 1H), 3.19 (br. s., 1H), 1.60 (br. s., 2H), 1.37-1.37 (m, 11H), 0.9 (t, J=6.6 Hz, 3H). LC-MS: m/z 468.6 (M+H)⁺

Compound 132 (General procedure 6, Step C)

N-(4-(4-hydroxy-4-((1-methylcyclopropyl)methyl)piperidine-1-carbonyl)phenyl)benzo[d]thiazole-4-sulfonamide

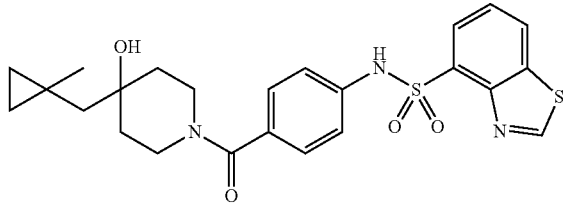 [SMILES: CC1(CC2(O)CCN(C(=O)c3ccc(NS(=O)(=O)c4cccc5scnc45)cc3)CC2)CC1]

¹H NMR (CHLOROFORM-d) δ: 9.31 (s, 1H), 8.15-8.23 (m, 1H), 8.06-8.13 (m, 1H), 7.92 (s, 1H), 7.54 (t, J=7.8 Hz, 1H), 7.16-7.24 (m, J=8.3 Hz, 2H), 7.07-7.14 (m, J=8.3 Hz, 2H), 4.34 (br. s., 1H), 3.29 (br. s., 3H), 1.66 (br. s., 2H), 1.47 (s, 2H), 1.33 (br. s., 1H), 1.28 (s, 1H), 1.17 (s, 3H), 0.25-0.38 (m, 4H). LC-MS: m/z 480.6 (M+H)⁺

Compound 121 (General procedure 6, Step C)

N-(4-(4-hydroxy-4-((1-methylcyclopropyl)methyl)piperidine-1-carbonyl)phenyl)quinoline-8-sulfonamide

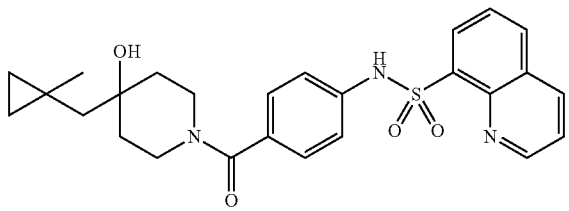 [SMILES: CC1(CC2(O)CCN(C(=O)c3ccc(NS(=O)(=O)c4cccc5cccnc45)cc3)CC2)CC1]

¹H NMR (CHLOROFORM-d) δ: 9.16 (dd, J=4.3, 1.6 Hz, 1H), 8.56 (br. s., 1H), 8.38 (dd, J=7.5, 1.3 Hz, 1H), 8.32 (dd, J=8.3, 1.6 Hz, 1H), 8.06 (dd, J=8.2, 1.2 Hz, 1H), 7.58-7.67 (m, 2H), 7.14-7.20 (m, J=8.6 Hz, 2H), 7.04-7.11 (m, J=8.6 Hz, 2H), 4.36 (br. s., 1H), 3.44 (br. s., 1H), 3.36 (br. s., 1H), 3.17 (br. s., 1H), 1.74 (br. s., 1H), 1.70 (br. s., 1H), 1.63 (d, J=6.7 Hz, 3H), 1.46 (s, 2H), 1.17 (s, 3H), 0.24-0.37 (m, 4H). LC-MS: m/z 480.6 (M+H)⁺

Compound 198 (General procedure 6, Step C)

N-(4-(4-(cyclopropylmethyl)-4-hydroxypiperidine-1-carbonyl)phenyl)benzo[d]thiazole-4-sulfonamide

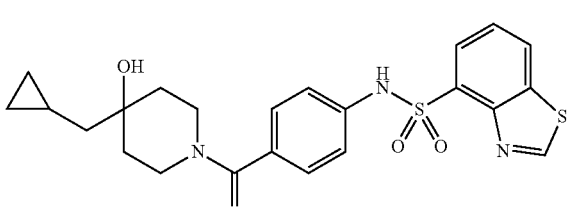

¹H NMR (CHLOROFORM-d) δ: 9.31 (br. s., 1H), 8.19 (d, J=7.8 Hz, 1H), 8.10 (d, J=7.3 Hz, 1H), 7.94 (s, 1H), 7.54 (t, J=7.7 Hz, 1H), 7.20 (br. s., 2H), 7.12 (br. s., 2H), 4.38 (br. s., 1H), 3.51 (br. s., 1H), 3.36 (br. s., 2H), 2.06 (br. s., 2H), 1.69 (d, J=8.6 Hz, 2H), 1.43 (br. s., 2H), 0.74 (br. s., 1H), 0.53 (d, J=7.5 Hz, 2H), 0.11 (d, J=4.3 Hz, 2H). LC-MS: m/z 472.6 (M+H)⁺

Compound 201 (General procedure 6, Step C)

N-(4-(4-(cyclobutylmethyl)-4-hydroxypiperidine-1-carbonyl)phenyl)-5-fluoroquinoline-8-sulfonamide

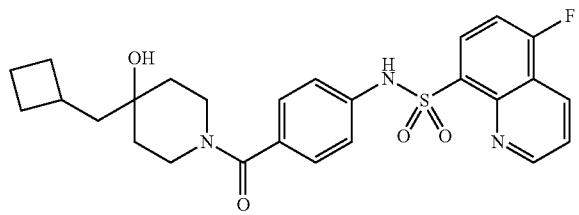 [SMILES: O=C(c1ccc(NS(=O)(=O)c2ccc(F)c3cccnc23)cc1)N1CCC(O)(CC2CCC2)CC1]

¹H NMR (CHLOROFORM-d) δ: 9.21 (dd, J=4.2, 1.5 Hz, 1H), 8.57 (dd, J=8.5, 1.5 Hz, 1H), 8.37 (dd, J=8.2, 5.7 Hz, 2H), 7.70 (dd, J=8.5, 4.3 Hz, 1H), 7.26 (d, J=8.7 Hz, 1H), 7.17 (d, J=8.4 Hz, 2H), 7.07 (d, J=8.4 Hz, 2H), 4.33 (s, 1H), 3.54-3.08 (m, 4H), 2.49 (dd, J=15.5, 7.7 Hz, 1H), 2.13-2.01 (m, 2H), 1.91 (dd, J=18.4, 9.4 Hz, 1H), 1.83-1.75 (m, 1H), 1.60 (d, J=7.0 Hz, 5H), 1.48-1.51 (m, 2H), 1.42 (s, 2H), 1.27 (s, 2H). LC-MS: m/z 498.6 (M+H)⁺

Compound 134 (General procedure 6, Step C)

N-(4-(4-hydroxy-4-neopentylpiperidine-1-carbonyl)phenyl)benzo[d]thiazole-4-sulfonamide

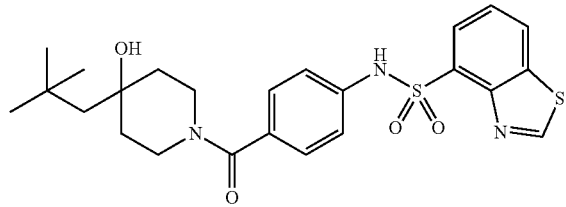 [SMILES: CC(C)(C)CC1(O)CCN(C(=O)c2ccc(NS(=O)(=O)c3cccc4scnc34)cc2)CC1]

¹H NMR (CHLOROFORM-d) δ: 9.31 (s, 1H), 8.19 (d, J=8.3 Hz, 1H), 8.10 (d, J=8.3 Hz, 1H), 7.91 (s, 1H), 7.54 (t, J=7.9 Hz, 1H), 7.18-7.22 (m, J=8.3 Hz, 2H), 7.09-7.13 (m, J=8.3 Hz, 2H), 1.65 (br. s., 4H), 1.50 (s, 2H), 1.28 (s, 4H), 1.05 (s, 9H). LC-MS: m/z 488.6 (M+H)⁺

Compound 187 (General procedure 6, Step C)

5-fluoro-N-(4-(4-hydroxy-4-neopentylpiperidine-1-carbonyl)phenyl)quinoline-8-sulfonamide

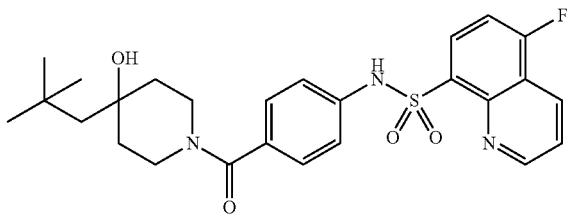 [SMILES: CC(C)(C)CC1(O)CCN(C(=O)c2ccc(NS(=O)(=O)c3ccc(F)c4cccnc34)cc2)CC1]

¹H NMR (CHLOROFORM-d) δ: 9.23 (dd, J=4.3, 1.5 Hz, 1H), 8.60 (dd, J=8.5, 1.5 Hz, 1H), 8.44 (s, 1H), 8.39 (dd, J=8.3, 5.7 Hz, 1H), 7.72 (dd, J=8.5, 4.3 Hz, 1H), 7.31-7.26 (m, 1H), 7.18 (d, J=8.5 Hz, 2H), 7.08 (d, J=8.5 Hz, 2H), 4.36 (s, 1H), 3.50-3.02 (m, 3H), 1.70-1.58 (m, 4H), 1.49 (s, 2H), 1.06 (d, J=8.3 Hz, 9H). LC-MS: m/z 500.71 (M+H)⁺

Compound 208 (General procedure 6, Step C)

5-fluoro-N-(4-(4-hydroxy-4-(2-(trifluoromethyl)benzyl)piperidine-1-carbonyl)phenyl)quinoline-8-sulfonamide

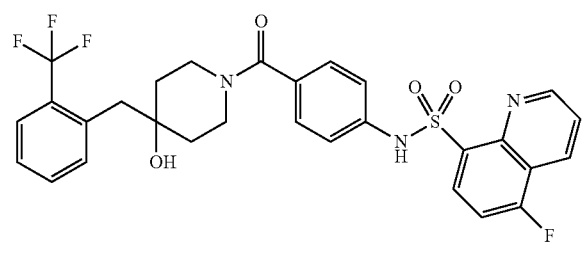 [SMILES: O=C(c1ccc(NS(=O)(=O)c2ccc(F)c3cccnc23)cc1)N1CCC(O)(Cc2ccccc2C(F)(F)F)CC1]

¹H NMR (CHLOROFORM-d) δ: 1.46-1.64 (m, 3H), 1.81 (br. s., 1H), 2.98 (s, 2H), 3.05 (br. s., 1H), 3.28 (br. s., 1H), 3.38-3.51 (m, 1H), 4.42 (br. s., 1H), 7.06 (m, J=8.33 Hz, 2H), 7.16 (m, J=8.33 Hz, 2H), 7.23-7.27 (m, 1H), 7.32-7.39 (m, 1H), 7.44-7.53 (m, 2H), 7.64-7.72 (m, 2H), 8.37 (dd, J=8.19, 5.78 Hz, 1H), 8.41 (s, 1H), 8.55 (dd, J=8.60, 1.61 Hz, 1H), 9.20 (dd, J=4.30, 1.61 Hz, 1H). LC-MS: m/z 588.7 (M+H)⁺

Compound 412 (General procedure 6, Step C)

N-(4-(4-hydroxy-4-(2-(trifluoromethyl)benzyl)piperidine-1-carbonyl)phenyl)benzo[d]thiazole-4-sulfonamide

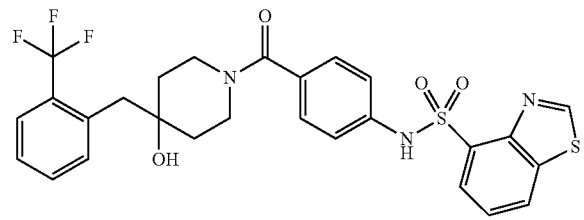 [SMILES: O=C(c1ccc(NS(=O)(=O)c2cccc3scnc23)cc1)N1CCC(O)(Cc2ccccc2C(F)(F)F)CC1]

¹H NMR (CHLOROFORM-d) δ: 1.44 (br. s., 1H), 1.51-1.70 (m, 3H), 2.99 (s, 2H), 3.06 (br. s., 1H), 3.30 (br. s., 1H), 3.39-3.47 (m, 1H), 4.42 (br. s., 1H), 7.10 (m, J=8.60 Hz, 2H), 7.17 (m, J=8.60 Hz, 2H), 7.33-7.40 (m, 1H), 7.45-7.56 (m, 3H), 7.67 (d, J=7.79 Hz, 1H), 8.10 (dd, J=7.52, 1.07 Hz, 1H), 8.17 (dd, J=8.06, 0.81 Hz, 1H), 8.22 (s, 1H), 9.29 (s, 1H). LC-MS: m/z 576.7 (M+H)⁺

Compound 181 (General procedure 6, Step C)

N-(4-(4-hydroxy-4-(2-methylallyl)piperidine-1-carbonyl)phenyl)benzo[d]thiazole-4-sulfonamide

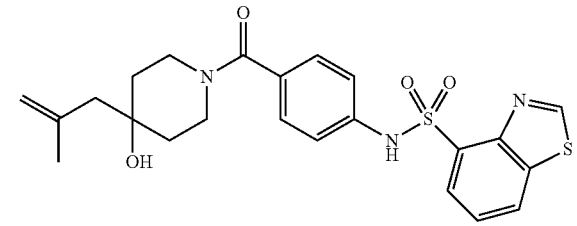 [SMILES: C=C(C)CC1(O)CCN(C(=O)c2ccc(NS(=O)(=O)c3cccc4scnc34)cc2)CC1]

¹H NMR (CHLOROFORM-d) δ: 9.30 (s, 1H), 8.18 (dd, J=8.1, 0.8 Hz, 1H), 8.08-8.14 (m, 1H), 8.06 (s, 1H), 7.53 (t, J=7.8 Hz, 1H), 7.17-7.24 (m, 2H), 7.06-7.15 (m, 2H), 4.96-5.03 (m, 1H), 4.78 (s, 1H), 4.36 (br. s., 1H), 3.44 (br. s., 1H), 3.35 (br. s., 1H), 3.17 (br. s., 1H), 2.18-2.22 (m, 2H), 1.82 (s, 3H), 1.63 (br. s., 2H), 1.48 (br. s., 2H). LC-MS: m/z 472.69 (M+H)+

Compound 414 (General procedure 6, Step C)

(E)-N-(4-(4-(3,3-difluoroprop-1-en-1-yl)-4-hydroxypiperidine-1-carbonyl)phenyl)quinoline-8-sulfonamide

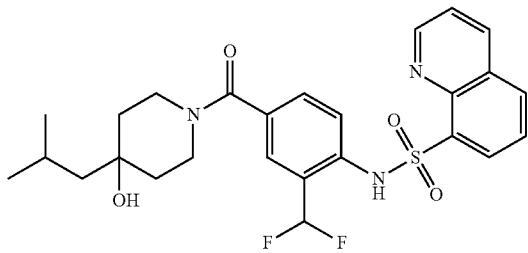 [SMILES: CC(C)CC1(O)CCN(C(=O)c2ccc(NS(=O)(=O)c3cccc4cccnc34)c(C(F)F)c2)CC1]

¹H NMR (CHLOROFORM-d) δ: 9.14 (d, J=5.6 Hz, 1H), 8.80 (br. s., 1H), 8.43 (d, J=7.3 Hz, 1H), 8.36 (d, J=8.3 Hz, 1H), 8.13 (d, J=8.1 Hz, 1H), 7.62-7.72 (m, 2H), 7.53 (s, 1H), 7.23-7.33 (m, 2H), 6.84 (t, J=56 Hz, 1H), 4.36 (br. s., 1H), 3.42 (br. s., 2H), 3.22 (br. s., 1H), 1.84 (dt, J=12.9, 6.4 Hz, 1H), 1.64 (br. s., 2H), 1.52 (br. s., 2H), 1.42 (d, J=5.9 Hz, 2H), 0.98 (d, J=6.7 Hz, 6H). LC-MS: m/z 518.7 (M+H)+

Compound 415 (General procedure 6, Step C)

(E)-N-(4-(4-(3,3-difluoroprop-1-en-1-yl)-4-hydroxypiperidine-1-carbonyl)phenyl)quinoline-8-sulfonamide

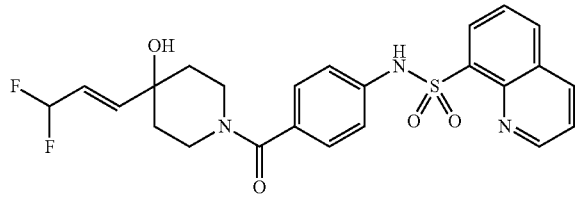 [SMILES: O=C(c1ccc(NS(=O)(=O)c2cccc3cccnc23)cc1)N1CCC(O)(/C=C/C(F)F)CC1]

¹H NMR (CHLOROFORM-d) δ: 9.21 (dd, J=4.4, 1.7 Hz, 1H), 8.85 (s, 1H), 8.40 (ddd, J=9.9, 7.9, 1.4 Hz, 2H), 8.09 (dd, J=8.2, 1.2 Hz, 1H), 7.72-7.61 (m, 2H), 7.19 (d, J=8.6 Hz, 2H), 7.13 (d, J=8.6 Hz, 2H), 6.28-5.84 (m, 3H), 4.43 (s, 1H), 3.51 (s, 1H), 3.30 (d, J=69.3 Hz, 2H), 1.82-1.52 (m, 4H). LC-MS: m/z 488.63 (M+H)+

Compound 386 (General procedure 6, Step C)

N-(4-(4-hydroxy-4-((2,2,2-trifluoroethoxy)methyl)piperidine-1-carbonyl)phenyl)benzo[d]thiazole-4-sulfonamide

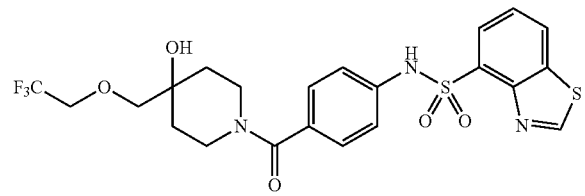

¹H NMR (METHANOL-d₄) δ: 9.47 (s, 1H), 8.31 (dd, J=8.1, 1.1 Hz, 1H), 8.07-8.14 (m, 1H), 7.55 (t, J=7.8 Hz, 1H), 7.11-7.25 (m, 4H), 4.18-4.37 (m, 1H), 3.98 (q, J=9.0 Hz, 2H), 3.48 (s, 2H), 3.35-3.43 (m, 2H), 3.19 (br. s., 1H), 1.65 (br. s., 2H), 1.38-1.59 (m, 2H). LC-MS: m/z 530.7 (M+H)+

Compound 387 (General procedure 6, Step C)

N-(4-(4-(3,3-difluorobutyl)-4-hydroxypiperidine-1-carbonyl)phenyl)benzo[d]thiazole-4-sulfonamide

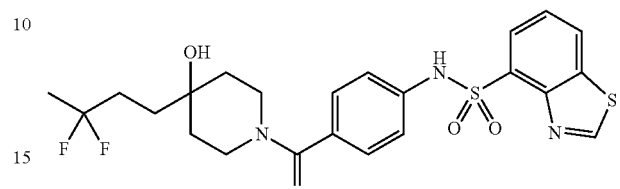

¹H NMR (CHLOROFORM-d) δ: 9.31 (s, 1H), 8.19 (d, J=8.1 Hz, 1H), 8.10 (d, J=7.3 Hz, 1H), 7.92 (s, 1H), 7.55 (t, J=7.8 Hz, 1H), 7.16-7.24 (m, J=8.1 Hz, 2H), 7.06-7.15 (m, J=8.3 Hz, 2H), 5.37 (br. s., 1H), 4.36 (br. s., 1H), 3.34 (br. s., 2H), 3.22 (br. s., 1H), 1.93-2.08 (m, 2H), 1.56-1.71 (m, 9H). LC-MS: m/z 510.7 (M+H)+

Compound 388 (General procedure 6, Step C)

4-hydroxy-N-(4-(4-hydroxy-4-isobutylpiperidine-1-carbonyl)phenyl)quinazoline-8-sulfonamide

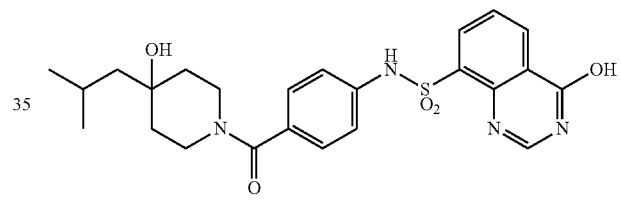

¹H NMR (METHANOL-d₄) δ: 0.97 (d, J=6.72 Hz, 6H), 1.39 (d, J=5.91 Hz, 2H), 1.49 (br. s., 2H), 1.56 (br. s., 1H), 1.66 (br. s., 1H), 1.80-1.91 (m, 1H), 7.21-7.26 (m, 4H), 7.58 (t, J=7.92 Hz, 1H), 8.28 (s, 1H), 8.39 (ddd, J=7.72, 6.11, 1.48 Hz, 2H). LC-MS: m/z 485.7 (M+H)+

Compound 389 (General procedure 6, Step C)

N-(4-(4-(4,4-difluorobutyl)-4-hydroxypiperidine-1-carbonyl)phenyl)benzo[d]thiazole-4-sulfonamide

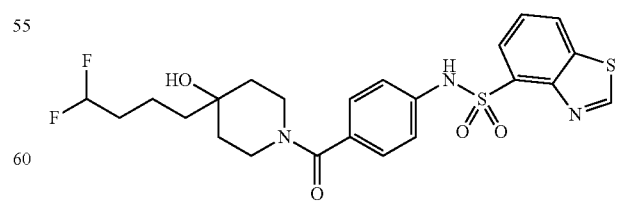

¹H NMR (400 MHz, CHLOROFORM-d) δ: 1.22-1.37 (m, 2H), 1.59 (br. s., 6H), 1.75-1.94 (m, 2H), 3.19 (d, J=4.57 Hz, 1H), 3.32 (br. s., 1H), 3.47 (br. s., 1H), 5.84 (t, J=4.30 Hz, 1H), 7.11 (m, J=8.33 Hz, 2H), 7.19 (m, J=8.33 Hz, 2H), 7.54 (t,

J=7.92 Hz, 1H), 7.96 (s, 1H), 8.10 (d, J=7.52 Hz, 1H), 8.19 (d, J=8.06 Hz, 1H), 9.31 (s, 1H). LC-MS: m/z 510.5 (M+H)$^+$

Compound 390 (General procedure 6, Step C)

N-(4-(4-hydroxy-4-(2-(trifluoromethyl)allyl)piperidine-1-carbonyl)phenyl)benzo[d]thiazole-4-sulfonamide

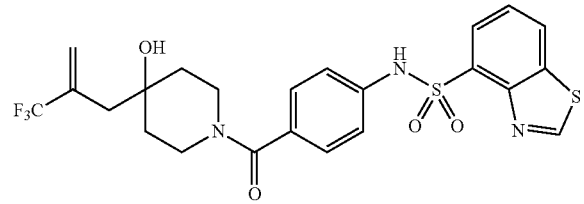 [SMILES: C=C(CC1(O)CCN(C(=O)c2ccc(NS(=O)(=O)c3cccc4scnc34)cc2)CC1)C(F)(F)F]

$^1$H NMR (CHLOROFORM-d) δ: 9.31 (s, 1H), 8.19 (dd, J=8.1, 0.8 Hz, 1H), 8.10 (dd, J=7.5, 1.1 Hz, 1H), 7.92 (s, 1H), 7.53-7.59 (m, 1H), 7.17-7.23 (m, J=8.6 Hz, 2H), 7.09-7.14 (m, J=8.6 Hz, 2H), 5.93 (d, J=1.3 Hz, 1H), 5.60 (s, 1H), 4.42 (br. s., 1H), 3.50 (br. s., 1H), 3.35 (br. s., 1H), 3.17 (br. s., 1H), 2.42 (s, 2H), 1.65 (br. s., 2H), 1.45 (br. s., 2H). LC-MS: m/z 526.7 (M+H)$^+$

Compound 421 (General procedure 6, Step C)

N-(4-(4-hydroxy-4-(3,3,3-trifluoro-2-methylpropyl)piperidine-1-carbonyl)phenyl)benzo[d]thiazole-4-sulfonamide

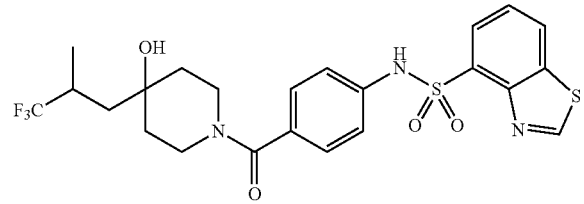 [SMILES: CC(CC1(O)CCN(C(=O)c2ccc(NS(=O)(=O)c3cccc4scnc34)cc2)CC1)C(F)(F)F]

$^1$H NMR (CHLOROFORM-d) δ: 9.31 (s, 1H), 8.19 (d, J=7.5 Hz, 1H), 8.10 (d, J=7.5 Hz, 1H), 7.98 (s, 1H), 7.54 (t, J=7.8 Hz, 1H), 7.15-7.24 (m, J=8.3 Hz, 2H), 7.05-7.15 (m, J=8.3 Hz, 2H), 4.34 (br. s., 1H), 3.51 (s, 1H), 3.12-3.41 (m, 2H), 2.44 (d, J=7.0 Hz, 1H), 1.87 (dd, J=14.9, 2.0 Hz, 1H), 1.58 (br.s., 4H), 1.42 (dd, J=14.9, 7.4 Hz, 2H), 1.21 (d, J=7.0 Hz, 3H). LC-MS: m/z 528.6 (M+H)

Compound 442 (General procedure 6, Step C)

N-(4-(4-(2-chlorophenyl)-4-hydroxypiperidine-1-carbonyl)naphthalen-1-yl)quinoline-8-sulfonamide

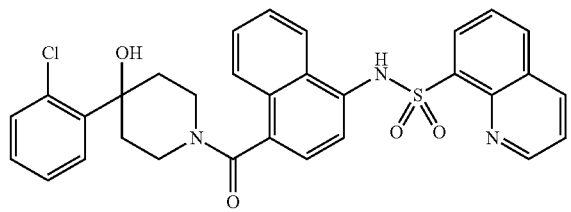 [SMILES: O=C(c1ccc(NS(=O)(=O)c2cccc3cccnc23)c2ccccc12)N1CCC(O)(c2ccccc2Cl)CC1]

$^1$H NMR (CHLOROFORM-d) δ: 9.27 (d, J=4.3 Hz, 2H), 8.39-8.48 (m, 2H), 8.29-8.38 (m, 1H), 8.12 (dd, J=7.5, 4.3 Hz, 1H), 7.83-7.92 (m, 1H), 7.65-7.76 (m, 2H), 7.48-7.57 (m, 3H), 7.39 (d, J=7.5 Hz, 1H), 7.20-7.27 (m, 2H), 7.16 (d, J=2.4 Hz, 1H), 4.88 (br. s., 1H), 3.33-3.59 (m, 2H), 3.17-3.33 (m, 2H), 2.56 (d, J=5.1 Hz, 1H), 2.45 (d, J=4.8 Hz, 1H), 1.85 (d, J=11.0 Hz, 1H), 1.73 (d, J=16.1 Hz, 1H). LC-MS: m/z 573.1 (M+H)$^+$

General Procedure 7:

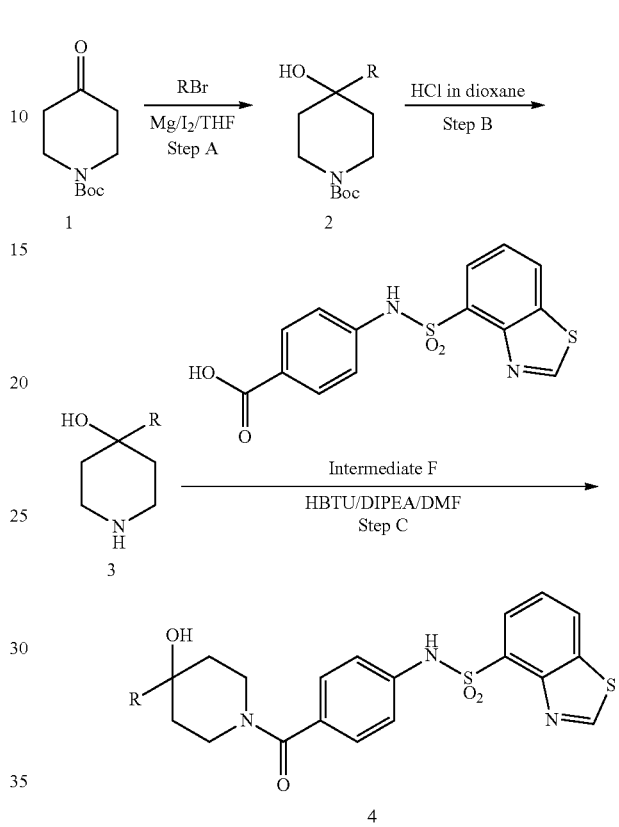

Step A:

To a mixture of RBr (0.08 mol) and magnesium turnings (4.8 g, 0.2 mol) in dry tetrahydrofuran (80 mL) was added a crystal of iodine and the mixture was stirred at room temperature until complete reaction had occurred. To this mixture was added tert-butyl 4-oxopiperidine-1-carboxylate (7.7 g, 0.039 mol) in tetrahydrofuran (20 mL) at 0° C. After 1 h at 0° C., and 3 h at room temperature the reaction mixture was diluted with ammonium chloride solution, and the mixture was extracted with ethyl acetate. After drying over Na$_2$SO$_4$, the solvent was removed in vacuo and the residue was purified via flash chromatography with 20% ethyl acetate/hexane to afford the title compound 2.

Step B:

A solution of the corresponding compound 2 (3.0 mmol) in the solution of HCl in 1,4-dioxane (3M, 5 mL) was stirred at room temperature for 3 hours. The solution was evaporated to dryness under reduced pressure to give the crude product 3 which was used in the next step without further purification.

Step C:

To a solution of compound 3 (0.2 mmol) in DMF (5 mL) was added HBTU (91 mg, 0.24 mmol) and the mixture was stirred at r.t. for 20 min, then Intermediate F (0.2 mmol) and DIPEA (0.6 mmol) were added. After stirring overnight, the reaction was partitioned between satd. Na$_2$CO$_3$ solution and DCM. The organic layer was separated and washed with water and brine, dried over Na₂SO₄ and concentrated, and then purified by a standard method to give title product 4.

Compound 392 (General procedure 7, Step C)

N-(4-(4-hydroxy-4-isopentylpiperidine-1-carbonyl) phenyl)benzo[d]thiazole-4-sulfonamide

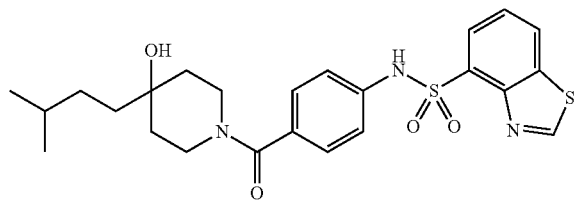 [SMILES: CC(C)CCC1(O)CCN(C(=O)c2ccc(NS(=O)(=O)c3cccc4scnc34)cc2)CC1]

¹H NMR (CHLOROFORM-d) δ: 10.76 (s, 1H), 9.65 (s, 1H), 8.49 (d, J=8.1 Hz, 1H), 8.10 (d, J=7.5 Hz, 1H), 7.63 (t, J=7.9 Hz, 1H), 7.16 (d, J=8.3 Hz, 2H), 7.09 (d, J=8.4 Hz, 2H), 4.18 (s, 1H), 4.08 (s, 1H), 3.16 (m, 3H), 1.05-1.3 (m, 9H), 0.82 (d, J=6.6 Hz, 6H). LC-MS: m/z 488.6 (M+H)⁺

Compound 393 (General procedure 7, Step C)

N-(4-(4-(4,4-difluorobut-3-en-1-yl)-4-hydroxypiperidine-1-carbonyl)phenyl)benzo[d]thiazole-4-sulfonamide

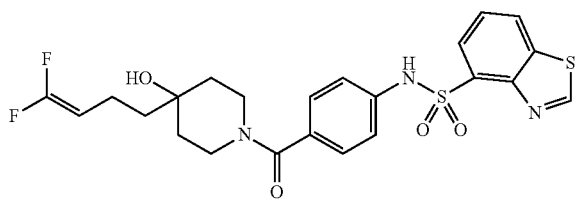 [SMILES: O=C(c1ccc(NS(=O)(=O)c2cccc3scnc23)cc1)N1CCC(O)(CCC=C(F)F)CC1]

¹H NMR (400 MHz, CHLOROFORM-d) δ: 0.89 (d, J=6.98 Hz, 2H), 1.56 (d, J=8.60 Hz, 2H), 1.70 (br. s., 2H), 1.76 (br. s., 2H), 2.02-2.13 (m, 2H), 4.09-4.23 (m, 1H), 7.11 (d, J=8.33 Hz, 2H), 7.19 (d, J=8.33 Hz, 2H), 7.54 (t, J=7.79 Hz, 1H), 8.02-8.14 (m, 2H), 8.19 (d, J=8.33 Hz, 1H), 9.30 (s, 1H). LC-MS: m/z 508.5 (M+H)⁺

Compound 394 (General procedure 7, Step C)

N-(4-(4-hydroxy-4-(4,4,4-trifluorobutyl)piperidine-1-carbonyl)phenyl)benzo[d]thiazole-4-sulfonamide

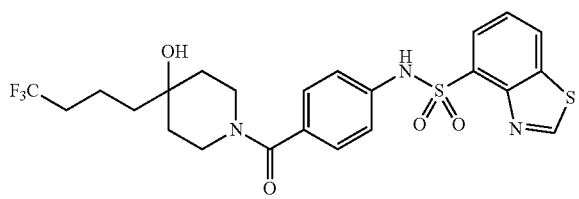 [SMILES: O=C(c1ccc(NS(=O)(=O)c2cccc3scnc23)cc1)N1CCC(O)(CCCC(F)(F)F)CC1]

¹H NMR (CHLOROFORM-d) δ: 9.31 (s, 1H), 8.19 (d, J=8.3 Hz, 1H), 8.10 (d, J=6.7 Hz, 1H), 7.98 (s, 1H), 7.54 (t, J=7.8 Hz, 1H), 7.16-7.21 (m, J=8.6 Hz, 2H), 7.07-7.15 (m, J=8.3 Hz, 2H), 4.37 (br. s., 1H), 3.46 (br. s., 1H), 3.34 (br. s., 1H), 3.21 (br. s., 1H), 2.10 (br. s., 3H), 1.54 (br. s., 4H), 1.33 (br. s., 4H). LC-MS: m/z 528.8 (M+H)⁺

Compound 395 (General procedure 7, Step C)

N-(4-(4-hydroxy-4-(3,4,4-trifluorobut-3-enyl)piperidine-1-carbonyl)phenyl)benzo[d]thiazole-4-sulfonamide

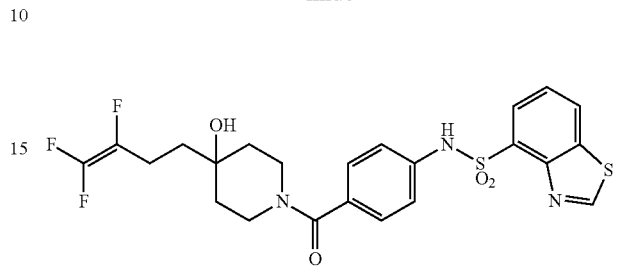

¹H NMR (CHLOROFORM-d) δ: 1.38 (br. s., 3H), 1.50 (br. s., 1H), 1.54-1.63 (m, 2H), 2.33 (br. s., 1H), 2.39 (br. s., 1H), 2.98-3.14 (m, 2H), 3.14-3.28 (m, 2H), 4.07 (br. s., 1H), 7.10 (m, J=8.60 Hz, 2H), 7.17 (m, J=8.60 Hz, 2H), 7.64 (t, J=7.92 Hz, 1H), 8.11 (d, J=6.72 Hz, 1H), 8.50 (d, J=8.06 Hz, 1H), 9.65 (s, 1H), 10.76 (s, 1H). LC-MS: m/z 526.7 (M+H)⁺

Compound 233 (General procedure 7, Step C)

N-(4-(4-hydroxy-4-(3,3,3-trifluoropropyl)piperidine-1-carbonyl)phenyl)benzo[d]thiazole-4-sulfonamide

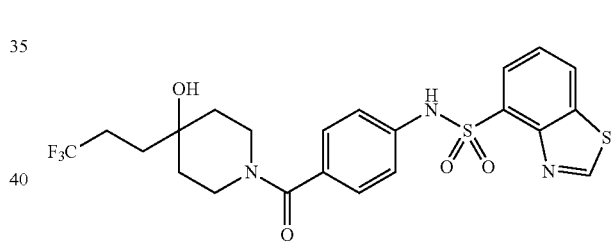

¹H NMR (CHLOROFORM-d) δ: 9.31 (s, 1H), 8.20 (d, J=7.3 Hz, 1H), 8.10 (d, J=7.8 Hz, 1H), 7.94 (s, 1H), 7.55 (t, J=7.8 Hz, 1H), 7.20 (d, J=8.6 Hz, 2H), 7.12 (d, J=8.6 Hz, 2H), 4.33 (s, 1H), 3.73 (s, 1H), 3.53-3.44 (m, 1H), 3.19 (s, 2H), 2.29-2.18 (m, 2H), 1.55-1.50 (m, 2H), 1.47 (d, J=6.7 Hz, 2H), 0.9 (t, J=6.8 Hz, 2H). LC-MS: m/z 514.6 (M+H)⁺

Compound 212 (General procedure 7, Step C)

N-(4-(4-(cyclobutylmethyl)-4-hydroxypiperidine-1-carbonyl)phenyl)benzo[d]thiazole-4-sulfonamide

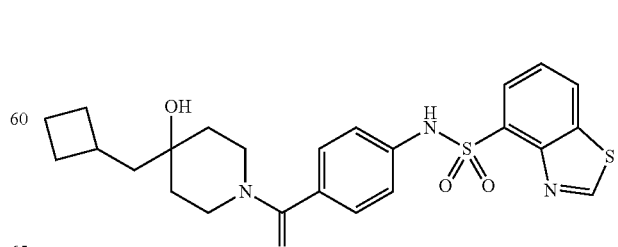

¹H NMR (CHLOROFORM-d) δ: 9.32 (s, 1H), 8.24-8.15 (m, 1H), 8.13-8.07 (m, 1H), 7.96 (s, 1H), 7.55 (t, J=7.8 Hz, 1H), 7.19 (d, J=8.5 Hz, 2H), 7.12 (d, J=8.5 Hz, 2H), 4.34 (s, 1H), 3.70 (dd, J=10.2, 6.4 Hz, 2H), 3.16 (dd, J=7.4, 4.2 Hz, 2H), 2.55-2.43 (m, 1H), 1.62 (s, 1H), 1.43-1.45 (m, 5H), 1.40-1.36 (m, 2H), 1.26-1.31 (m, 4H). LC-MS: m/z 486.6 (M+H)⁺

General Procedure 8:

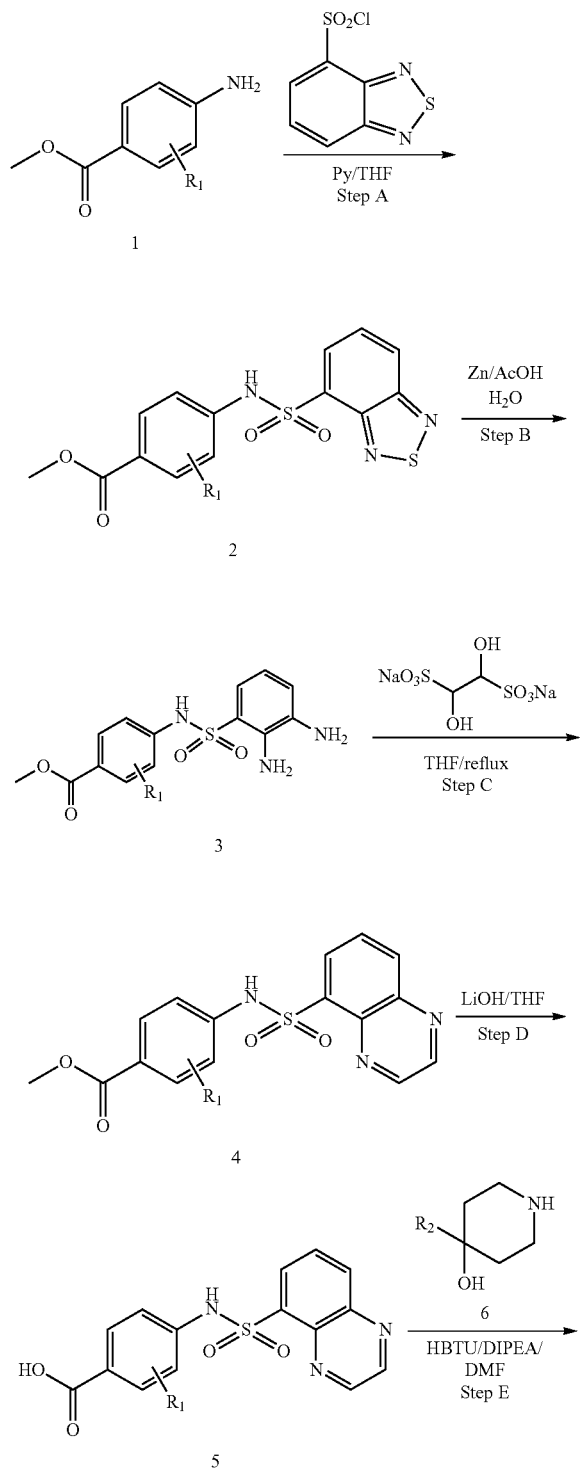

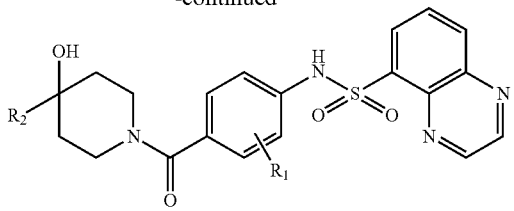

Step A:

To a solution of the corresponding methyl 4-aminobenzoate (1, 2.5 mmol) in 20 mL of DCM was added pyridine (600 mg, 7.5 mmol) and benzo[c][1,2,5]thiadiazole-4-sulfonyl chloride (585 mg, 2.5 mmol). The resulting mixture was stirred at 50° C. overnight. After removal of DCM, the residue was partitioned between water and EtOAc. The organic layer was washed with 2 N HCl, water and brine, dried over $Na_2SO_4$ and concentrated to give crude product 2, which was confirmed by LCMS, and used in the next reaction without further purification.

Step B:

To a solution of the corresponding compound 2 (1.0 mmol) in $AcOH/H_2O$ (8 mL/3 mL) at 70° C. was added zinc powder (975 mg, 15 mmol) and the resulting suspension was stirred at 70° C. for 1 h. The solid was filtered off and washed with EtOAc. The filtrate was partitioned between satd. $NaHCO_3$ and EtOAc. The organic layer was separated and washed with water and brine, dried over anhydrous $Na_2SO_4$ and concentrated to give crude product 3, which was confirmed by LCMS, and used in the next reaction without further purification.

Step C:

To a solution of the corresponding compound 3 (0.9 mmol) in ethanol/water (30 mL/4 mL) was added glyoxal sodium bisulfite hydrate (975 mg, 15 mmol) and the resulting suspension was stirred at 100° C. overnight. The solvent was removed in vacuo and the residue was partitioned between water and EtOAc. The organic layer was separated and washed with water and brine, dried over $Na_2SO_4$ and concentrated, purified by flash column to give title product 4, which was confirmed by LCMS.

Step D:

To a solution of the corresponding compound 4 (0.2 mmol) in $EtOH/H_2O$ (10 mL/3 mL) was added $LiOH.H_2O$ (37 mg, 0.9 mmol) and the resulting suspension was stirred at 70° C. overnight. The solvent was concentrated and the residue was partitioned between aqueous 2 N HCl and EtOAc. The organic layer was separated and washed with water and brine, dried over $Na_2SO_4$ and concentrated to give the desired crude product 5, which was confirmed by LCMS, and used in subsequent reaction without further purification.

Step E:

To a solution of compound 5 (0.2 mmol) and in DCM (10 mL) was added HBTU (91 mg, 0.24 mmol) and stirred at r.t. for 20 min, then the corresponding compound 6 (0.2 mmol) and DIPEA (0.6 mmol) were added. After stirring for 30 mins, the reaction was partitioned between satd. $Na_2CO_3$ solution and DCM. The organic layer was separated and washed with water and brine, dried over Na₂SO₄ and concentrated, and then purified by a standard method to give title product 7.

Compound 251 (General procedure 8, Step E)

N-(4-(4-(2-chlorophenyl)-4-hydroxypiperidine-1-carbonyl)-2-fluorophenyl)quinoxaline-5-sulfonamide

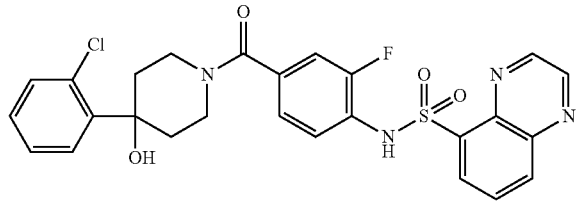

¹H NMR (CHLOROFORM-d) δ: 9.06 (s, 2H), 8.46 (d, J=7.3 Hz, 1H), 8.33-8.40 (m, 2H), 7.83-7.88 (m, 1H), 7.75 (t, J=8.1 Hz, 1H), 7.51 (d, J=7.5 Hz, 1H), 7.39 (d, J=7.5 Hz, 1H), 7.29 (br. s., 1H), 7.25 (m, 1H), 7.11 (d, J=8.3 Hz, 1H), 6.98 (d, J=8.9 Hz, 1H), 4.58 (br. s., 1H), 3.58 (br. s., 2H), 3.31 (br. s., 1H), 2.36 (br. s., 2H), 2.18 (br. s., 2H). LC-MS: m/z 542.0 (M+H)⁺

Compound 262 (General procedure 8, Step E)

N-(4-(4-(2,3-difluorophenyl)-4-hydroxypiperidine-1-carbonyl)-2-fluorophenyl)quinoxaline-5-sulfonamide

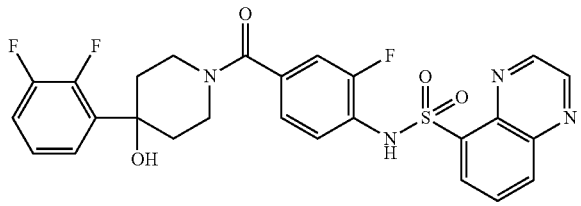 [SMILES: O=C(c1ccc(NS(=O)(=O)c2cccc3nccnc23)c(F)c1)N1CCC(O)(c2cccc(F)c2F)CC1]

¹H NMR (CHLOROFORM-d) δ: 9.06 (s, 2H), 8.47 (d, J=8.5 Hz, 1H), 8.34-8.40 (m, 2H), 7.83-7.89 (m, 1H), 7.76 (t, J=8.2 Hz, 1H), 7.24 (t, J=7.0 Hz, 1H), 7.08-7.16 (m, 3H), 6.99 (d, J=10.5 Hz, 1H), 4.59 (br. s., 1H), 3.57 (br. s., 2H), 3.28 (br. s., 1H), 2.25 (br. s., 2H), 2.13 (br. s., 1H), 1.88 (br. s., 2H). LC-MS: m/z 543.5 (M+H)⁺

Compound 160 (General procedure 8, Step E)

N-(4-(4-hydroxy-4-isobutylpiperidine-1-carbonyl)phenyl)quinoxaline-5-sulfonamide

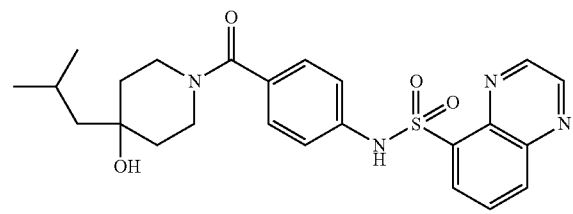 [SMILES: CC(C)CC1(O)CCN(C(=O)c2ccc(NS(=O)(=O)c3cccc4nccnc34)cc2)CC1]

¹H NMR (CHLOROFORM-d) δ: 9.07 (s, 2H), 8.45 (dd, J=7.3, 1.3 Hz, 1H), 8.35 (dd, J=8.5, 1.2 Hz, 1H), 8.03 (s, 1H), 7.82-7.88 (m, 1H), 7.16-7.21 (m, J=8.6 Hz, 2H), 7.06-7.11 (m, J=8.3 Hz, 2H), 4.33 (br. s., 1H), 3.35 (br. s., 2H), 3.19 (br. s., 1H), 1.82 (dt, J=12.8, 6.3 Hz, 1H), 1.50 (br. s., 4H), 1.40 (d, J=5.9 Hz, 2H), 0.97 (d, J=6.7 Hz, 6H). LC-MS: m/z 469.5 (M+H)⁺

Compound 243 (General procedure 8, Step E)

N-(4-(4-hydroxy-4-phenylpiperidine-1-carbonyl)phenyl)quinoxaline-5-sulfonamide

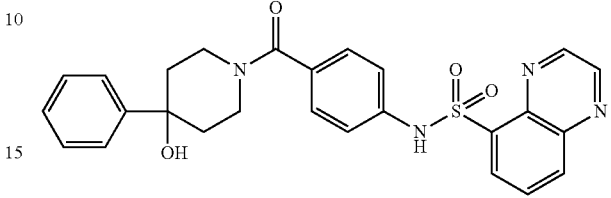

¹H NMR (CHLOROFORM-d) δ: 9.03-9.08 (m, 2H), 8.45 (dd, J=7.3, 1.5 Hz, 1H), 8.34 (dd, J=8.5, 1.5 Hz, 1H), 8.14 (s, 1H), 7.84 (dd, J=8.4, 7.5 Hz, 1H), 7.41-7.46 (m, 2H), 7.33-7.38 (m, 2H), 7.29-7.31 (m, 1H), 7.25-7.28 (m, 1H), 7.19-7.23 (m, J=8.5 Hz, 2H), 7.07-7.11 (m, J=8.5 Hz, 2H), 4.54 (br. s., 1H), 3.53 (br. s., 2H), 3.20-3.36 (m, 1H), 1.93 (br. s., 2H), 1.84 (br. s., 2H). LC-MS: m/z 488.6 (M+H)⁺

Compound 162 (General procedure 8, Step E)

N-(4-(4-(2-chlorophenyl)-4-hydroxypiperidine-1-carbonyl)phenyl)quinoxaline-5-sulfonamide

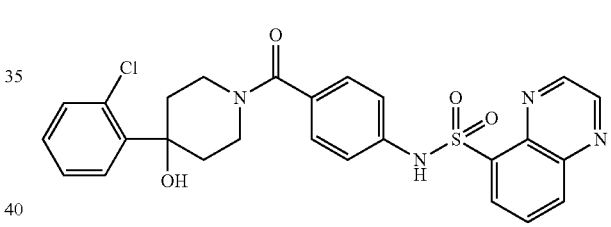

¹H NMR (CHLOROFORM-d) δ: 9.05-9.10 (m, 2H), 8.45 (dd, J=7.5, 1.3 Hz, 1H), 8.36 (dd, J=8.6, 1.3 Hz, 1H), 8.02-8.09 (m, 1H), 7.85 (dd, J=8.3, 7.5 Hz, 1H), 7.52 (dd, J=7.8, 1.9 Hz, 1H), 7.38 (dd, J=7.8, 1.6 Hz, 1H), 7.25-7.28 (m, 1H), 7.24 (s, 1H), 7.21-7.23 (m, 1H), 7.10 (d, J=8.6 Hz, 2H), 4.60 (d, J=10.7 Hz, 1H), 3.56 (br. s., 2H), 3.50 (s, 1H), 1.86-2.09 (m, 2H), 1.72 (br. s., 2H). LC-MS: m/z 523.6 (M+H)⁺

Compound 119 (General procedure 8, Step E)

N-(4-(4-(2-chlorophenyl)-4-hydroxypiperidine-1-carbonyl)-2-methylphenyl)quinoxaline-5-sulfonamide

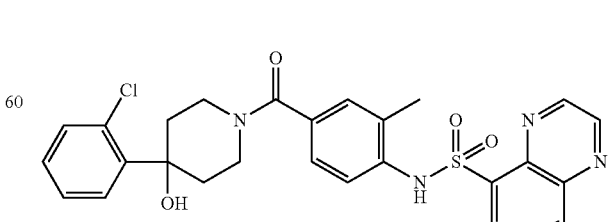

¹H NMR (CHLOROFORM-d) δ: 9.02-9.07 (m, 2H), 8.51 (d, J=7.3 Hz, 1H), 8.38 (d, J=8.3 Hz, 1H), 7.89 (t, J=7.9 Hz, 1H), 7.76 (s, 1H), 7.50-7.54 (m, 1H), 7.39 (dd, J=7.5, 1.3 Hz, 1H), 7.29-7.32 (m, 1H), 7.22-7.28 (m, 2H), 7.16 (s, 1H), 7.06 (d, J=8.1 Hz, 1H), 4.60 (br. s., 1H), 3.61 (br. s., 1H), 3.55 (br. s., 1H), 3.31 (d, J=11.3 Hz, 1H), 2.35 (d, J=7.5 Hz, 1H), 2.25 (s, 3H), 2.20 (d, J=14.8 Hz, 1H), 2.01-2.12 (m, 1H), 1.97 (br. s., 1H). LC-MS: m/z 537.6 (M+H)⁺

Compound 175 (General procedure 8, Step E)

N-(4-(4-(2,3-difluorophenyl)-4-hydroxypiperidine-1-carbonyl)-2-methylphenyl)quinoxaline-5-sulfonamide

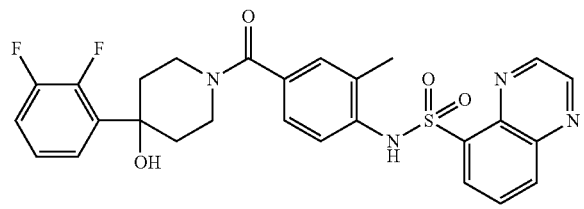 [SMILES: Cc1cc(C(=O)N2CCC(O)(c3cccc(F)c3F)CC2)ccc1NS(=O)(=O)c1cccc2nccnc12]

¹H NMR (CHLOROFORM-d) δ: 9.05 (dd, J=9.2, 1.6 Hz, 2H), 8.51 (dd, J=7.3, 1.3 Hz, 1H), 8.38 (dd, J=8.4, 1.1 Hz, 1H), 7.89 (dd, J=8.3, 7.5 Hz, 1H), 7.76 (s, 1H), 7.22-7.27 (m, 1H), 7.03-7.17 (m, 4H), 4.58 (br. s., 1H), 3.60 (br. s., 1H), 3.39-3.57 (m, 1H), 3.24 (br. s., 1H), 2.05-2.19 (m, 1H), 1.83 (br. s., 1H), 1.75 (br. s., 2H). LC-MS: m/z 538.6 (M+H)⁺

Compound 213 (General procedure 8, Step E)

N-(3-(difluoromethoxy)-4-(4-hydroxy-4-isobutylpiperidine-1-carbonyl)phenyl)quinoxaline-5-sulfonamide

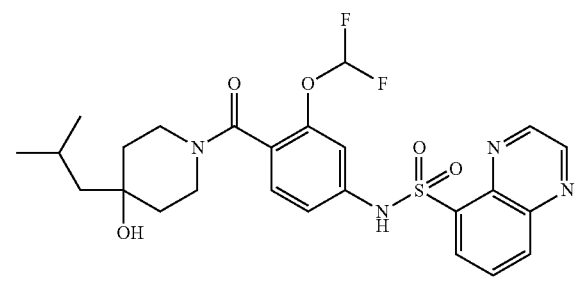 [SMILES: CC(C)CC1(O)CCN(C(=O)c2ccc(NS(=O)(=O)c3cccc4nccnc34)cc2OC(F)F)CC1]

¹H NMR (CHLOROFORM-d) δ: 9.07 (d, J=5.4 Hz, 2H), 8.48 (d, J=7.3 Hz, 1H), 8.38 (d, J=8.6 Hz, 1H), 8.04 (s, 1H), 7.85-7.93 (m, 1H), 6.99-6.90 (m, 3H), 6.36 (t, J=73.2 Hz, 1H), 4.39 (br. s., 1H), 3.25-3.16 (m, 3H), 1.82 (m, 1H), 1.63 (m., 5H), 0.98 (d, J=6.7 Hz, 6H). LC-MS: m/z 535.8 (M+H)⁺

Compound 114 (General procedure 8, Step E)

N-(4-(4-hydroxy-4-(2-(trifluoromethyl)benzyl)piperidine-1-carbonyl)phenyl)quinoxaline-5-sulfonamide

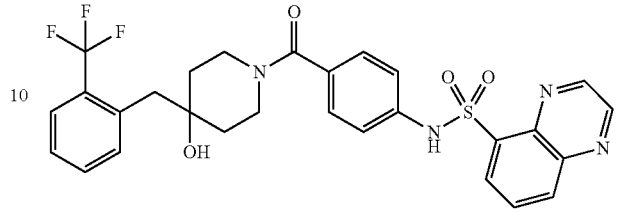

¹H NMR (CHLOROFORM-d) δ: 1.60 (br. s., 4H), 3.01 (s, 2H), 3.12 (br. s., 1H), 3.30 (br. s., 1H), 3.48 (br. s., 1H), 4.47 (br. s., 1H), 7.08 (m, J=7.79 Hz, 2H), 7.20 (m, J=8.06 Hz, 2H), 7.39 (dd, J=8.33, 3.76 Hz, 1H), 7.47-7.53 (m, 2H), 7.69 (d, J=7.79 Hz, 1H), 7.82-7.89 (m, 1H), 7.99 (s, 1H), 8.36 (dd, J=8.46, 1.21 Hz, 1H), 8.45 (dd, J=7.39, 1.21 Hz, 1H), 9.08 (s, 2H). LC-MS: m/z 571.7 (M+H)⁺

Compound 221 (General procedure 8, Step E)

N-(4-(4-hydroxy-4-(3,3,3-trifluoropropyl)piperidine-1-carbonyl)phenyl)quinoxaline-5-sulfonamide

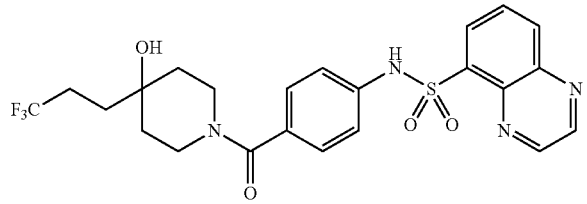 [SMILES: O=C(c1ccc(NS(=O)(=O)c2cccc3nccnc23)cc1)N1CCC(O)(CCC(F)(F)F)CC1]

¹H NMR (CHLOROFORM-d) δ: 9.12 (d, J=1.9 Hz, 1H), 9.03 (d, J=1.9 Hz, 1H), 8.50 (dd, J=7.3, 1.3 Hz, 1H), 8.32 (dd, J=8.3, 1.3 Hz, 1H), 7.91 (dd, J=8.3, 7.5 Hz, 1H), 7.15-7.26 (m, 4H), 3.18 (br. s., 1H), 2.25 (td, J=11.1, 5.9 Hz, 2H), 1.62-1.78 (m, 3H), 1.56 (br. s., 1H), 1.46 (br. s., 2H), 1.31 (d, J=2.1 Hz, 1H). LC-MS: m/z 509.62 (M+H)⁺

Compound 130 (General procedure 8, Step E)

N-(4-(4-hydroxy-4-neopentylpiperidine-1-carbonyl)phenyl)quinoxaline-5-sulfonamide

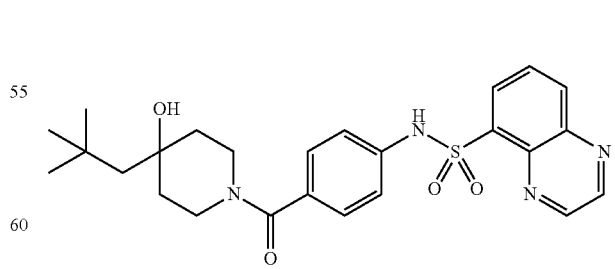

¹H NMR (CHLOROFORM-d) δ: 9.08 (s, 2H), 8.45 (dd, J=7.4, 1.2 Hz, 1H), 8.36 (dd, J=8.6, 1.3 Hz, 1H), 8.00 (s, 1H), 7.85 (dd, J=8.3, 7.5 Hz, 1H), 7.15-7.22 (m, J=8.3 Hz, 2H), 7.03-7.11 (m, J=8.6 Hz, 2H), 4.36 (br. s., 1H), 3.40 (br. s.,

2H), 3.17 (dd, J=12.6, 5.9 Hz, 2H), 1.62 (br. s., 4H), 1.49 (s, 2H), 1.05 (s, 9H). LC-MS: m/z 483.6 (M+H)⁺

Compound 188 (General procedure 8, Step E)

N-(4-(4-(cyclopropylmethyl)-4-hydroxypiperidine-1-carbonyl)phenyl)quinoxaline-5-sulfonamide

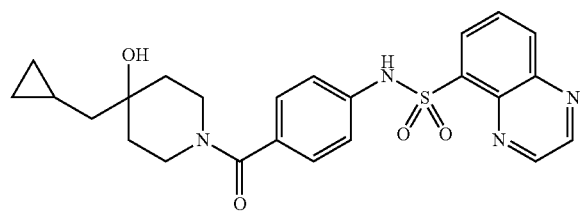 [SMILES: O=C(c1ccc(NS(=O)(=O)c2cccc3nccnc23)cc1)N1CCC(O)(CC2CC2)CC1]

¹H NMR (CHLOROFORM-d) δ: 9.07 (q, J=1.7 Hz, 2H), 8.45 (dd, J=7.3, 1.3 Hz, 1H), 8.35 (dd, J=8.6, 1.3 Hz, 1H), 8.06 (s, 1H), 7.85 (dd, J=8.5, 7.4 Hz, 1H), 7.15-7.22 (m, J=8.3 Hz, 2H), 7.04-7.13 (m, J=8.3 Hz, 2H), 4.37 (br. s., 1H), 3.49 (br. s., 1H), 3.27 (br. s., 3H), 1.76 (br. s., 1H), 1.51-1.66 (m, 3H), 1.41 (d, J=6.4 Hz, 2H), 0.65-0.80 (m, 1H), 0.46-0.58 (m, 2H), 0.05-0.13 (m, 2H). LC-MS: m/z 467.6 (M+H)⁺

Compound 396 (General procedure 8, Step E)

N-(4-(4-(3,3-difluorobutyl)-4-hydroxypiperidine-1-carbonyl)phenyl)quinoxaline-5-sulfonamide

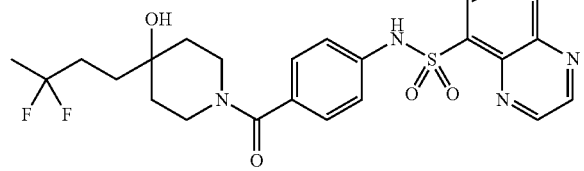

¹H NMR (CHLOROFORM-d) δ: 9.08 (s, 2H), 8.45 (dd, J=7.3, 1.1 Hz, 1H), 8.36 (dd, J=8.5, 1.2 Hz, 1H), 8.03 (s, 1H), 7.86 (dd, J=8.3, 7.5 Hz, 1H), 7.14-7.24 (m, J=8.1 Hz, 2H), 7.04-7.13 (m, J=8.1 Hz, 2H), 4.33 (br. s., 1H), 3.51 (s, 1H), 3.28 (br. s., 3H), 1.88-2.02 (m, 2H), 1.56-1.69 (m, 9H). LC-MS: m/z 505.6 (M+H)⁺

Compound 397 (General procedure 8, Step E)

N-(4-(4-hydroxy-4-(4,4,4-trifluorobutyl)piperidine-1-carbonyl)phenyl)quinoxaline-5-sulfonamide

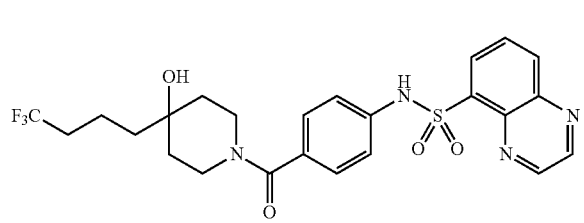 [SMILES: O=C(c1ccc(NS(=O)(=O)c2cccc3nccnc23)cc1)N1CCC(O)(CCCC(F)(F)F)CC1]

¹H NMR (CHLOROFORM-d) δ: 9.08 (s, 2H), 8.45 (dd, J=7.3, 1.3 Hz, 1H), 8.36 (dd, J=8.6, 1.3 Hz, 1H), 8.04 (s, 1H), 7.82-7.89 (m, 1H), 7.16-7.22 (m, J=8.6 Hz, 2H), 7.06-7.12 (m, J=8.6 Hz, 2H), 4.35 (br. s., 1H), 3.43 (br. s., 1H), 3.34 (br. s., 1H), 3.17 (br. s., 1H), 2.04-2.14 (m, 2H), 1.48-1.58 (m, 4H), 1.32 (br. s., 2H), 1.24 (br. s., 2H). LC-MS: m/z 523.7 (M+H)⁺

Compound 398 (General procedure 8, Step E)

N-(4-(4-hydroxy-4-(3,4,4-trifluorobut-3-enyl)piperidine-1-carbonyl)phenyl)quinoxaline-5-sulfonamide

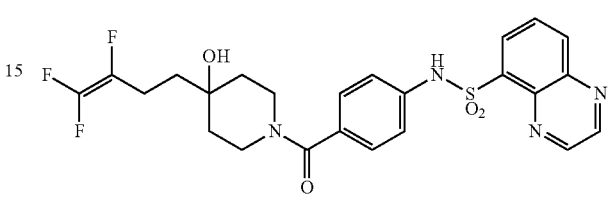

¹H NMR (CHLOROFORM-d) δ: 1.44 (br. s., 1H), 1.49-1.65 (m, 3H), 2.31-2.45 (m, 2H), 2.57 (d, J=6.45 Hz, 1H), 3.10-3.38 (m, 3H), 7.08 (m, J=8.60 Hz, 2H), 7.18 (m, J=8.60 Hz, 2H), 7.84 (dd, J=8.33, 7.52 Hz, 1H), 8.34 (dd, J=8.46, 1.21 Hz, 1H), 8.45 (dd, J=7.39, 1.21 Hz, 1H), 9.03-9.10 (m, 2H). LC-MS: m/z 521.7 (M+H)⁺

Compound 399 (General procedure 8, Step E)

N-(4-(4-(4,4-difluorobut-3-en-1-yl)-4-hydroxypiperidine-1-carbonyl)phenyl)quinoxaline-5-sulfonamide

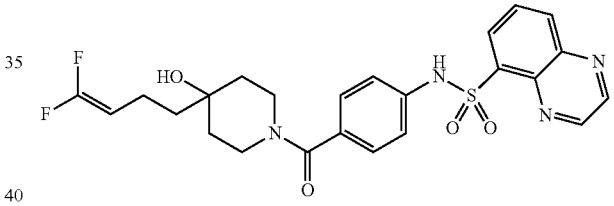

¹H NMR (400 MHz, CHLOROFORM-d) δ: 0.79-0.93 (m, 2H), 1.51-1.57 (m, 3H), 1.59-1.74 (m, 4H), 1.98-2.17 (m, 2H), 3.33 (br. s., 2H), 3.50 (s, 1H), 4.08-4.24 (m, 1H), 7.08 (m, J=8.33 Hz, 2H), 7.19 (m, J=8.33 Hz, 2H), 7.85 (dd, J=8.46, 7.39 Hz, 1H), 8.04 (s, 1H), 8.36 (dd, J=8.46, 1.21 Hz, 1H), 8.45 (dd, J=7.39, 1.21 Hz, 1H), 9.08 (s, 2H). LC-MS: m/z 503.5 (M+H)⁺

Compound 400 (General procedure 8, Step E)

N-(4-(4-(4,4-difluorobutyl)-4-hydroxypiperidine-1-carbonyl)phenyl)quinoxaline-5-sulfonamide

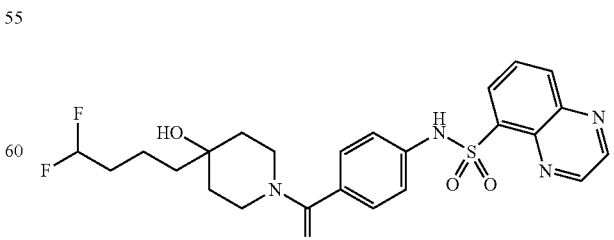

¹H NMR (400 MHz, CHLOROFORM-d) δ: 1.25-1.29 (m, 2H), 1.51-1.69 (m, 7H), 1.78-1.87 (m, 2H), 3.06-3.24 (m,

1H), 3.24-3.36 (m, 1H), 3.41 (br. s., 1H), 4.32 (br. s., 1H), 5.81 (t, J=4.30 Hz, 1H), 7.08 (m, J=8.60 Hz, 2H), 7.18 (m, J=8.33 Hz, 2H), 7.84 (dd, J=8.33, 7.52 Hz, 1H), 8.12 (s, 1H), 8.34 (dd, J=8.46, 1.21 Hz, 1H), 8.45 (dd, J=7.39, 1.21 Hz, 1H), 8.98-9.14 (m, 2H). LC-MS: m/z 505.5 (M+H)+

General Procedure 9:

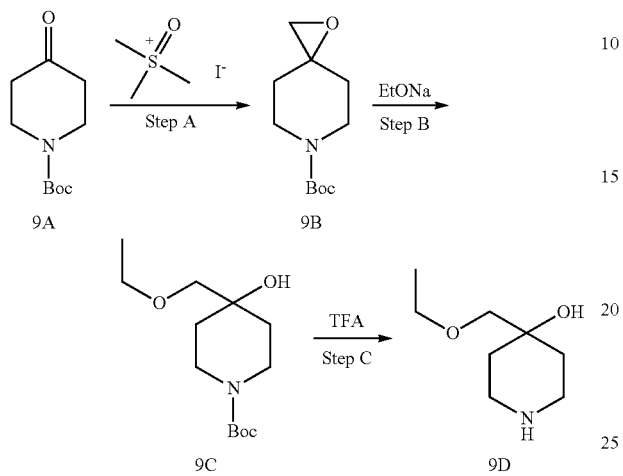

Step A: tert-butyl 1-oxa-6-azaspiro[2.5]octane-6-carboxylate (9B)

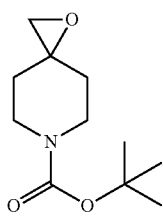

To a solution of tert-butyl 4-oxopiperidine-1-carboxylate (5 g, 25 mmol) in BuOH (20 mL) was added potassium tert-butoxide (4.125 g, 18.75 mmol). The mixture was stirred at 50° C. for 1 h. Then trimethyl sulfoxonium iodide (11 g, 50 mmol) was added to the mixture, and the resulting reaction mixture was stirred at 50° C. overnight. When TLC showed that s.m. was consumed, the mixture was cooled and filtered. The filtrate was concentrated to give the crude product which was used in the next step without further purification.

$^1$H NMR (CHLOROFORM-d) δ: 3.75 (d, J=13.8 Hz, 2H), 3.45 (dd, J=13.2, 9.4, 3.8 Hz, 2H), 2.72 (s, 2H), 2.01-2.07 (m, 2H), 1.78-1.86 (m, 2H), 1.50 (s, 9H)

Step B: tert-butyl 4-(ethoxymethyl)-4-hydroxypiperidine-1-carboxylate (9C)

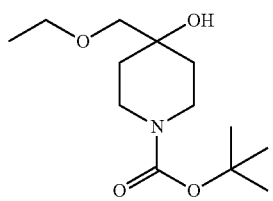 [SMILES: CCOCC1(O)CCN(C(=O)OC(C)(C)C)CC1]

To anhydrous EtOH (20 mL) was added slowly NaH (124 mg, 52 mmol) at 0° C., and after the addition was complete the mixture was stirred for 1.5 h. Then tert-butyl 1-oxa-6-azaspiro[2.5]octane-6-carboxylate (9B, 45 mmol) was added, and the resulting mixture was stirred at 50° C. for 1 h, when TLC showed that s.m. was consumed. Then the mixture was neutralized with 1N aq. HCl, and concentrated. The residue was purified by prep-TLC to give the desired product 9C as colorless oil (600 mg) $^1$H NMR (METHANOL-d$^4$) δ: 3.78 (d, J=12.6 Hz, 2H), 3.51 (q, J=7.0 Hz, 2H), 3.22-3.29 (m, 2H), 3.15 (br. s., 2H), 1.48-1.60 (m, 4H), 1.43 (s, 9H), 1.18 (t, J=7.0 Hz, 3H).

Step C: 4-(ethoxymethyl)piperidin-4-ol (9D)

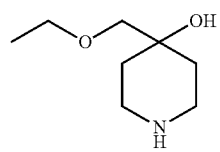

To a solution of tert-butyl 4-(ethoxymethyl)-4-hydroxypiperidine-1-carboxylate (9C, 1 eq.) in DCM was added TFA (10 eq.). The mixture was stirred at r.t. for 0.5 hr, when TLC showed that s.m. was consumed. The mixture was concentrated to give the crude product which was used to the next step without further purification. LC-MS: m/z 160.2 (M+H)+

General Procedure 10:

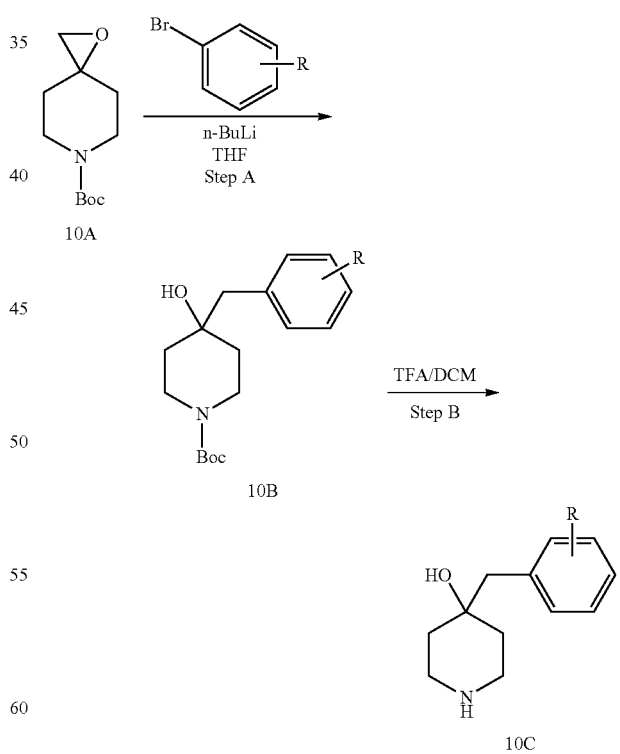

Step A:

To a solution of the corresponding bromobenzene (4.7 mmol) in 30 mL of anhydrous THF was added dropwise n-BuLi (7.04 mmol) at −78° C. under N$_2$. After stirring for 1 h at −78° C., tert-butyl 1-oxa-6-azaspiro[2.5]octane-6-carboxylate (7.04 mmol) in THF (5 mL) was added drop wise to the above obtained solution at −78° C. under N₂. The resulting mixture was stirred at −78° C. under N₂ for 2 h, then allowed to warm to r.t. and stirred overnight. The reaction mixture was cooled to −78° C. and quenched by satd. NH₄Cl solution, then the resulting mixture was extracted with EtOAc (50 mL, 30 mL). The combined organic phase was washed with brine, dried over anhydrous Na₂SO₄ and concentrated in vacuo to give the title compound 10B.

Step B:

A solution of compound 10B (1.62 mmol) in 13 mL of 6N HCl in dioxane was stirred at room temperature for 30 min. The reaction mixture was concentrated in vacuo to give the title product 10C as a yellow liquid which was used in the next step directly.

General Procedure 11:

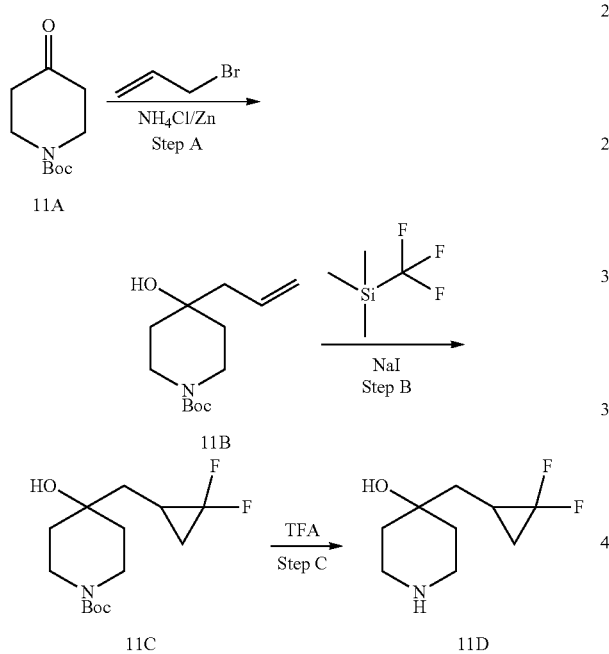

Step A: tert-butyl 4-allyl-4-hydroxypiperidine-1-carboxylate (11B)

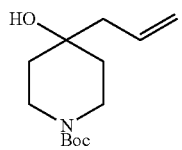

To a solution of tert-butyl 4-oxopiperidine-1-carboxylate (10 g, 50.2 mmol), allyl bromide (10.8 mL, 124 mmol) in THF (10 mL), and saturated ammonium chloride solution (50 mL) was added Zn dust (6.5 g, 100 mmol) portionwise below 10° C. After addition was complete, the reaction mixture was stirred overnight, when TLC indicated consumption of s.m. The reaction mixture was diluted with water (50 mL) and acidified with several drops of 10% H₂SO₄ to pH=6. The reaction mixture was extracted with EtOAc (3×200 mL). The organic layers were combined and washed with a saturated solution of NaHCO₃, brine and evaporated, to give the crude product which was purified by chromatography to give title compound 11B as colorless oil.

¹H NMR (CHLOROFORM-d) δ: 5.77-5.92 (m, 1H), 5.05-5.21 (m, 2H), 3.76 (br. s., 2H), 3.05-3.22 (m, 2H), 2.21 (d, J=7.6 Hz, 2H), 2.01 (br. s., 1H), 1.50 (dd, J=7.2, 4.0 Hz, 3H), 1.47 (s, 1H), 1.43 (s, 9H).

Step B: tert-butyl 4-((2,2-difluorocyclopropyl)methyl)-4-hydroxypiperidine-1 carboxylate (11C)

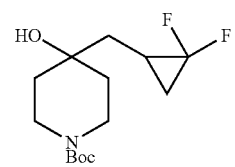

To a sealed tube was added tert-butyl 4-allyl-4-hydroxypiperidine-1-carboxylate 11B (280 mg, 1.16 mmol), NaI (112 mg, 0.74 mmol), trimethyl(trifluoromethyl)silane (0.6 mL) and THF (10 mL). The tube was sealed, and then the mixture was stirred at 80° C. overnight. The resulting mixture was diluted with DCM, filtered, and the filtrate was concentrated in vacuo to give the crude product 11C which was used for next step without further purification. LC-MS: m/z 292.3 (M+H)⁺

Step C: 4((2,2-difluorocyclopropyl)me piperidin-4-ol (11D)

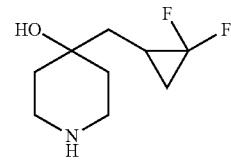

To a solution of compound 11C (1 eq.) in DCM, was added TFA (10 eq.), the reaction mixture was stirred at room temperature for about 2 hours, when TLC detected no s.m. The reaction mixture was concentrated to afford the desired product 11D. The crude product was used for the next step directly without further purification. LC-MS: m/z 192.3 (M+H)⁺

General Procedure 12:

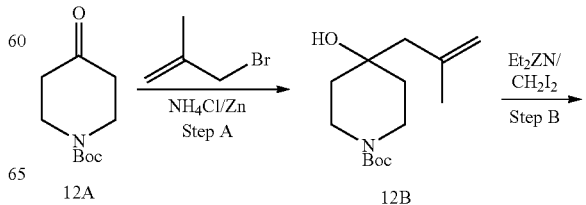

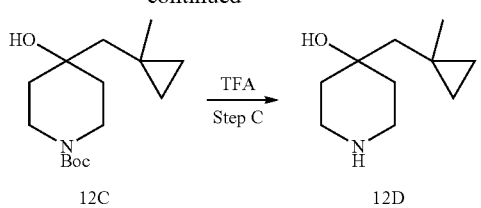

Step A: tert-butyl 4-hydroxy-4-(2-methylallyl)piperidine-1-carboxylate (12B)

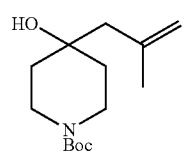

t-butyl-4-oxopiperidine-1-carboxylate (10 g, 0.05 mol) was dissolved in 3-bromo-2-methylprop-1-ene (16.9 g, 0.126 mol), THF (100 mL) and saturated ammonium chloride solution (500 mL). The reaction was cooled to 10° C. and zinc dust (6.6 g, 0.01 mol) was added portionwise. After addition, the reaction mixture was stirred overnight, when TLC (heptane/EtOAc 7:1) indicated that the reaction was complete. The reaction mixture was then diluted with water and acidified with 10% $H_2SO_4$ to pH 6. The reaction mixture was extracted with ethyl acetate (3×50 mL). The organic layers were combined and washed with saturated solution of $NaHCO_3$, brine and evaporated to give tert-butyl 4-hydroxy-4-(2-methylallyl)piperidine-1-carboxylate (12.28 g). $^1$H NMR (CHLOROFORM-d) δ: 4.94-5.04 (m, 1H), 4.80 (s, 1H), 3.85 (dt, J=13.0, 3.4 Hz, 2H), 3.08-3.26 (m, 2H), 2.21 (s, 2H), 1.86 (s, 3H), 1.52-1.60 (m, 4H), 1.43-1.50 (m, 9H).

Step B: tert-butyl 4-hydroxy-4-((1-methylcyclopropyl)methyl)piperidine-1-carboxylate (12C)

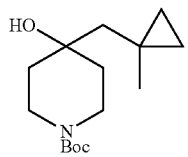

To $CH_2Cl_2$ (20 mL) at 0° C. was added 1M solution of diethylzinc in hexane (11.75 mL, 11.75 mmol), followed by dropwise addition of a solution of trifluoroacetic acid (0.6 mL, 7.83 mmol) in $CH_2Cl_2$ (8 mL). After stirring for 15 min, a solution of diiodomethane (0.65 mL, 7.83 mmol) in $CH_2Cl_2$ (8 mL) was added. The mixture was stirred for 15 min and a clear solution resulted. tert-Butyl 4-hydroxy-4-(2-methylallyl)piperidine-1-carboxylate (12B) (1 g, 3.92 mmol) was added and the mixture was stirred at room temperature overnight. After quenching with 0.1 M aqueous HCl (50 mL), the $CH_2Cl_2$ layer was separated, washed with brine, dried ($Na_2SO_4$) and concentrated to give the crude product, which was used directly for the next step without purification.

Step C: 4-((1-methylcyclopropyl)methyl)piperidin-4-ol (12D)

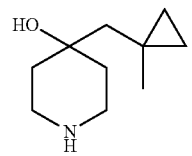

To a solution of compound 12C (1 eq.) in DCM, was added TFA (10 eq.), the reaction mixture was stirred at room temperature for about 2 hours, when TLC detected no s.m. The reaction mixture was concentrated to afford the desired product 12D. The crude product was used for the next step directly without further purification. LC-MS: m/z 170.3 (M+H)$^+$ General Procedure 13:

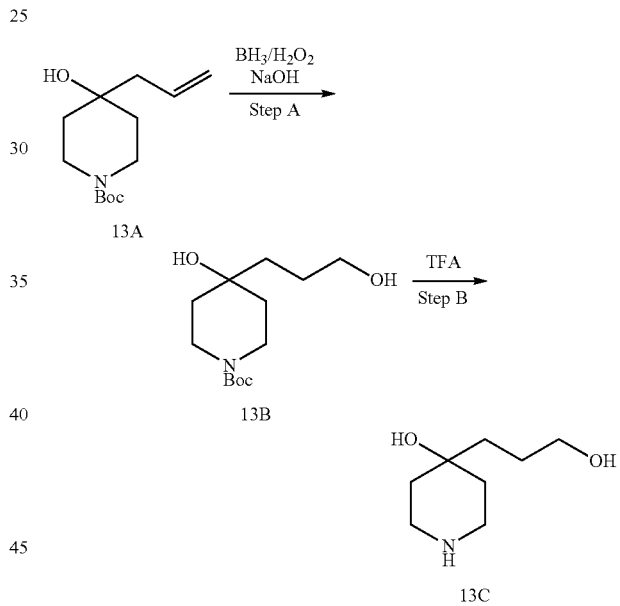

Step A: tert-butyl 4-hydroxy-4-(3-hydroxypropyl)piperidine-1-carboxylate (13B)

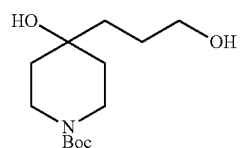

A mixture of $BH_3$ in THF (21 mL, 21.0 mmol) was added slowly to a mixture of tert-butyl 4-allyl-4-hydroxypiperidine-1-carboxylate (500 mg, 2.07 mmol) and THF (5 mL) at 0° C. under nitrogen, and then stirred for 30 min. The resulting mixture was allowed to warm to room temperature and stirred overnight. The mixture was cooled to 0° C. and 3N sodium hydroxide (1 mL) was added followed by the addition of 30% hydrogen peroxide (1 mL). The resulting mixture was allowed to warm to room temperature and stirred for 2.5 hours. The mixture was then treated with water (10 mL) and extracted with EA (3×20 mL). The combined organic extracts were dried over $Na_2SO_4$ and the solvent was removed in vacuo. The residue was purified by column chromatography on silica gel with (30% EtOAc/PE) to give tert-butyl 4-hydroxy-4-(3-hydroxypropyl)piperidine-1-carboxylate 13B (6:29 mg) as a colorless oil. $^1$H NMR (CHLOROFORM-d) δ: 3.65 (t, J=5.7 Hz, 4H), 3.36 (br. s., 2H), 3.16 (br. s., 2H), 1.63-1.71 (m, 2H), 1.53-1.62 (m, 4H), 1.41-1.48 (m, 9H).

Step B: 4-(3-hydroxypropyl)piperidin-4-ol (13C)

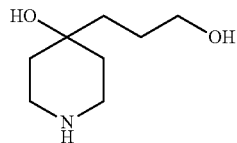

To a solution of compound 2 (1 eq.) in DCM, was added TFA (10 eq.), the reaction mixture was stirred at room temperature for about 2 hours, when TLC detected no s.m. The reaction mixture was concentrated to afford the desired product 3. The crude product was used for the next step directly without further purification. LC-MS: m/z 160.2 $(M+H)^+$ General Procedure 14:

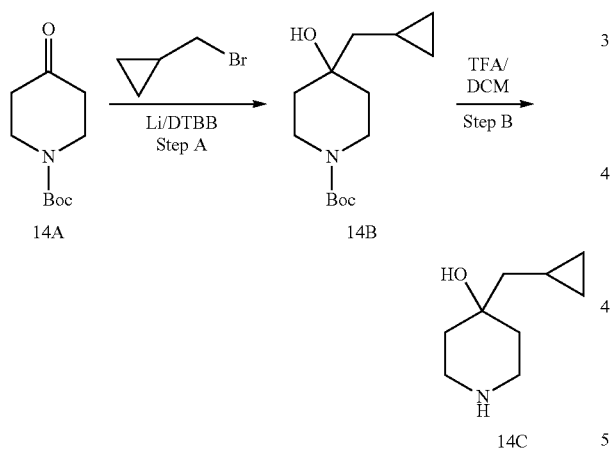

Step A: tert-butyl 4-(cyclopropylmethyl)-4-hydroxypiperidine-1-carboxylate (14B)

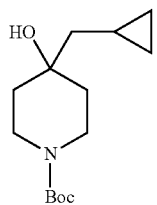

To a suspension of 4,4'-di-tert-butylbiphenyl (DTBB, 30.33 mg, 0.114 mmol) and Li (56.7 mg, 8.09 mmol) in 50 mL of anhydrous THF was added dropwise a solution of (bromomethyl)cyclopropane (307.9 mg, 2.28 mmol) and tert-butyl 4-oxopiperidine-1-carboxylate (500 mg, 2.5 mmol) in anhydrous THF (5 mL) at −78° C. under $N_2$. The resulting mixture was stirred at −78° C. under $N_2$ for 8 h. The reaction mixture was quenched by satd. $NH_4Cl$ solution at −78° C. The resulting mixture was extracted with EtOAc (50 mL×2). The combined organic phase was washed with brine, dried over anhy. $Na_2SO_4$ and concentrated in vacuo. Column chromatography (15% PE/EtOAc) afforded 262.5 mg of title compound as a colorless oil. $^1$H NMR (CHLOROFORM-d) δ: 3.90-3.78 (m, 2H), 3.25-3.12 (m, 2H), 1.60 (dd, J=9.4, 4.3 Hz, 4H), 1.48 (s, 9H), 1.42 (d, J=6.9 Hz, 2H), 0.82-0.70 (m, 1H), 0.57-0.47 (m, 2H), 0.16-0.06 (m, 2H).

Step B: 4-(cyclopropylmethyl)piperidin-4-ol (14C)

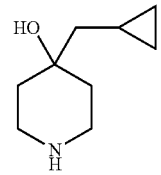

To a solution of compound 14B (1 eq.) in DCM, was added TFA (10 eq.), the reaction mixture was stirred at room temperature for about 2 hours, when LCMS detected no s.m. The reaction mixture was concentrated to afford the desired product 14C. The crude product was used for the next step directly without further purification. LC-MS: m/z 156.2 $(M+H)^+$ General Procedure 15:

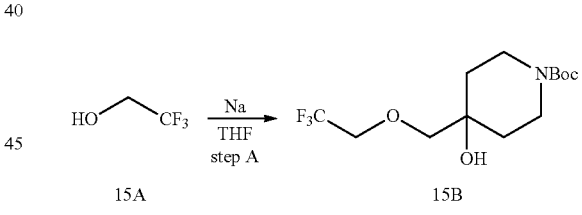

Step A:

Sodium (90 mg, 3.9 mmol) was added (in small pieces) into 2,2,2-trifluoroethanol (2 mL) at room temperature, then the mixture was stirred at room temperature until Na was totally consumed, and the resulting mixture was then added dropwise into a solution of tert-butyl 1-oxa-6-azaspiro[2.5]octane-6-carboxylate (500 mg, 2.35 mmol) in 10 mL of anhydrous THF at room temperature. After the addition was complete, the mixture was stirred at 60° C. overnight when TLC (petroleum ether: ethyl acetate=2:1) ($I_2$ stained) indicated formation of a new spot, and consumption of tert-butyl 1-oxa-6-azaspiro[2.5]octane-6-carboxylate. The resulting mixture was then cooled to room temperature, $H_2O$ was added to quench the reaction, and the mixture was extracted with ethyl acetate. The organic layer was dried over anhydrous $Na_2SO_4$, and concentrated to give crude title compound which was used in the next step without further purification.

General Procedure 16:

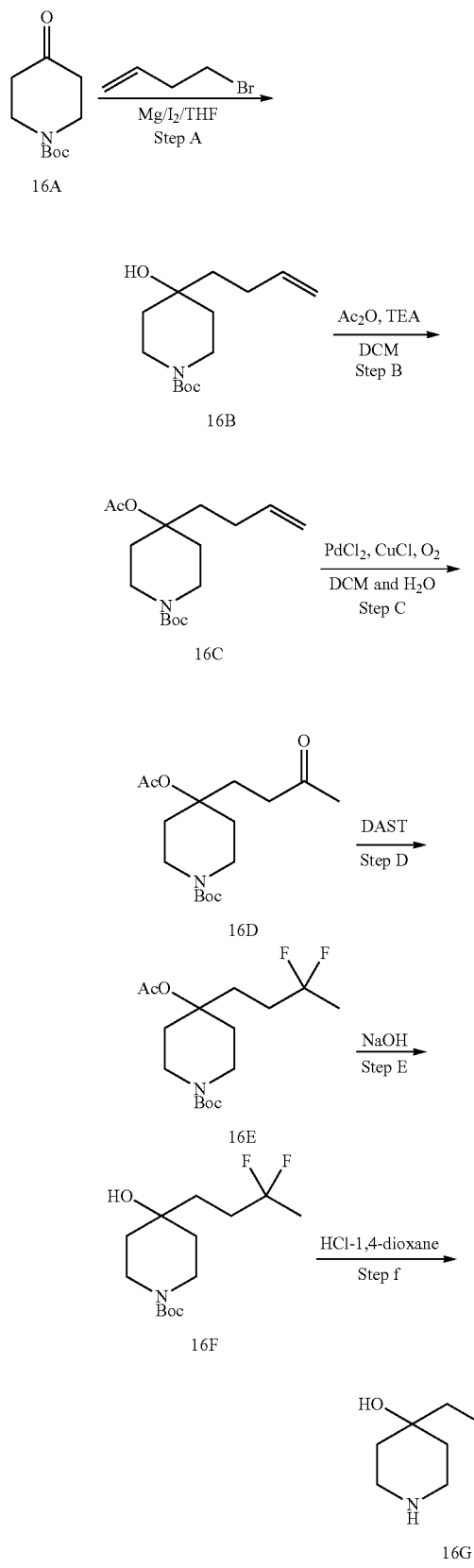

Step A: tert-butyl-4-(but-3-en-1-yl)-4-hydroxypiperidine-1-carboxylate (16B)

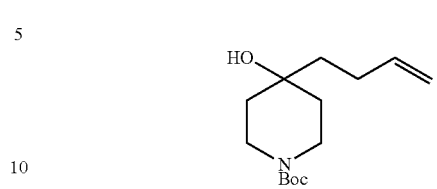

To a mixture of 4-bromobut-1-ene (10.9 g, 0.08 mol) and magnesium turnings (4.8 g, 0.2 mol) in dry tetrahydrofuran (80 mL) was added a crystal of iodine and the mixture was stirred at room temperature until complete reaction had occurred. To this mixture was added tert-butyl 4-oxopiperidine-1-carboxylate (7.7 g, 0.039 mol) in tetrahydrofuran (20 mL) at 0° C. After 1 h at 0° C., and 3 h at room temperature the reaction mixture was diluted with ammonium chloride solution and extracted with ethyl acetate. After drying over $Na_2SO_4$, the solvent was removed in vacuo and the residue was purified via flash chromatography with 25% ethyl actetate/hexane to afford the title compound 16B (3.63 g) as an oil. $^1$H NMR (CHLOROFORM-d) δ 5.84 (d, J=6.7 Hz, 1H), 4.89-5.11 (m, 2H), 3.16 (br. s., 2H), 2.16 (d, J=9.4 Hz, 2H), 1.48-1.66 (m, 6H), 1.45 (s, 9H).

Step B: tert-butyl-4-acetoxy-4-(but-3-en-1-yl)piperidine-1-carboxylate (16C)

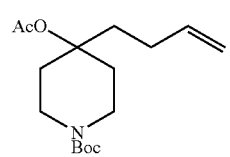

A solution of tert-butyl-4-(but-3-en-1-yl)-4-hydroxypiperidine-1-carboxylate (3.7 g, 14.51 mmol) in dichloromethane (20 mL) was treated with dimethylaminopyridine (1.8 g, 14.51 mmol), acetic anhydride (4.1 mL, 43.53 mmol) and triethylamine (6.1 mL, 43.53 mmol), stirred overnight at 20° C. The solvent was removed under reduced pressure and the residue was partitioned between water and ethyl acetate. The aqueous layer was extracted twice with ethyl acetate. Combined organic extracts were washed with water, dried ($Na_2SO_4$) and filtered. The filtrate was concentrated under reduced pressure, purified by flash chromatography to provide the title compound 16C as colorless oil (3.4 g).

Step C: tert-butyl-4-acetoxy-4-(3-oxobutyl)piperidine-1-carboxylate (16D)

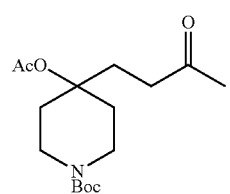

To a solution of tert-butyl-4-acetoxy-4-(but-3-en-1-yl)piperidine-1-carboxylate (1 g, 3.36 mmol) in DMF (6 mL) and H₂O (2 mL) was added CuCl (0.77 g, 7.73 mmol) and PdCl₂ (0.16 g, 0.91 mmol) and the resulting suspension was stirred under an oxygen atmosphere at room temperature for 24 h. The insoluble materials were removed by filtration, and washed with ethyl acetate. The filtrate was dried over anhydrous Na₂SO₄, filtered, and concentrated under reduced pressure. The residue was purified by flash chromatography on silica gel to give 16D (540 mg) as a colorless oil. ¹H NMR (CHLOROFORM-d) δ: 3.84 (br. s., 2H), 2.97 (t, J=12.1 Hz, 2H), 2.38-2.47 (m, 2H), 2.17-2.24 (m, 2H), 2.15 (s, 3H), 2.04 (s, 3H), 1.39-1.51 (m, 9H).

Step D: tert-butyl-4-acetoxy-4-(3,3-difluorobutyl)piperidine-1-carboxylate (16E)

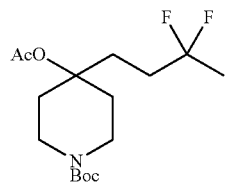

To a solution of tert-butyl-4-acetoxy-4(3-oxobutyl)piperidine-1-carboxylate (2.66 g, 8.5 mmol), in CH₂Cl₂ (15 mL) was added DAST (4.5 mL, 34 mmol) and the resulting mixture was stirred for 24 h room temperature. A saturated aqueous NaHCO₃ solution was added and the resulting biphasic mixture was stirred vigorously for 15 min. The two layers were separated and the aqueous phase was extracted with CH₂Cl₂. The combined organic phase were dried over Na₂SO₄ and concentrated in vacuo. The residue was purified by flash chromatography on silica gel to give the title compound 16E (1.27 g).

Step E: tert-butyl-4-(3,3-difluorobutyl)-4-hydroxypiperidine-1-carboxylate (16F)

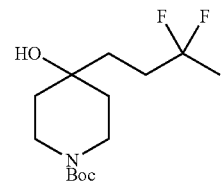 [SMILES: CC(F)(F)CCC1(O)CCN(C(=O)OC(C)(C)C)CC1]

To a solution of tert-butyl-4-acetoxy-4-(3,3-difluorobutyl) piperidine-1-carboxylate (100 mg, 0.426 mmol) in MeOH (10 mL) and H₂O (2 mL) was added NaOH (145 mg, 8.45 mmol). The resulting mixture was stirred at 40° C. for 4 h. After cooling to room temperature, the mixture was acidified with 2N HCl solution. After removal of MeOH, the resulting solution was extracted with ethyl acetate. The organic layer was dried over Na₂SO₄, filtered, and evaporated to dryness under reduced pressure to give the crude product which was used in the next step without further purification.

Step F: 4-(3,3-difluorobutyl)piperidin-4-ol (16G)

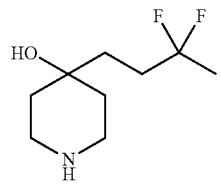

The solution of tert-butyl-4-(3,3-difluorobutyl)-4-hydroxypiperidine-1-carboxylate (0.932 g, 3.2 mmol) in the solution of HCl in 1,4-dioxane (3M, 5 mL) was stirred at room temperature for 1 hour. The solution was evaporated to dryness under reduced pressure to give the product which was used in the next step without further purification. LC-MS: m/z 194.3 (M+H)⁺.

General Procedure 17:

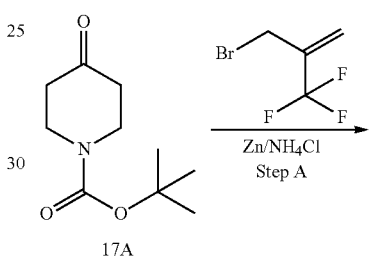

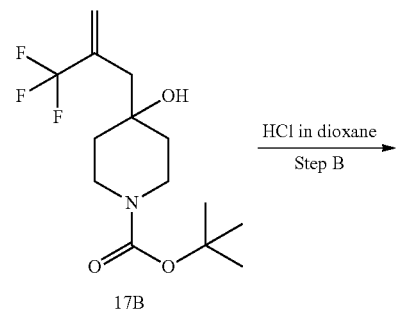

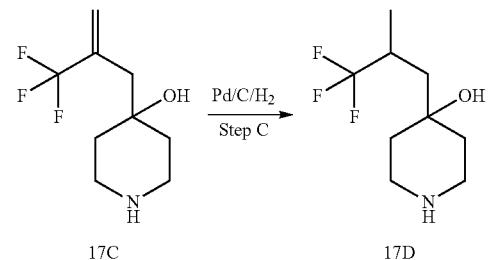

Step A: tert-butyl-4-hydroxy-4-(2-(trifluoromethyl)allyl)piperidine-1-carboxylate (17B)

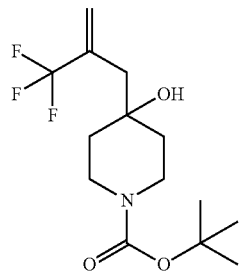 [SMILES: C=C(CC1(O)CCN(C(=O)OC(C)(C)C)CC1)C(F)(F)F]

A solution of tert-butyl 4-oxopiperidine-1-carboxylate (500 mg, 2.51 mmol) and allylbromide (1.2 g, 6.3 mol, 2.5 eq.) in THF (5 mL) and saturated ammonium chloride solution (20 mL) was cooled to 10° C., and zinc dust (328 mg, 5.0 mol, 2 eq.) was added portion wise. After the addition was complete, the reaction mixture was stirred at room temperature overnight, when TLC (heptane/EtOAc 7:1) indicated complete conversion. The reaction mixture was diluted with water (5 mL), and then extracted with EtOAc. The organic layer was washed with saturated NaHCO$_3$ solution, brine, and evaporated to give the title compound, which was used in the next step without further purification.

Step B: 4-(2-(trifluoromethyl)allyl)piperidin-4-ol (17C)

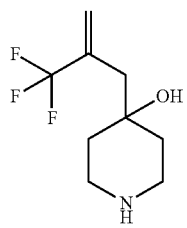

To a solution of tert-butyl-4-hydroxy-4-(2-(trifluoromethyl)allyl)piperidine-1-carboxylate 17B (300 mg, 0.97 mmol), in DCM (5 mL) was added a solution of HCl in dioxane (3 M, 1 mL, 3 mmol), and then the mixture was stirred at room temperature for 16 hrs. The mixture was concentrated in vacuo to get the desired compound which was used directly for the next step. LC-MS: m/z 210.2 (M+H)$^+$

Step C: 4-(3,3,3-trifluoro-2-methylpropyl)piperidin-4-ol (17D)

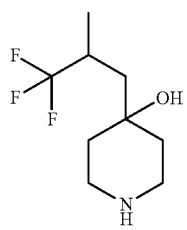

To a mixture of tert-butyl-4-hydroxy-4-(2-(trifluoromethyl)allyl)piperidine-1-carboxylate (100 mg, 0.32 mmol) in EtOH (5 mL) was added 10% Pd/C (20 mg) and a drop of AcOH. The mixture was stirred at 40° C. for 16 hrs under H$_2$ atmosphere. The reaction mixture was filtered through a celite pad; the filtrate was concentrated to get the title compound which was used directly for the next step without purification. LC-MS: m/z 212.2 (M+H)$^+$ General Procedure 18:

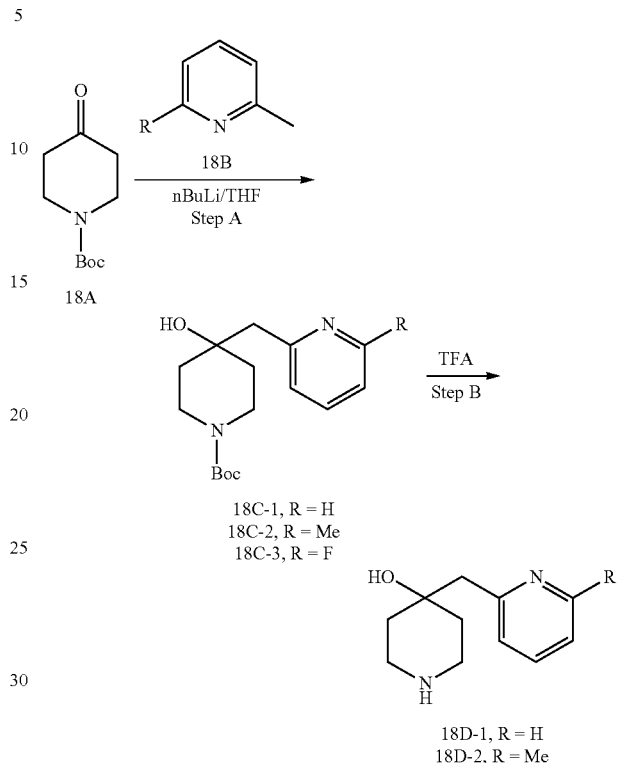

18C-1, R = H
18C-2, R = Me
18C-3, R = F 18D-1, R = H
18D-2, R = Me
18D-3, R = F

Step A:

Compound 18B (1 eq.) was taken in dry THF and cooled to −78° C. when a solution of n-Butyllithium (1.2 eq.) in hexane was added over a period of 15 min at −78° C. under nitrogen atmosphere. The reaction mixture was stirred for 30 min −78° C., and then allowed to stir at −5° C. for 30 min. The resulting mixture was then cooled again to −78° C., and tert-butyl 4-oxopiperidine-1-carboxylate (18A, 0.9 eq.) in THF was added over a period of 15 min. The resulting reaction mixture was then allowed to warm up to room temperature and stirred at r.t. for 16 hrs. The progress of the reaction was monitored by TLC. Upon completion of reaction, the mixture was quenched with satd. NH$_4$Cl solution (500 mL) and extracted with EtOAc. The combined organic layers were washed with water, dried over Na$_2$SO$_4$ and concentrated under reduced pressure. The crude product was purified by column chromatography using silica gel (100-200 mesh) and 10% EtOAc in hexane to afford the corresponding compounds 18C-1, 18C-2 and 18C-3 as light yellow oils. tert-butyl 4-hydroxy-4-(pyridin-2-ylmethyl)piperidine-1-carboxylate (18C-1)

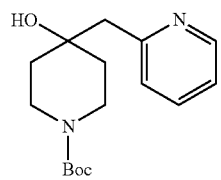 [SMILES: CC(C)(C)OC(=O)N1CCC(O)(Cc2ccccn2)CC1]

$^1$H NMR (CHLOROFORM-d) δ: 8.49-8.48 (m, 1H), 7.64 (t, 1H, J=8 Hz), 7.18 (t, 1H, J=8 Hz), 7.12 (d, 1H, J=7.6 Hz), 3.80-3.77 (m, 2H), 3.24-3.22 (m, 2H), 2.90 (s, 2H), 1.54-1.47 (m, 4H), 1.45 (s, 9H).

tert-butyl 4-hydroxy-4-((6-methylpyridin-2-yl)methyl)piperidine-1-carboxylate (18C-2)

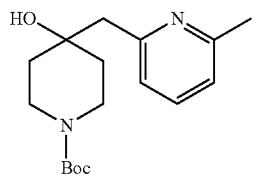 [SMILES: Cc1cccc(CC2(O)CCN(C(=O)OC(C)(C)C)CC2)n1]

$^1$H NMR (CHLOROFORM-d) δ: 7.51 (t, 1H, J=7.6 Hz), 7.02 (d, 1H, J=7.6 Hz), 6.90 (d, 1H, J=7.6 Hz), 6.36 (bs, 1H), 3.79-3.77 (m, 2H), 3.24-3.22 (m, 2H), 2.84 (s, 2H), 2.51 (s, 3H), 1.51-1.47 (m, 4H), 1.45 (s, 9H).

tert-butyl 4-((6-fluoropyridin-2-yl)methyl)-4-hydroxypiperidine-1-carboxylate (18C-3)

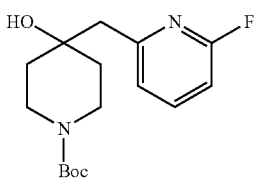 [SMILES: CC(C)(C)OC(=O)N1CCC(O)(Cc2cccc(F)n2)CC1]

$^1$H NMR (CHLOROFORM-d) δ: 7.76-7.70 (m, 1H), 7.02 (d, 1H, J=7.2 Hz), 6.82 (d, 1H, J=8 Hz), 4.44 (s, 1H), 3.80-3.78 (m, 2H), 3.21-3.20 (m, 2H), 2.87 (s, 2H), 1.63-1.49 (m, 4H), 1.45 (s, 9H).

Step B:

Compound 18C (1 eq.) was dissolved in DCM, cooled to 0° C., and TFA (10 eq.) was added at 0° C. and the reaction mixture was then stirred for 3-4 hrs at room temperature until LCMS and TLC confirmed completion of the reaction. The reaction mixture was concentrated to dryness, triturated 3 to 4 times with DCM and washed with n-pentane to afford compound 18D as colorless oil. The crude product was used for the next step directly without further purification.

General Procedure 19:

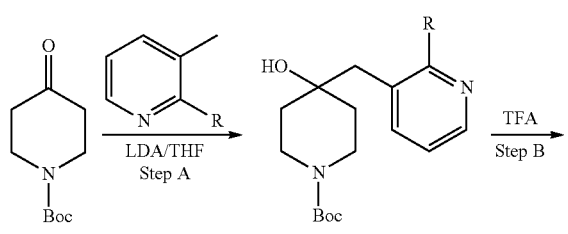

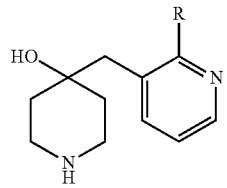

19C-1, R = H
19C-3, R = F

Step A:

The corresponding 2-R-3-methylpyridine (1 eq.) was taken in dry THF and cooled to −78° C. A solution of lithium diisopropylamide (1.8 eq.) 2.5M in THF was added to the above reaction mixture over 15 min at −78° C. under nitrogen atmosphere and stirred for 30 min at same temperature. The reaction mixture was then stirred at −5° C. for 30 min before cooling it again to −78° C. when tert-butyl 4-oxopiperidine-1-carboxylate (19A, 0.9 eq.) in THF was added over 15 min. The resulting mixture was then allowed to stir at room temperature for 16 hrs. The progress of the reaction was monitored by TLC. Upon completion of reaction, the mixture was quenched with satd. NH$_4$Cl solution (500 mL) and extracted with EtOAc. The combined organic layers was washed with water, dried over Na$_2$SO$_4$ and concentrated under reduced pressure. The crude product was purified by column chromatography using silica gel (100-200 mesh) and 10% EtOAc in Hexane to afford the title compound 19B as light yellow oil.

tert-butyl 4-hydroxy-4-(pyridin-3-ylmethyl)piperidine-1-carboxylate (19B-1)

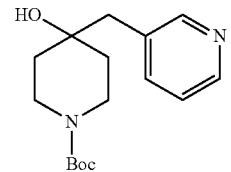 [SMILES: CC(C)(C)OC(=O)N1CCC(O)(Cc2cccnc2)CC1]

$^1$H NMR (CHLOROFORM-d) δ: 8.51-8.46 (m, 2H), 7.56 (d, 1H, J=8 Hz), 7.27-7.24 (m, 1H), 3.88-3.81 (m, 2H), 3.12-3.07 (m, 2H), 2.76 (s, 2H), 1.63-1.61 (m, 2H), 1.49-1.47 (m, 2H), 1.45 (s, 9H).

Step B:

compound 19B-1 or 19B-2 (1eq.) was dissolved in DCM, cooled to 0° C. to which TFA (10 eq.) was added at 0° C. and the reaction mixture was then stirred for 3-4 hrs at room temperature until LCMS and TLC confirmed completion of the reaction. The reaction mixture was concentrated to dryness, triturated 3 to 4 times with DCM and washed with n-pentane to afford compound 19C-1 or 19C-2, respectively, as colorless oil. The crude product was used for the next step without purification.

General Procedure 20:

-continued

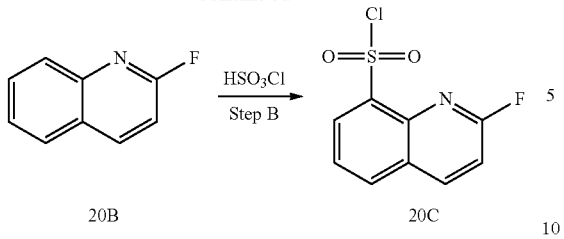

Step A: 2-fluoroquinoline (20B)

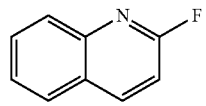 [SMILES: Fc1ccc2ccccc2n1]

To a solution of 2-chloroquinoline (4.9 g, 30 mmol) in 200 mL of anhydrous DMSO was added cesium fluoride (9.13 g, 60 mmol), and the resulting mixture was stirred at 130° C. overnight, when LC-MS showed completion of the reaction. After cooling, the reaction mixture was diluted with water, and then extracted with ethyl acetate. The organic layer was then washed with brine, dried over anhy. $Na_2SO_4$, and concentrated in vacuo. Column chromatography (6% EtOAc/PE) afforded 3.34 g of title compound. $^1H$ NMR (CHLOROFORM-d) δ: 8.23 (d, J=8.6 Hz, 1H), 7.89 (d, J=8.6 Hz, 1H), 7.82-7.86 (m, 1H), 7.67 (d, J=8.5, 7.0, 1.5 Hz, 1H), 7.47-7.53 (m, 1H), 7.35 (d, J=8.6 Hz, 1H). LC-MS: m/z 148.2 (M+H)$^+$ Step B: 2-fluoroquinoline-8-sulfonyl chloride (20C)

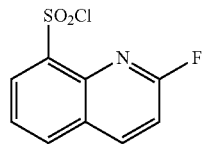 [SMILES: O=S(=O)(Cl)c1cccc2ccc(F)nc12]

A solution of 2-fluoroquinoline (1.3 g, 8.9 mmol) in chlorosulfonic acid (15 mL) was stirred at −5-0° C. for 15 minutes and at 130° C. overnight. The resulting reaction mixture was poured into an ice-water mixture (300 mL), stirred at room temperature for 20 min, and extracted with EtOAc. The organic layer was then washed with brine, dried over $Na_2SO_4$ and solvent was removed. The residue was purified by column chromatography using a gradient elution from 100% PE to PE/EtOAc (100:6) to afford 1.1 g of title compound. $^1H$ NMR (CHLOROFORM-d) δ: 8.56 (d, J=7.5 Hz, 1H), 8.43 (t, J=8.3 Hz, 1H), 8.25 (d, J=8.3 Hz, 1H), 7.72 (t, J=7.8 Hz, 1H), 7.32 (dd, J=8.9, 3.0 Hz, 1H). LC-MS: m/z 246.3 (M+H)$^+$ General Procedure 21:

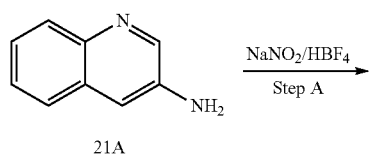

-continued

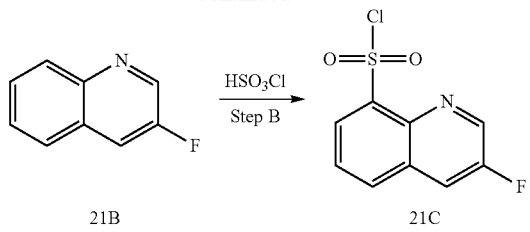

Step A: 3-fluoroquinoline (21B)

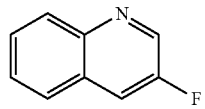 [SMILES: Fc1cnc2ccccc2c1]

Quinolin-3-amine (4 g, 27.7 mmol) was added to $HBF_4$ (26 mL, 48% aqueous solution) portionwise at room temperature, and the mixture was stirred at room temperature until it became homogeneous. The mixture was then cooled to 0° C., and a solution of $NaNO_2$ (2.4 g, 34.8 mmol) in $H_2O$ (8 mL) was added dropwise, when the reaction mixture became heterogeneous. The mixture was stirred at 0° C. for 1 hour, then the mixture was filtered, and the filtered cake was washed with cold EtOH, then $Et_2O$. The resulting solid was dried under vacuum, then suspended in toluene in a round bottom flask and was refluxed for 1.5 hours. The resulting mixture was cooled to room temperature, and then poured into cold water. The organic layer was dried over $Na_2SO_4$, and then concentrated in vacuo to obtain the desired product (1.6 g). LC-MS: m/z 148.1 (M+H)$^+$ Step B: 3-fluoroquinoline-8-sulfonyl chloride (21C)

A mixture of 3-fluoroquinoline (0.6 g, 4.08 mmol) and $HSO_3Cl$ (2 mL) in a round bottom flask equipped with a cooling condenser was stirred at 130° C. overnight. When TLC indicated that the reaction was complete, the resulting mixture was carefully poured into crushed ice, the mixture was extracted with DCM (100 mL×3), and the combined organic layers were dried over $Na_2SO_4$, and concentrated. The crude mixture was purified by chromatography (5% Ethyl Acetate/PE) to give the desired 3-fluoroquinoline-8-sulfonyl chloride. $^1H$ NMR (CHLOROFORM-d) δ: 9.15 (d, J=2.6 Hz, 1H), 8.53 (d, J=7.6 Hz, 1H), 8.23 (dd, J=8.2, 0.9 Hz, 1H), 7.97 (dd, J=8.1, 2.8 Hz, 1H), 7.69-7.83 (m, 1H). LC-MS: m/z 246.7 (M+H)$^+$ General Procedure 22:

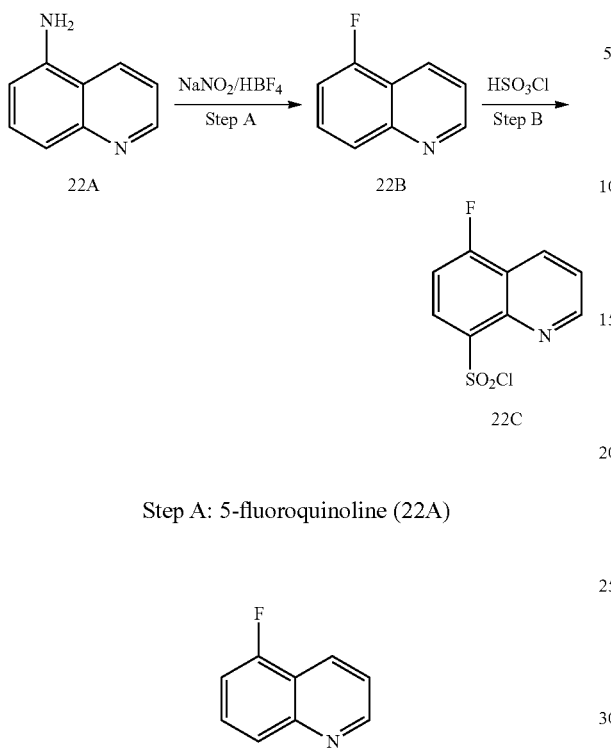

Step A: 5-fluoroquinoline (22A)

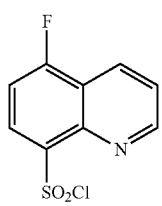

To a solution of quinolin-5-amine (2 g, 13.9 mmol) in 10 mL of 48% HBF$_4$ at 0° C. was added sodium nitrite (933 mg, 13.5 mmol) portionwise. This was stirred for 1 hour and then poured into 1:1 ethyl acetate diethyl ether mixture (50 mL). The resulting suspension was filtered and the solid was dried. This solid was added portionwise to refluxing xylene (30 mL) and stirred for 3 hours, then allowed to cool. The xylene was decanted off and the residue was dissolved in 1N HCl (50 mL). After neutralization with NaHCO$_3$, the mixture was extracted with ethyl acetate (3×50 mL). The extracts were dried over sodium sulfate, filtered and the volatiles were removed under reduced pressure. The residue was purified by silica gel chromatography (3% EtOAc/PE) to afford 800 mg of title compound as colorless oil. LC-MS: m/z 148.2 (M+H)$^+$ Step B: 5-fluoroquinoline-8-sulfonyl chloride (22C)

5-fluoroquinoline (800 mg, 5.4 mmol) was added slowly to 10 mL of chlorosulfonic acid at 0° C. When the addition was complete, the reaction mixture was heated at 130° C. overnight. The solution was allowed to cool and was slowly poured over ice. The aqueous layer was extracted with ethyl acetate (3×50 mL). The combined organic extracts were dried and evaporated to give the crude product, which was purified by column chromatography (5% EtOAc/PE) to afford 400 mg of title compound. $^1$H NMR (CHLOROFORM-d) δ: 7.40 (t, J=8.46 Hz, 1H), 7.74 (dd, J=8.60, 4.30 Hz, 1H), 8.55-8.64 (m, 2H), 9.32 (dd, J=4.30, 1.88 Hz, 1H). LC-MS: m/z 4.246 (M+H)$^+$ General Procedure 23:

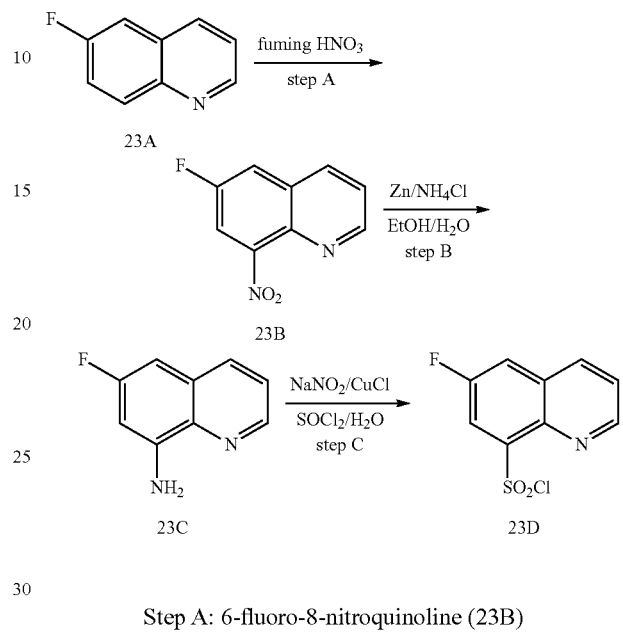

Step A: 6-fluoro-8-nitroquinoline (23B)

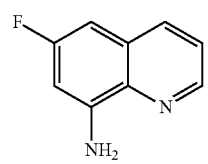 [SMILES: O=[N+]([O-])c1cc(F)cc2cccnc12]

A mixture of 6-fluoroquinoline (2 g, 13.6 mmol) and fuming HNO$_3$ (15 mL) in a round bottom flask equipped with a cooling condenser was refluxed for 100 hours, the resulting mixture was cooled to r.t., poured slowly into crushed ice/H$_2$O, and then the mixture was extracted with DCM (200 mL×3). The combined organic layers were dried over Na$_2$SO$_4$, and concentrated. The residue was passed through a short pad of silica gel to give 1.6 g of title compound. $^1$H NMR (CHLOROFORM-d) δ: 9.08 (dd, J=4.1, 1.5 Hz, 1H), 8.25 (dd, J=8.5, 1.5 Hz, 1H), 7.89 (dd, J=7.5, 2.8 Hz, 1H), 7.72 (dd, J=8.1, 2.8 Hz, 1H), 7.62 (dd, J=8.4, 4.3 Hz, 1H). LC-MS: m/z 466.6 (M+H)$^+$ Step B: 6-fluoroquinolin-8-amine (23C)

To a mixture of 6-fluoro-8-nitroquinoline (1.6 g, 8.3 mmol), and NH$_4$Cl (2 g, 41.5 mmol) in EtOH/H$_2$O (10 mL/10 mL) in a round bottom flask equipped with a refluxing condenser was added Zn (5.4 g, 16.6 mmol) dust in portions at room temperature, and the resulting mixture was stirred at 60° C. overnight. The reaction mixture was filtered, and the filtrate was extracted with EtOAc. The combined organic layers were dried over Na$_2$SO$_4$, and concentrated to give 1.0 g of crude product, which was used directly for the next step without further purification. LC-MS: m/z 163.2 (M+H)$^+$ Step C: 6-fluoroquinoline-8-sulfonyl chloride (23D)

(a) Thionyl chloride (2.1 mL) was added dropwise to water (12.5 mL) at 5° C. This mixture was allowed to warm to room temperature and stirred overnight. CuCl (10 mg) was then added and the resulting yellow solution was cooled to 0° C. (b) Concentrated hydrochloric acid (6.75 mL) was cooled to 0° C. while 6-fluoroquinolin-8-amine (1 g) was added portionwise. The mixture was allowed to warm up slightly between additions, during which time the reaction mixture turned yellow. After the addition was complete, the reaction mixture was cooled to −5° C. and a solution of NaNO$_2$ (0.5 g) in water (2 mL) was added dropwise. After complete addition and at −5° C., the resulting mixture was added slowly to the cooled thionyl chloride/CuCl mixture from part (a). Then the mixture was stirred at 0° C. for about 1 hour. The resulting mixture was extracted with DCM, combined organic layers were dried over Na$_2$SO$_4$, concentrated to yield 500 mg of title compound which was used for the next step without further purification. LC-MS: m/z 246.7 (M+H)$^+$ General Procedure 24-1:

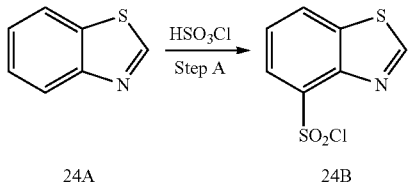

Step A: Benzo[d]thiazole-4-sulfonyl chloride (24B)

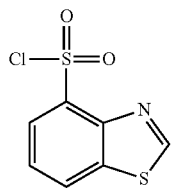 [SMILES: O=S(=O)(Cl)c1cccc2scnc12]

Benzo[d]thiazole (1 g, 7.45 mol) was added dropwise to chlorosulfonic acid (5.5 mmol) at 0° C. After the addition was complete, the mixture was stirred at room temperature for 0.5 h and then heated at 105° C. and stirred overnight. The resulting mixture was cooled to −10° C. and quenched by pouring on crushed ice slowly. The resulting mixture was extracted with EtOAc (100 mL×2). The combined organic phase was washed with brine, dried over anhy. Na$_2$SO$_4$ and concentrated in vacuo. Column chromatography (15% PE/EtOAc) afforded 218 mg of title compound. $^1$H NMR (CHLOROFORM-d) δ: 9.41 (s, 1H), 8.41 (dd, J=8.1, 1.0 Hz, 1H), 8.29 (dd, J=7.7, 1.1 Hz, 1H), 7.68 (t, J=7.9 Hz, 1H). LC-MS: m/z 234.7 (M+H)$^+$ General Procedure 24:

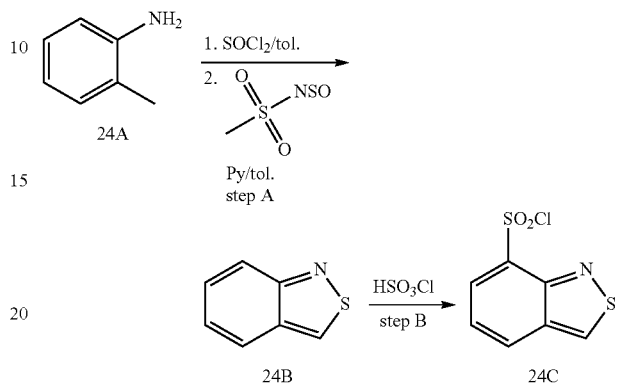

Step A: benzo[c]isothiazole (24B)

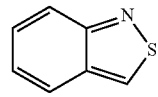

To a solution of o-toluidine (10 g, 93.4 mmol) in 50 mL toluene was added SOCl$_2$ (12.1 g, 102 mmol) dropwise at 0° C. After the addition was complete, the reaction mixture was heated to reflux and stirred overnight. The reaction mixture was cooled to room temperature, and concentrated under reduced pressure to give a yellow oil. The oil was dissolved in toluene (100 mL), then a solution of N-sulfinylmethanesulfonamide (20.6 g, 146 mmol) was added dropwise, followed by pyridine (7.3 g, 93.4 mmol). The mixture was heated to reflux and stirred at that temperature overnight. Toluene was then removed under reduced pressure, the residue was dissolved in EtOAc (200 mL) and washed with water (2×200 mL). The organic layer was washed with brine, dried and evaporated to give the crude product. The crude product was purified by column chromatography (3% EtOAc/PE) to afford 6.2 g title compound as colorless oil. $^1$H NMR (CHLOROFORM-d) δ 9.22 (s, 1H), 7.88 (d, J=9.7 Hz, 1H), 7.80 (d, J=8.6 Hz, 1H), 7.46 (ddd, J=8.9, 6.5, 1.2 Hz, 1H), 7.26 (dd, J=7.9, 6.6 Hz, 1H).

Step B: benzo[c]isothiazole-7-sulfonyl chloride (24C)

Benzo[c]isothiazole 24B (1 g, 7.45 mmol) was added dropwise to chlorosulfonic acid (5.5 mmol) at 0° C. After the addition was complete, the mixture was stirred at room temperature for 0.5 h and then heated at 105° C. and stirred overnight. The resulting mixture was cooled to −10° C. and quenched by pouring on crushed ice slowly. The resulting mixture was extracted with EtOAc (100 mL×2). The combined organic phase was washed with brine, dried over anhy. Na$_2$SO$_4$ and concentrated in vacuo. Column chromatography (15% PE/EtOAc) afforded 200 mg of title compound. $^1$H NMR (CHLOROFORM-d) δ: 9.68 (s, 1H), 8.66 (d, J=1.9 Hz, 1H), 8.10 (d, J=9.4 Hz, 1H), 7.99 (dd, J=9.4, 2.1 Hz, 1H).

General Procedure 25:

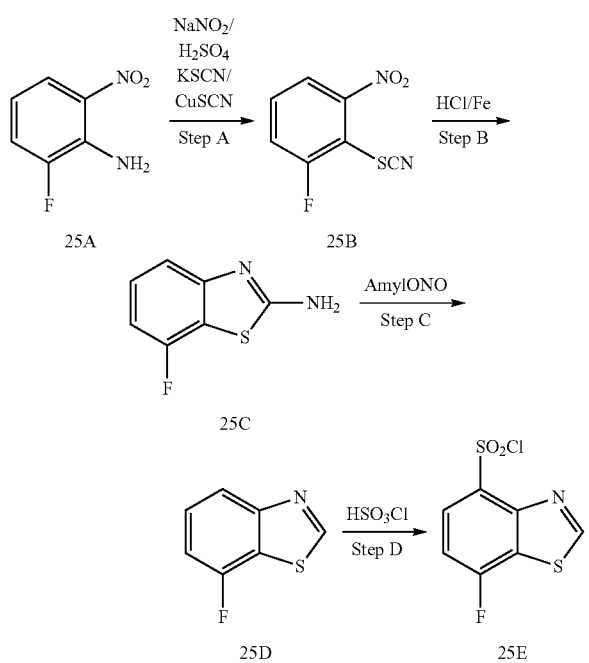

Step A: 1-fluoro-3-nitro-2-thiocyanatobenzene (25B)

A solution of 2-fluoro-6-nitroaniline (3 g, 0.02 mol) in conc. sulphuric acid (30 mL) and water (30 mL) was diazotized at 0-3° C. for 90 min with aqueous sodium nitrite (1.45 g, 0.021 mol). After addition of potassium thiocyanate (2.522 g, 0.026 mol) in water (10 mL), the diazo-liquor was stirred vigorously into a suspension of cuprous thiocyanate (6.05 g, 0.05 mol) in water (20 mL) at 5° C. After stirring at 5° C. for 2 hr, the mixture was then heated at 70° C. for 20 min, then was cooled overnight, filtered, and the cake extracted with EtOAc to get the crude product (3.96 g) which was used in the next step without further purification. LC-MS: m/z 199.2 (M+H)$^+$ Step B: 7-fluorobenzo[d]thiazol-2-amine (25C)

A mixture of 1-fluoro-3-nitro-2-thiocyanatobenzene 2 (3.96 g, 0.02 mol), ethanol (30 mL), water (25 mL) and conc. hydrochloric acid (25 mL) was refluxed gently during the addition of hydrogen-reduced iron powder (8 g). After refluxing for 16 hr, the liquor was filtered hot, cooled, the residue filtered, dissolved in hot water, and neutralized with ammonia and then extracted with EtOAc to get the compound 7-fluorobenzo[d]thiazol-2-amine (1 g) as a colorless oil. LC-MS: m/z 169.2 (M+H)$^+$ Step C: 7-fluorobenzo[d]thiazole (25D)

To a solution of 7-fluorobenzo[d]thiazol-2-amine 25C (1 g, 5.95 mmol) in THF (10 mL) was added isoamyl nitrite (1.51 g, 12.9 mmol) at room temperature. After refluxing for 3 hr, the reaction mixture was then allowed to cool to room temperature and poured into ice water (50 mL), and then extracted with EtOAc. The organic extract was washed with water and brine, dried and evaporated. The residue was chromatographed on silica gel to get the 7-fluorobenzo[d]thiazole as colorless oil. LC-MS: m/z 154.2 (M+H)$^+$ Step D: 7-fluorobenzo[d]thiazole-4-sulfonyl chloride (25E)

7-fluorobenzo[d]thiazole 25D (500 mg, 3.26 mmol) was added dropwise to chlorosulfonic acid (2.5 mmol) at 0° C. After the addition was complete, the mixture was stirred at room temperature for 0.5 h and then heated at 105° C. and stirred overnight. The resulting mixture was cooled to −10° C. and quenched by pouring on crushed ice slowly. The resulting mixture was extracted with EtOAc (20 mL×2). The combined organic phase was washed with brine, dried over anhy. Na$_2$SO$_4$ and concentrated in vacuo. Column chromatography (15% PE/EtOAc) afforded 200 mg of title compound. $^1$H NMR (CHLOROFORM-d) δ: 9.44 (s, 1H), 8.32 (dd, J=8.6, 4.6 Hz, 1H), 7.38 (t, J=8.5 Hz, 1H).

General Procedure 26:

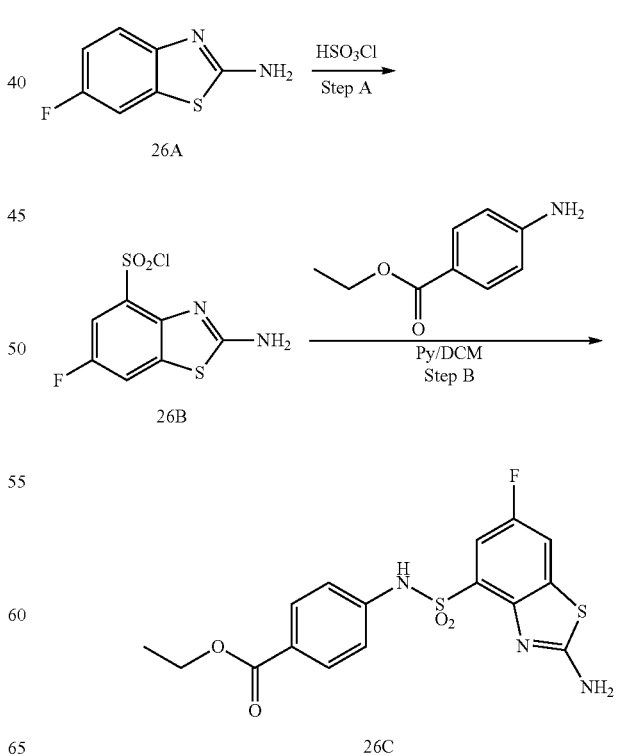

Step A: 2-amino-6-fluorobenzo[d]thiazole-4-sulfonyl chloride (26B)

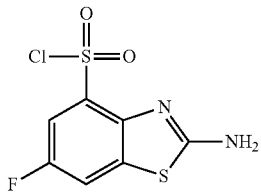 [SMILES: Nc1nc2c(S(=O)(=O)Cl)cc(F)cc2s1]

6-fluorobenzo[d]thiazol-2-amine (1 g, 5.95 mol) was added dropwise to chlorosulfonic acid (5.0 mmol) at 0° C. After the addition was complete, the mixture was stirred at room temperature for 0.5 h and then heated at 105° C. and stirred overnight. The resulting mixture was cooled to −10° C. and quenched by pouring on crushed ice slowly. The resulting mixture was extracted with EtOAc (100 mL×2). The combined organic phase was washed with brine, dried over anhy. $Na_2SO_4$ and concentrated in vacuo. Column chromatography (50% PE/EtOAc) afforded 200 mg of title compound. LC-MS: m/z 266.7 $(M+H)^+$

Step B: ethyl 4-(2-amino-6-fluorobenzo[d]thiazole-4-sulfonamido)benzoate (26C)

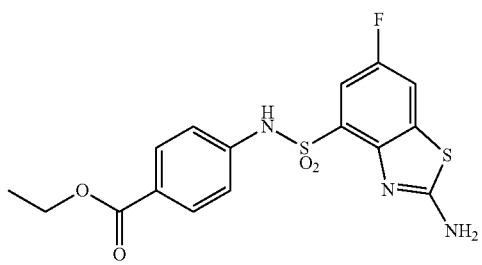 [SMILES: CCOC(=O)c1ccc(NS(=O)(=O)c2cc(F)cc3sc(N)nc23)cc1]

To a solution of the ethyl 4-aminobenzoate (413 mg, 2.5 mmol) in 20 mL of DCM was added pyridine (600 mg, 7.5 mmol) and 2-amino-6-fluorobenzo[d]thiazole-4-sulfonyl chloride (668 mg, 2.5 mmol). The resulting mixture was stirred at 50° C. overnight. After removal of DCM, the residue was partitioned between water and EtOAc. The organic layer was washed with 2 N HCl, water and brine, dried over $Na_2SO_4$ and concentrated to give crude product, which was purified by chromatography to give pure compound 26C. $^1$H NMR (CHLOROFORM-d) δ: 8.10 (s, 1H), 7.93-7.82 (m, 2H), 7.59 (dd, J=8.2, 2.6 Hz, 1H), 7.47 (dd, J=7.5, 2.6 Hz, 1H), 7.20-7.09 (m, 2H), 5.73 (s, 2H), 4.32 (q, J=7.1 Hz, 2H), 1.35 (t, J=7.1 Hz, 3H). LC-MS: m/z 396.5 $(M+H)^+$ General Procedure 27:

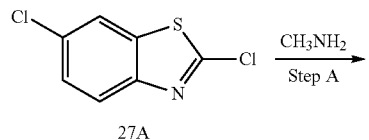

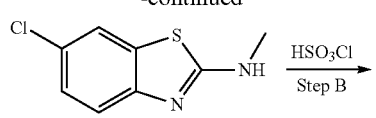

Step A: 6-chloro-N-methylbenzo[d]thiazol-2-amine (27B)

To a solution of 2,6-dichlorobenzo[d]thiazole (2 g, 10 mmol) in 10 mL THF was added 25% $MeNH_2$ in water (3 mL) dropwise. After the addition complete, the reaction mixture was stirred at room temperature overnight. Filter off the product and washed with methanol. Drying in vacuo to yield 1.5 g of the desired compound. LC-MS: m/z 204.2 $(M+H)^+$

Step B: 6-chloro-2-(methylamino)benzo[d]thiazole-4-sulfonyl chloride (27C)

A solution of 6-chloro-N-methylbenzo[d]thiazol-2-amine (500 mg, 2.53 mmol) in chlorosulfonic acid (5 mL) was stirred at 130° c. overnight. The solution was allowed to cool and slowly added to a large excess of ice. The aqueous layer was extracted with EtOAc (3×50 mL). The combined organic layers were washed with brine, dried over $Na_2SO_4$ and concentrated under reduced pressure. The residue was purified by chorography (silica gel) eluting with PE/EA=1:1 to get the title compound. $^1$H NMR (CHLOROFORM-d) δ: 7.95 (d, J=1.9 Hz, 1H), 7.89 (d, J=2.1 Hz, 1H), 6.70 (br. s., 1H), 3.16 (d, J=4.3 Hz, 3H). LC-MS: m/z 297 $(M+H)^+$ General Procedure 28:

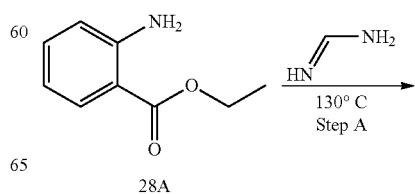

-continued

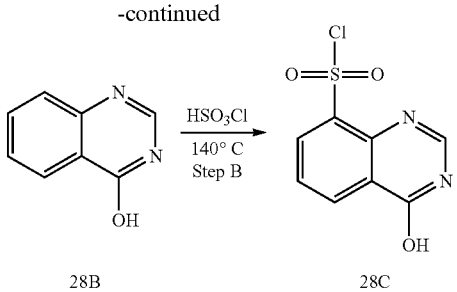

Step A: quinazolin-4-ol (28B)

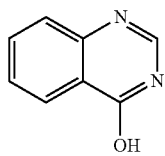 [SMILES: Oc1ncnc2ccccc12]

A solution of ethyl 2-aminobenzoate (5.0 g, 30 mmol) in methoxyethanol (20 mL) was treated with formamidine acetate (8 g, 77 mmol) under reflux for 17 h. A second portion of formamidine acetate (8 g, 77 mmol) was then added, and the reflux was continued for 7 more hours. The mixture was cooled, and the solvent was removed under vacuum. The residue was taken in saturated NaHCO$_3$ and extracted with ethyl acetate. The organic layers were combined, washed with saturated NaHCO$_3$, and dried with magnesium sulfate, and the solvent was removed under vacuum to give the desired compound (4.84 g, 91%), which was used for the next step without further purification. LC-MS: m/z 147.7 (M+H)$^+$ Step B: 4-hydroxyquinazoline-8-sulfonyl chloride (28C)

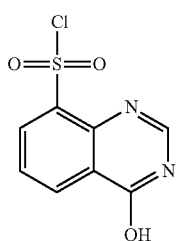 [SMILES: O=S(=O)(Cl)c1cccc2c(O)ncnc12]

Chlorosulfonic acid (4.10 mL, 62.6 mmol) was slowly added to quinazolin-4-ol (1.09 g, 0.26 mmol). The resulting mixture was heated to 140° C. and stirred for 3 hours at the same temperature. After cooling to room temperature, the reaction mixture was poured into crushed ice. The mixture was extracted with DCM (100 mL×3), the combined organic layers were dried over Na$_2$SO$_4$, filtered, and the filtrate was concentrated in vacuo. The residue was purified via flash chromatography (5% PE: Ethyl Acetate) to give 370 mg of 4-hydroxyquinazoline-8-sulfonyl chloride. $^1$H NMR (400 MHz, DMSO-d$_6$) δ: 7.76 (t, J=7.79 Hz, 1H) 8.26 (ddd, J=9.67, 7.92, 1.48 Hz, 2H) 9.02 (s, 1H). LC-MS: m/z 245.7 (M+H)$^+$ General Procedure 29:

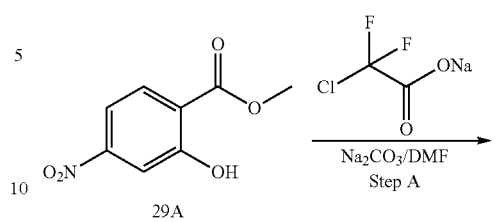

Step A: methyl 2-(difluoromethoxy)-4-nitrobenzoate (29B)

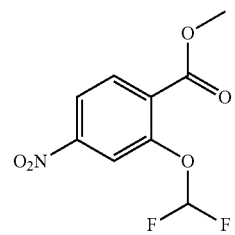 [SMILES: COC(=O)c1ccc([N+](=O)[O-])cc1OC(F)F]

A mixture of methyl 2-hydroxy-4-nitrobenzoate (1.1 g, 5.6 mmol), sodium 2-chloro-2,2-difluoroacetate (1.0 g, 6.6 mmol) and Na$_2$CO$_3$ (710 mg, 6.7 mmol) in DMF (10 mL) was stirred at 100° C. overnight. After cooling to rt, the mixture was partitioned between water and EtOAc. The organic layer was separated and washed with twice with water, then brine, dried over Na$_2$SO$_4$ and concentrated, and purified by a standard method to give the title product (330 mg). $^1$H NMR (CHLOROFORM-d) δ: 8.15-8.19 (m, 1H), 8.13 (s, 1H), 8.06 (d, J=8.6 Hz, 1H), 6.68 (s, 1H), 3.98 (t, J=72.8 Hz, 1H).

Step B: Methyl 4-amino-2-(difluoromethoxy)benzoate (29C)

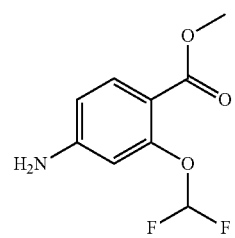

A mixture of methyl 2-(difluoromethoxy)-4-nitrobenzoate (330 mg, 1.3 mmol) and 10% Pd on carbon (50 mg) in THF (10 mL) was stirred at room temperature under hydrogen atmosphere for 6 hours. The solid was removed by filtration and the solvent was concentrated to give the crude aniline. LC-MS: m/z 218.1 (M+H)⁺

General Procedure 30:

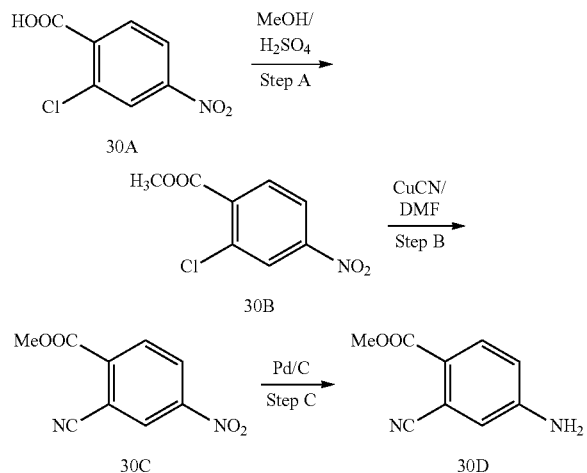

Step A: methyl 2-chloro-4-nitrobenzoate (30B)

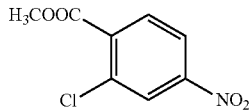

To a solution of 2-chloro-4-nitrobenzoic acid (10 g, 0.06 mol) in MeOH (120 mL) was added H₂SO₄ (5 mL). The resulting mixture was stirred at 60° C. overnight. After cooling to room temperature, the mixture was brought to pH=8 using sodium bicarbonate solution. After removal of MeOH, the resulting crude mixture was purified by column chromatography (20% CH₂Cl₂/PE) to afford 4 g of the title compound. LC-MS: m/z 216.6 (M+H)⁺

Step B: methyl 2-cyano-4-nitrobenzoate (30C)

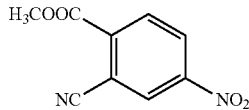

A mixture of methyl 2-chloro-4-nitrobenzoate (2 g, 9.3 mmol), CuCN (3.3 g, 37.2 mmol), and Pd(PPh₃)₄ (1.075 g, 0.93 mmol) was suspended in DMF (15 mL) and then subjected to microwave irradiation at 150° C. for 4 hours. After the mixture was concentrated under reduced pressure, the residue was partitioned between ethyl acetate and water. The organic layer was dried over Na₂SO₄, filtered, and the filtrate was evaporated to dryness under reduced pressure. The crude material was purified by column chromatography (20% EA/PE) to afford 0.9 g of title compound. LC-MS: m/z 207.1 (M+H)⁺.

Step C: methyl 4-amino-2-cyanobenzoate (30D)

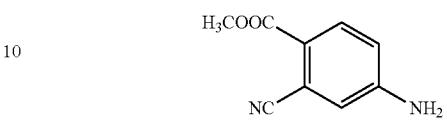

To a solution of methyl 2-cyano-4-nitrobenzoate (0.9 g, 4.4 mmol) in MeOH (5 mL) was added Pd/C (0.1 g). The resulting mixture was stirred at room temperature for 2 hours under hydrogen atmosphere. The mixture was filtered, and the filtrate was evaporated to dryness under reduced pressure to give the title product (0.77 g), which was used in the next step without further purification. LC-MS: m/z 177.2 (M+H)⁺

General Procedure 31:

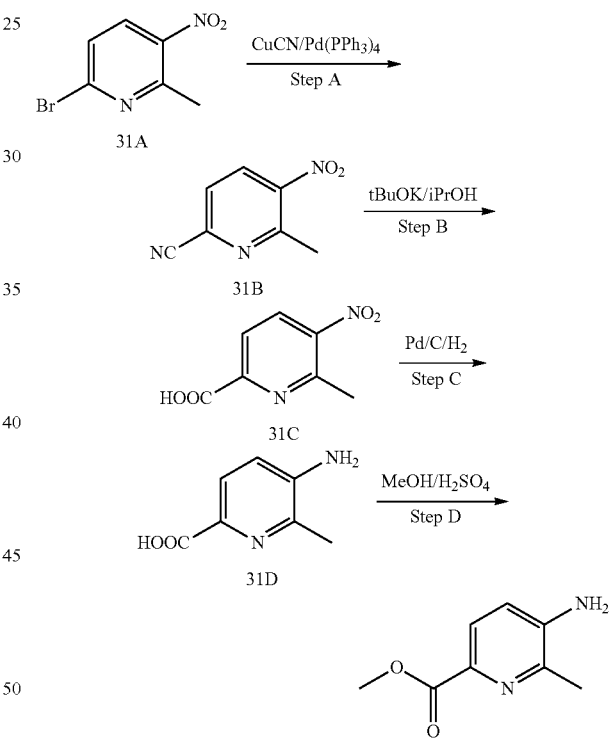

Step A: 6-methyl-5-nitropicolinonitrile (31B)

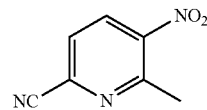

To a mixture of methyl 2-bromo-4-nitrobenzoate (31A, 4 g, 18.4 mmol) in 10 mL DMA was added CuCN (6.6 g, 74 mmol), and Pd(PPh₃)₄ (1.06 g, 0.92 mmol) under N₂. The mixture was stirred at 150° C. under microwave irradiation for 4 hrs. Then the mixture was diluted water and filtered. The filtrate was extracted with EtOAc (20 mL). The organic layer was dried, concentrated, and purified by silica gel chromatography (PE: EtOAc=3:1) to give 500 mg the title compound. ¹H NMR (CHLOROFORM-d) δ: 8.08 (d, J=7.9 Hz, 1H), 7.68 (d, J=7.9 Hz, 1H), 2.85 (s, 3H).

Step B: 6-methyl-5-nitropicolinic acid (31C)

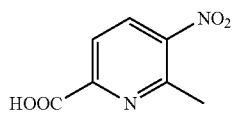

To a solution of 6-methyl-5-nitropicolinonitrile (31B, 500 mg, 3.1 mmol) in 2-propanol (1 mL) and water (5 mL) was added potassium tert-butoxide (687 mg, 6.13 mmol). The mixture was stirred at 100° C. overnight, when LCMS indicated that the reaction was complete. The mixture diluted with water, and then extracted with DCM (10 mL×3). The aqueous phase was acidified with 1N HCl solution, and extracted with DCM. The organic layer was dried and concentrated to give the crude product which was used to the next step without further purification. LC-MS: m/z 181 (M−H)⁺

Step C: 5-amino-6-methylpicolinic acid (31D)

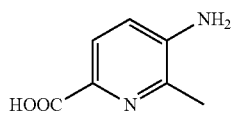

To a solution of 6-methyl-5-nitropicolinic acid (31C, 500 mg, 2.75 mmol) in methanol (10 ml) was added Pd/C (50 mg). The solution was stirred at r.t. under H₂ atmosphere for 1 h, when LC-MS showed that s.m. was consumed. Then the mixture was filtered and concentrated to give the crude product which was used to the next step without further purification. LC-MS: m/z 153 (M+H)⁺

Step D: methyl 5-amino-6-methylpicolinate (31E)

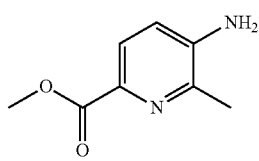

To a solution of 5-amino-6-methylpicolinic acid (31D, 240 mg, 1.5 mmol) in methanol was added conc. H₂SO₄. The solution was stirred at 60° C. overnight, when LC-MS showed that s.m. was consumed. Then the mixture was concentrated and neutralized with Na₂CO₃ solution to pH=7. The mixture was extracted with DCM (10 mL×3). The organic layer was dried and concentrated to give the title compound 31E. LC-MS: m/z 167 (M+H)⁺

General Procedure 36:

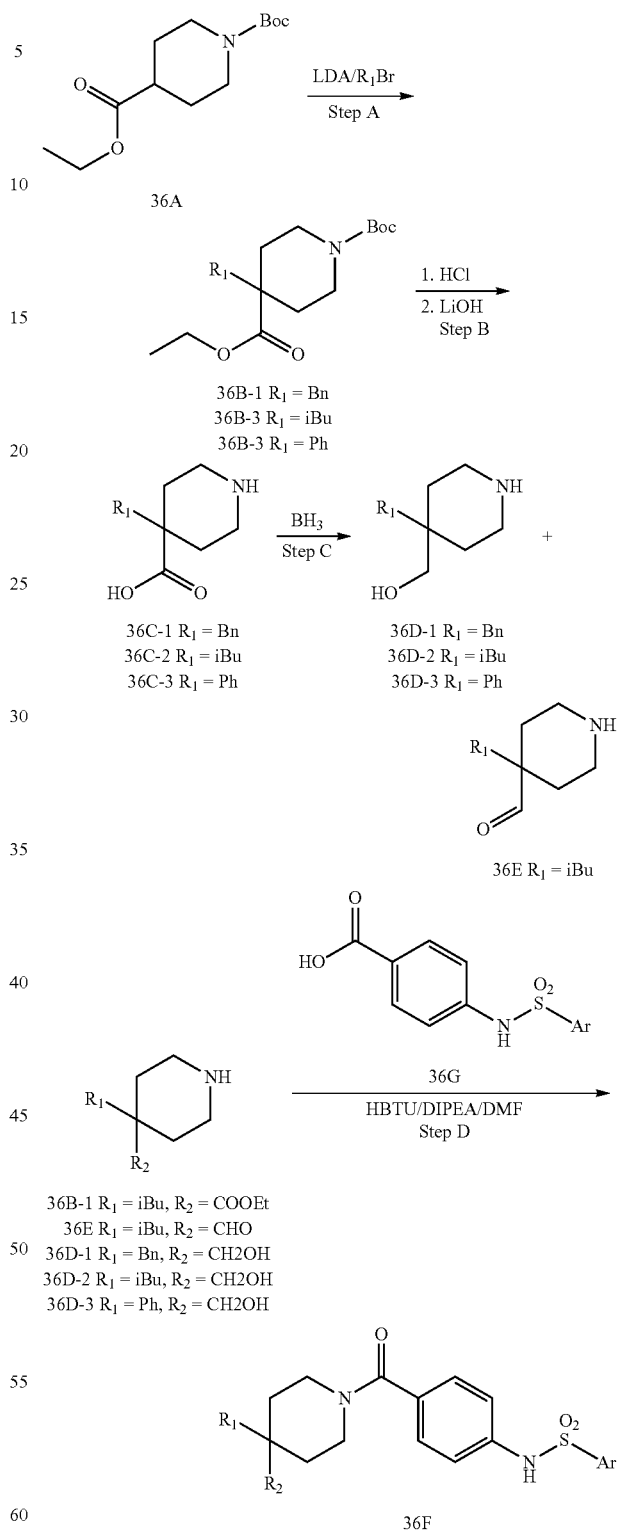

Step A:

To a solution of 1-tert-butyl 4-ethyl piperidine-1,4-dicarboxylate (36A, 1.24 g, 4.0 mmol) in anhydrous THF (50 mL) was added LDA solution (2.1 mL, 5.2 mmol) dropwise at −65° C. for 30 min, and the resulting mixture was stirred at −65° C. for 15 min, and then stirred at −30° C. for another 30 min. After the addition of RBr (4.8 mmol, 1.2 eq) at −65° C., the mixture was stirred for another 15 min at −65° C., and then it was allowed to warm up to r.t. for 2 hrs. The reaction was quenched by adding 50 mL NH₄Cl solution (1 M), the organic phase was concentrated and the crude product purified by a standard method to give the title compound 36B.

Step B:

A mixture of the corresponding compound 36B (2.0 mol) and HCl (10 mL, 4M solution in 1,4-dioxane) was stirred at r.t. for 4 hrs. The solvent was then removed, and the residue was dissolved in 3.0 mL NaOH solution and 2.0 mL of methanol. The mixture was stirred under microwave irradiation at 110° C. for 10 min and then concentrated. The residue was purified by a standard method to give the title compound 36C.

Step C:

To a vial was added compound 36C (24.36 mmol) in 10 mL THF, then borane-tetrahydrofuran complex (3.3 mL, 32.88 mmol) was added, and the mixture was heated at reflux for 3 h. After washing with satd. NaHCO₃, brine, the combined organic layer was dried over anhy. Na₂SO₄ and concentrated in vacuo to get the crude product 36D and 36E, which was used directly for the next step without purification.

Step D:

To a round-bottomed flask was added compound 36E (or 36B-1 or 36D-1, or 36D-2, or 36D-3) (0.2 mmol, 1 eq.), DMF (5 mL), DIPEA (0.6 mmol, 3.0 eq.), HBTU (2.4 mmol, 1.2 eq.), and Intermediate 36G (e.g., Ar-8-quinoline) (0.2 mmol, 1.0 eq.) sequentially. The reaction mixture was stirred at room temperature overnight or until TLC showed that s.m. was consumed. The mixture was diluted with brine, extracted with ethyl acetate, the organic layer was dried with anhydrous Na₂SO₄, filtered, and the filtrate was concentrated in vacuo. The desired product 36F was purified by a standard method.

Compound 149 (General procedure 36, Step D)

N-(4-(4-benzyl-4-(hydroxymethyl)piperidine-1-carbonyl)phenyl)quinoline-8-sulfonamide

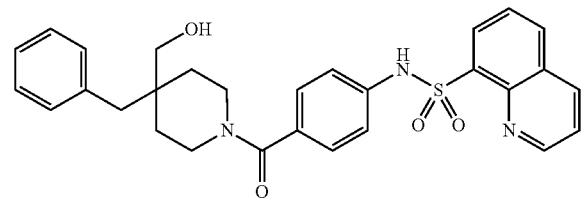 [SMILES: O=C(c1ccc(NS(=O)(=O)c2cccc3cccnc23)cc1)N1CCC(CO)(Cc2ccccc2)CC1]

$^1$H NMR (400 MHz, CDCl₃) δ: 9.17 (dd, J=4.4, 1.7 Hz, 1H), 8.52 (dd, J=8.4, 1.6 Hz, 1H), 8.43 (dd, J=7.3, 1.3 Hz, 1H), 8.26-8.19 (m, 1H), 7.78-7.65 (m, 2H), 7.29-7.15 (m, 10H), 4.17-4.06 (m, 1H), 3.75 (s, 1H), 3.60 (t, J=5.7 Hz, 2H), 2.74 (s, 2H), 2.08-2.01 (m, 1H), 1.64-1.60 (m, 3H), 1.48-1.38 (m, 2H). LC-MS: m/z 516.6 (M+H)

Compound 250 (General procedure 36, Step D)

Ethyl 4-isobutyl-1-(4-(quinoline-8-sulfonamido)benzoyl)piperidine-4-carboxylate

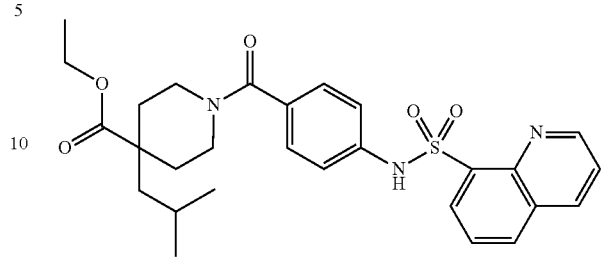

$^1$H NMR (CHLOROFORM-d) δ: 9.16 (dd, J=4.3, 1.6 Hz, 1H), 8.38 (dd, J=7.3, 1.1 Hz, 1H), 8.32 (dd, J=8.3, 1.6 Hz, 1H), 8.06 (dd, J=8.3, 1.1 Hz, 1H), 7.59-7.67 (m, 2H), 7.13-7.19 (m, J=8.6 Hz, 2H), 7.04-7.11 (m, J=8.6 Hz, 2H), 4.17 (q, J=7.0 Hz, 2H), 3.51 (br. s., 1H), 3.10 (br. s., 1H), 2.93 (br. s., 1H), 2.15-2.24 (m, 1H), 2.08 (d, J=10.2 Hz, 1H), 1.61-1.74 (m, 4H), 1.47 (d, J=12.9 Hz, 2H), 1.29-1.36 (m, 2H), 1.26 (s, 1H), 0.83-0.91 (m, 6H). LC-MS: m/z 524.7 (M+H)⁺

Compound 137 (General procedure 36, Step D)

N-(4-(4-formyl-4-isobutylpiperidine-1-carbonyl)phenyl)quinoline-8-sulfonamide

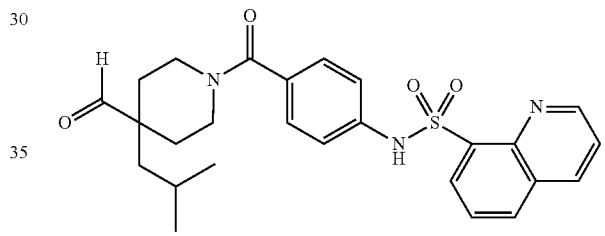

$^1$H NMR (CHLOROFORM-d) δ: 9.50 (s, 1H), 9.16 (dd, J=4.3, 1.3 Hz, 1H), 8.27-8.41 (m, 2H), 8.02-8.11 (m, 1H), 7.55-7.68 (m, 2H), 7.12-7.19 (m, J=8.3 Hz, 2H), 7.05-7.11 (m, J=8.6 Hz, 2H), 3.48 (s, 1H), 2.93-3.17 (m, 2H), 1.96 (br. s., 2H), 1.64 (tt, J=13.1, 6.5 Hz, 1H), 1.48 (br. s., 3H), 1.22-1.42 (m, 2H), 0.82-0.94 (m, 6H). LC-MS: m/z 480.7 (M+H)⁺

Compound 172 (General procedure 36, Step D)

N-(4-(4-(hydroxymethyl)-4-isobutylpiperidine-1-carbonyl)phenyl)quinoline-8-sulfonamide

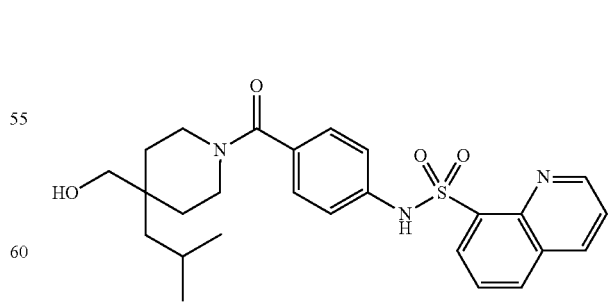

$^1$H NMR (CHLOROFORM-d) δ: 9.17 (dd, J=4.3, 1.6 Hz, 1H), 8.27-8.42 (m, 2H), 8.06 (dd, J=8.1, 1.3 Hz, 1H), 7.58-7.67 (m, 2H), 7.13-7.21 (m, 2H), 7.05-7.12 (m, 2H), 3.54 (s, 3H), 3.30 (br. s., 2H), 1.69 (dd, J=12.6, 6.2 Hz, 2H), 1.47 (d,

J=11.6 Hz, 3H), 1.34 (d, J=5.4 Hz, 3H), 0.95 (d, J=6.7 Hz, 6H). LC-MS: m/z 482.7 (M+H)⁺

Compound 238 (General procedure 36, Step D)

(N-(4-(4-(hydroxymethyl)-4-phenylpiperidine-1-carbonyl)phenyl)quinoline-8-sulfonamide

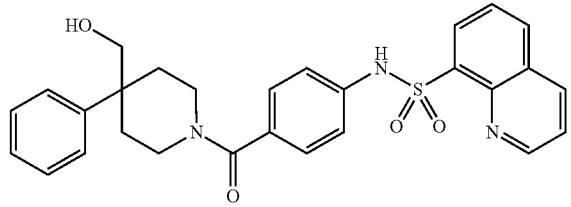 [SMILES: O=C(c1ccc(NS(=O)(=O)c2cccc3cccnc23)cc1)N1CCC(CO)(c2ccccc2)CC1]

¹H NMR (CHLOROFORM-d) δ: 9.14 (dd, J=4.3, 1.6 Hz, 1H), 8.36 (dd, J=7.4, 1.2 Hz, 1H), 8.31 (dd, J=8.5, 1.5 Hz, 1H), 8.02-8.07 (m, 1H), 7.57-7.65 (m, 2H), 7.36-7.42 (m, 2H), 7.30-7.34 (m, 2H), 7.23-7.28 (m, 1H), 7.11-7.16 (m, J=8.6 Hz, 2H), 7.04-7.09 (m, J=8.6 Hz, 2H), 3.53 (s, 2H), 3.06-3.16 (m, 2H), 2.16-2.30 (m, 1H), 2.10-2.16 (m, 1H), 1.71-1.91 (m, 3H), 1.67 (dt, J=5.7, 2.9 Hz, 1H). LC-MS: m/z 502.7 (M+H)⁺

Compound 216 (General procedure 36, Step D)

N-(4-(4-(hydroxymethyl)-4-isobutylpiperidine-1-carbonyl)phenyl)benzo[d]thiazole-4-sulfonamide

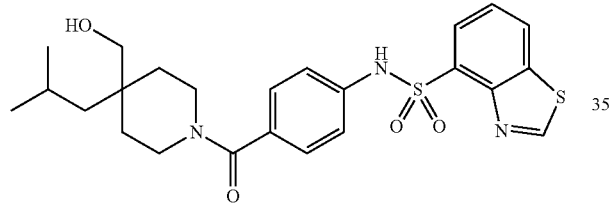

¹H NMR (CHLOROFORM-d) δ: 9.49 (s, 1H), 8.34 (dd, J=8.2, 0.9 Hz, 1H), 8.12 (dd, J=7.7, 0.9 Hz, 1H), 7.58 (t, J=7.8 Hz, 1H), 7.19 (s, 4H), 4.62 (s, 1H), 3.71 (br. s, 1H), 3.58 (br. s., 1H), 3.47 (s, 2H), 1.75 (s, 1H), 1.59 (br. s., 1H), 1.42-1.51 (m, 2H), 1.35 (d, J=5.1 Hz, 3H), 1.31 (br. s., 2H), 0.95 (d, J=6.7 Hz, 6H) LC-MS: m/z 488.7 (M+H)⁺

Compound 219 (General procedure 36, Step D)

N-(4-(4-(hydroxymethyl)-4-isobutylpiperidine-1-carbonyl)phenyl)quinoxaline-5-sulfonamide

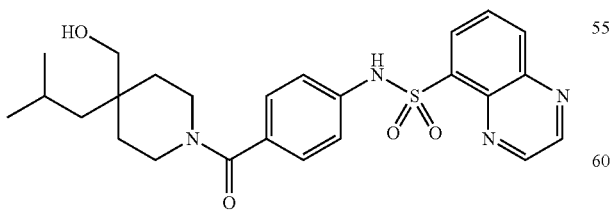

¹H NMR (CHLOROFORM-d) δ: 9.11 (d, J=1.9 Hz, 1H), 9.02 (d, J=1.9 Hz, 1H), 8.50 (dd, J=7.5, 1.3 Hz, 1H), 8.31 (dd, J=8.3, 1.3 Hz, 1H), 7.91 (dd, J=8.5, 7.4 Hz, 1H), 7.14-7.24 (m, 4H), 3.70 (br. s., 1H), 3.57 (br. s., 1H), 3.46 (s, 2H), 3.37 (s, 1H), 3.28 (br. s., 2H), 1.66-1.77 (m, 1H), 1.55 (br. s., 1H), 1.43 (br. s., 2H), 1.24-1.37 (m, 3H), 0.95 (s, 3H), 0.93 (s, 3H). LC-MS: m/z 483.6 (M+H)⁺

General Procedure 37:

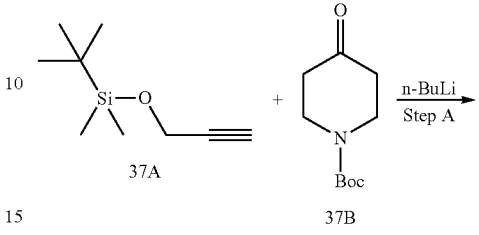

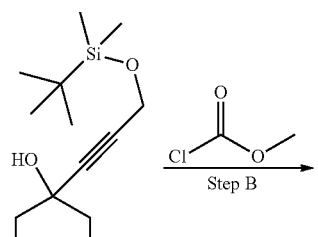

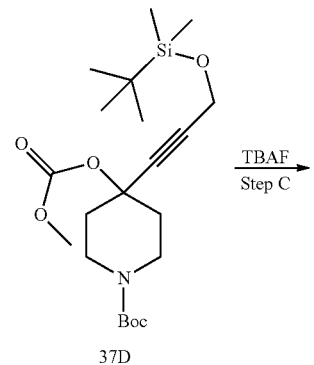

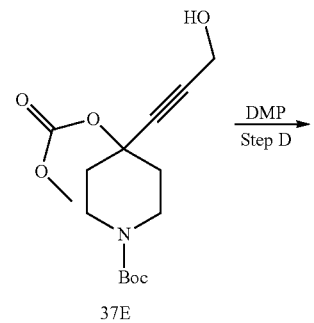

227
-continued

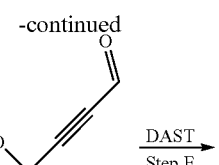

37F

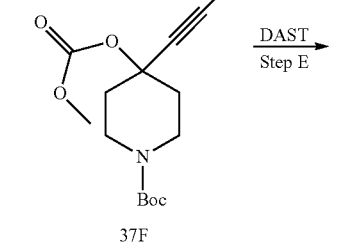

37G

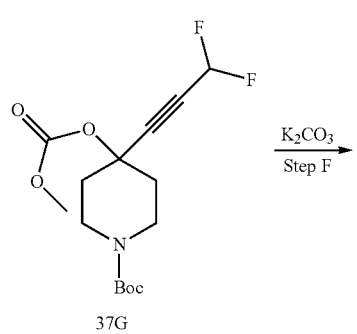

37H    37I

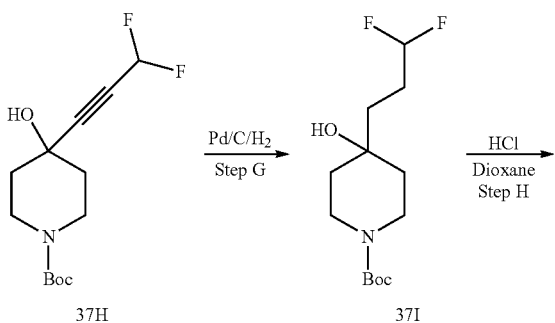

37J

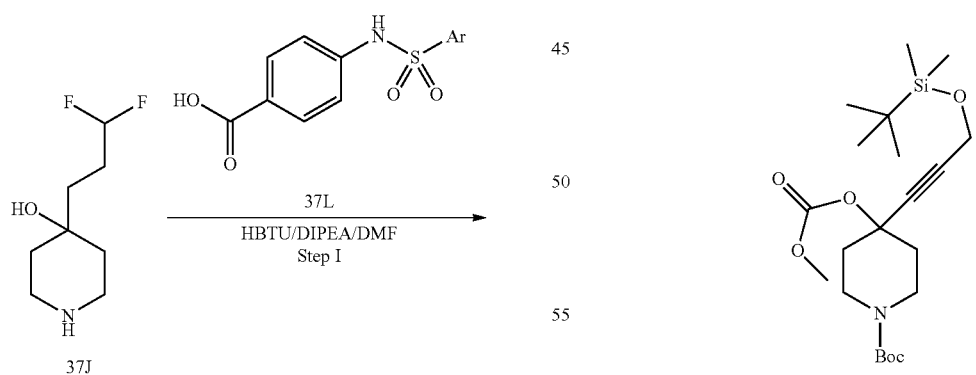

37K

228

Step A: tert-butyl 4-(3-((tert-butyldimethylsilyl)oxy)prop-1-yn-1-yl)-4-hydroxypiperidine-1-carboxylate (37C)

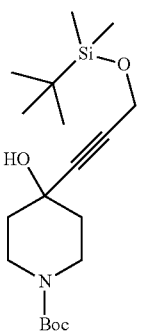

To a solution of tert-butyldimethyl(prop-2-yn-1-yloxy)silane (0.5 mL, 2.46 mmol) in 30 mL of anhydrous THF was added dropwise n-BuLi (1.2 mL, 2.95 mmol) at −78° C. under $N_2$. After stirring for 1 h at −78° C., tert-butyl 4-oxopiperidine-1-carboxylate (588.4 mg, 2.95 mmol) in THF (2 mL) was added dropwise to the above solution at −78° C. under $N_2$. The resulting mixture was stirred at −78° C. under $N_2$ for 2 h, then allowed to warm to r.t. and stirred for another 1.5 h. The reaction mixture was cooled to −78° C. and quenched by sat. $NH_4Cl$ aq., and the resulting mixture was extracted with EtOAc (50 mL, 30 mL). The combined organic phase was washed with brine, dried over anhy. $Na_2SO_4$ and concentrated in vacuo to afford 1.10 g of title compound. LC-MS: m/z 370.7 $(M+H)^+$. $^1H$ NMR (CHLOROFORM-d) δ: 4.37 (s, 2H), 3.74 (d, J=6.2 Hz, 2H), 3.35-3.24 (m, 2H), 2.46 (t, J=6.2 Hz, 1H), 1.92-1.84 (m, 2H), 1.71 (ddd, J=12.9, 9.1, 3.8 Hz, 2H), 1.47 (s, 9H), 0.92 (s, 9H), 0.13 (s, 6H).

Step B: tert-butyl-4-(3-((tert-butyldimethylsilyl)oxy)prop-1-yn-1-yl)-4-((methoxycarbonyl)oxy)piperidine-1-carboxylate (37D)

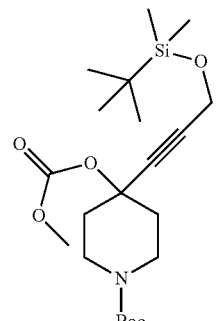

To a solution of tert-butyl 4-(3-((tert-butyldimethylsilyl)oxy)prop-1-yn-1-yl)-4-hydroxypiperidine-1-carboxylate (500 mg, 1.353 mmol) in 30 mL of anhydrous THF was added dropwise n-BuLi (0.65 mL, 1.623 mmol) at −78° C. under $N_2$. After stirring for 1 h at −78° C., methyl carbonochloridate (176.2 mg, 1.623 mmol) in THF (1 mL) was added dropwise to the above solution at −78° C. under $N_2$. The resulting mixture was stirred at −78° C. under $N_2$ for 2 h, then allowed to warm to r.t. and stirred for another 8 h. The reaction mixture was cooled to −78° C. and quenched by sat. NH₄Cl aq., and the resulting mixture was extracted with EtOAc (50 mL, 30 mL). The combined organic phase was washed with brine, dried over anhy. Na₂SO₄ and concentrated in vacuo. Column chromatography (15% PE/EtOAc) afforded 453 mg of title compound. ¹H NMR (CHLOROFORM-d) δ: 4.40 (s, 2H), 4.26-4.15 (m, 2H), 3.80-3.67 (m, 2H), 3.41-3.28 (m, 2H), 2.27-2.14 (m, 2H), 2.00 (ddd, J=13.1, 9.2, 3.9 Hz, 2H), 1.48 (s, 9H), 1.33 (t, J=7.1 Hz, 4H), 0.92 (s, 9H), 0.14 (s, 6H).

Step C: tert-butyl 4-(3-hydroxyprop-1-yn-1-yl)-4-((methoxycarbonyl)oxy)piperidine-1-carboxylate (37E)

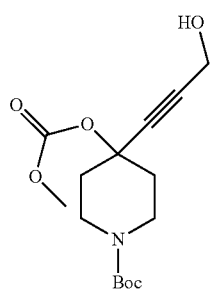 [SMILES: COC(=O)OC1(C#CCO)CCN(C(=O)OC(C)(C)C)CC1]

To a solution of tert-butyl 4-(3-((tert-butyldimethylsilyl)oxy)prop-1-yn-1-yl)-4-((methoxycarbonyl)oxy)piperidine-1-carboxylate (450 mg, 1.02 mmol) in 30 mL of anhydrous THF was added TBAF (800.5 mg, 3.06 mmol) at 0° C. under N₂. After stirring for 1 h at 0° C., the reaction mixture was quenched by sat. NH₄Cl aq., and the resulting mixture was extracted with EtOAc (50 mL, 30 mL). The combined organic phase was washed with brine, dried over anhy. Na₂SO₄ and concentrated in vacuo. Column chromatography (15% PE/EtOAc) afforded 290 mg of title compound. MS (ES) M+H expected 313.25. found 313.47. ¹H NMR (CHLOROFORM-d) δ: 4.36 (s, 2H), 4.21 (q, J=7.1 Hz, 2H), 3.80-3.70 (m, 2H), 3.41-3.29 (m, 2H), 2.24-2.13 (m, 2H), 2.00 (ddd, J=13.2, 9.3, 3.9 Hz, 2H), 1.95 (s, 1H), 1.48 (s, 9H), 1.34 (t, J=7.1 Hz, 3H).

Step D: tert-butyl 4-((methoxycarbonyl)oxy)-4-(3-oxoprop-1-yn-1-yl)piperidine-1-carboxylate (37F)

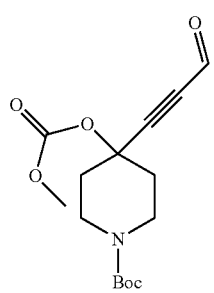 [SMILES: COC(=O)OC1(C#CC=O)CCN(C(=O)OC(C)(C)C)CC1]

To a solution of tert-butyl 4-(3-hydroxyprop-1-yn-1-yl)-4-((methoxycarbonyl)oxy) piperidine-1-carboxylate (130 mg, 0.398 mmol) in 30 mL of DCM was added NaHCO₃ (334 mg, 3.98 mmol), DMP (338 mg. 0.796 mmol) at r.t. The reaction mixture was stirred at r.t. for 8 h. The reaction mixture was filtered and the residue mixture was extracted with EtOAc (50 mL, 30 mL). The combined organic phase was washed with brine, dried over anhy. Na₂SO₄ and concentrated in vacuo. Column chromatography (15% PE/EtOAc) afforded 110 mg of title compound. ¹H NMR (CHLOROFORM-d) δ: 9.29 (s, 1H), 4.25 (q, J=7.1 Hz, 2H), 3.80-3.64 (m, 2H), 3.49-3.35 (m, 2H), 2.30-2.18 (m, 2H), 2.17-2.03 (m, 2H), 1.48 (s, 9H), 1.36 (t, J=7.1 Hz, 3H).

Step E: tert-butyl 4-(3,3-difluoroprop-1-yn-1-yl)-4-((methoxycarbonyl)oxy)piperidine-1-carboxylate (37G)

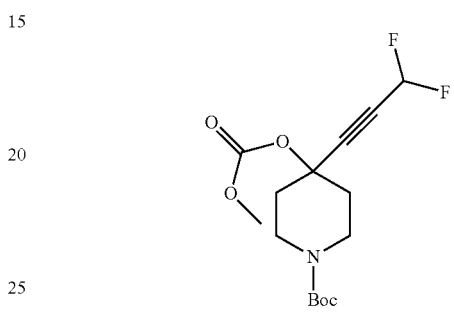

To a solution of tert-butyl 4-((methoxycarbonyl)oxy)-4-(3-oxoprop-1-yn-1-yl)piperidine-1-carboxylate (60 mg, 0.1846 mmol) in 5 mL of DCM was added DAST (89.3 mg, 0.5583 mmol) at 0° C. under N₂. After stirring for 8 h at r.t., the reaction mixture was quenched by sat. NH₄Cl aq., and the resulting mixture was extracted with DCM (50 mL, 30 mL). The combined organic phase was washed with brine, dried over anhy. Na₂SO₄ and concentrated in vacuo. Column chromatography (15% PE/EtOAc) afforded 63 mg of title compound. ¹H NMR (CHLOROFORM-d) δ: 6.27 (t, J=54.4 Hz, 1H), 4.30-4.18 (m, 2H), 3.75 (d, J=7.0 Hz, 2H), 3.46-3.28 (m, 2H), 2.32-2.14 (m, 2H), 2.10-1.99 (m, 2H), 1.48 (s, 9H), 1.35 (t, J=7.1 Hz, 3H).

Step F: tert-butyl 4-(3,3-difluoroprop-1-yn-1-yl)-4-hydroxypiperidine-1-carboxylate (37H)

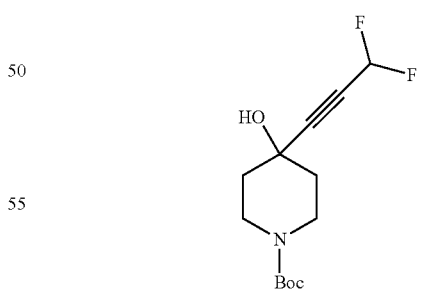

To a solution of tert-butyl 4-(3,3-difluoroprop-1-yn-1-yl)-4-((methoxycarbonyl)oxy) piperidine-1-carboxylate (6.0 g, 18.5 mmol) in 100 mL of MeOH and 15 mL of water was added K₂CO₃ (3.822 g, 27.7 mmol) at r.t. The reaction mixture was stirred at 48° C. for 3 h. The reaction mixture was cooled to r.t., and was extracted with EtOAc (150 mL, 100 mL). The combined organic phase was washed with brine, Step G: tert-butyl 4-(3,3-difluoropropyl)-4-hydroxypiperidine-1-carboxylate (37I)

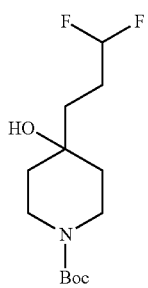

A solution of tert-butyl 4-(3,3-difluoroprop-1-yn-1-yl)-4-hydroxypiperidine-1-carboxylate (350 mg, 1.273 mmol) in 30 mL of anhydrous THF was stirred with Pd/C (200 mg) under H$_2$ atmosphere at 15 psi at 48° C. for 8 h. The reaction mixture was cooled to r.t. and filtered, and the resulting mixture was concentrated in vacuo to afforde 293 mg of title compound. $^1$H NMR (CHLOROFORM-d) δ: 5.89 (tt, J=56.9, 4.3 Hz, 1H), 3.84 (dd, J=9.8, 3.5 Hz, 2H), 3.24-3.10 (m, 2H), 2.05-1.89 (m, 2H), 1.67-1.60 (m, 2H), 1.55 (m, 4H), 1.47 (s, 9H).

Step H: 4-(3,3-difluoropropyl)piperidin-4-ol (37J)

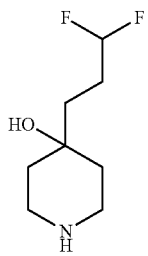

A solution of tert-butyl 4-(3,3-difluoropropyl)-4-hydroxypiperidine-1-carboxylate (293 mg, 1.075 mmol) in 5 mL of 3.5 N HCl in dioxane was stirred at r.t. for 30 min. The reaction mixture was concentrated in vacuo to give 301 mg of the title product which was used in the next step directly.

Step I:

To a solution of the corresponding (aryl-sulfonamido)benzoic acid (1.05 mmol) in 15 mL of DMF was added HBTU (479 mg, 1.26 mmol), DIPEA (203 mg, 1.58 mmol) and 4-(3,3-difluoropropyl)piperidin-4-ol (226.3 mg, 1.05 mmol), sequentially at room temperature. The reaction mixture was stirred at room temperature for 1 hour. The mixture was poured into water and extracted with EtOAc (50 mL) twice. The combined organic layer was washed with brine and dried over anhy. Na$_2$SO$_4$. The combined organic layer was concentrated in vacuo. The title compound was purified by a standard method.

Compound 204

N-(4-(4-(3,3-difluoropropyl)-4-hydroxypiperidine-1-carbonyl)phenyl)quinoline-8-sulfonamide

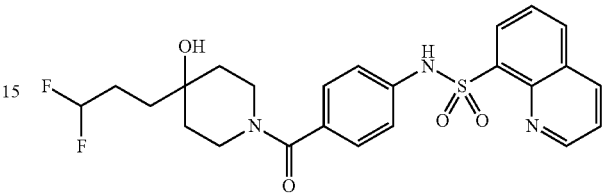

$^1$H NMR (CHLOROFORM-d) δ: 10.41 (s, 1H), 9.13 (dd, J=4.2, 1.7 Hz, 1H), 8.52 (dd, J=8.4, 1.7 Hz, 1H), 8.42 (dd, J=7.3, 1.3 Hz, 1H), 8.36-8.24 (m, 1H), 7.80-7.64 (m, 2H), 7.11 (q, J=8.7 Hz, 4H), 6.06 (td, J=59.4, 55.3 Hz, 1H), 4.44 (m, 1H), 4.16-3.92 (m, 1H), 3.16-2.91 (m, 2H), 1.84 (dqt, J=19.9, 13.0, 6.6 Hz, 2H), 1.51-1.40 (m, 3H), 1.40-1.29 (m, 3H). LC-MS: m/z 490.68 (M+H)$^+$ Compound 235

N-(4-(4-(3,3-difluoropropyl)-4-hydroxypiperidine-1-carbonyl)phenyl)benzo[d]thiazole-4-sulfonamide

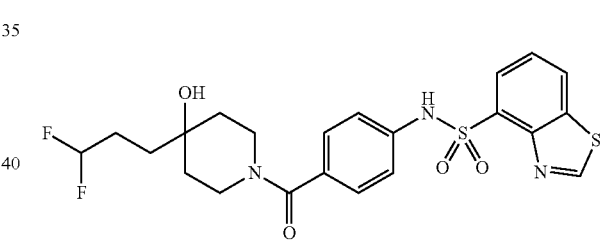

$^1$H NMR (CHLOROFORM-d) δ: 10.76 (s, 1H), 9.66 (s, 1H), 8.50 (dd, J=8.1, 1.0 Hz, 1H), 8.11 (dd, J=7.6, 1.0 Hz, 1H), 7.65 (t, J=7.9 Hz, 1H), 7.17 (d, J=8.7 Hz, 2H), 7.10 (d, J=8.7 Hz, 2H), 6.06 (tt, J=57.1, 4.3 Hz, 1H), 4.10 (d, J=5.3 Hz, 1H), 3.11 (dd, J=51.3, 35.5 Hz, 3H), 1.83 (dd, J=18.4, 11.9 Hz, 2H), 1.55-1.28 (m, 6H). LC-MS: m/z 496.59 (M+H)$^+$

Compound 230

N-(4-(4-(3,3-difluoropropyl)-4-hydroxypiperidine-1-carbonyl)phenyl)quinoxaline-5-sulfonamide

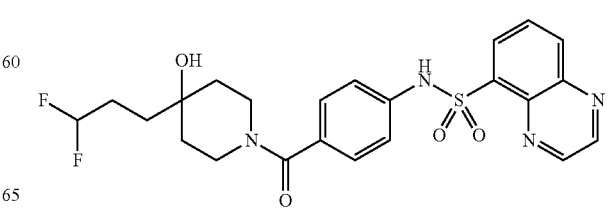

¹H NMR (CHLOROFORM-d) δ: 10.65 (s, 1H), 9.13 (dd, J=13.1, 1.8 Hz, 2H), 8.50 (dd, J=7.4, 1.3 Hz, 1H), 8.37 (dd, J=8.4, 1.2 Hz, 1H), 8.05-7.93 (m, 1H), 7.12 (dd, J=25.5, 8.7 Hz, 4H), 6.06 (tt, J=57.1, 4.2 Hz, 1H), 4.10-3.93 (m, 1H), 3.04 (m, 3H), 1.84 (m, 2H), 1.54-1.27 (m, 6H). LC-MS: m/z 491.58 (M+H)⁺

General Procedure 38:

Step A: (E)-tert-butyl 4-(3,3-difluoroprop-1-enyl)-4-hydroxypiperidine-1-carboxylate (38B)

To a solution of tert-butyl 4-(3,3-difluoroprop-1-yn-1-yl)-4-hydroxypiperidine-1-carboxylate (280 mg, 1.016 mmol) in 30 mL of anhydrous THF was added dropwise sodium dihydro-bis-(2-methoxyethoxy)aluminate (587 mg, 2.032 mmol, 70%) at −78° C. under N₂. After the addition, the reaction mixture was stirred at −78° C. under N₂ for 5 h. The reaction mixture was quenched by sat. NH₄Cl aq., and the resulting mixture was extracted with EtOAc (50 mL, 30 mL). The combined organic phase was washed with brine, dried over anhy. Na₂SO₄ and concentrated in vacuo to afford 291 mg of title compound. MS (ES) M+H expected 278.15. found 178.30. ¹H NMR (CHLOROFORM-d) δ: 6.29-6.08 (m, 2H), 6.01-5.84 (m, 1H), 3.98-3.84 (m, 2H), 3.20 (t, J=11.4 Hz, 2H), 1.76-1.62 (m, 4H), 1.48 (s, 9H).

Step B: (E)-4-(3,3-difluoroprop-1-enyl)piperidin-4-ol (38C)

A solution of (E)-tert-butyl 4-(3,3-difluoroprop-1-enyl)-4-hydroxypiperidine-1-carboxylate (38C) (293 mg, 1.075 mmol) in 5 mL of 3.5 N HCl in dioxane was stirred at r.t. for 30 min. The reaction mixture was concentrated in vacuo to give 300 mg of the title product as a yellow liquid which was used in the next step directly.

General Procedure 39:

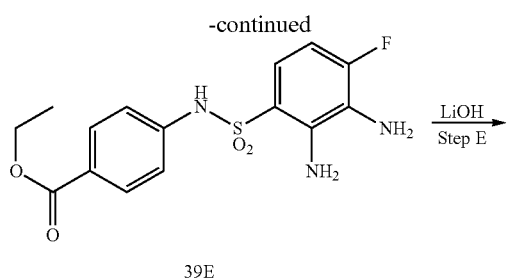

39E

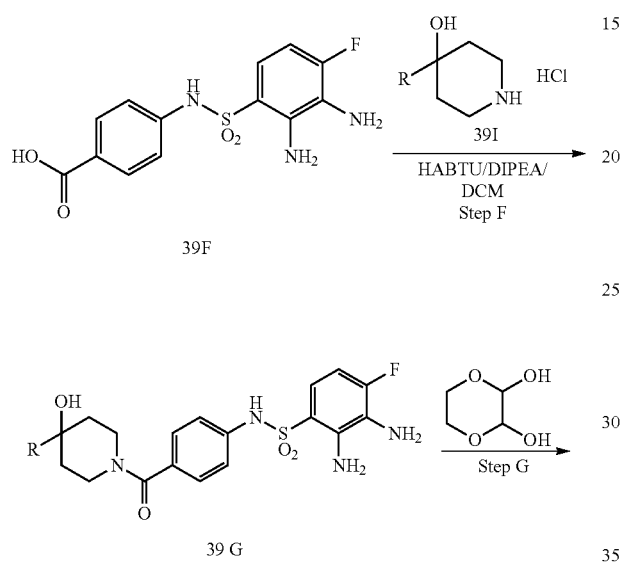

39F

39 G

39H

Step A: N,N'-disulfinyl-3-fluoro-1,2-diaminobenzene (39B)

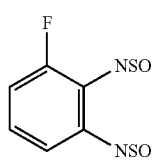

To a solution of 3-fluorobenzene-1,2-diamine (7.9 g, 62.7 mmol) in 80 mL of pyridine was added dropwise SOCl₂ (16 mL) at 0° C. The reaction mixture was stirred at 100° C. for 8 hours. The mixture was poured into water and extracted with EtOAc (50 mL) twice. The combined organic layer was washed with brine and dried over anhy. Na₂SO₄. The combined organic layer was concentrated in vacuo. Column chromatography (15% Petroleum/EtOAc) afforded 11.5 g of title compound.

Step B: 7-fluorobenzo[c][1,2,5]thiadiazole-4-sulfonyl chloride (39C)

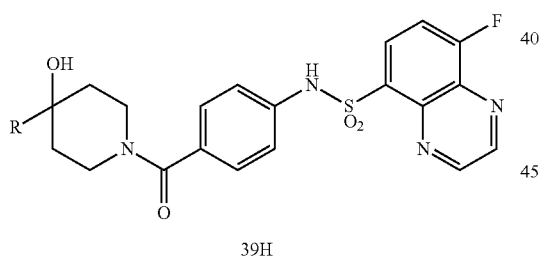

A solution of N,N'-disulfinyl-3-fluoro-1,2-diaminobenzene 39B (11.5 g, 52.75 mmol) in 80 mL of chlorosulfonic acid was heated at 110° C. for 8 hours. The mixture was cooled to r.t. and poured into water and extracted with EtOAc (50 mL) twice. The combined organic layer was washed with brine and dried over anhy. Na₂SO₄. The combined organic layer was concentrated in vacuo. Column chromatography (15% Petroleum/EtOAc) afforded 7.1 g of title compound. $^1$H NMR (CHLOROFORM-d) δ: 8.48 (dd, J=8.4 Hz, 4.4 Hz, 1H), 7.45 (t, J=8.4 Hz, 1H). LC-MS: m/z 253.2 (M+H)⁺.

Step C: Ethyl 4-(7-fluorobenzo[c][1,2,5]thiadiazole-4-sulfonamido)benzoate (39D)

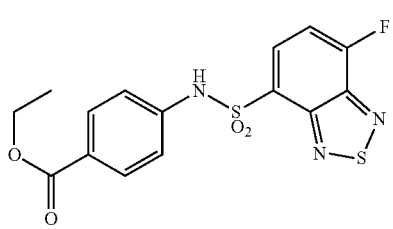 [SMILES: CCOC(=O)c1ccc(NS(=O)(=O)c2ccc(F)c3nsnc23)cc1]

To a solution of ethyl 4-aminobenzoate (412 mg, 2.5 mmol) in 20 mL of DCM was added pyridine (600 mg, 7.5 mmol) and 7-fluorobenzo[c][1,2,5]thiadiazole-4-sulfonyl chloride (39C) (633 mg, 2.5 mmol). The resulting mixture was stirred at 50° C. overnight. After removal of DCM, the residue was partitioned between water and EtOAc. The organic layer was washed with 2 N HCl, water and brine, dried over Na₂SO₄ and concentrated to give crude product 39D, which was confirmed by LCMS, and used in the next reaction without further purification. $^1$H NMR (CHLOROFORM-d) δ: 8.33 (dd, J=8.0, 4.6 Hz, 1H), 7.85 (d, J=8.7 Hz, 2H), 7.66 (s, 1H), 7.35-7.30 (m, 1H), 7.12 (d, J=8.7 Hz, 2H), 4.31 (q, J=7.1 Hz, 2H), 1.34 (t, J=7.1 Hz, 3H). LC-MS: m/z 382.4 (M+H)+.

Step D: ethyl 4-(2,3-diamino-4-fluorophenylsulfonamido)benzoate (39E)

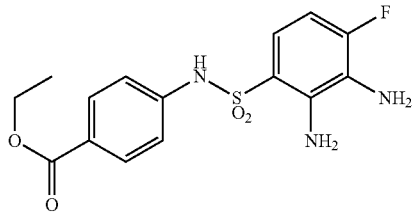 [SMILES: CCOC(=O)c1ccc(NS(=O)(=O)c2ccc(F)c(N)c2N)cc1]

To a solution of the compound 39D (382 mg, 1.0 mmol) in AcOH/H$_2$O (8 mL/3 mL) at 70° C. was added zinc powder (975 mg, 15 mmol) and the resulting suspension was stirred at 70° C. for 1 h. The solid was filtered off and washed with EtOAc. The filtrate was partitioned between satd. NaHCO$_3$ and EtOAc. The organic layer was separated and washed with water and brine, dried over anhydrous Na$_2$SO$_4$ and concentrated to give crude product 39E, which was confirmed by LCMS, and used in the next reaction without further purification. LC-MS: m/z 354.4 (M+H)+.

Step E: 4-(2,3-diamino-4-fluorophenylsulfonamido)benzoic acid (39F)

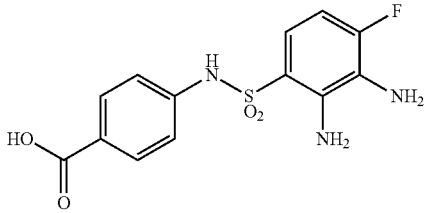 [SMILES: Nc1c(F)ccc(S(=O)(=O)Nc2ccc(C(=O)O)cc2)c1N]

To a solution of the compound 39E (350 mg, 1 mmol) in EtOH/H$_2$O (10 mL/3 mL) was added LiOH.H$_2$O (200 mg, 5 mmol) and the resulting suspension was stirred at 70° C. overnight. The solvent was concentrated and the residue was partitioned between aqueous 2 N HCl and EtOAc. The organic layer was separated and washed with water and brine, dried over Na$_2$SO$_4$ and concentrated to give the desired crude product 39F, which was confirmed by LCMS, and used in subsequent reaction without further purification. LC-MS: m/z 326.3 (M+H)+.

Step F:
To a solution of compound 39F (0.2 mmol) and in DCM (10 mL) was added HBTU (91 mg, 0.24 mmol) and stirred at r.t. for 20 min, then the corresponding compound 7 (0.2 mmol) and DIPEA (0.6 mmol) were added. After stirring for 30 mins, the reaction was partitioned between satd. Na$_2$CO$_3$ solution and DCM. The organic layer was separated and washed with water and brine, dried over Na$_2$SO$_4$ and concentrated, and then purified by a standard method to give title product 39G.

Compound 256

2,3-diamino-N-(4-(4-(2-chlorophenyl)-4-hydroxypiperidine-1-carbonyl)phenyl)-4-fluorobenzenesulfonamide

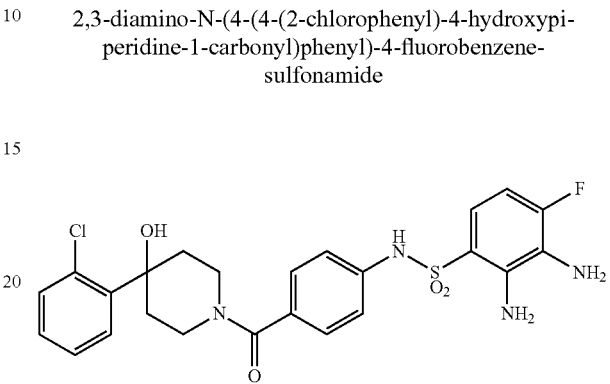

$^1$H NMR (CHLOROFORM-d) δ: 10.56 (s, 1H), 7.81 (dd, J=7.9, 1.6 Hz, 1H), 7.42-7.33 (m, 2H), 7.27 (m, 3H), 7.08 (d, J=8.6 Hz, 2H), 6.99 (dd, J=9.0, 5.9 Hz, 1H), 6.46 (dd, J=9.2 Hz, 1H), 5.71 (s, 2H), 5.43 (s, 1H), 4.87 (s, 2H), 4.35 (s, 1H), 3.45 (s, 2H), 3.12 (s, 1H), 1.78-1.12 (m, 4H). LC-MS: m/z 519.70 (M+H)+

Compound 254

2,3-diamino-4-fluoro-N-(4-(4-hydroxy-4-isobutylpiperidine-1-carbonyl)phenyl)benzenesulfonamide

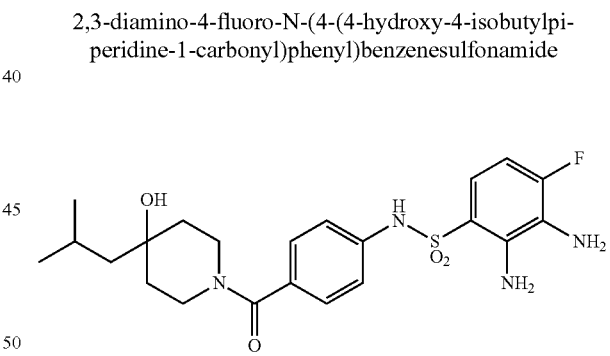

$^1$H NMR (CHLOROFORM-d) δ: 7.27 (d, J=8.5 Hz, 2H), 7.20 (dd, J=9.0, 5.9 Hz, 1H), 7.15 (s, 1H), 7.06 (d, J=8.5 Hz, 2H), 6.49 (t, J=9.1 Hz, 1H), 4.38 (s, 1H), 3.44 (s, 2H), 3.25 (s, 1H), 1.85 (td, J=12.9, 6.5 Hz, 1H), 1.67 (s, 4H), 1.44 (d, J=6.0 Hz, 2H), 1.00 (d, J=6.6 Hz, 6H). LC-MS: m/z 465.66 (M+H)+

Step G:
To a solution of the corresponding compound 39G (0.9 mmol) in ethanol/water (30 mL/4 mL) was added 1,4-dioxane-2,3-diol (130 mg, 1.08 mmol) and the resulting suspension was stirred at 30° C. overnight. The solvent was removed in vacuo and the residue was partitioned between water and EtOAc. The organic layer was separated and washed with

Compound 444

8-fluoro-N-(4-(4-hydroxy-4-isobutylpiperidine-1-carbonyl)phenyl)quinoxaline-5-sulfonamide

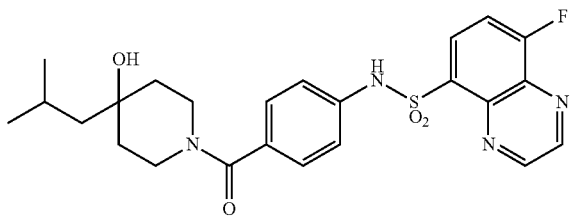 [SMILES: CC(C)CC1(O)CCN(C(=O)c2ccc(NS(=O)(=O)c3ccc(F)c4nccnc34)cc2)CC1]

¹H NMR (CHLOROFORM-d) δ: 9.14 (d, J=8.8 Hz, 2H), 8.46 (dd, J=8.3, 5.2 Hz, 1H), 7.88 (s, 1H), 7.54 (t, J=8.5 Hz, 1H), 7.20 (d, J=8.1 Hz, 2H), 7.07 (d, J=8.1 Hz, 2H), 4.31 (s, 1H), 3.29 (s, 3H), 1.82 (td, J=12.9, 6.5 Hz, 1H), 1.57 (s, 4H), 1.41 (d, J=6.0 Hz, 2H), 0.98 (d, J=6.6 Hz, 6H). LC-MS: m/z 487.68 (M+H)⁺

Compound 234

N-(4-(4-(2-chlorophenyl)-4-hydroxypiperidine-1-carbonyl)phenyl)-8-fluoroquinoxaline-5-sulfonamide

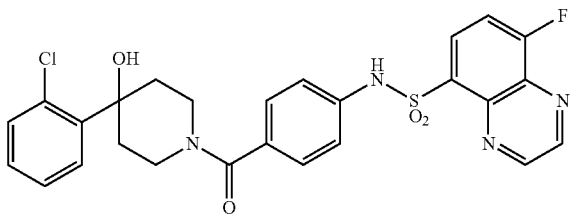 [SMILES: O=C(c1ccc(NS(=O)(=O)c2ccc(F)c3nccnc23)cc1)N1CCC(O)(c2ccccc2Cl)CC1]

¹H NMR (CHLOROFORM-d) δ: 9.15 (d, J=9.5 Hz, 2H), 8.47 (dd, J=8.3, 5.1 Hz, 1H), 7.87 (s, 1H), 7.53 (dd, J=17.0, 8.5 Hz, 2H), 7.40 (d, J=7.6 Hz, 1H), 7.31 (d, J=7.8 Hz, 1H), 7.25 (d, J=7.2 Hz, 3H), 7.09 (d, J=7.2 Hz, 2H), 4.61 (s, 1H), 3.58 (m, 2H), 3.32 (m, 1H), 2.38-2.01 (m, 4H). LC-MS: m/z 541.79 (M+H)⁺

General Procedure 40: Compound 202

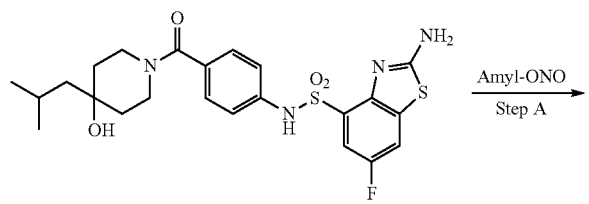

Amyl-ONO
Step A

-continued

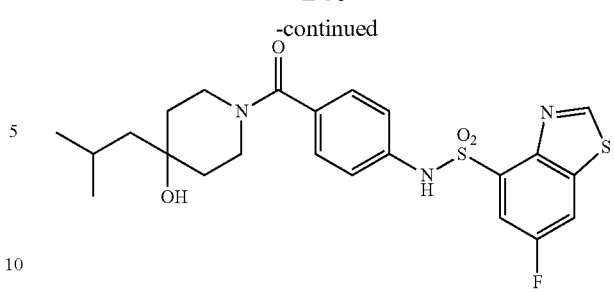

Step A:

To a solution of 2-amino-6-fluoro-N-(4-(4-hydroxy-4-isobutylpiperidine-1-carbonyl)phenyl)benzo[d]thiazole-4-sulfonamide (Compound 145) (200 mg, 0.4 mmol) in THF (5 mL) was added isoamyl nitrite (94 mg, 0.8 mmol). The reaction mixture was stirred at 70° C. for 3 hrs under nitrogen atmosphere. After completion of the reaction (monitored by TLC), the reaction mixture was concentrated in vacuo. The residue was dissolved in water, and extracted with ethyl acetate (3×50 mL). Combined organic extracts were washed with brine (20 mL), dried over anhydrous sodium sulfate, filtered and concentrated under reduced pressure to obtain the crude product, which was purified by a standard method.

Compound 446: 6-fluoro-N-(4-(4-hydroxy-4-isobutylpiperidine-1-carbonyl)phenyl)benzo[d]thiazole-4-sulfonamide

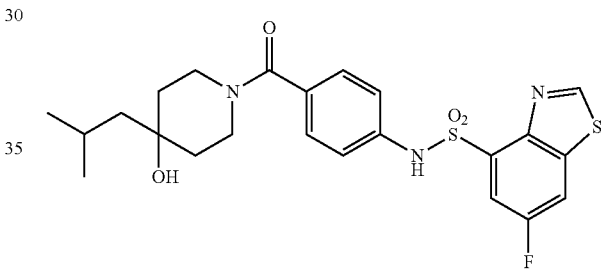

¹H NMR (CHLOROFORM-d) δ: 9.26 (s, 1H), 7.89 (s, 1H), 7.88-7.84 (m, 2H), 7.22 (d, J=8.4 Hz, 2H), 7.11 (d, J=8.5 Hz, 2H), 4.33 (s, 1H), 3.30 (s, 3H), 1.90-1.79 (m, 1H), 1.52 (d, J=51.2 Hz, 4H), 1.42 (d, J=6.0 Hz, 2H), 0.98 (d, J=6.6 Hz, 6H). LC-MS: m/z 492.68 (M+H)⁺

Compound 401 (General procedure 39, started from Compound 154)

N-(4-(4-(2-chlorophenyl)-4-hydroxypiperidine-1-carbonyl)phenyl)-6-fluorobenzo[d]thiazole-4-sulfonamide

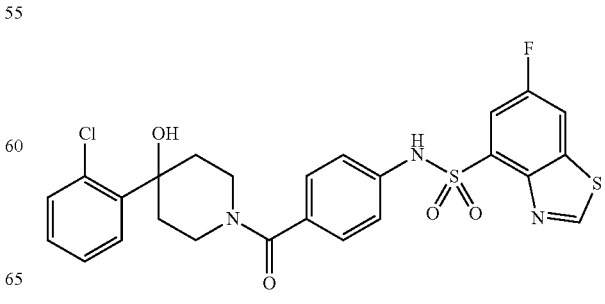

¹H NMR (CHLOROFORM-d) δ: 9.26 (s, 1H), 7.89 (s, 1H), 7.87 (d, J=7.6 Hz, 2H), 7.52 (dd, J=7.8, 1.7 Hz, 1H), 7.40 (dd, J=7.7, 1.6 Hz, 1H), 7.34-7.29 (m, 1H), 7.25 (dd, J=10.0, 5.0 Hz, 3H), 7.13 (d, J=8.5 Hz, 2H), 4.64 (s, 1H), 3.60 (s, 2H), 3.31 (s, 1H), 2.39-1.99 (m, 4H). LC-MS: m/z 546.7 (M+H)⁺

General Procedure 42:

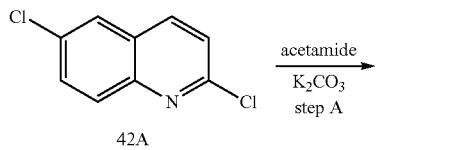

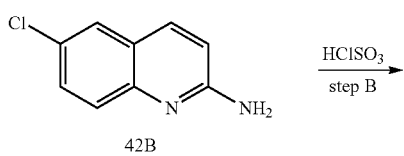

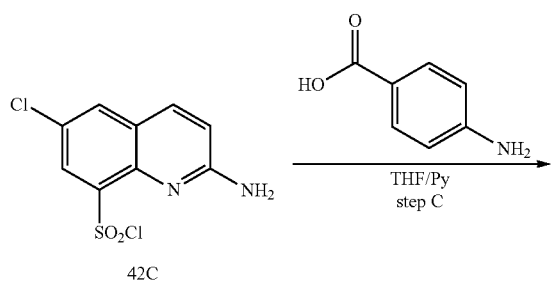

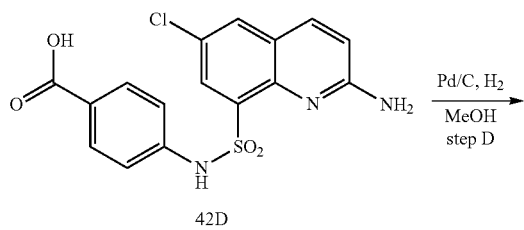

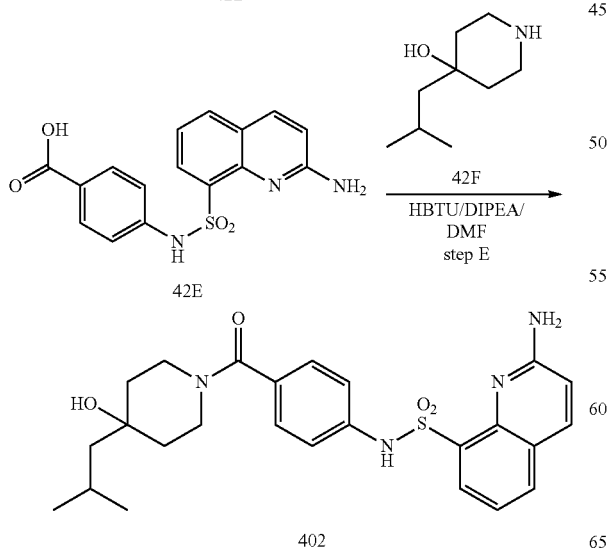

Step A: 6-chloroquinolin-2-amine (42B)

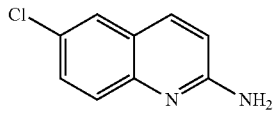 [SMILES: Nc1ccc2cc(Cl)ccc2n1]

A mixture of 2,6-dichloroquinoline (500 mg, 2.5 mmol), acetamide (3 g, 50.8 mmol) and K₂CO₃ (1.75 g, 12.7 mmol) in a round bottom flask was stirred at 200° C. for 1.5 hours until TLC indicated that 2,6-dichloroquinoline was consumed. The resulting mixture was cooled to room temperature, and was partitioned between dichloromethane and H₂O, the organic layer was dried over anhydrous Na₂SO₄, concentrated, and the residue was purified by a standard method to give 440 mg of the title compound. LCMS (m/z): 179.7 (M+1)⁺

Step B: 2-amino-6-chloroquinoline-8-sulfonyl chloride (42C)

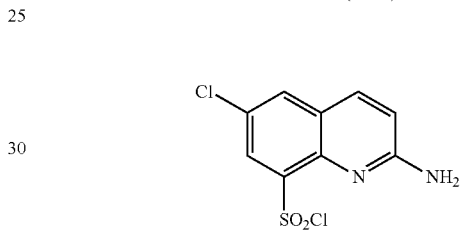

6-chloroquinolin-2-amine (350 mg) was added to 5 mL of HClSO₃ at 0° C. in portions, and then the mixture was stirred at 100° C. for 1 hour. The resulting mixture was cooled to room temperature, then it was poured with caution into crushed ice and H₂O, and the resulting mixture was extracted with dichloromethane. The combined organic layers were dried over anhydrous Na₂SO₄, concentrated to provide the crude title compound which was used in the next step without further purification. LCMS (m/z): 278.1 (M+1)⁺

Step C: 4-(2-amino-6-chloroquinoline-8-sulfonamido)benzoic acid (42D)

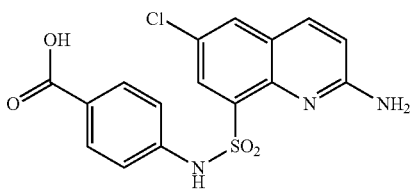 [SMILES: Nc1ccc2cc(Cl)cc(S(=O)(=O)Nc3ccc(C(=O)O)cc3)c2n1]

A mixture of 2-amino-6-chloroquinoline-8-sulfonyl chloride (500 mg, 1.8 mmol), 4-aminobenzoic acid (300 mg, 2.2 mmol) and pyridine (1 mL) in 10 mL of THF was stirred at 30° C. overnight, when LCMS indicated that the reaction was complete. The resulting mixture was concentrated, and the Step D: 4-(2-aminoquinoline-8-sulfonamido)benzoic acid (42E)

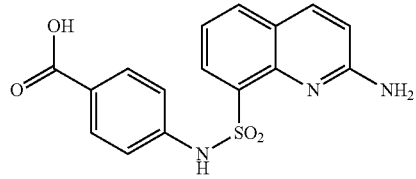 [SMILES: Nc1ccc2cccc(S(=O)(=O)Nc3ccc(C(=O)O)cc3)c2n1]

A mixture of 4-(2-amino-6-chloroquinoline-8-sulfonamido)benzoic acid (150 mg, 0.44 mmol), 10% Pd/C (20 mg) in methanol (5 mL) was stirred under H$_2$ atmosphere overnight when LCMS indicated that the reaction was complete. The resulting mixture was filtered, and the filtrate was concentrated to yield 100 mg of title compound, which was used in the next step without further purification. LCMS (m/z): 344.6 (M+1)$^+$ Step E: Compound 402: 2-amino-N-(4-(4-hydroxy-4-isobutylpiperidine-1-carbonyl)phenyl)quinoline-8-sulfonamide

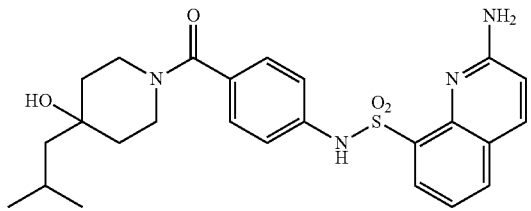 [SMILES: CC(C)CC1(O)CCN(C(=O)c2ccc(NS(=O)(=O)c3cccc4ccc(N)nc34)cc2)CC1]

To a mixture of 4-isobutylpiperidin-4-ol (70 mg, 0.44 mmol), 4-(2-aminoquinoline-8-sulfonamido)benzoic acid (100 mg, 0.44 mmol), and HBTU (134 mg, 0.53 mmol) in DCM (5 mL) was added DIPEA (1 mL) dropwise at room temperature, and then the mixture was stirred at room temperature for 1 hour. The resulting mixture was concentrated, purified by a standard method to yield the title compound. $^1$H NMR (CHLOROFORM-d) δ: 8.10-8.20 (m, 1H), 7.89 (d, J=9.1 Hz, 1H), 7.69-7.82 (m, 1H), 7.06-7.26 (m, 5H), 6.80 (d, J=9.1 Hz, 1H), 5.41 (s, 2H), 4.33 (br. s., 1H), 3.41-3.19 (m., 3H), 1.82 (dt, J=12.9, 6.4 Hz, 1H), 1.63-1.46 (m, 4H), 1.40 (d, J=5.9 Hz, 2H), 0.97 (d, J=6.7 Hz, 6H). LCMS (m/z): 483.7 (M+1)$^+$ General Procedure 43:

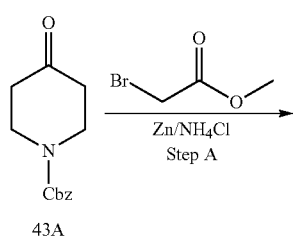

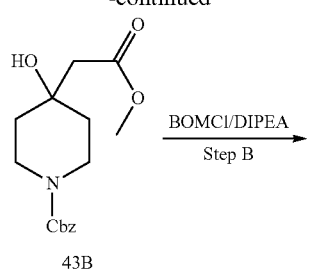

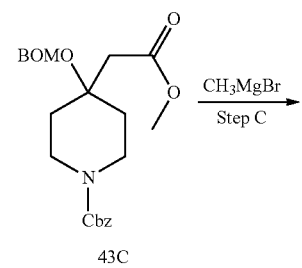

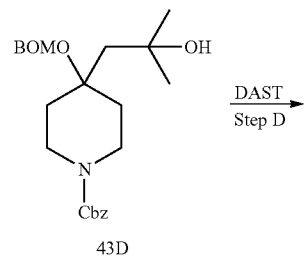

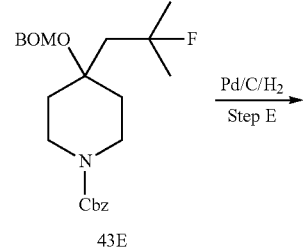

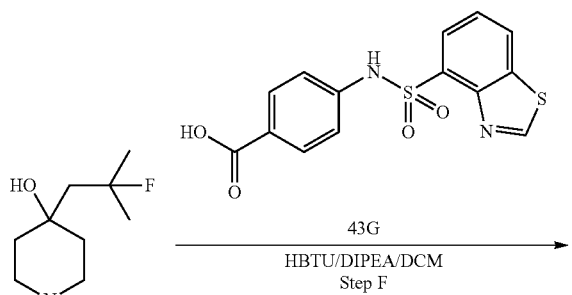

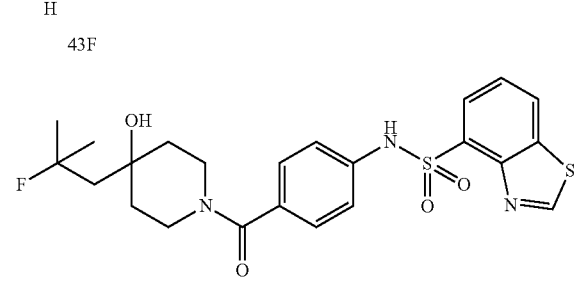

Step A: Benzyl 4-hydroxy-4-(2-methoxy-2-oxoethyl)piperidine-1-carboxylate (43B)

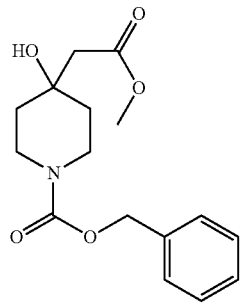 [SMILES: COC(=O)CC1(O)CCN(C(=O)OCc2ccccc2)CC1]

To a round-bottom flask containing Zn dust (2.3 g, 36 mmol) was added dibromoethane (585 mg, 3.11 mmol). The resulting mixture was warmed to 60° C. and allowed to cool for 1 min. This heating-cooling process was repeated three more times, and then the flask was allowed to cool for an additional 3 min. Trimethylsilylchloride (456 mg, 4.2 mmol) in THF (5 mL) was added, followed by addition of ethyl-2-bromoacetate (2 g, 12 mmol) in THF (8 mL). The reaction was warmed to 60° C. for an additional two hours until a dark grey suspension was obtained. The mixture was cooled to room temperature; benzyl 4-oxopiperidine-1-carboxylate (1.9 g, 8.2 mmol) in THF (20 mL) was then added. The resulting mixture was stirred for 3 days, and then quenched with water. The solid was filtered off, and the aqueous was extracted with ethyl acetate. The combined organic layers were washed with brine and dried over Na$_2$SO$_4$. Purification by a standard method gave the desired product. $^1$H NMR (CHLOROFORM-d) δ: 7.33-7.43 (m, 5H), 5.14 (s, 2H), 3.89-4.05 (m, 2H), 3.68-3.79 (m, 3H), 3.22-3.36 (m, 2H), 2.49 (s, 2H), 2.19 (s, 1H), 1.71 (d, J=12.6 Hz, 2H), 1.53 (dd, J=12.5, 4.2 Hz, 2H). LCMS (m/z): 308.1 (M+1)$^+$

Step B: benzyl 4-(benzyloxymethoxy)-4-(2-methoxy-2-oxoethyl)piperidine-1-carboxylate (43C)

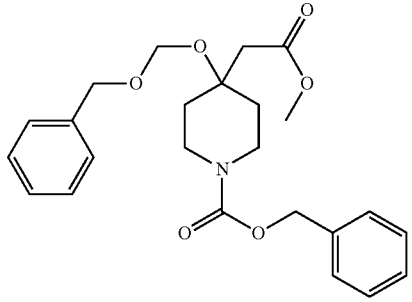 [SMILES: COC(=O)CC1(OCOCc2ccccc2)CCN(C(=O)OCc2ccccc2)CC1]

A solution of compound 43B (0.5 g, 1.63 mmol) and diisopropylethylamine (1.26 g, 9.8 mmol) in CH$_2$Cl$_2$ (10 mL) was treated with benzyl chloromethylether (636 mg 4.1 mmol) and stirred at room temperature for 16 h. Purification a standard method gave the desired product. $^1$H NMR (CHLOROFORM-d) δ: 7.30-7.44 (m, 9H), 5.15 (s, 2H), 4.92 (s, 2H), 4.69 (s, 2H), 3.91 (br. s., 2H), 3.65 (s, 3H), 3.29 (br. s., 2H), 2.63 (s, 2H), 2.20 (s, 1H), 2.02 (d, J=13.7 Hz, 2H), 1.69 (ddd, J=14.1, 11.7, 4.6 Hz, 3H). LC-MS: m/z 428.6 (M+H)$^+$

Step C: benzyl 4-(benzyloxymethoxy)-4-(2-hydroxy-2-methylpropyl)piperidine-1-carboxylate (43D)

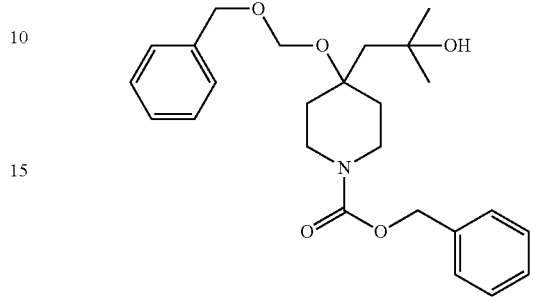

To a solution of benzyl 4-(benzyloxymethoxy)-4-(2-methoxy-2-oxoethyl)piperidine-1-carboxylate (500 mg, 1.17 mmol) in anhydrous THF (15 mL) was added dropwise a solution of methylmagnesium bromide (2 mL, 6 mmol) in diethyl ether at 0° C. After the addition was complete, the mixture was stirred at room temperature for 1.5 h, and then cooled again in an ice bath. Saturated ammonium chloride solution was added dropwise. The resulting precipitate was dissolved by the addition of water (30 mL). The mixture was extracted three times with EtOAc. The combined organic layers were dried over Na$_2$SO$_4$ and evaporated to get the crude product which was used directly for next step without further purification. LCMS (m/z): 428.2 (M+1)$^+$

Step D: benzyl 4-(benzyloxymethoxy)-4-(2-fluoro-2-methylpropyl)piperidine-1-carboxylate (43E)

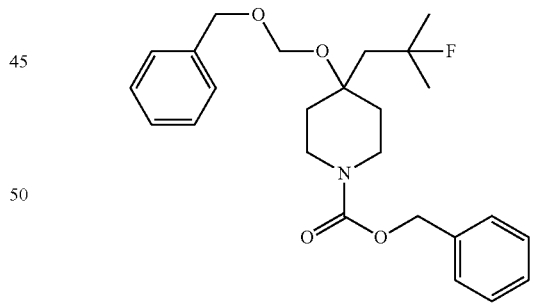

To a solution of (4-hydroxy-4-(isothiazol-4-yl)piperidin-1-yl)(4-((quinolin-8-ylsulfonyl)methyl)phenyl)methanone (500 mg, 1.17 mmol) in DCM (10 mL) was added dropwise DAST (282 mg, 1.75 mmol) while cooling on an ice-water bath. The mixture was allowed to warm up from 0° C. to room temperature, and was stirred for 16 hrs. The reaction was quenched by dropwise addition of saturated ammonium chloride solution, then was washed with saturated NaHCO$_3$ and extracted with EtOAc. The organic layer was washed with brine, and then concentrated to get the crude product. Purification by a standard method gave the desired product. ¹H NMR (CHLOROFORM-d) δ: 7.30-7.59 (m, 10H), 5.15 (s, 2H), 4.85 (s, 2H), 4.71 (s, 2H), 3.83 (br. s., 2H), 3.38 (br. s., 2H), 1.91-2.05 (m, 3H), 1.59-1.70 (m, 2H), 1.47 (s, 3H), 1.42 (s, 3H), 1.36 (s, 1H).

Step E: 4-(2-fluoro-2-methylpropyl)piperidin-4-ol (43F)

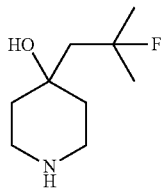

To a round bottom flask was added benzyl-4-(benzyloxymethoxy)-4-(2-fluoro-2-methylpropyl)piperidine-1-carboxylate (50 mg, 0.12 mmol), Pd/C (20 mg), and methanol (5 mL). The mixture was stirred at room temperature for 16 hrs under hydrogen atmosphere. The reaction mixture was filtered to get a solution, which was concentrated to give the desired product. The crude product was used directly for the next step. LC-MS: m/z 176.2 (M+H)⁺

Step F: Compound 403: N-(4-(4-(2-fluoro-2-methylpropyl)-4-hydroxypiperidine-1-carbonyl)phenyl)benzo[d]thiazole-4-sulfonamide

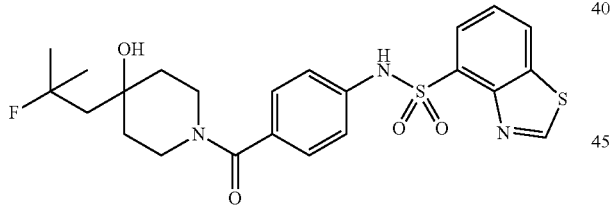

To a round-bottom flask was added with 4-(2-fluoro-2-methylpropyl)piperidin-4-ol (25 mg 0.143 mmol), 4-(benzo[d]thiazole-4-sulfonamido)benzoic acid (47 mg, 0.143 mmol), DIPEA (110 mg, 0.85 mmol), HATU (54 mg, 0.143 mmol), and DCM (5 mL). The mixture was stirred at r.t. for 16 hours. After washing with satd. NaHCO₃, brine, the combined organic layer was dried over anhy. Na₂SO₄ and concentrated in vacuo. Purification by a standard method gave the desired compound. ¹H NMR (CHLOROFORM-d) δ: 9.31 (s, 1H), 8.19 (dd, J=8.1, 0.8 Hz, 1H), 8.10 (dd, J=7.5, 1.1 Hz, 1H), 7.93 (s, 1H), 7.54 (t, J=7.9 Hz, 1H), 7.16-7.23 (m, J=8.3 Hz, 2H), 7.05-7.15 (m, J=8.3 Hz, 2H), 4.19-4.47 (m, 1H), 3.46 (d, J=15.6 Hz, 1H), 3.35 (d, J=15.3 Hz, 2H), 1.89 (s, 3H), 1.84 (s, 3H), 1.49-1.55 (m, 3H), 1.46 (s, 3H). LC-MS: m/z 492.65 (M+H)⁺

General Procedure 44:

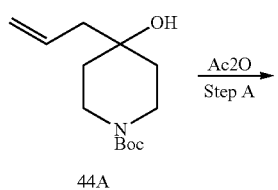

44A

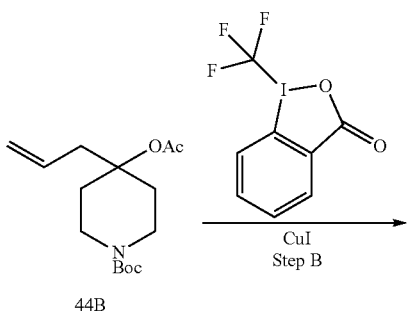

44B

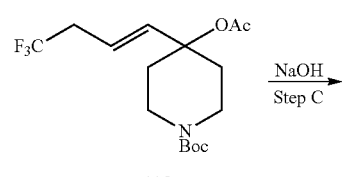

44C

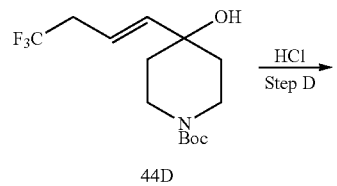

44D

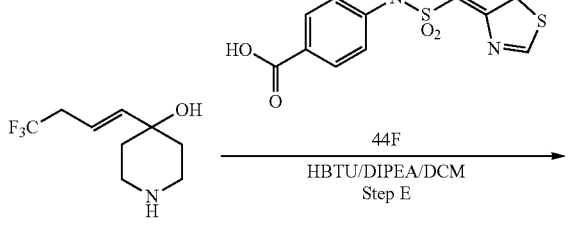

44E

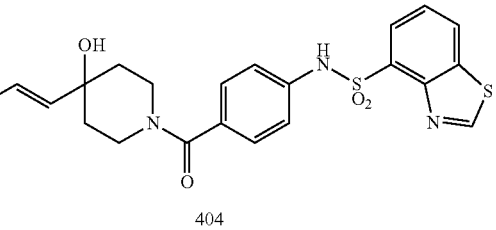

404

Step A: tert-butyl 4-acetoxy-4-allylpiperidine-1-carboxylate (44B)

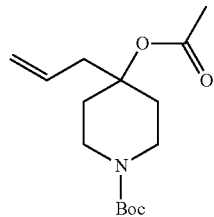 [SMILES: C=CCC1(OC(C)=O)CCN(C(=O)OC(C)(C)C)CC1]

A solution of tert-butyl 4-allyl-4-hydroxypiperidine-1-carboxylate (3.7 g, 14.51 mmol) in dichloromethane (20 mL) was treated with dimethylaminopyridine (1.8 g, 14.51 mmol), acetic anhydride (4.1 mL, 43.53 mmol) and triethylamine (6.1 mL, 43.53 mmol), and was stirred overnight at 20° C. The solvent was removed under reduced pressure and the residue was partitioned between water and ethyl acetate. The aqueous layer was extracted twice with ethyl acetate. Combined organic extracts were washed with water, dried ($Na_2SO_4$) and filtered. The filtrate was concentrated under reduced pressure, and purified by a standard method to provide the title compound 44B (3.4 g). LC-MS: m/z 284.4 (M+H)

Step B: (E)-tert-butyl 4-acetoxy-4-(4,4,4-trifluorobut-1-enyl)piperidine-1-carboxylate (44C)

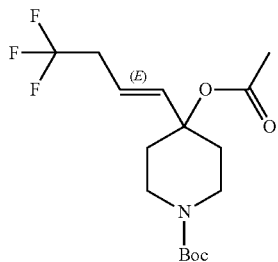 [SMILES: CC(=O)OC1(/C=C/CC(F)(F)F)CCN(C(=O)OC(C)(C)C)CC1]

A flame-dried vial equipped with a magnetic stir bar was charged with Togni reagent (2.0 g, 7.0 mmol) and CuI (34 mg, 0.35 mmol), and was sealed with a septum. The vial was evacuated and backfilled with $N_2$ for three times. MeOH (8 mL) and tert-butyl 4-acetoxy-4-allylpiperidine-1-carboxylate (4.5 g, 14 mmol) were then added via syringe. The vial was kept at 80° C. for 2 h. The reaction mixture was concentrated in vacuo and the crude residue was purified by a standard method to afford the product (2.1 g). $^1$H NMR (400 MHz, CHLOROFORM-d) δ: 1.47 (s, 9H), 1.66-1.77 (m, 2H), 2.00-2.07 (m, 3H), 2.22 (d, J=13.43 Hz, 2H), 2.85 (qdd, J=10.61, 10.61, 10.61, 7.25, 1.21 Hz, 2H), 3.11 (t, J=11.82 Hz, 2H), 3.81 (br. s., 2H), 5.58 (dt, J=15.98, 7.19 Hz, 1H), 6.05 (d, J=16.12 Hz, 1H).

Step C: (E)-tert-butyl 4-hydroxy-4-(4,4,4-trifluorobut-1-enyl)piperidine-1-carboxylate (44D)

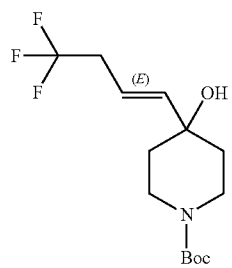 [SMILES: CC(C)(C)OC(=O)N1CCC(O)(/C=C/CC(F)(F)F)CC1]

To a mixture of (E)-tert-butyl 4-acetoxy-4-(4,4,4-trifluorobut-1-enyl)piperidine-1-carboxylate (200 mg, 0.57 mmol) in methanol (5 mL) was added 2M NaOH (2 mL, 4 mmol), the mixture was held stirring at r.t. for 16 hrs, when TLC (20% EA/PE) indicated completion of the reaction. The mixture was concentrated in vacuo, the residue was diluted with brine and extracted with EtOAc, and the organic layer was concentrated in vacuo to get the crude product, which was used directly for the next step.

Step D: (E)-4-(4,4,4-trifluorobut-1-enyl)piperidin-4-ol (44E)

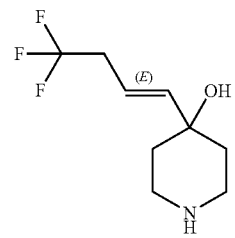

A solution of (E)-tert-butyl 4-hydroxy-4-(4,4,4-trifluorobut-1-enyl)piperidine-1-carboxylate (200 mg, 0.65 mmol) in 3M HCl/1,4-dioxane (5 mL) was stirred at room temperature for 2 hours. The solution was evaporated to dryness under reduced pressure to give the product which was used in the next step without further purification. LC-MS: m/z 210.2 (M+H)$^+$.

Step E: Compound 404: (E)-N-(4-(4-hydroxy-4-(4,4,4-trifluorobut-1-enyl)piperidine-1-carbonyl)phenyl)benzo[d]thiazole-4-sulfonamide

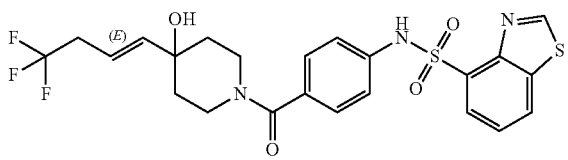 [SMILES: O=C(c1ccc(NS(=O)(=O)c2cccc3scnc23)cc1)N1CCC(O)(/C=C/CC(F)(F)F)CC1]

To a round-bottom flask was added with (E)-4-(4,4,4-trifluorobut-1-enyl)piperidin-4-ol (50 mg 0.24 mmol), 4-(benzo[d]thiazole-4-sulfonamido)benzoic acid (80 mg, 0.24 mmol), DIPEA (155 mg, 1.2 mmol), HATU (110 mg, 0.29 mmol), and DCM (5 mL). The mixture was stirred at r.t. for 16 hours. After washing with brine, the combined organic layer was dried over anhy. $Na_2SO_4$ and concentrated in vacuo. Purification by a standard method gave the desired compound. $^1$H NMR (CHLOROFORM-d) δ: 9.31 (s, 1H), 8.19 (d, J=8.1 Hz, 1H), 8.10 (d, J=7.5 Hz, 1H), 7.99 (s, 1H), 7.54 (t, J=7.8 Hz, 1H), 7.17-7.24 (m, J=8.3 Hz, 2H), 7.08-7.15 (m, J=8.1 Hz, 2H), 5.78-5.94 (m, 1H), 5.64-5.76 (m, 1H), 4.28-4.47 (m, 1H), 3.51 (s, 1H), 3.32-3.48 (m, 1H), 3.27 (br. s., 1H), 2.84 (dd, J=10.5, 7.0 Hz, 1H), 1.66 (br. s., 4H), 1.46 (d, J=9.7 Hz, 2H). LC-MS: m/z 526.7 (M+H)$^+$

General Procedure 45:

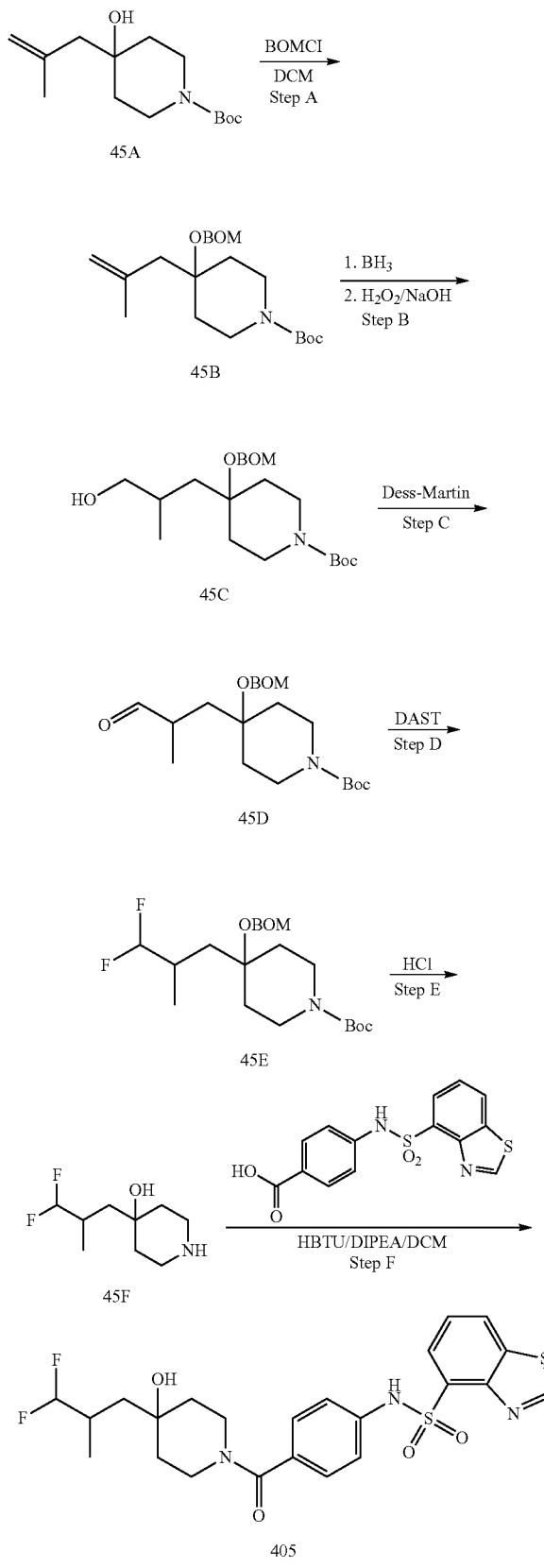

Step A: tert-butyl 4-((benzyloxy)methoxy)-4-(2-methylallyl)piperidine-1-carboxylate (45B)

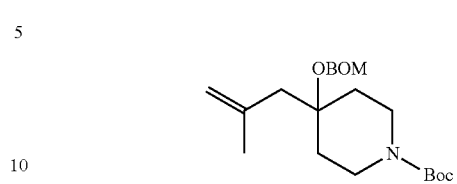

To a solution of tert-butyl 4-((benzyloxy)methoxy)-4-(2-methylallyl)piperidine-1-carboxylate (2.55 g, 10.0 mmol) in dichloromethane (50 mL) was added BOMCl (3.12 g, 20.0 mmol) and TEA (3.03 g, 30.0 mmol), and the mixture was stirred at 45° C. for 16 hrs. The solvent was then removed and the residue was purified by a standard method to obtain the desired product (3 g). LC-MS: m/z 376.6 (M+H)$^+$

Step B: tert-butyl 4-((benzyloxy)methoxy)-4-(3-hydroxy-2-methylpropyl)piperidine-1-carboxylate (45C)

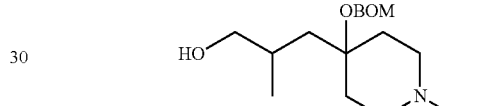

To a solution of tert-butyl 4-((benzyloxy)methoxy)-4-(2-methylallyl)piperidine-1-carboxylate (3.05 g, 8.1 mmol) in THF (50 mL) was added BH$_3$ solution in THF (32 mL, 1 mol/L, 32.4 mmol), and the mixture was stirred at room temperature for 16 hrs. Then 30% H$_2$O$_2$ solution (30 mL) and 10% sodium hydroxide solution (50 mL) were added slowly to the mixture, and the mixture was stirred for another 2 hrs. The mixture was then treated with water (10 mL) and extracted with EtOAc (3×20 mL). The combined organic extracts were dried over Na$_2$SO$_4$ and the solvent was removed in vacuo. The residue was purified by a standard method to give the product (1.97 g). LC-MS: m/z 394.5 (M+H)$^+$

Step C: tert-butyl-4-((benzyloxy)methoxy)-4-(2-methyl-3-oxopropyl)piperidine-1-carboxylate (45D)

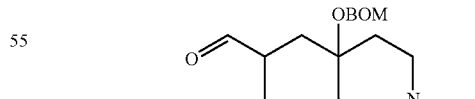

A mixture of tert-butyl-4-((benzyloxy)methoxy)-4-(3-hydroxy-2-methylpropyl)piperidine-1-carboxylate (1.97 g, 5.0 mmol) and Dess-martin reagent (3.18 g) was stirred in dichloromethane (60 mL) at r.t for 16 hrs. The reaction mixture was quenched by adding 25% sodium bicarbonate solution (100 mL), then the mixture was extracted by EtOAc (60 mL×2). The organic phase was combined and concentrated to give a residue, which was further purified by a standard method to give the product (0.88 g). LC-MS: m/z 392.5 (M+H)+

Step D: tert-butyl 4-((benzyloxy)methoxy)-4-(3,3-difluoro-2-methylpropyl)piperidine-1-carboxylate (45E)

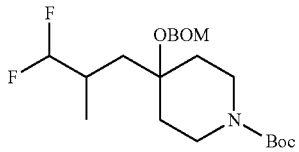

A mixture of tert-butyl 4-((benzyloxy)methoxy)-4-(2-methyl-3-oxopropyl)piperidine-1-carboxylate (0.88 g, 2.25 mmol) and DAST (0.8 g) in DCM (5 mL) was stirred at r.t for 20 hrs. The reaction mixture was quenched by adding 25% sodium bicarbonate solution (20 mL). The mixture was then extracted with DCM twice. The organic phase was combined and concentrated to give a residue, which was further purified by a standard method to obtain the title compound (0.33 g). LC-MS: m/z 414.5 (M+H)+

Step E:
4-(3,3-difluoro-2-methylpropyl)piperidin-4-ol (45F)

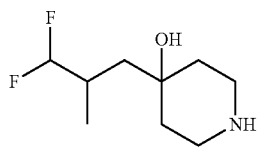

A mixture of tert-butyl 4-((benzyloxy)methoxy)-4-(3,3-difluoro-2-methylpropyl)piperidine-1-carboxylate (0.33 g) and 5 M HCl in MeOH (4 mL) was stirred in methanol (15 mL) for 3 hrs. The solvent was then removed under vacuum to obtain crude product (4-(3,3-difluoro-2-methylpropyl)piperidin-4-ol (0.11 g). LC-MS: m/z 194.2 (M+H)+

Step F: Compound 405: N-(4-(4-(3,3-difluoro-2-methylpropyl)-4-hydroxypiperidine-1-carbonyl)phenyl)benzo[d]thiazole-4-sulfonamide

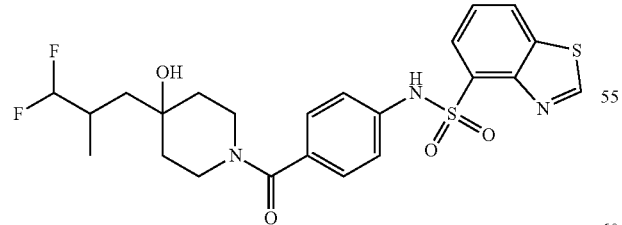

To a round-bottom flask was added 4-(3,3-difluoro-2-methylpropyl)piperidin-4-ol (110 mg 0.57 mmol), 4-(benzo[d]thiazole-4-sulfonamido)benzoic acid (190 mg, 0.57 mmol), DIPEA (367 mg, 2.8 mmol), HATU (261 mg, 0.69 mmol), and DCM (5 mL). The mixture was stirred at r.t. for 16 hours. After washing with brine, the combined organic layer was dried over anhy. Na2SO4 and concentrated in vacuo. Purification by a standard method gave the desired compound. 1H NMR (CHLOROFORM-d) δ: 9.31 (s, 1H), 8.20 (d, J=8.1 Hz, 1H), 8.10 (d, J=7.5 Hz, 1H), 7.94 (s, 1H), 7.55 (t, J=7.9 Hz, 1H), 7.20 (d, J=8.5 Hz, 2H), 7.12 (d, J=8.6 Hz, 2H), 5.90-5.61 (m, 1H), 4.36 (s, 1H), 3.57-3.42 (m, 1H), 3.21 (s, 2H), 2.24 (d, J=7.6 Hz, 1H), 2.05 (s, 1H), 1.86-1.77 (m, 2H), 1.36 (dd, J=14.8, 6.3 Hz, 4H), 1.10 (d, J=7.0 Hz, 3H). LC-MS: m/z 510.5 (M+H)+

General Procedure 46:

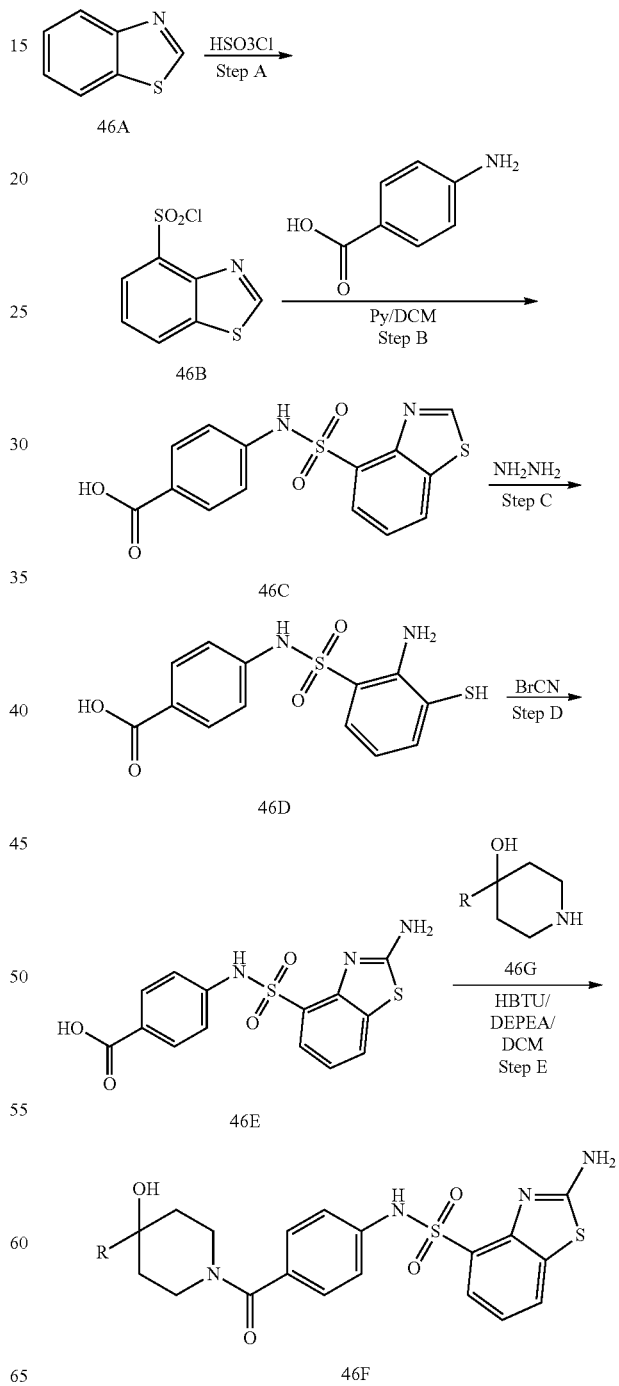

Step A: Benzo[d]thiazole-4-sulfonyl chloride (46B)

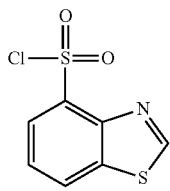 [SMILES: O=S(=O)(Cl)c1cccc2scnc12]

Benzo[d]thiazole (1 g, 7.45 mol) was added dropwise to chlorosulfonic acid (5.5 mmol) at 0° C. After the addition was complete, the mixture was stirred at room temperature for 0.5 h and then heated at 105° C. and stirred overnight. The resulting mixture was cooled to −10° C. and quenched by pouring on crushed ice slowly. The resulting mixture was extracted with EtOAc (100 mL×2). The combined organic phase was washed with brine, dried over anhy. $Na_2SO_4$ and concentrated in vacuo. Column chromatography (15% PE/EtOAc) afforded 218 mg of title compound. $^1$H NMR (CHLOROFORM-d) δ: 9.41 (s, 1H), 8.41 (dd, J=8.1, 1.0 Hz, 1H), 8.29 (dd, J=7.7, 1.1 Hz, 1H), 7.68 (t, J=7.9 Hz, 1H). LC-MS: m/z 234.7 (M+H)$^+$

Step B: 4-(benzo[d]thiazole-4-sulfonamido)benzoic acid (46C)

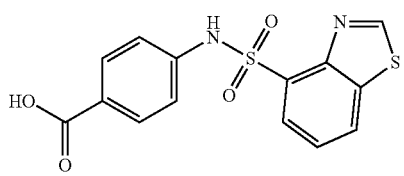 [SMILES: O=C(O)c1ccc(NS(=O)(=O)c2cccc3scnc23)cc1]

To a solution of 4-aminobenzoic acid (10 g, 73 mmol) in DCM (100 mL) was added pyridine (29 g, 365 mmol), then aryl-sulfonyl chloride (20 g, 88 mmol). The resulting mixture was heated at 40° C. for 16 hrs, when LC-MS showed that the reaction was complete. The mixture was then filtered, and the filter cake was washed with $Et_2O$, and dried to afford title product (23 g). $^1$H NMR (DMSO-$d_6$) δ: 12.56 (br. s., 1H), 11.05 (s, 1H), 9.63-9.68 (m, 1H), 8.51 (dd, J=8.1, 1.1 Hz, 1H), 8.12-8.18 (m, 1H), 7.70 (d, J=8.6 Hz, 2H), 7.64-7.69 (m, 1H), 7.11-7.20 (m, 2H). LC-MS: m/z 335.2 (M+H)$^+$

Step C: 4-(2-amino-3-mercaptophenylsulfonamido)benzoic acid (46D)

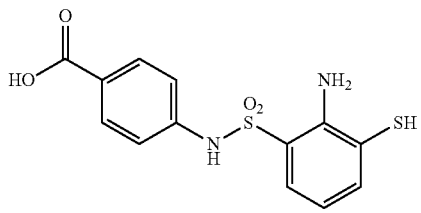 [SMILES: Nc1c(S)cccc1S(=O)(=O)Nc1ccc(C(=O)O)cc1]

To a solution of 4-(benzo[d]thiazole-4-sulfonamido)benzoic acid (500 mg, 1.5 mmol) in 6 mL of EtOH was added hydrazine hydrate (479 mg, 15 mmol) at r.t. The reaction mixture was then stirred at 130° C. in microwave for 1.5 h. The resulting mixture was then cooled, and partitioned between water and EtOAc. The organic phase was washed with brine, dried over anhy. $Na_2SO_4$ and concentrated in vacuo to afford the title compound (449.0 mg). LC-MS: m/z 323.4 (M+H)$^+$

Step D: 4-(2-aminobenzo[d]thiazole-4-sulfonamido)benzoic acid (46E)

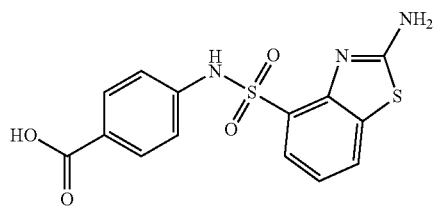 [SMILES: Nc1nc2c(S(=O)(=O)Nc3ccc(C(=O)O)cc3)cccc2s1]

To a solution of 4-(2-amino-3-mercaptophenylsulfonamido)benzoic acid (671 mg, 2.07 mmol) in THF (15 mL) was added cyanic bromide (439.1 mg, 4.14 mmol) at r.t. The reaction mixture was stirred at 80° C. for 8 h. The resulting mixture was then cooled, and partitioned between water and EtOAc. The organic phase was washed with brine, dried over anhy. $Na_2SO_4$ and concentrated in vacuo to afford the title compound (730 mg). LC-MS: m/z 348.7 (M+H)$^+$

Step E: Same procedure as General Procedure 2, Step C

Compound 406: 2-amino-N-(4-(4-hydroxy-4-isobutylpiperidine-1-carbonyl)phenyl)benzo[d]thiazole-4-sulfonamide

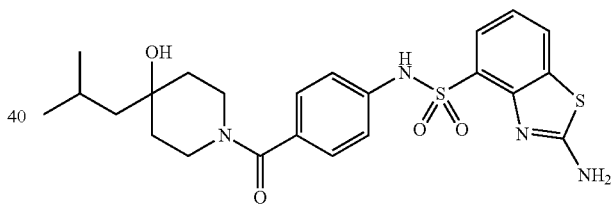

$^1$H NMR (CHLOROFORM-d) δ: 7.93 (s, 1H), 7.82 (dd, J=7.8, 1.0 Hz, 1H), 7.75 (dd, J=7.9, 1.0 Hz, 1H), 7.23 (d, J=8.5 Hz, 2H), 7.16 (t, J=7.6 Hz, 1H), 7.13 (d, J=8.6 Hz, 2H), 5.71 (s, 2H), 4.36 (s, 1H), 3.47-3.19 (m, 3H), 1.84 (dt, J=13.0, 6.4 Hz, 1H), 1.67 (s, 2H), 1.51 (s, 2H), 1.42 (d, J=6.0 Hz, 2H), 0.99 (d, J=6.6 Hz, 6H). LC-MS: m/z 489.70 (M+H)$^+$

Compound 407: 2-amino-N-(4-(4-(2-chlorophenyl)-4-hydroxypiperidine-1-carbonyl)phenyl)benzo[d]thiazole-4-sulfonamide

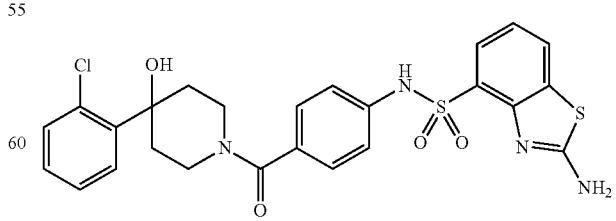

$^1$H NMR (CHLOROFORM-d) δ: 7.81 (d, J=7.9 Hz, 1H), 7.76 (dd, J=16.1, 7.8 Hz, 2H), 7.38 (d, J=7.8 Hz, 1H), 7.33 (t, J=7.6 Hz, 1H), 7.30-7.19 (m, 5H), 7.07 (t, J=7.8 Hz, 1H), 4.51

(d, J=13.9 Hz, 1H), 3.52 (d, J=16.0 Hz, 2H), 2.84-2.72 (m, 1H), 2.68-2.56 (m, 1H), 1.72 (d, J=18.4 Hz, 1H), 1.56 (d, J=15.3 Hz, 1H), 1.34 (d, J=14.7 Hz, 1H). LC-MS: m/z 543.67 (M+H)$^+$

General Procedure 47:

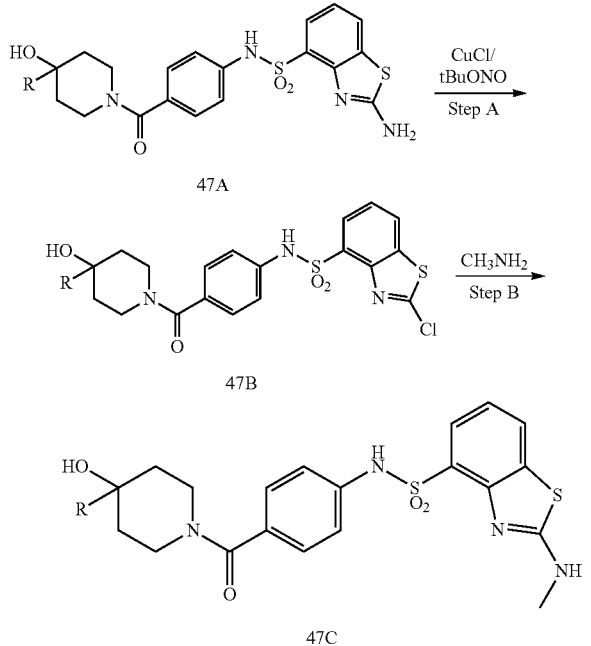

Step A:

A solution of compound 47A (1.23 mol) in MeCN (10 mL) was mixed with water (5 mL), CuCl (243 mg, 2.46 mmol), NaCl (500 mg) and 18-crown-6 (0.5 mL). A solution of tert-butyl-nitrite (165 mg) was then added dropwise with stirring, the solution was heated at reflux for 15 hrs. Then the resulting mixture was poured into water (20 mL), the aqueous layer was extracted with EtOAc (3×50 mL). The combined organic layers were washed with brine, dried over Na$_2$SO$_4$ and evaporated to get the title compound. The crude product was used in the next step without further purification.

Step B:

To a solution of compound 47B (0.6 mmol) in THF (10 mL) was added 25% MeNH$_2$ in water (3 mL) dropwise. After the addition was complete, the reaction mixture was stirred at room temperature overnight. The crude product was filtered off, washed with methanol, then dried thoroughly and was then purified by a standard method to give the desired product.

Compound 408: N-(4-(4-hydroxy-4-isobutylpiperidine-1-carbonyl)phenyl)-2-(methylamino)benzo[d]thiazole-4-sulfonamide

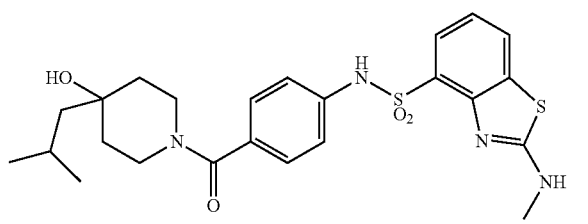 [SMILES: CNc1nc2c(S(=O)(=O)Nc3ccc(C(=O)N4CCC(O)(CC(C)C)CC4)cc3)cccc2s1]

$^1$H NMR (CHLOROFORM-d) δ: 8.33 (br. s., 1H), 7.77-7.84 (m, 1H), 7.70-7.77 (m, 1H), 7.22 (d, J=8.3 Hz, 2H), 7.13 (d, J=8.6 Hz, 2H), 7.07-7.11 (m, 1H), 6.25 (br. s., 1H), 4.35 (br. s., 1H), 3.44 (br. s., 1H), 3.36 (br. s., 1H), 3.22 (br. s., 1H), 3.13 (s, 3H), 1.83 (dd, J=12.9, 6.4 Hz, 2H), 1.65 (br. s., 2H), 1.49 (br. s., 1H), 1.41 (d, J=5.9 Hz, 2H), 0.98 (d, J=6.7 Hz, 6H). LC-MS: m/z 503.6 (M+H)$^+$

Compound 409: 2-chloro-N-(4-(4-(2-chlorophenyl)-4-hydroxypiperidine-1-carbonyl)phenyl)benzo[d]thiazole-4-sulfonamide

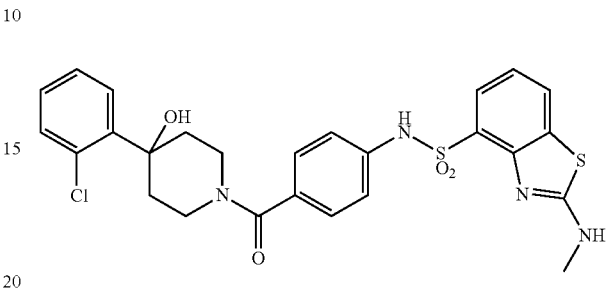

$^1$H NMR (CHLOROFORM-d) δ: 8.25 (br. s., 1H), 7.82 (d, J=7.8 Hz, 1H), 7.75 (d, J=8.1 Hz, 1H), 7.52 (dd, J=7.7, 1.7 Hz, 1H), 7.40 (dd, J=7.7, 1.5 Hz, 1H), 7.29-7.33 (m, 1H), 7.23-7.28 (m, 3H), 7.10-7.19 (m, 3H), 6.12 (br. s., 1H), 4.62 (br. s., 1H), 3.62 (br. s., 1H), 3.52 (br. s., 1H), 3.32 (br. s., 1H), 3.20 (s, 3H), 2.92 (s, 1H), 2.09 (br. s., 2H), 1.84 (br. s., 2H). LC-MS: m/z 558.1 (M+H)$^+$

General Procedure 48:

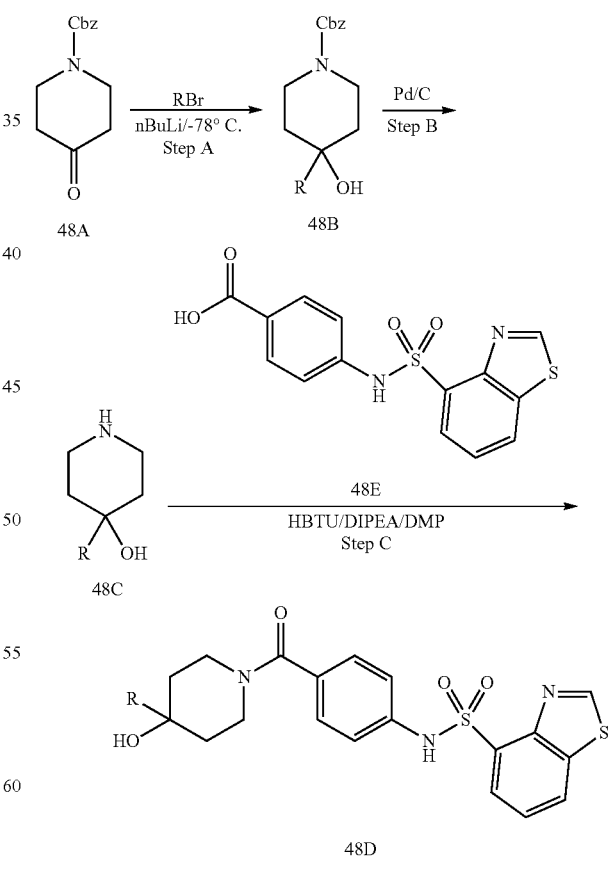

Step A:

To a solution of the corresponding Aryl Bromide (1.0 eq.) in anhydrous THF was added a solution of n-BuLi in THF (1.05 eq.) dropwise at −78° C. After the addition, the mixture was stirred at −78° C. for about 0.5 hour. Then a solution of Cbz-4-piperidone in THF was added dropwise via a syringe at −78° C. After the addition was complete, the resulting mixture was stirred at −78° C. under N₂ for 2 h, and then allowed to warm to r.t. The reaction mixture was quenched by addition of satd. NH₄Cl solution, and the resulting mixture was extracted with EtOAc (50 mL, 30 mL). The combined organic phase was washed with brine, dried over anhydrous Na₂SO₄ and concentrated in vacuo. The residue was purified a standard method to afford compound 48B, which was confirmed by LCMS.

Step B:

To a round bottom flask was added the corresponding compound 48B (0.2 mmol), Pd/C (20 mg), and methanol (5 mL). The mixture was stirred at room temperature for 16 hrs under hydrogen atmosphere. The reaction mixture was filtered, and the resulting solution was concentrated to give the desired product 48C. The crude product was used directly for the next step without further purification.

Step C:

To a round-bottomed flask was added compound 48C (0.1 mmol, 1 eq.), DMF (5 mL), DIPEA (0.3 mmol, 3.0 eq.), HBTU (0.12 mmol, 1.2 eq.), and 48E (0.1 mmol, 1 eq.) sequentially. The reaction mixture was stirred at room temperature overnight or until TLC indicated that s.m. was consumed. The mixture was diluted with brine, extracted with ethyl acetate, the organic layer was dried with anhydrous Na₂SO₄, filtered, and filtrate was concentrated. The desired product 48D was purified by a method.

Compound 410: N-[4-[4-hydroxy-4-(1H-pyrazol-4-yl)piperidine-1-carbonyl]phenyl]benzothiazole-4-sulfonamide

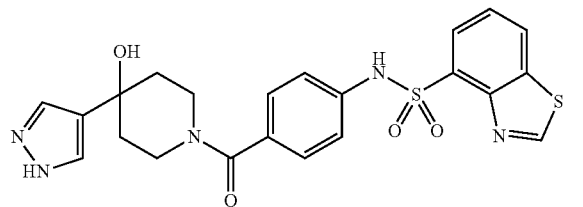 [SMILES: O=C(c1ccc(NS(=O)(=O)c2cccc3scnc23)cc1)N1CCC(O)(c2cn[nH]c2)CC1]

¹H NMR (CHLOROFORM-d) δ: 12.57 (s, 1H), 10.76 (s, 1H), 9.66 (s, 1H), 8.50 (dd, J=8.1, 1.0 Hz, 1H), 8.11 (dd, J=7.6, 1.0 Hz, 1H), 7.65 (t, J=7.9 Hz, 1H), 7.58 (s, 1H), 7.43 (s, 1H), 7.20 (d, J=8.6 Hz, 2H), 7.12 (t, J=9.8 Hz, 2H), 4.90 (s, 1H), 4.07 (s, 1H), 3.21 (s, 3H), 1.73 (s, 4H). LC-MS: m/z 484.7 (M+H)⁺

Compound 411: N-[4-[4-hydroxy-4-(1-methylpyrazol-4-yl)piperidine-1-carbonyl]phenyl]benzothiazole-4-sulfonamide

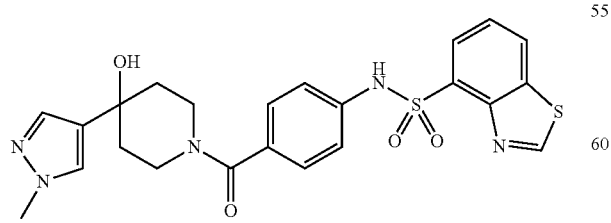

¹H NMR (CHLOROFORM-d) δ: 9.31 (s, 1H), 8.23-8.16 (m, 1H), 8.10 (dd, J=7.5, 0.9 Hz, 1H), 7.93 (s, 1H), 7.55 (t, J=7.9 Hz, 1H), 7.41 (d, J=2.0 Hz, 1H), 7.22 (d, J=8.5 Hz, 2H), 7.13 (d, J=8.6 Hz, 2H), 6.10 (d, J=2.0 Hz, 1H), 4.50 (s, 1H), 4.10 (s, 3H), 3.59 (s, 1H), 3.40 (m, 2H), 1.99 (s, 2H), 1.87 (s, 2H). LC-MS: m/z 498.7 (M+H)⁺

Compound 412

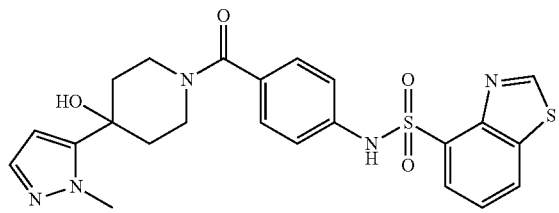 [SMILES: Cn1nccc1C1(O)CCN(C(=O)c2ccc(NS(=O)(=O)c3cccc4scnc34)cc2)CC1]

¹H NMR (METHANOL-d₄) δ: 9.47 (s, 1H), 8.29 (d, J=7.8 Hz, 1H), 8.11 (d, J=7.5 Hz, 1H), 7.54 (t, J=7.9 Hz, 1H), 7.29-7.37 (m, 1H), 7.12-7.26 (m, 4H), 6.10-6.21 (m, 1H), 4.27-4.48 (m, 1H), 4.03 (s, 3H), 3.39-3.60 (m, 2H), 1.81-2.11 (m, 5H). LC-MS: m/z 498.7 (M+H)⁺

The following compounds depicted in Table 4 below were prepared using the same general procedure as described above.

TABLE 4

| Compound No | LC-MS: m/z (M + H)⁺ |
|---|---|
| 267 | 440.2 |
| 268 | 520.2 |
| 270 | 606.1 |
| 271 | 604.1 |
| 272 | 504.2 |
| 273 | 546.2 |
| 274 | 456.2 |
| 275 | 470.2 |
| 276 | 518.2 |
| 277 | 560.1 |
| 278 | 513.2 |
| 281 | 485.1 |
| 283 | 502.2 |
| 284 | 546.2 |
| 285 | 519.2 |
| 286 | 507.1 |
| 287 | 519.2 |
| 288 | 495.2 |
| 290 | 524.1 |
| 292 | 498.2 |
| 293 | 542.1 |
| 294 | 495.1 |
| 296 | 426.1 |
| 297 | 519.2 |
| 298 | 489.2 |
| 299 | 485.1 |
| 300 | 488.2 |
| 301 | 469.2 |
| 302 | 524.1 |
| 304 | 519.2 |
| 306 | 489.2 |
| 307 | 535.1 |
| 308 | 551.1 |
| 310 | 493.2 |
| 311 | 506.1 |
| 313 | 523.1 |
| 315 | 452.2 |
| 316 | 511.1 |
| 317 | 476.2 |
| 318 | 511.1 |
| 319 | 488.2 |
| 320 | 516.2 |
| 321 | 519.2 |
| 323 | 490.2 |

TABLE 4-continued

| Compound No | LC-MS: m/z (M + H)+ |
|---|---|
| 325 | 535.1 |
| 326 | 522.2 |
| 327 | 495.2 |
| 330 | 558.2 |
| 331 | 476.2 |
| 269 | 474.6 |
| 280 | 529.0 |
| 289 | 485.6 |
| 303 | 547.0 |
| 309 | 492.6 |
| 312 | 457.6 |
| 314 | 475.6 |
| 322 | 487.0 |
| 324 | 432.6 |
| 384 | 472.6 |
| 413 | 496.6 |
| 414 | 514.7 |
| 415 | 459.6 |
| 416 | 485.6 |
| 417 | 530.0 |
| 418 | 562.0 |
| 419 | 475.6 |
| 443 | 531.7 |
| 444 | 546.6 |

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A compound of Formula (Ia) or a pharmaceutically acceptable salt thereof, wherein:

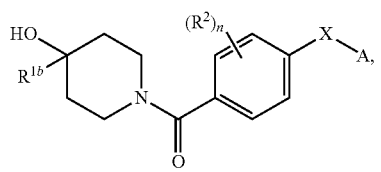

(Ia)

A is optionally substituted bicyclic heteroaryl;
X is selected from —NH—S(O)$_2$—, —NH—S(O)$_2$—CH$_2$—, —CH$_2$—S(O)—NH— or —CH$_2$—S(O)$_2$—NH—;
R$^{1b}$ is selected from C$_{1-8}$ alkyl optionally substituted with one to four R$^5$ groups; C$_{1-8}$ alkenyl optionally substituted with one to four R$^5$ groups; cycloalkyl; heterocycle; aryl; heteroaryl; cycloalkylalkyl; cycloalkylalkenyl; heterocyclylalkyl; heterocyclylalkenyl; aralkyl; aralkenyl; heteroaralkyl; and heteroaralkenyl; wherein each cycloalkyl, heterocycle, aryl, heteroaryl, cycloalkylalkyl, cycloalkylalkenyl, heterocyclylalkyl, heterocyclylalkenyl, aralkyl, aralkenyl, heteroaralkyl, or heteroaralkenyl is optionally substituted;
each R$^2$ is independently selected from halo, alkyl, CN, OH, and alkoxy, wherein said alkyl or alkoxy is optionally substituted with one to four R$^5$ groups; or two adjacent R$^2$ groups are taken together with the ring atoms they are attached to form a 5- or 6-membered carbocyclic, aryl, heterocyclic or heteroaryl ring;
each R$^5$ is independently selected from halo, OH, C$_{1-6}$ alkoxy, CN, NH$_2$, —SO$_2$—C$_{1-6}$ alkyl, —NH(C$_{1-6}$ alkyl), and —N(C$_{1-6}$ alkyl)$_2$; and
n is 0, 1, 2 or 3.

2. The compound of claim 1, wherein A is an optionally substituted quinolin-8-yl.

3. The compound of claim 1, wherein A is an optionally substituted quinoxalin-8-yl.

4. The compound of claim 1, wherein A is

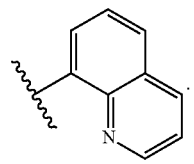 [SMILES: *c1cccc2cccnc12]

5. The compound of claim 1, wherein A is

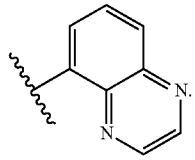 [SMILES: *c1cccc2nccnc12]

6. The compound of claim 1, wherein X is —NH—S(O)$_2$—.

7. The compound of claim 1, wherein R$^{1b}$ is C$_{1-8}$ alkyl optionally substituted with one to four R$^5$ groups; aryl; heteroaryl; aralkyl; or heteroaralkyl; wherein each aryl; heteroaryl; aralkyl; or heteroaralkyl; is optionally substituted.

8. The compound of claim 6, wherein each aryl; heteroaryl; aralkyl; or heteroaralkyl is optionally substituted with halo, C$_{1-6}$ alkyl, —OH, C$_{1-6}$ alkoxy, —CN, —NH$_2$, —SO$_2$—C$_{1-6}$ alkyl, —NH(C$_{1-6}$ alkyl), —N(C$_{1-6}$ alkyl)$_2$, aryl, haloalkyl, or haloalkoxy.

9. The compound of claim 1, wherein R$^{1b}$ is C$_{1-8}$ alkyl optionally substituted with one to four R$^5$ groups.

10. The compound of claim 1, wherein R$^{1b}$ is selected from methyl, ethyl, n-propyl, isopropyl, t-butyl, isobutyl, n-butyl, t-pentyl, 2-hydroxyethyl, 1-hydroxyethyl, 3-hydroxypropyl, 2-hydroxy-2-methylpropyl, 3-hydroxy-3-methylbutyl, 3,3,3-trifluoropropyl, 2-methoxyethyl, 3,3-difluoropropyl, ethoxymethyl, N,N-dimethylmethyl, pyrrollomethyl and 2-hydroxypropyl.

11. The compound of claim 1, wherein R$^{1b}$ is selected from methyl, ethyl, n-propyl, isopropyl, t-butyl, isobutyl, n-butyl, and t-pentyl.

12. The compound of claim 1, wherein n is 0.

13. The compound of claim 1, wherein the compound is selected from:

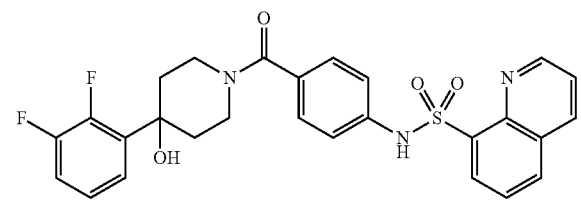

263
-continued
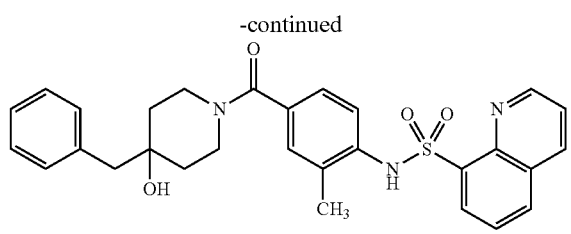
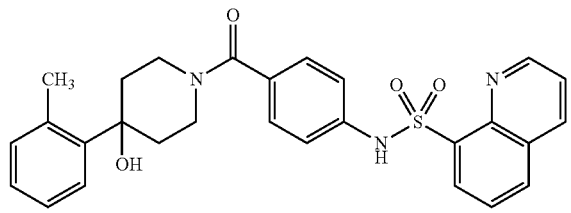
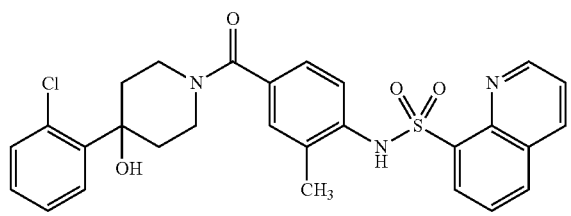
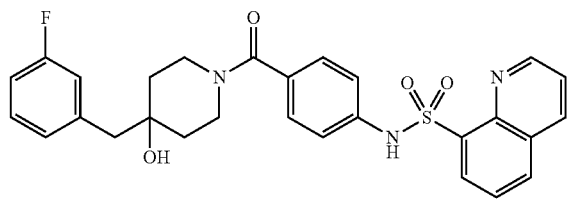
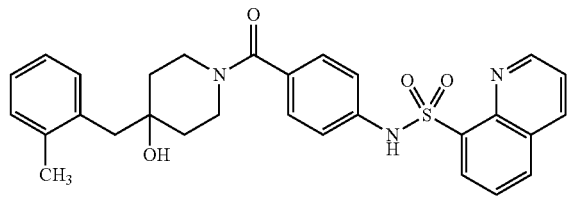
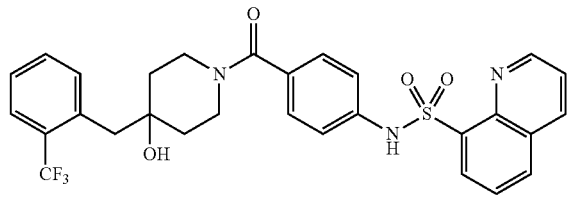
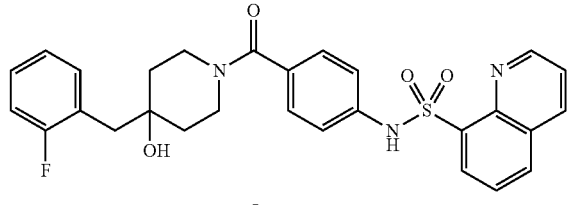
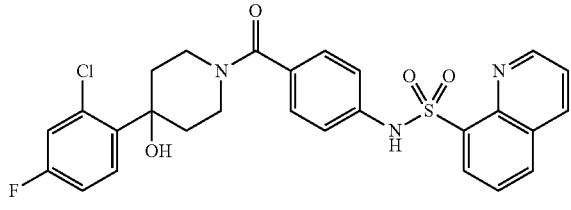
264
-continued
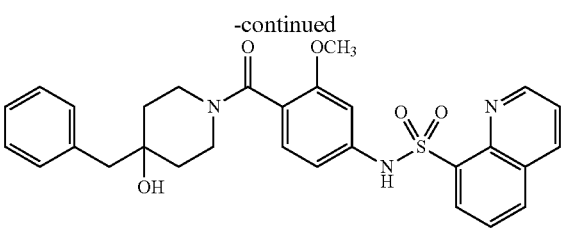
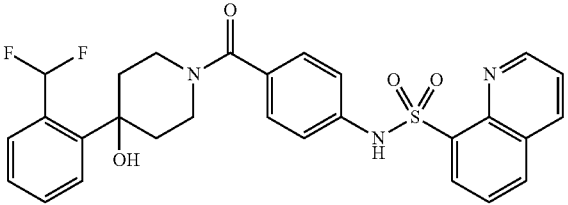
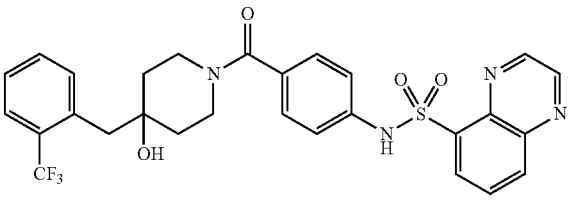 [SMILES: O=C(c1ccc(NS(=O)(=O)c2cccc3nccnc23)cc1)N1CCC(O)(Cc2ccccc2C(F)(F)F)CC1]
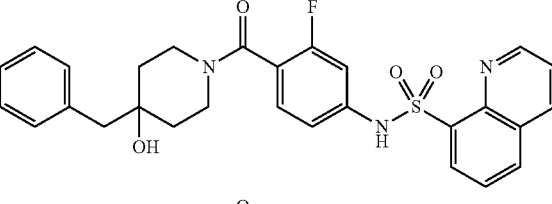
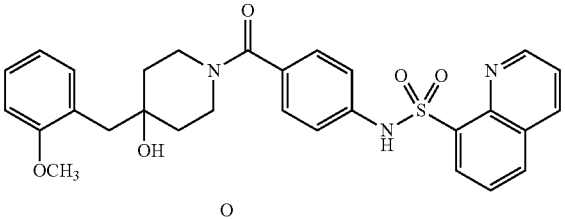
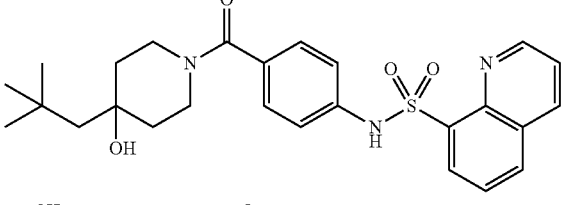
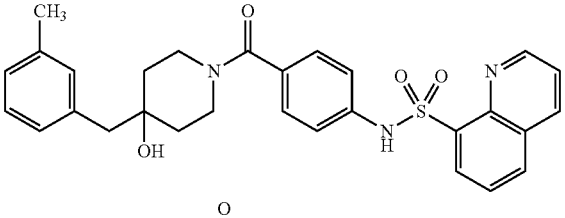
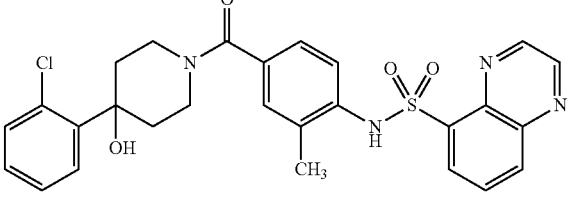

265
-continued
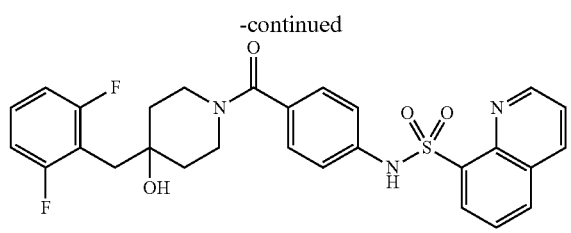
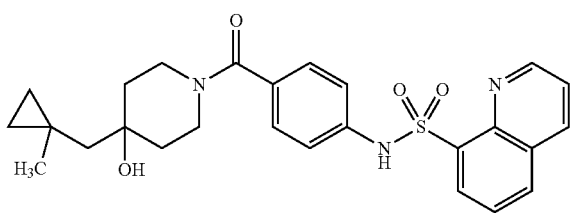
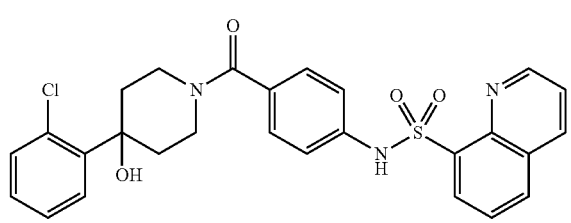
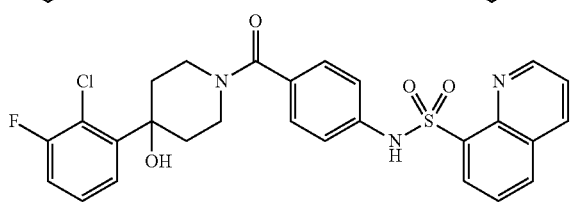
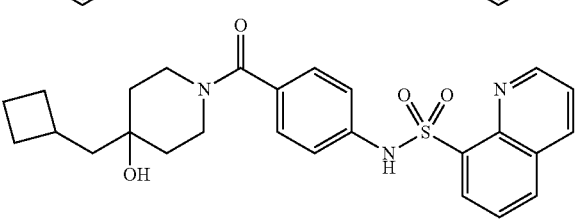
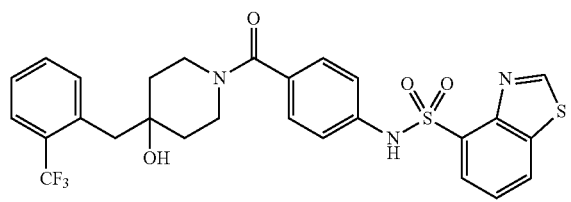
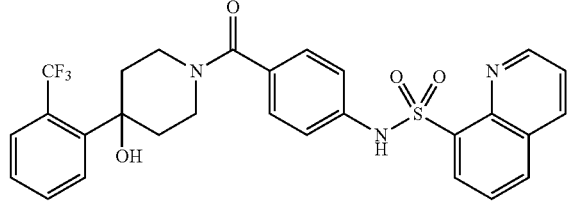
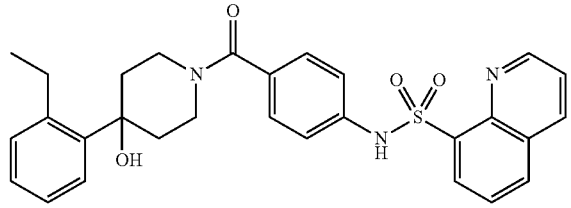
266
-continued
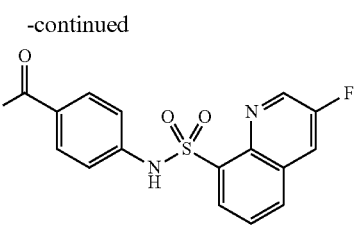
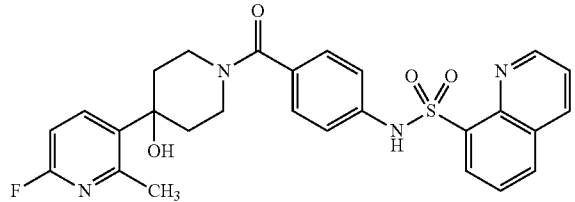
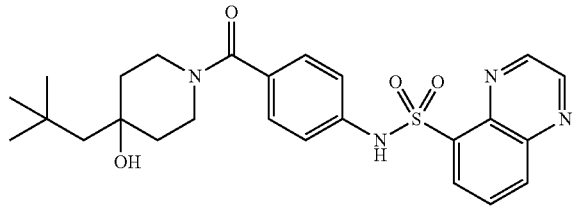
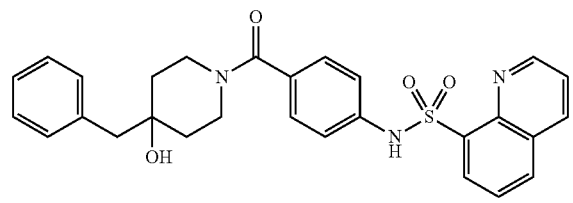
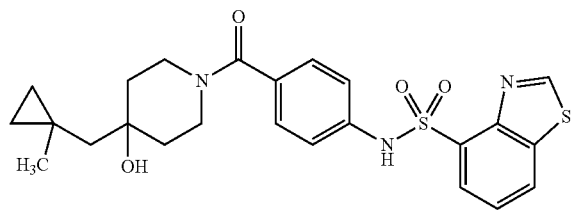
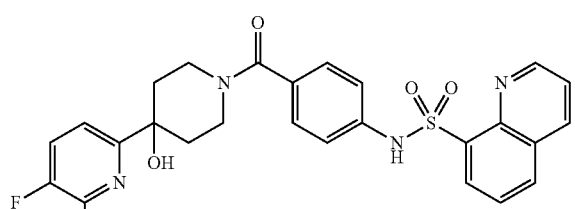
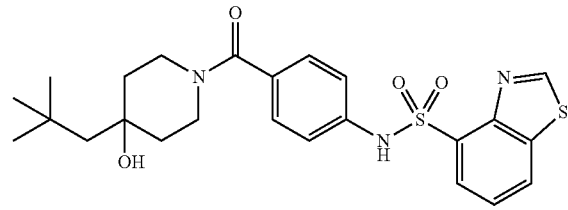

-continued

269
-continued
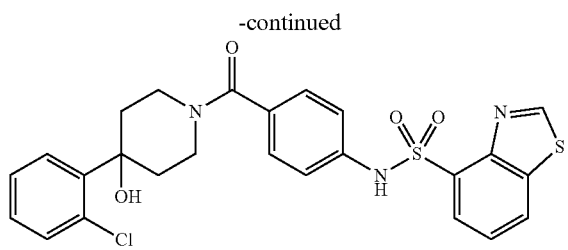
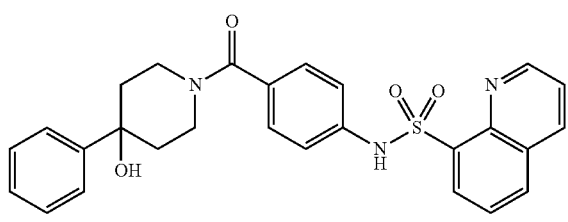
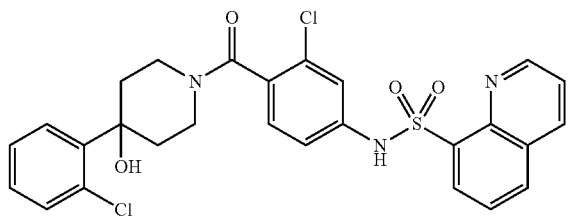
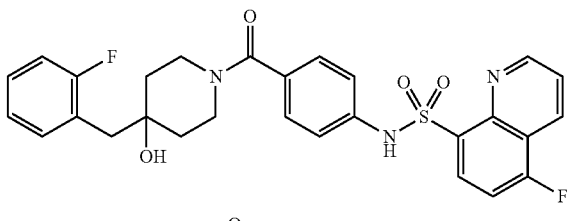
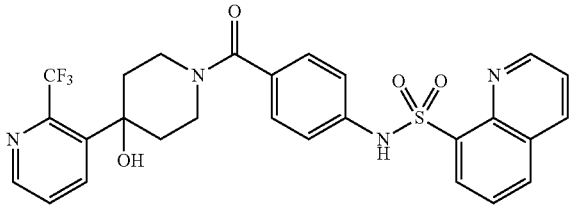
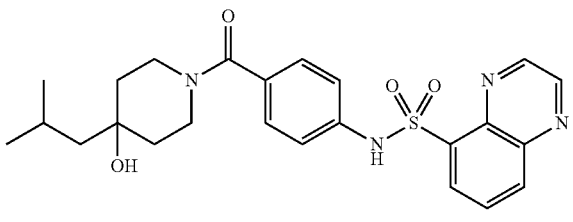
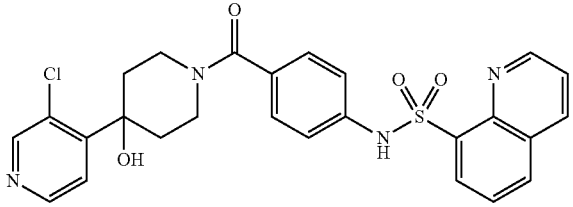
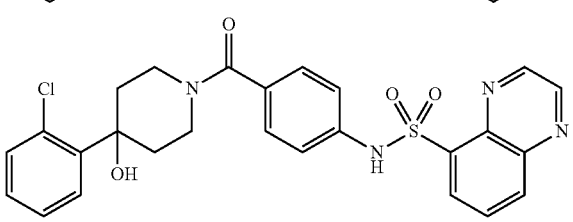
270
-continued
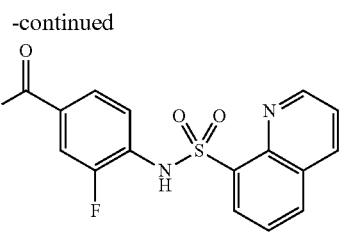
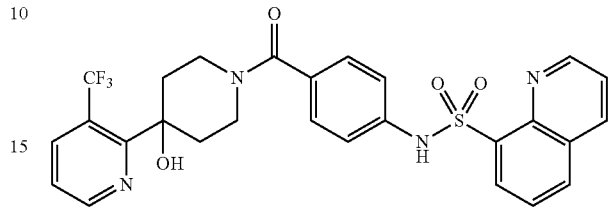
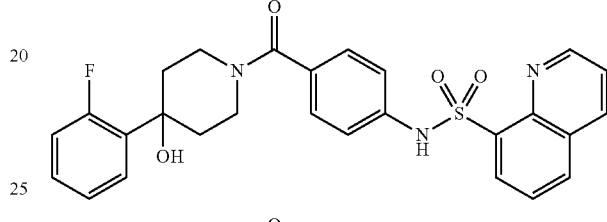
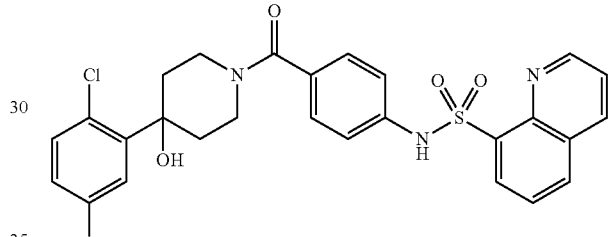
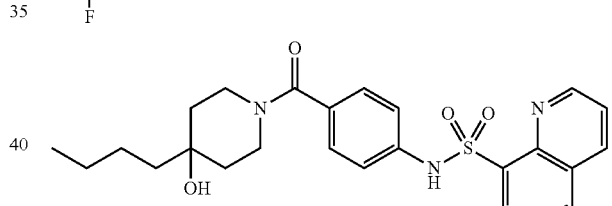
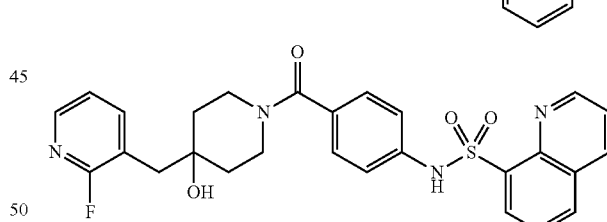
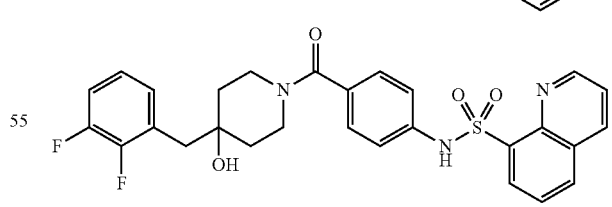
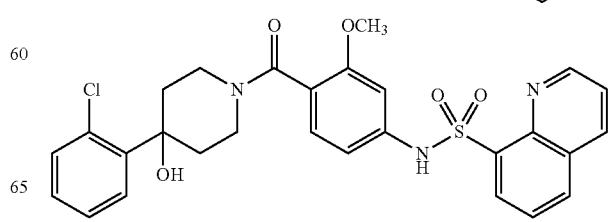

-continued

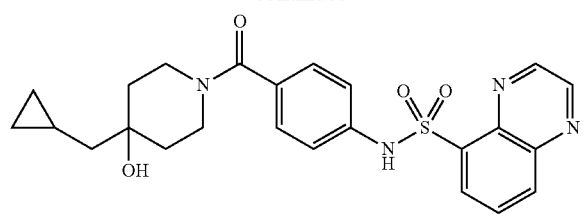
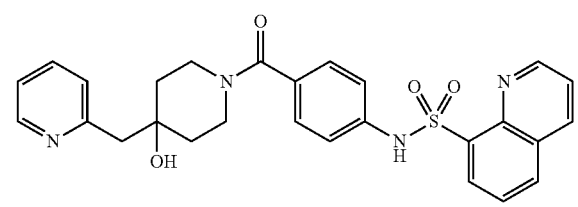
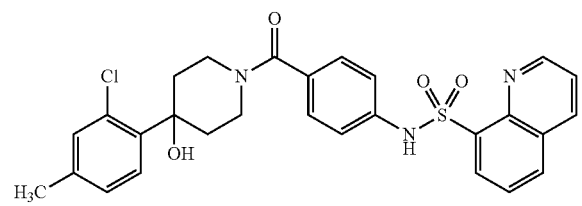
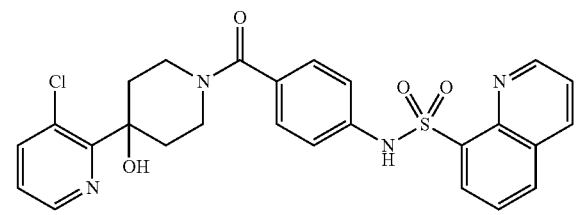
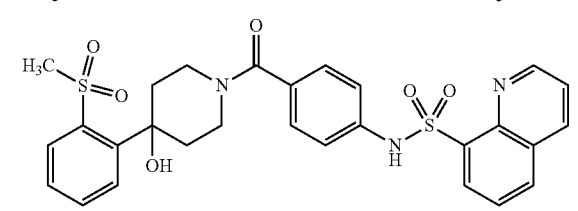
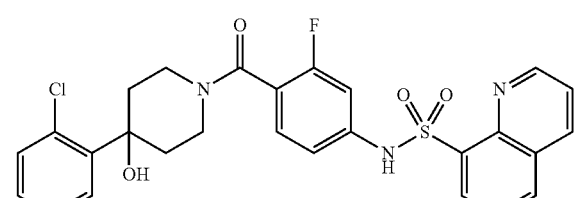
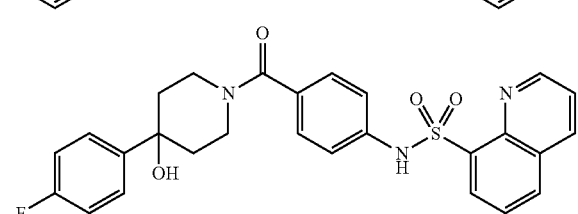
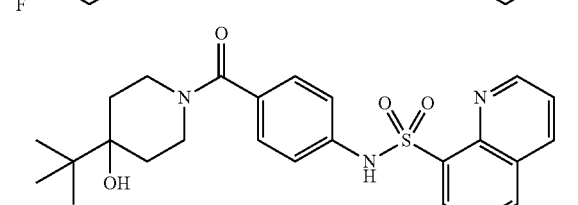
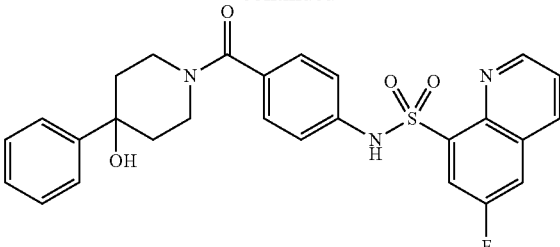
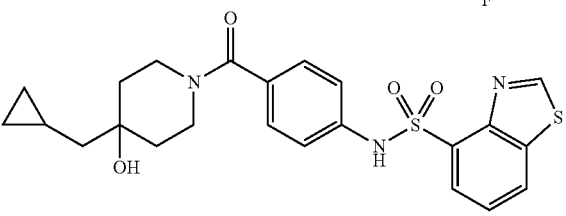
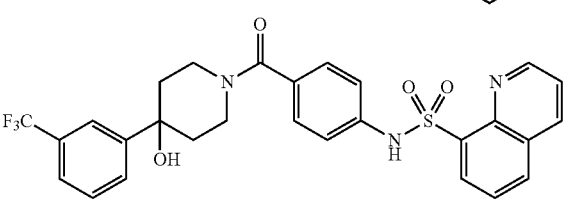
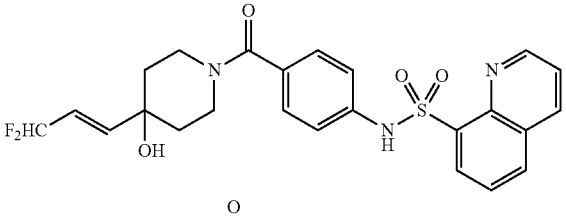
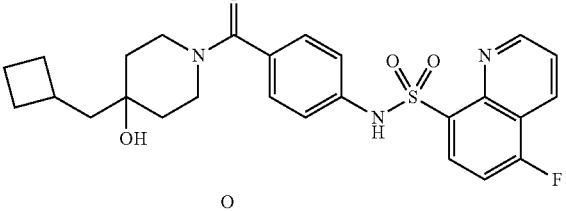
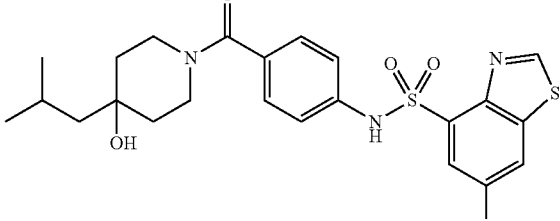
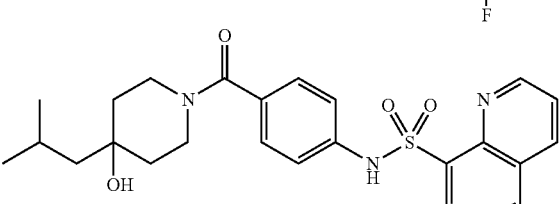
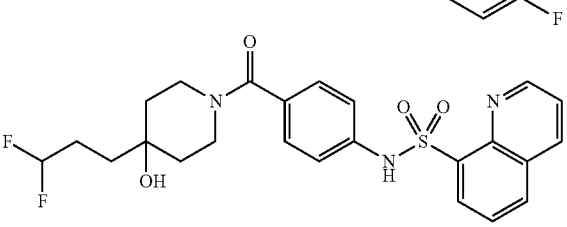

275
-continued
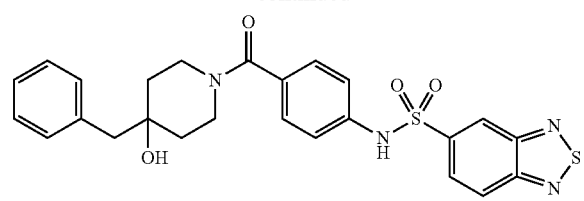
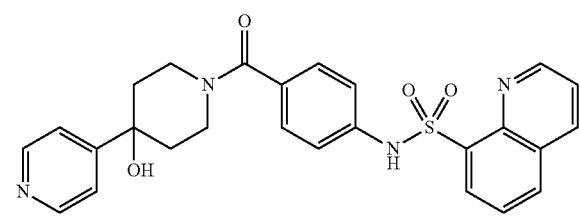
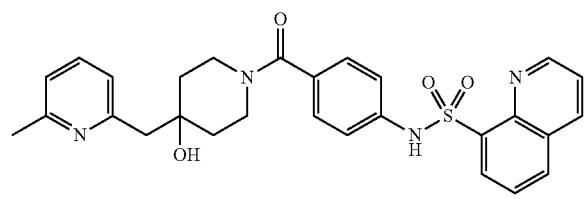
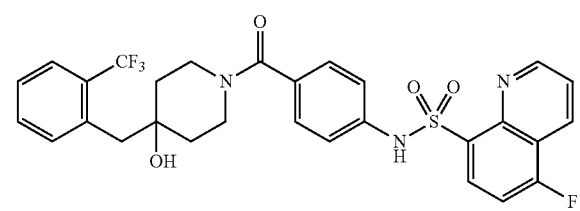
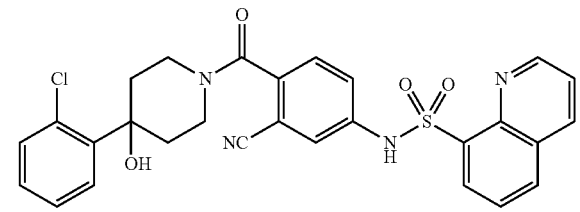
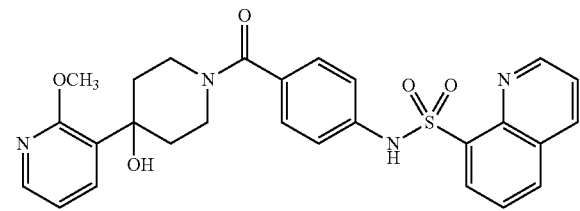
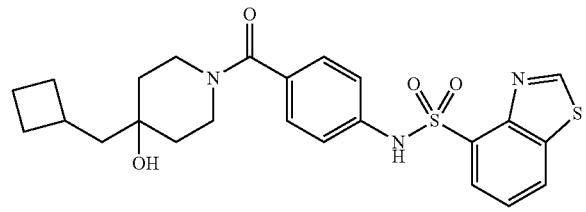
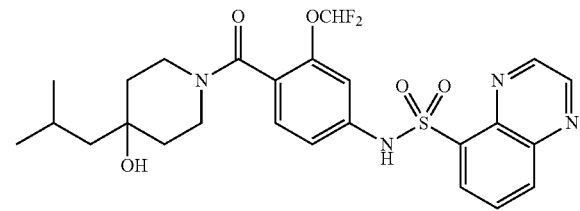
276
-continued
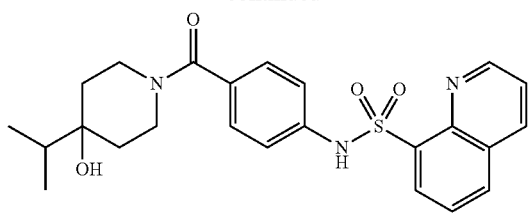
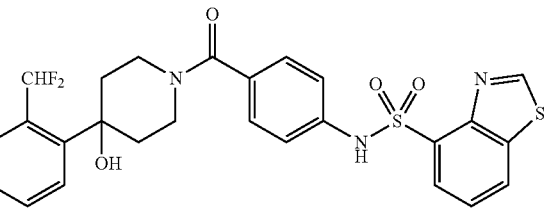
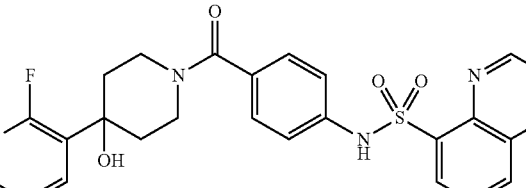
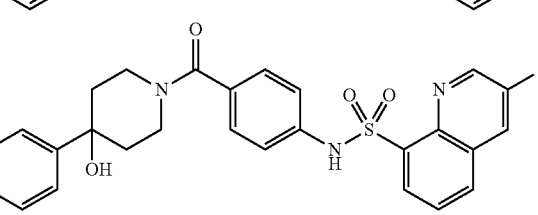
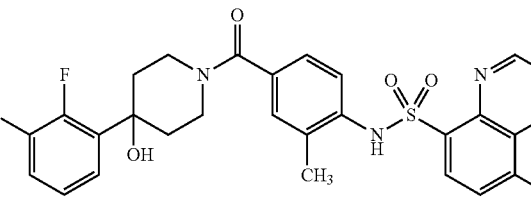
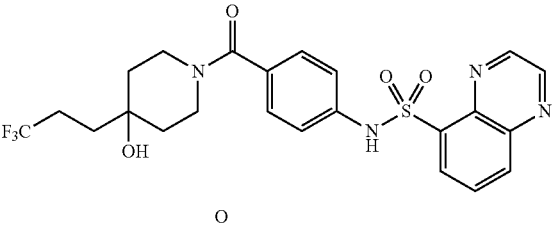
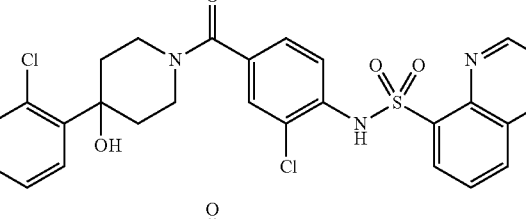
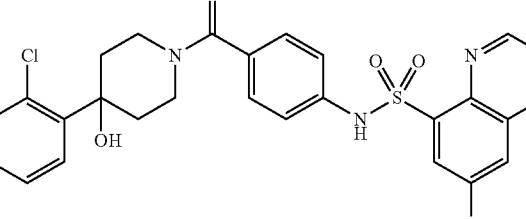

277
-continued
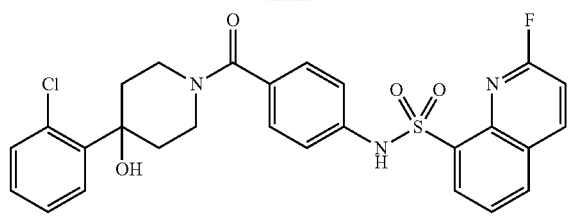
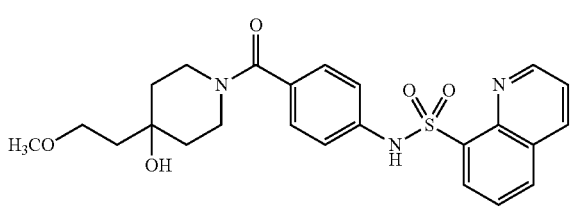
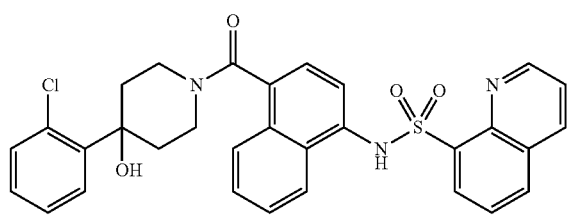
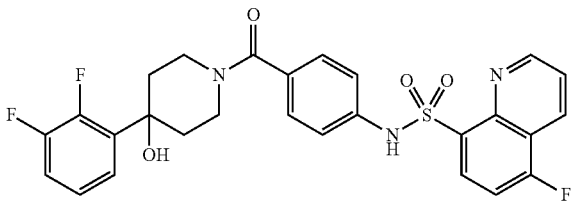
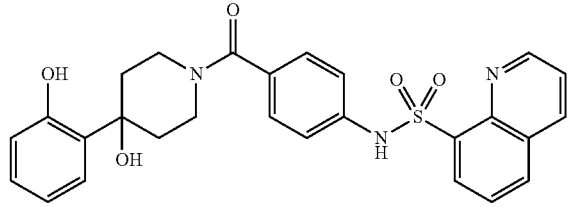
278
-continued
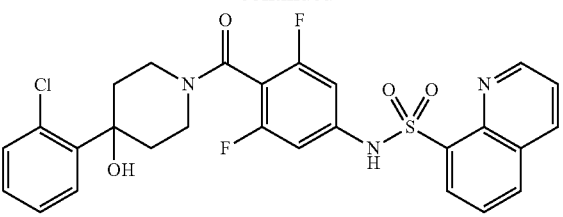
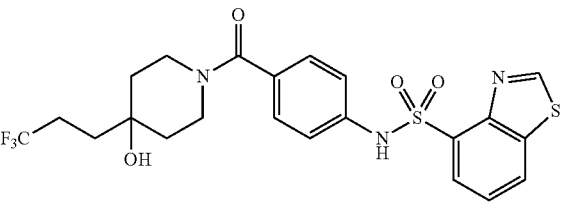
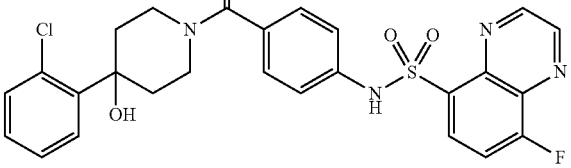
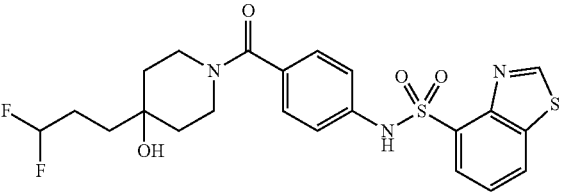
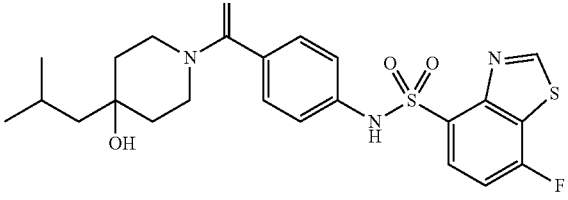
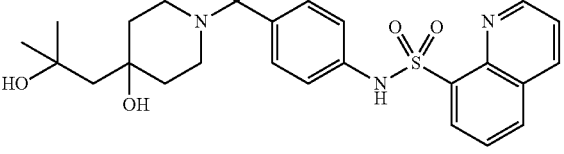
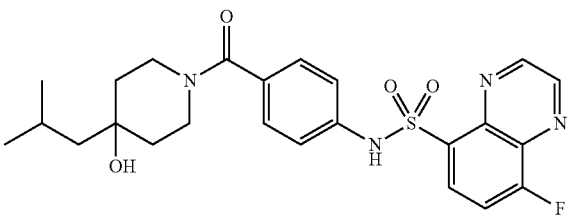
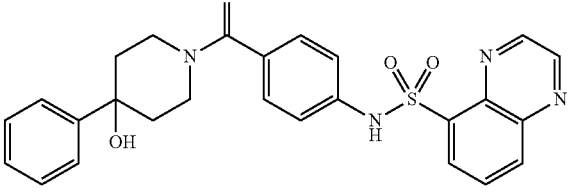

279
-continued
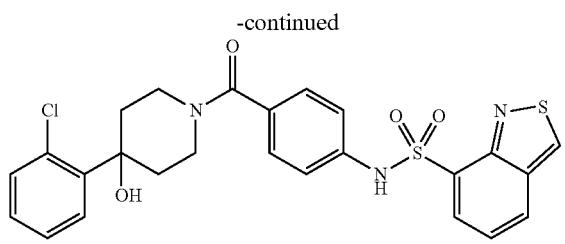
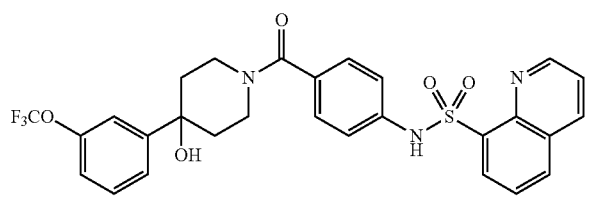
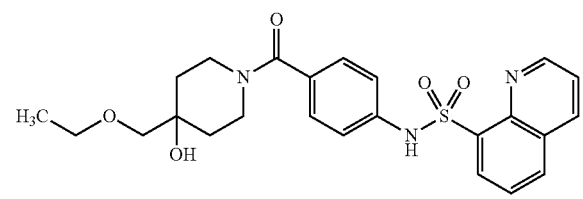
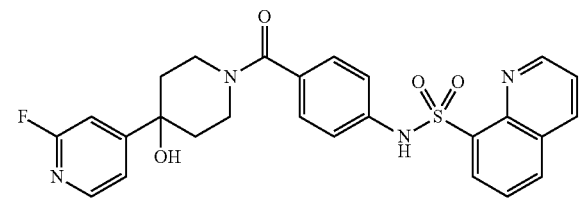
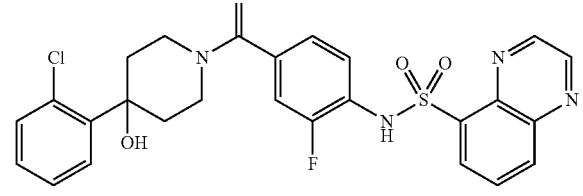
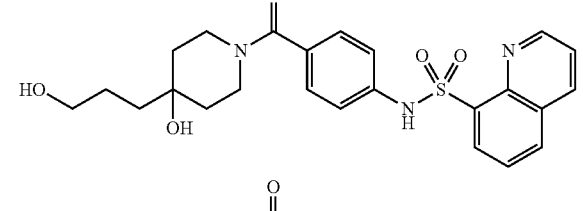
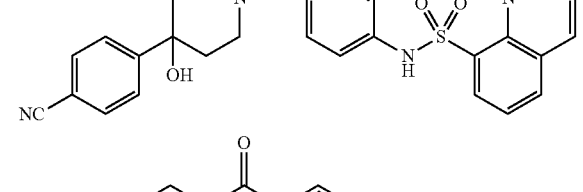
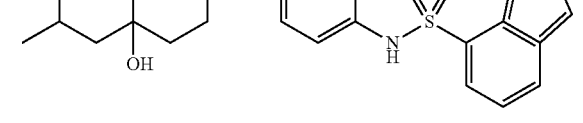
280
-continued
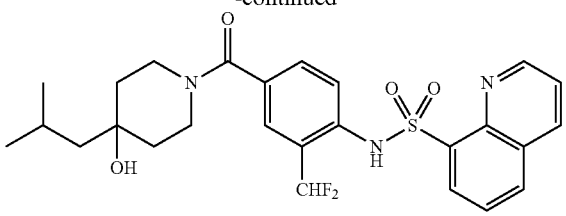
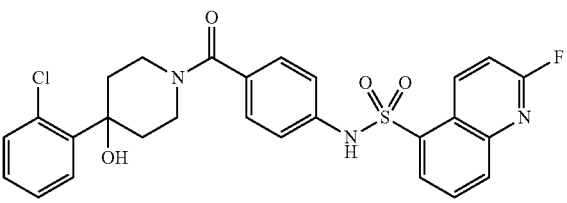
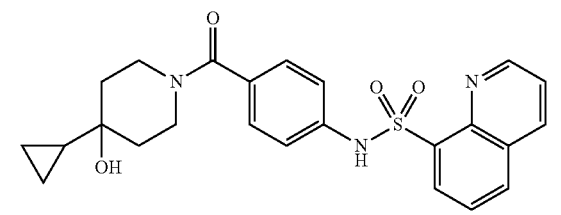
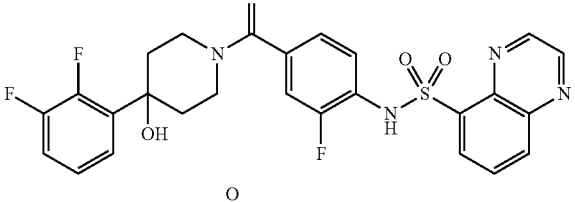
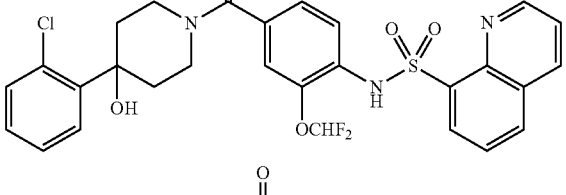
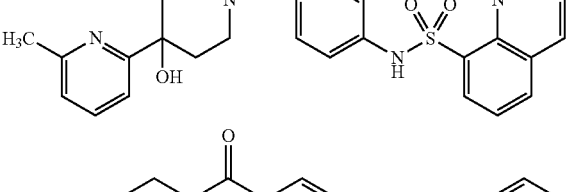
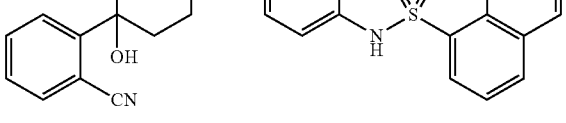

281
-continued

282
-continued

283
-continued
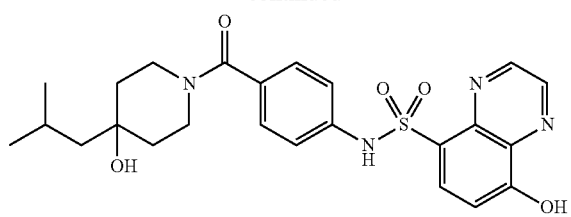
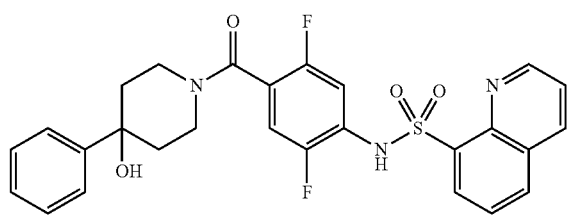
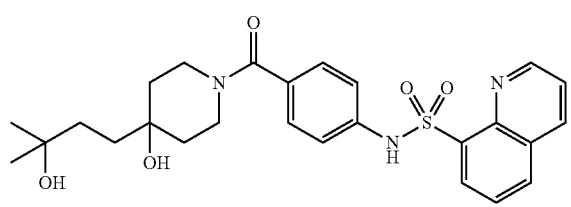
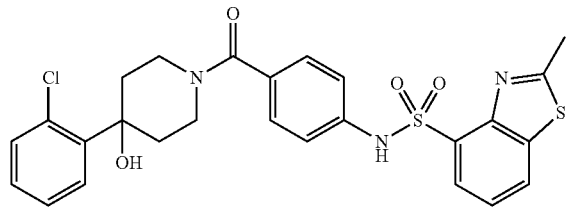
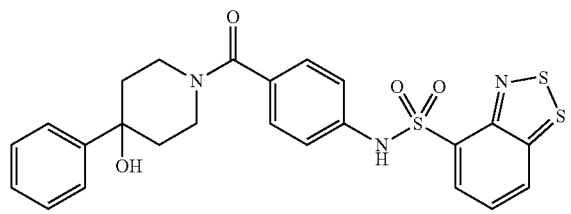
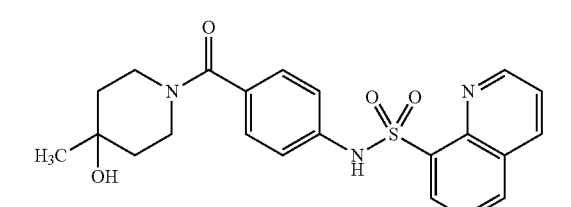
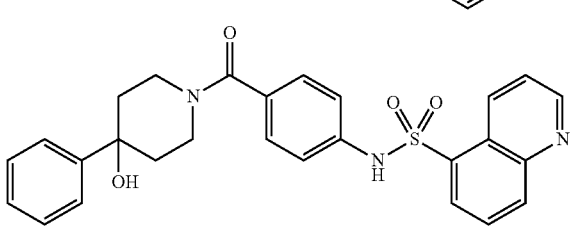
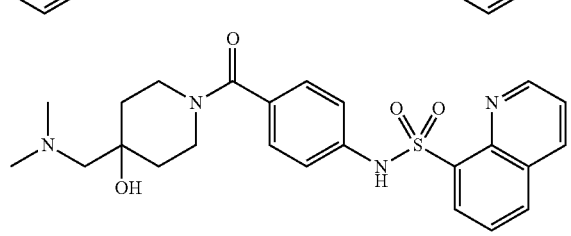
284
-continued
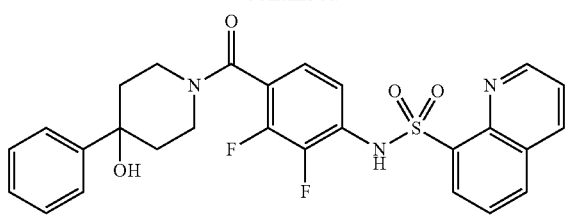
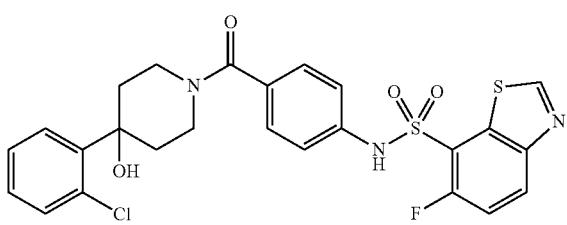
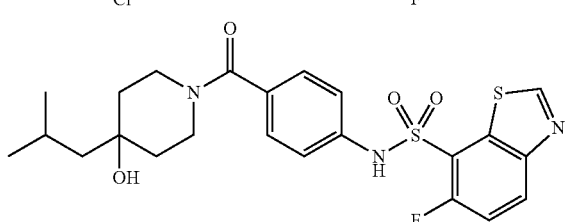
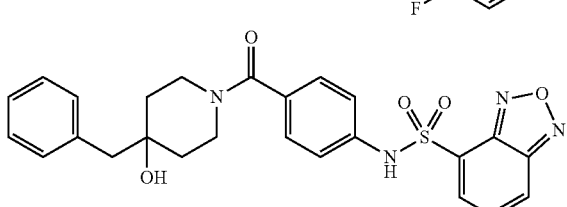
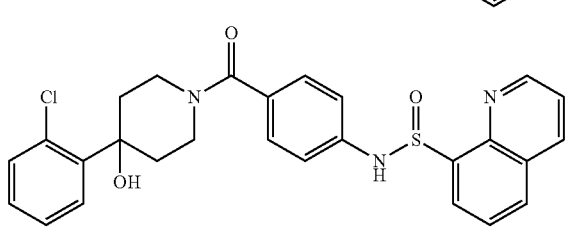
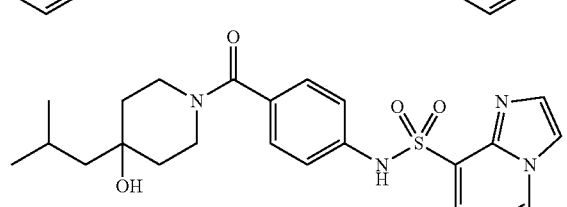
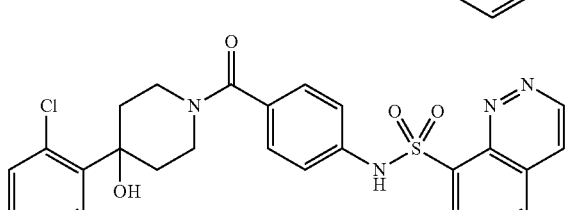
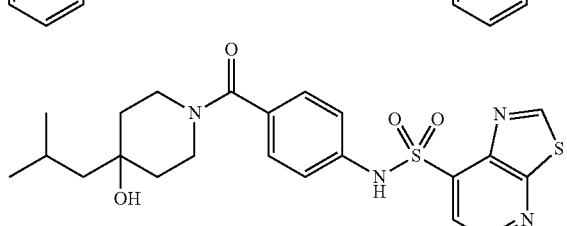

285
-continued
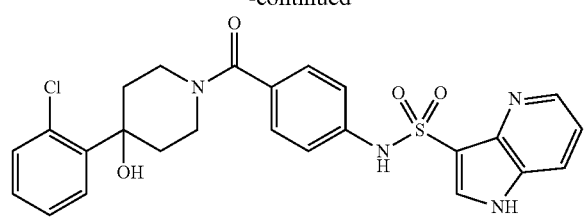
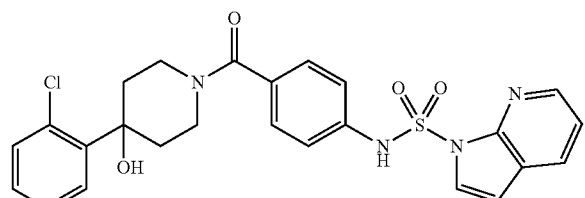
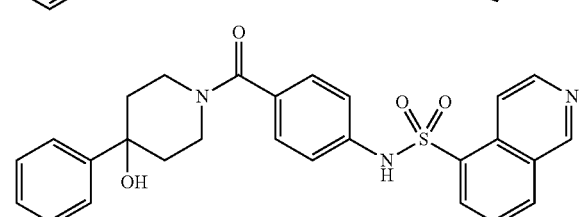
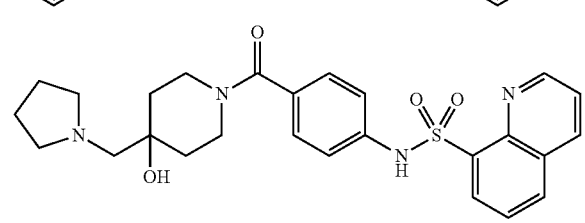
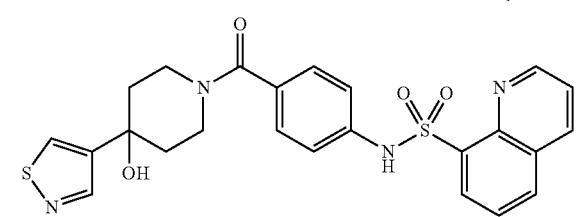
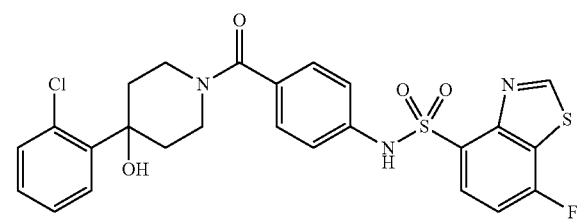
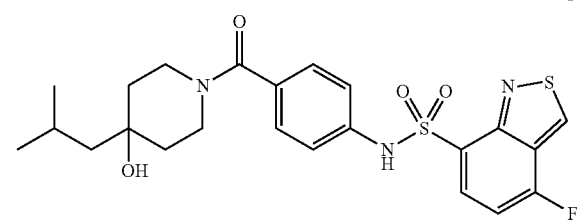
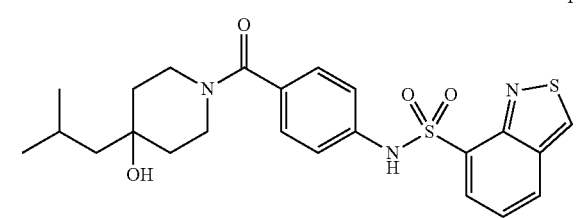
286
-continued
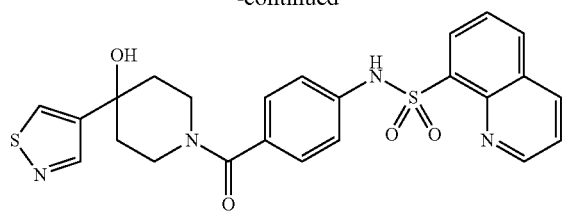
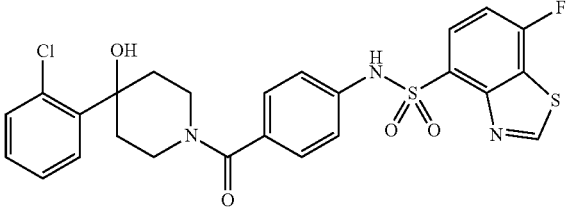
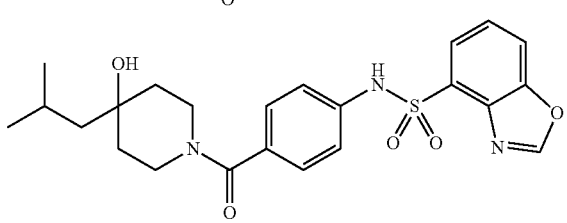
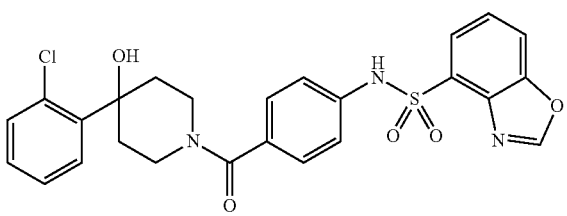
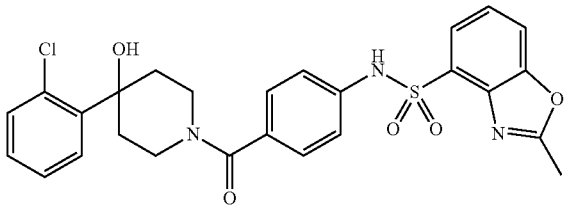
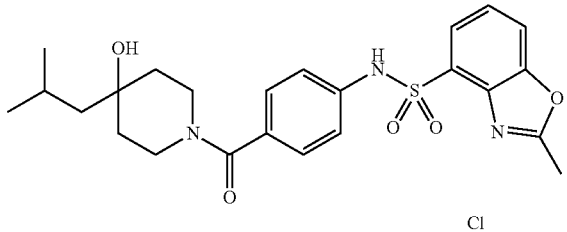
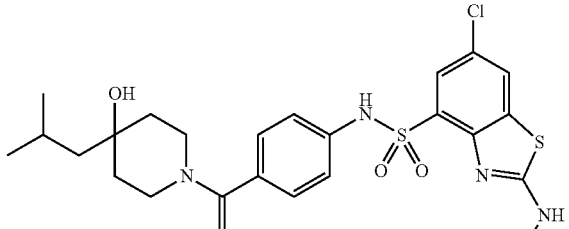
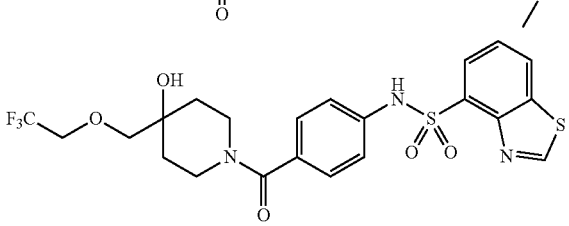

287
-continued
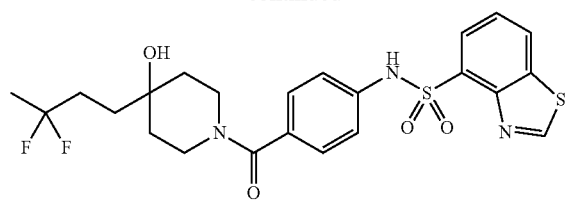
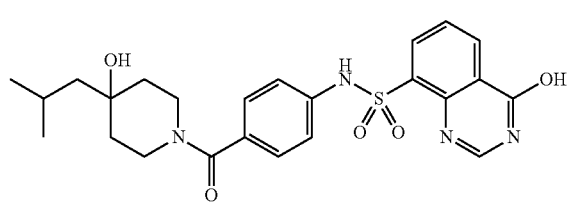
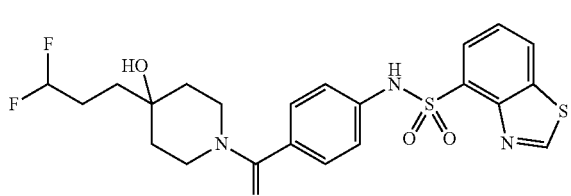
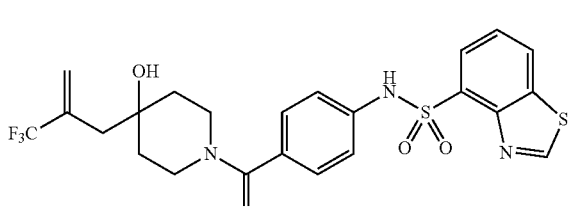
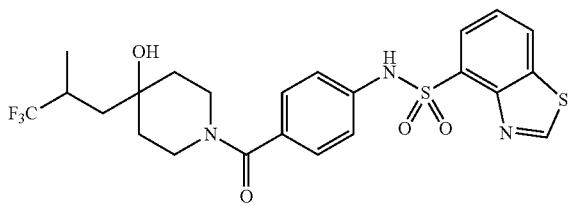
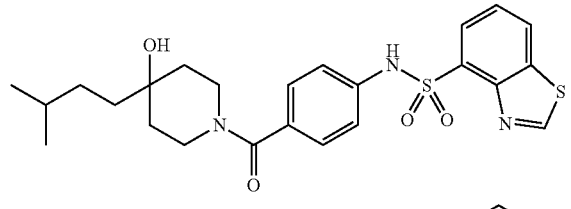
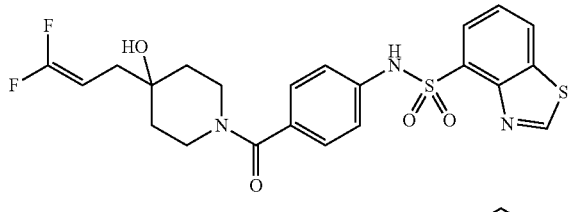
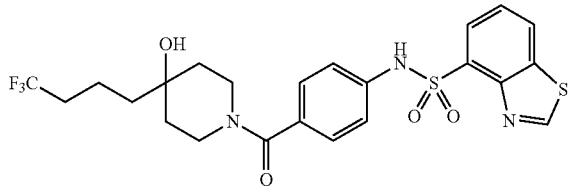
288
-continued
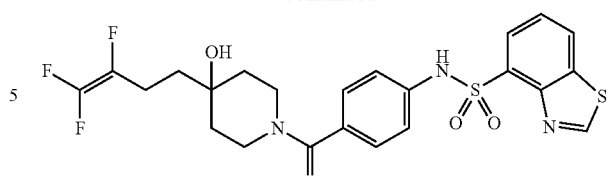
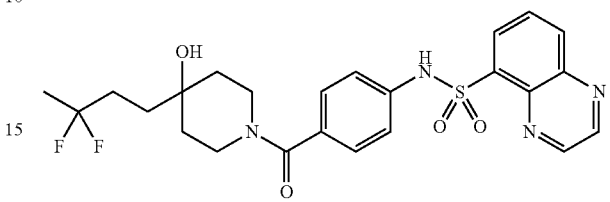
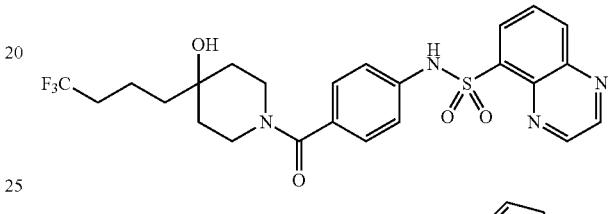
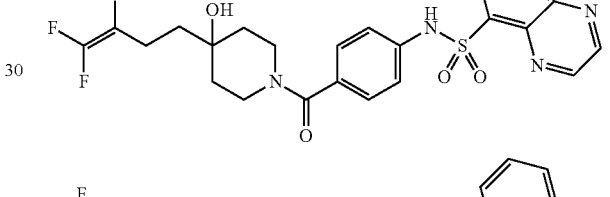
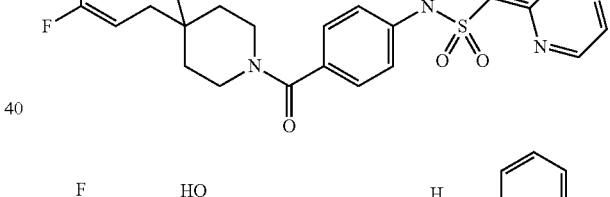
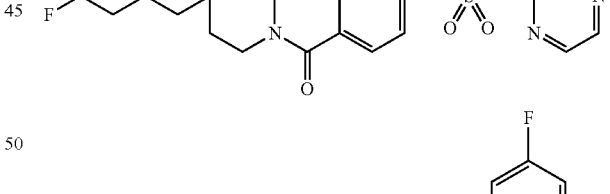
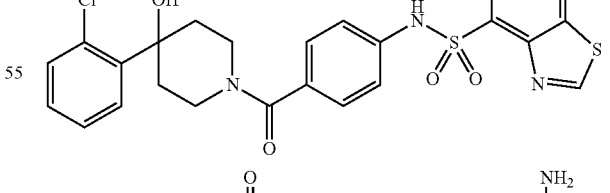
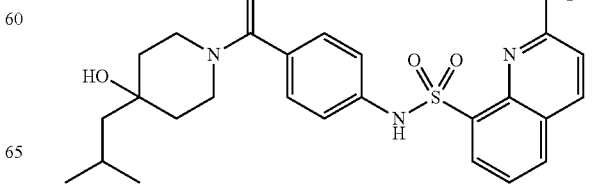

289 -continued

290 -continued

291
-continued
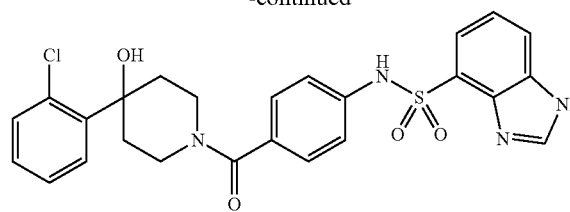
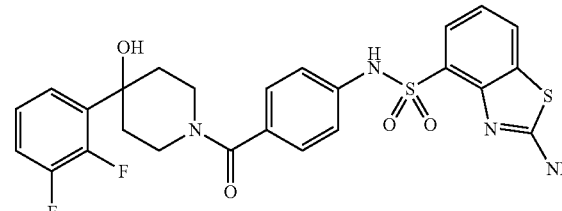
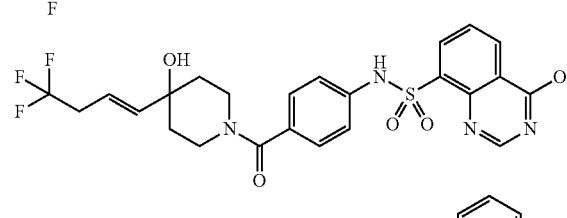
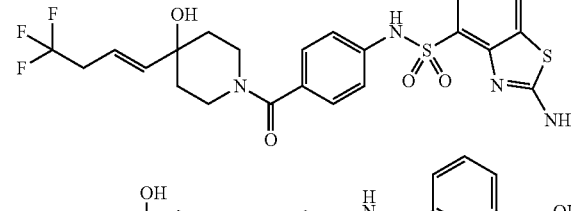
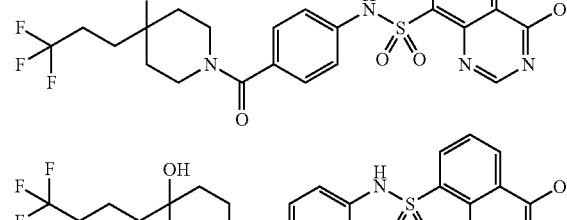
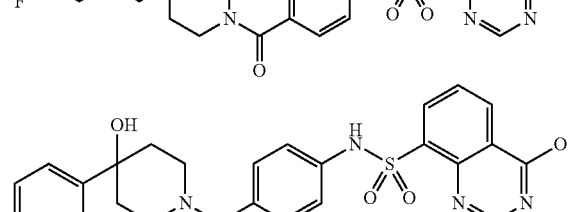
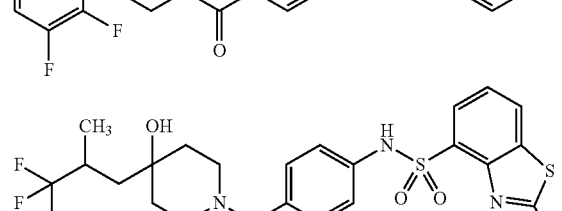
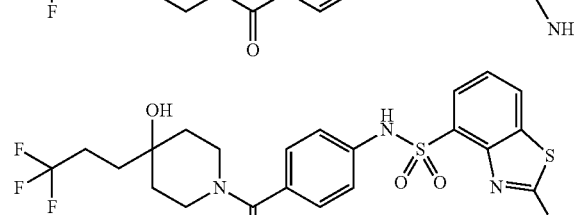
292
-continued
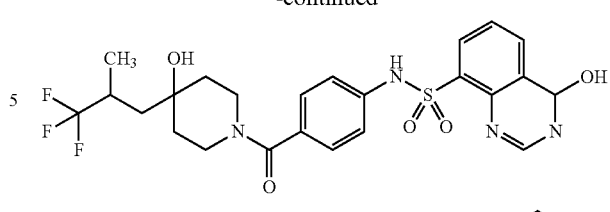
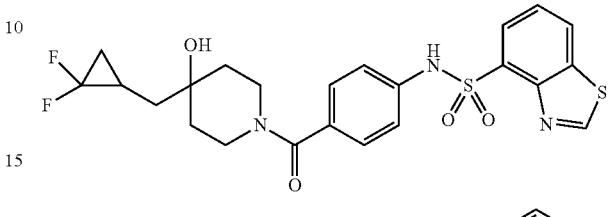
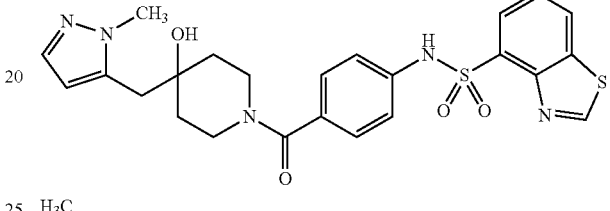
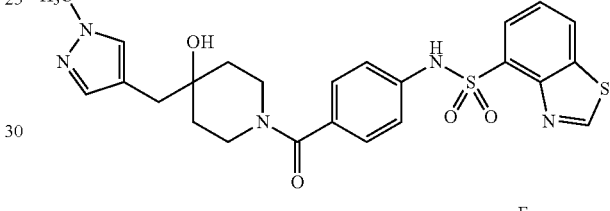
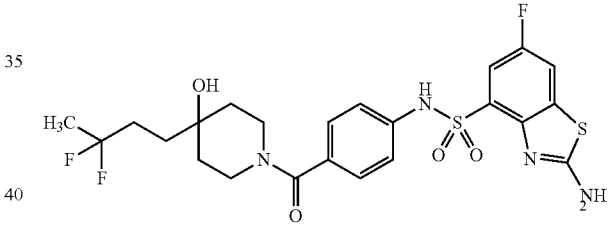
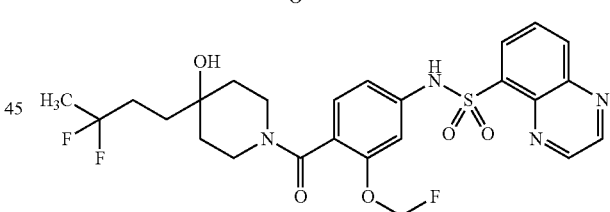
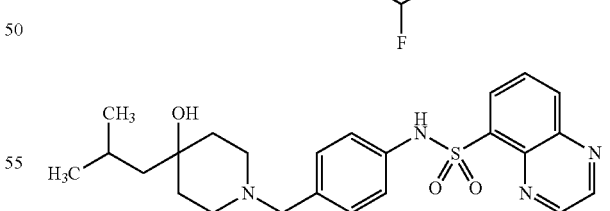
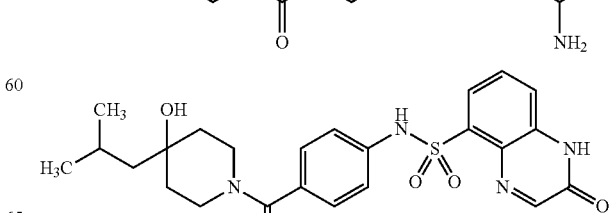

-continued
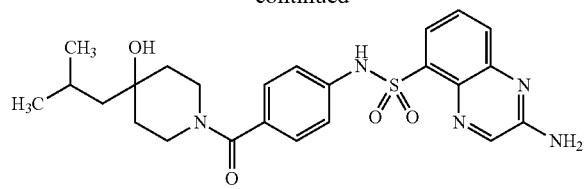
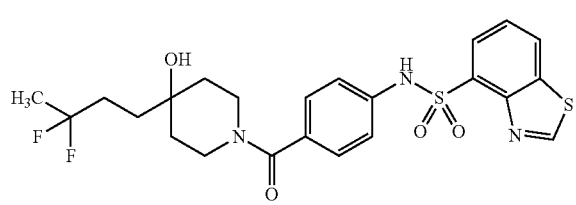
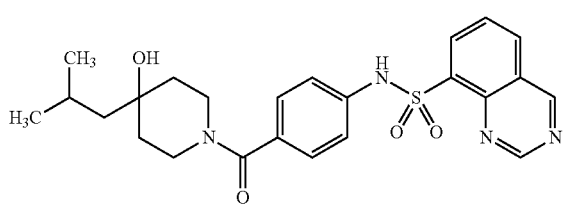
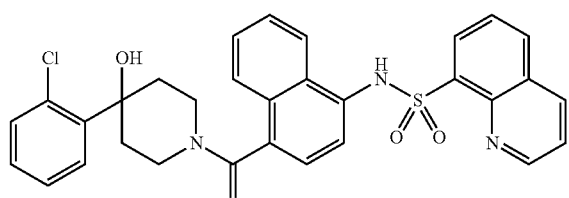
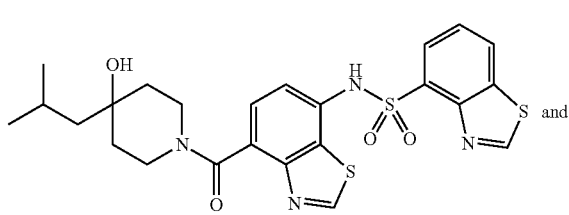
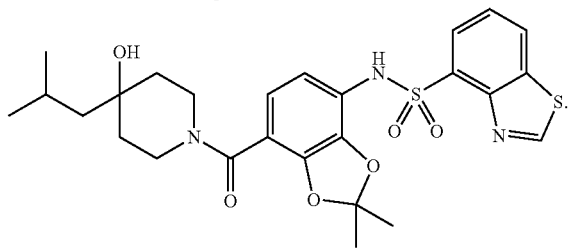
14. The compound of claim 1 having the following structure:
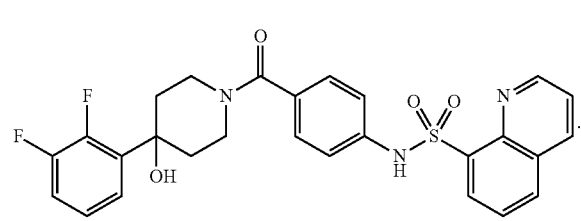
15. The compound of claim 1 having the following structure:
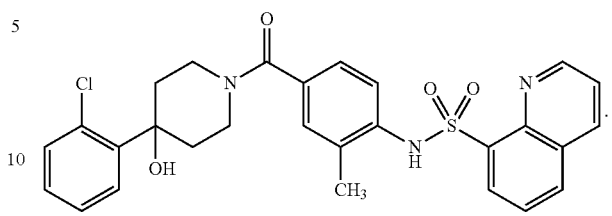
16. The compound of claim 1 having the following structure:
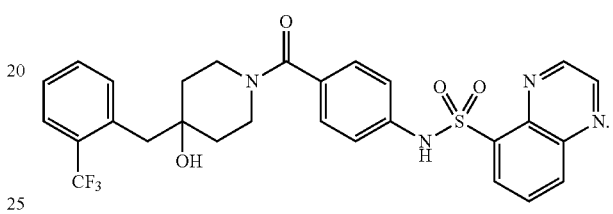
17. The compound of claim 1 having the following structure:
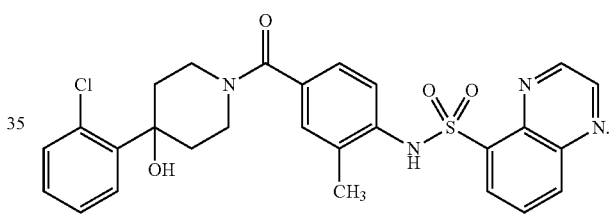
18. The compound of claim 1 having the following structure:
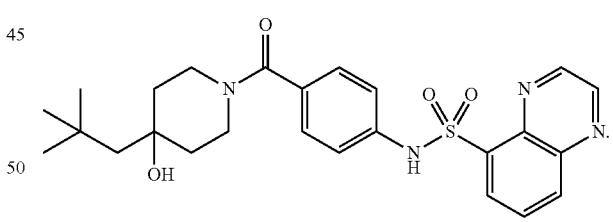
19. The compound of claim 1 having the following structure:
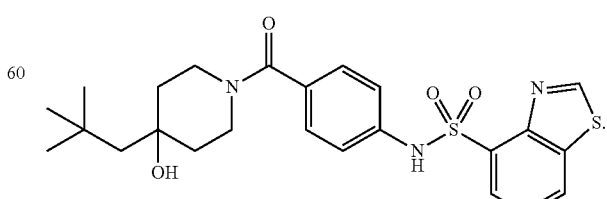

20. The compound of claim 1 having the following structure:

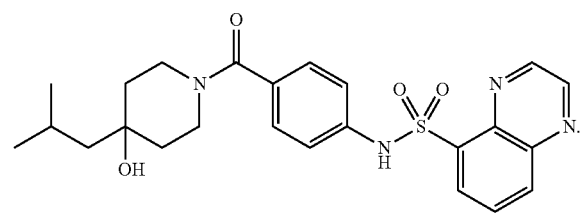 [SMILES: CC(C)CC1(O)CCN(C(=O)c2ccc(NS(=O)(=O)c3cccc4nccnc34)cc2)CC1]

21. The compound of claim 1 having the following structure:

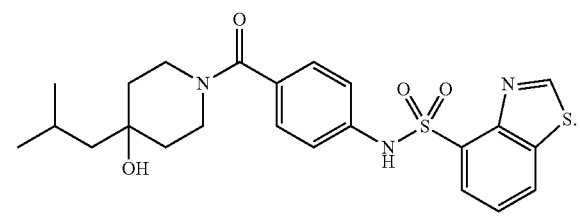 [SMILES: CC(C)CC1(O)CCN(C(=O)c2ccc(NS(=O)(=O)c3cccc4scnc34)cc2)CC1]

22. The compound of claim 1 having the following structure:

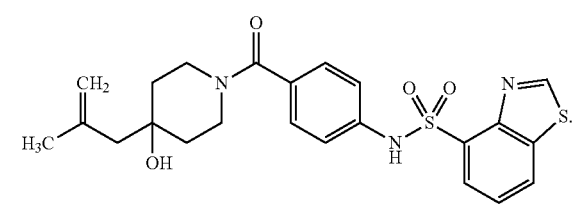 [SMILES: C=C(C)CC1(O)CCN(C(=O)c2ccc(NS(=O)(=O)c3cccc4scnc34)cc2)CC1]

23. The compound of claim 1 having the following structure:

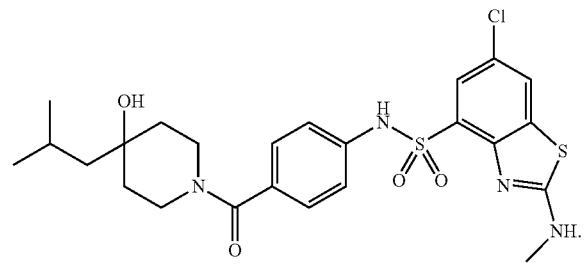 [SMILES: CNc1nc2c(S(=O)(=O)Nc3ccc(C(=O)N4CCC(O)(CC(C)C)CC4)cc3)cc(Cl)cc2s1]

24. The compound of claim 1 having the following structure:

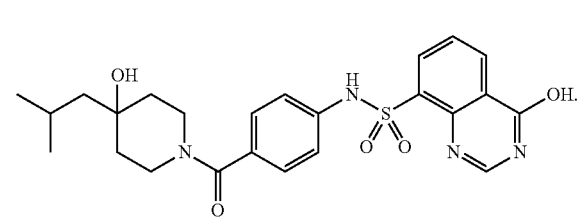 [SMILES: CC(C)CC1(O)CCN(C(=O)c2ccc(NS(=O)(=O)c3cccc4c(O)ncnc34)cc2)CC1]

25. The compound of claim 1 having the following structure:

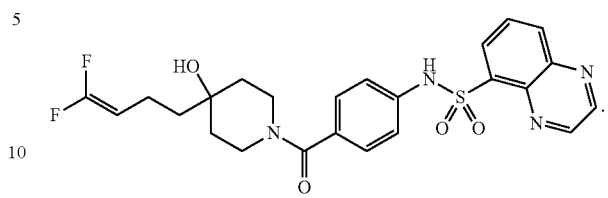

26. The compound of claim 1 having the following structure:

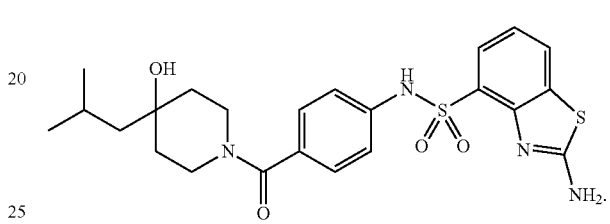 [SMILES: CC(CC1(O)CCN(C(=O)c2ccc(NS(=O)(=O)c3cccc4sc(N)nc34)cc2)CC1)C(F)(F)F]

27. The compound of claim 1 having the following structure:

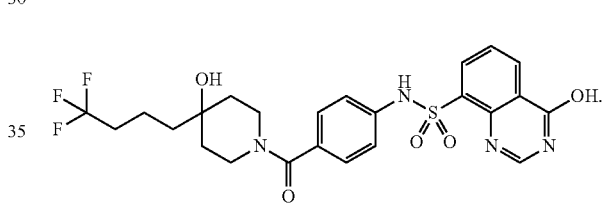

28. The compound of claim 1 having the following structure:

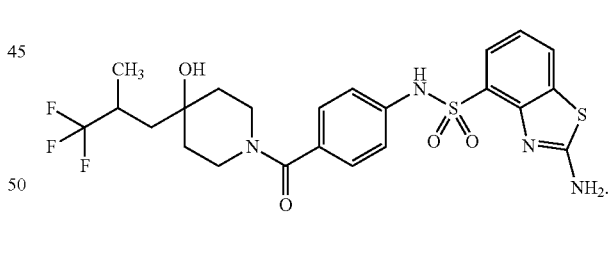

29. The compound of claim 1 having the following structure:

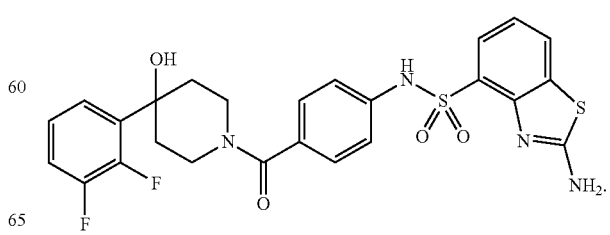

30. The compound of claim 1 having the following structure:
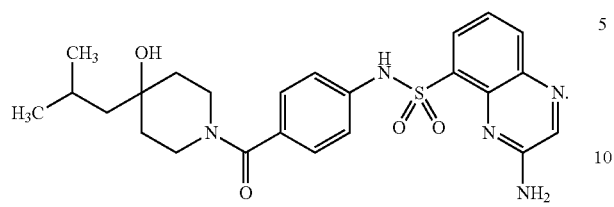
31. The compound of claim 1 having the following structure:
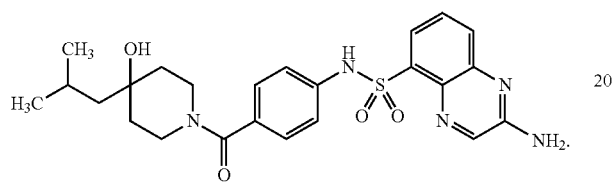
* * * * *